United States Patent
Abo et al.

(10) Patent No.: US 8,715,941 B2
(45) Date of Patent: May 6, 2014

(54) ANTIBODIES TO LRP6

(75) Inventors: Arie Abo, Oakland, CA (US); Minke Binners, San Francisco, CA (US)

(73) Assignee: Arca Biopharma, Inc., Broomfield, CO (US)

( * ) Notice: Subject to any disclaimer, the term of this patent is extended or adjusted under 35 U.S.C. 154(b) by 222 days.

(21) Appl. No.: 12/743,149

(22) PCT Filed: Nov. 14, 2008

(86) PCT No.: PCT/US2008/083486
§ 371 (c)(1),
(2), (4) Date: Jun. 23, 2011

(87) PCT Pub. No.: WO2009/064944
PCT Pub. Date: May 22, 2009

(65) Prior Publication Data
US 2011/0243963 A1   Oct. 6, 2011

Related U.S. Application Data

(60) Provisional application No. 60/988,647, filed on Nov. 16, 2007.

(51) Int. Cl.
*G01N 33/53* (2006.01)
*C12N 5/07* (2010.01)
*C07K 16/00* (2006.01)

(52) U.S. Cl.
USPC ............ 435/7.1; 435/326; 435/328; 435/331; 435/335; 435/336; 530/387.1; 530/387.3; 530/388.1; 530/388.15; 530/388.23; 530/388.24

(58) Field of Classification Search
None
See application file for complete search history.

(56) References Cited

U.S. PATENT DOCUMENTS

| | | | |
|---|---|---|---|
| 5,624,659 A | 4/1997 | Bigner et al. | |
| 7,442,534 B2 | 10/2008 | Abo et al. | 435/69.1 |
| 2003/0138804 A1 | 7/2003 | Boyle et al. | 435/6 |
| 2003/0194708 A1 | 10/2003 | Binnerts et al. | 435/6 |
| 2006/0094046 A1 | 5/2006 | Abo et al. | 435/6 |
| 2006/0127393 A1 | 6/2006 | Li et al. | |
| 2006/0127919 A1 | 6/2006 | Abo et al. | 435/6 |
| 2006/0198791 A2 | 9/2006 | Wu et al. | |
| 2009/0130113 A1 | 5/2009 | Kneissel et al. | 424/139.1 |
| 2009/0181009 A1 | 7/2009 | Abo et al. | 424/130.1 |
| 2010/0028335 A1 | 2/2010 | Lu et al. | 424/130.1 |
| 2012/0294871 A1* | 11/2012 | Cao et al. | 424/172.1 |

FOREIGN PATENT DOCUMENTS

| | | |
|---|---|---|
| EP | 0338395 A2 | 10/1989 |
| WO | 2006/055635 A2 | 5/2006 |
| WO | 2006/089114 A2 | 8/2006 |
| WO | WO 2009/051957 | 4/2009 |
| WO | WO 2009/051974 | 4/2009 |
| WO | 2009/056634 A2 | 5/2009 |

OTHER PUBLICATIONS van Meurs et al. (2006, J Bone Miner Res 21:141-150).*
van Meurs et al. (2008, JAMA 299:1277-1290).*
Tomaszewski et al. (2009, Arterioscler. Thromb. Vasc Biol. 29:1316-1321).*
Sarzani et al. (2011, Nutr. Metab. Cardiovasc. Dis. 21:150-156).*
Alarcón et al. (2013, Neurobiol. Aging 34:1709.e9-e18).*
Binnerts, Minke E. et al., "The First Propeller Domain of LRP6 Regulates Sensitivity to DKK1," Molecular Biology of the Cell, vol. 20:3552-3560 (2009).
GenBank Accession No. AAA53291, Marget, M. et al., "Cloning and characterization of cDNAs coding for the heavy and light chains of a monoclonal antibody specific for *Pseudomonas aeruginosa* outer membrane protein I," Gene, vol. 74:335-345 (1988), 2 pages, Nov. 28, 1994.
Khan, Zahid et al., "Analysis of Endogenous LRP6 Function Reveals a Novel Feedback Mechanism by Which Wnt Negatively Regulates Its Receptor," Molecular and Cellular Biology, vol. 27(20):7291-7301 (2007).
Li, Lin et al., "Second Cysteine-rich Domain of Dickkopf-2 Activates Canonical Wnt Signaling Pathway via LRP-6 Independently of Dishevelled," The Journal of Biological Chemistry, vol. 277(8):5977-5981 (2002).
Mao, Bingyu et al., "LDL-receptor-related protein 6 is a receptor for Dickkopf proteins," Nature, vol. 411 (6835):321-325 (2001).
Rudikoff, Stuart et al., "Single amino acid substitution altering antigen-binding specificity," Proc. Natl. Acad. Sci. USA, vol. 79:1979-1983 (1982).
Yaccoby, Shmuel et al., "Antibody-based inhibition of DKK1 suppresses tumor-induced bone resorption and multiple myeloma growth in vivo," Blood, vol. 109(5):2106-2111 (2007).
Supplementary European Search Report for Application No. 08850109.3, 20 pages, dated Sep. 26, 2011.
International Preliminary Report on Patentability and Written Opinion for Application No. PCT/US2008/083486, 6 pages, dated May 18, 2010.
International Search Report for Application No. PCT/US08/83486, 3 pages, dated Apr. 29, 2009.
Barker and Clevers, "Mining the Wnt pathway for cancer therapeutics," *Nat. Rev. Drug Discov.*, 5(12):997-1014, 2006.
Binnerts et al., "R-Spondin 1 regulates Wnt signaling by inhibiting internalization of LRP6," *Proc. Natl. Sci. USA*, 104:14700-14705, 2007.
Boyden et al., "High bone density due to a mutation in LDL-receptor-related protein 5," *New Engl. J. Med.*, 346:1513-1521, 2002.
DasGupta and Fuchs, "Multiple Roles for Activated LEF/TCF Transcription Complexes During Hair Follicle Development and Differentiation," *Development*, 126(20):4557-4568, 1998.

(Continued)

*Primary Examiner* — Elizabeth C Kemmerer
(74) *Attorney, Agent, or Firm* — Lando & Anastasi LLP

(57) ABSTRACT

Anti-LRP6 antibodies and antigen-binding fragments thereof, as well as pharmaceutical compositions comprising such antibodies and antigen-binding fragments are described. These anti-LRP6 antibodies can be used to enhance Wnt activity and/or antagonize Dkk1 activity. Also described are methods of therapy using such antibodies and antigen-binding regions to bind modulate Wnt/LRP6 signaling to promote tissue homeostasis, regeneration and repair in diseases such as, but not limited to, bone disorders, such as osteoporosis, rheumatoid arthritis, and osteolytic lesions caused by osteoarthritis and multiple myeloma, gastrointestinal disease and wound healing.

13 Claims, 32 Drawing Sheets

(56) References Cited

OTHER PUBLICATIONS

Diarra et al., "Dickkopf-1 is a master regulator of joint remodeling," *Nat. Med.*, 13:156-163, 2007.
Fathke et al., "Wnt signaling induces epithelial differentiation during cutaneous wound healing," *BMC Cell Biology*, 7:4, 2006.
Gong et al., "LDL receptor-related protein 5 (LRP5) affects bone accrual and eye development," *Cell*, 107:513-523, 2001.
He et al., "LDL receptor-related proteins 5 and 6 in Wnt/beta-catenin signaling: arrows point the way," *Development*, 131:1663-1677, 2004.
Ito et al., "Stem cells in the hair follicle bulge contribute to wound repair but not to homeostasis of the epidermis," *Nat. Med.*, 11:1351-4, 2005.
Jeon et al., "Implications for familial hypercholesterolemia from the structure of the LDL receptor YWTD-EGF domain pair," *Nat. Struct. Biol.*, 8:499-504, 2001.
Kirikoshi et al., "Expression profiles of 10 members of Frizzled gene family in human gastric cancer," *Int. J. Oncol.*, 19:767-771, 2001.
Korinek et al., "Depletion of epithelial stem-cell compartments in the small intestine of mice lacking Tcf-4," *Nat. Genet.*, 19:379-83, 1998.
Krishnan et al., "Regulation of bone mass by Wnt signaling," *J. Clin. Invest.*, 116:1202-1209, 2006.
Kuhnert et al., "Essential requirement for Wnt signaling in proliferation of adult small intestine and colon revealed by adenoviral expression of Dickkopf-1," *Proc. Natl. Acad. Sci. USA*, 101:266-71, 2004.
Kulkarni et al., "Orally bioavailable GSK-3alpha/beta dual inhibitor increases markers of cellular differentiation in vitro and bone mass in vivo," *J. Bone Miner. Res.*, 21:910-920, 2006.
Lo Celso et al., "Transient activation of beta-catenin signalling in adult mouse epidermis is sufficient to induce new hair follicles but continuous activation is required to maintain hair follicle tumours," *Development*, 131:1787-1799, 2004.
Maretto et al., "Mapping Wnt/beta-catenin signaling during mouse development and in colorectal tumors," *Proc. Natl. Acad. Sci. USA*, 100:3299-3304, 2003.
Mukhopadhyay et al., "Dickkopf1 is required for embryonic head induction and limb morphogenesis in the mouse," *Dev. Cell.*, 1:423-434, 2001.
Munroe et al., "Prototypic G protein-coupled receptor for the intestinotrophic factor glucagon-like peptide 2 ," *Proc. Natl. Acad. Sci USA*, 16:1569-1573, 1999.
Pinson et al., "An LDL-receptor-related protein mediates Wnt signalling in mice," *Nature*, 407:535-538, 2000.
Poilu et al., "Serum concentrations of Dickkopf-1 protein are increased in patients with multiple myeloma and reduced after autologous stem cell transplantation," *Int. J. Cancer*, 119:1728-1731, 2006.
Reya and Clevers, "Wnt signalling in stem cells and cancer," *Nature*, 434:843-850, 2005.
Reya et al., "A role for Wnt signalling in self-renewal of haematopoietic stem cells," *Nature*, 423:409-414, 2003.
Sato et al., "Maintenance of pluripotency in human and mouse embryonic stem cells through activation of Wnt signaling by a pharmacological GSK-3-specific inhibitor," *Nature Med.*, 10:55-63, 2004.
Semënov et al., "DKK1 antagonizes Wnt signaling without promotion of LRP6 internalization and degradation," *J. Biol. Chem.*, 283:21427-21432, 2008.
Sher et al., "Structure-based mutational analyses in FGF7 identify new residues involved in specific interaction with FGFR2IIIb," *FEBS Lett.*, 552:150-154, 2003.
Sick et al., "WNT and DKK determine hair follicle spacing through a reaction-diffusion mechanism," *Science*, 314:1447-50, 2006.
Springer et al., "An extracellular beta-propeller module predicted in lipoprotein and scavenger receptors, tyrosine kinases, epidermal growth factor precursor, and extracellular matrix components," *J. Mol. Biol.*, 283:837-862, 1998.
Tamai et al., "LDL-receptor-related proteins in Wnt signal transduction," *Nature*, 407:530-535, 2000.
Tian et al., "The role of the Wnt-signaling antagonist DKK1 in the development of osteolytic lesions in multiple myeloma," *New Engl. J. Med.*, 349:2483-2494, 2003.
van Genderen et al., "Development of several organs that require inductive epithelial-mesenchymal interactions is impaired in LEF-1-deficient mice," *Genes Dev.*, 8:2691-2703, 1994.
Xu et al., "Deletion of beta-catenin impairs T cell development," *Nature Immunol.*, 4:1177-1182, 2003.
Yacooby and Epstein, "The Proliferative Potential of Myeloma Plasma Cells Manifest in the SCID-hu Host," *Blood*, 94:3576-3582, 1999.
Yacooby et al., "Primary Myeloma Cells Growing in SCID-hu Mice: A Model for Studying the Biology and Treatment of Myeloma and Its Manifestations," *Blood*, 92:2908-2913, 1998.
Yata and Yaccoby, "The SCID-rab model: a novel in vivo system for primary human myeloma demonstrating growth of CD138-expressing malignant cells," *Leukemia*, 18:1891-1897, 2004.
Zecher et al., "beta-Catenin signals regulate cell growth and the balance between progenitor cell expansion and differentiation in the nervous system," *Dev. Biol.*, 258:406-418, 2003.

* cited by examiner

A.
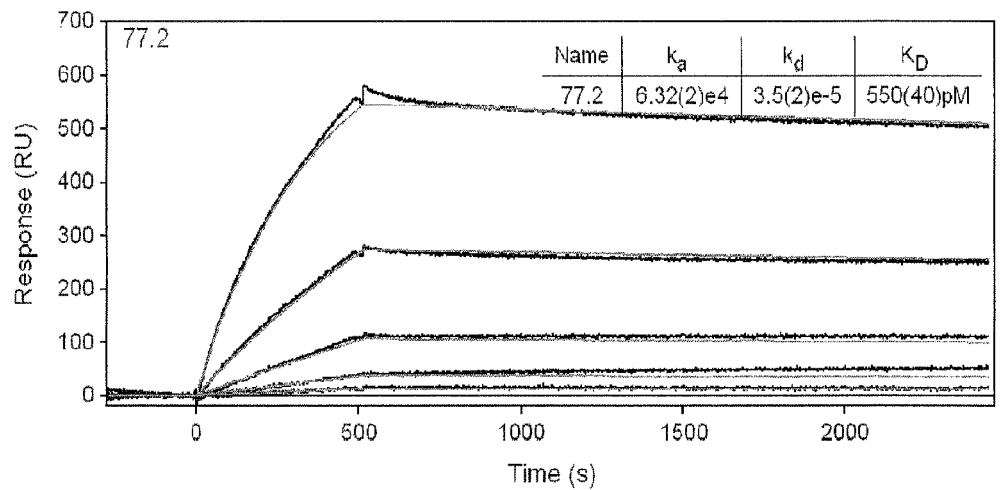
B.
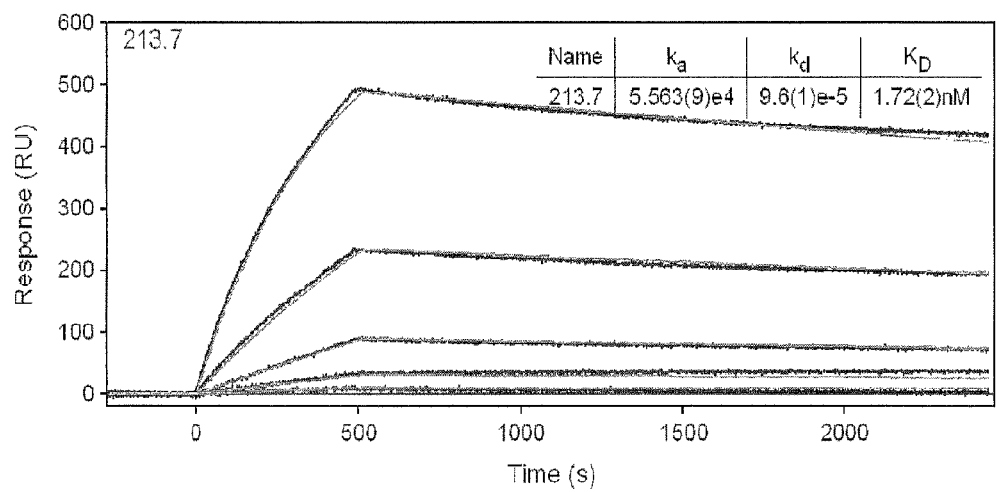
FIGURE 2

C.
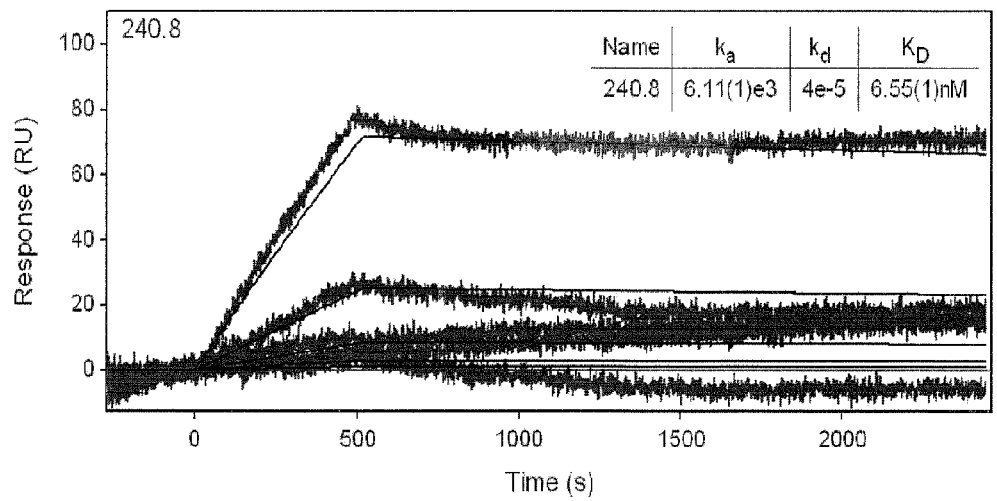
D.
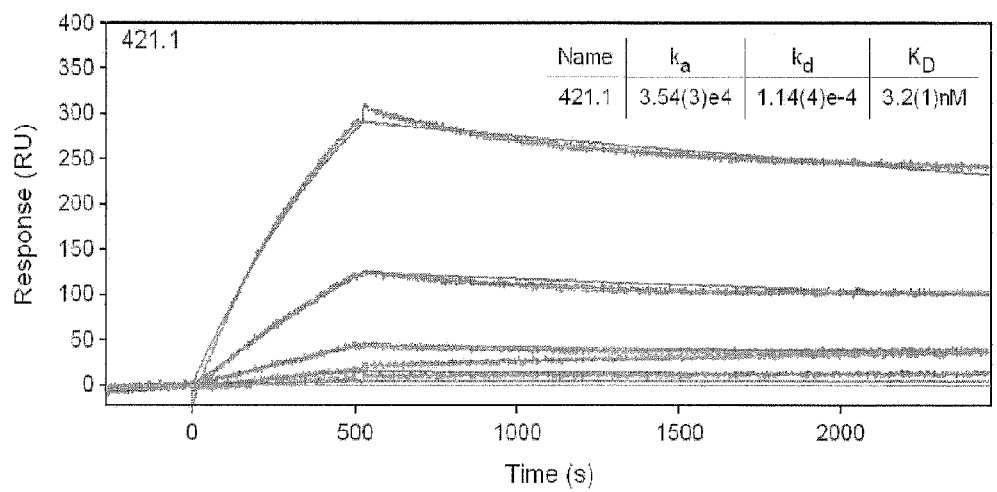
FIGURE 2, cont.

E.
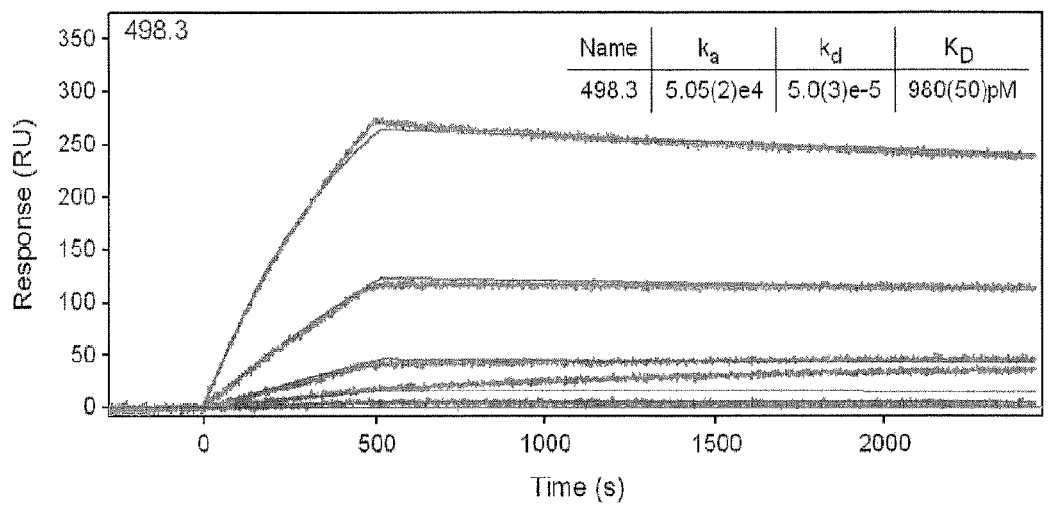
F.
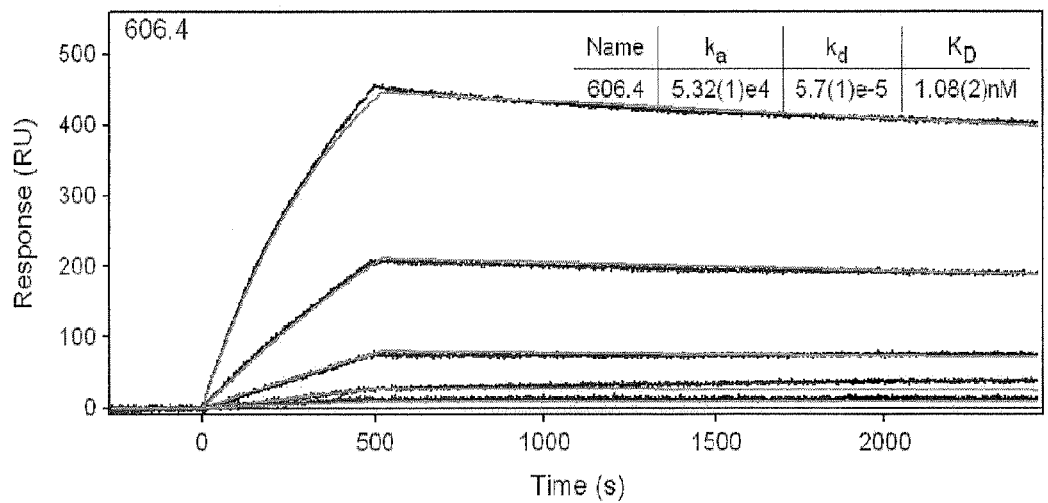
FIGURE 2, cont.

G.
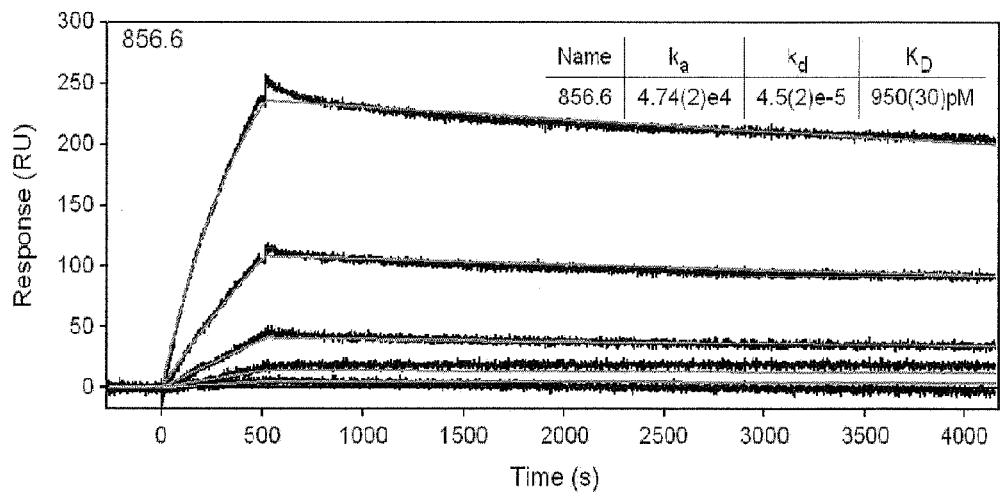
H.
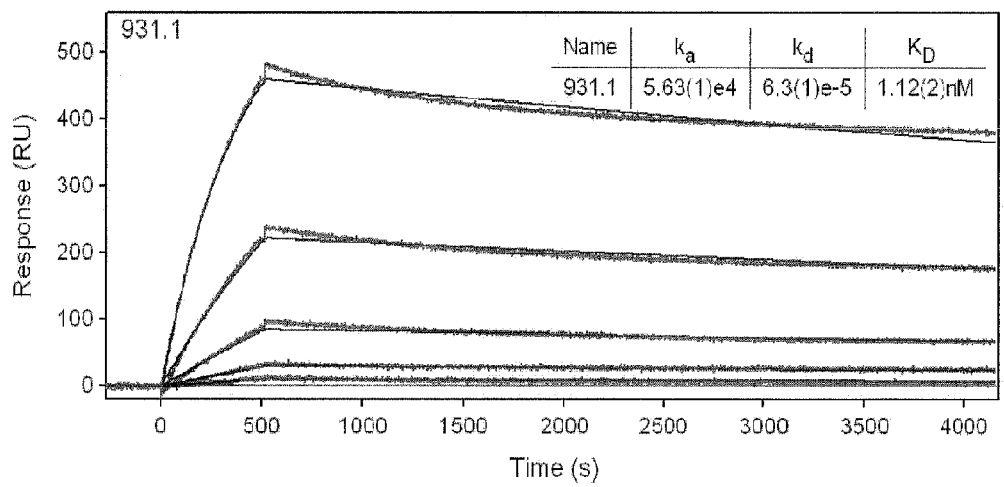
FIGURE 2, cont.

I.
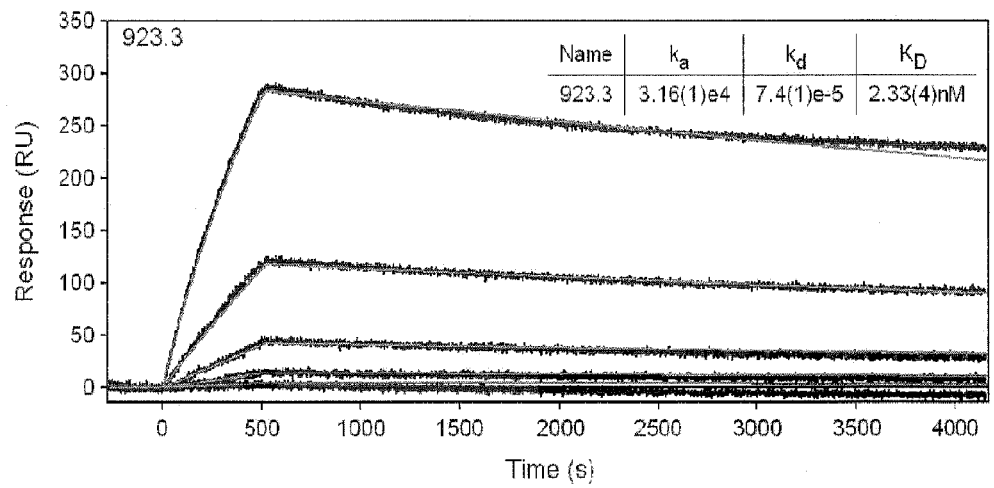
J.
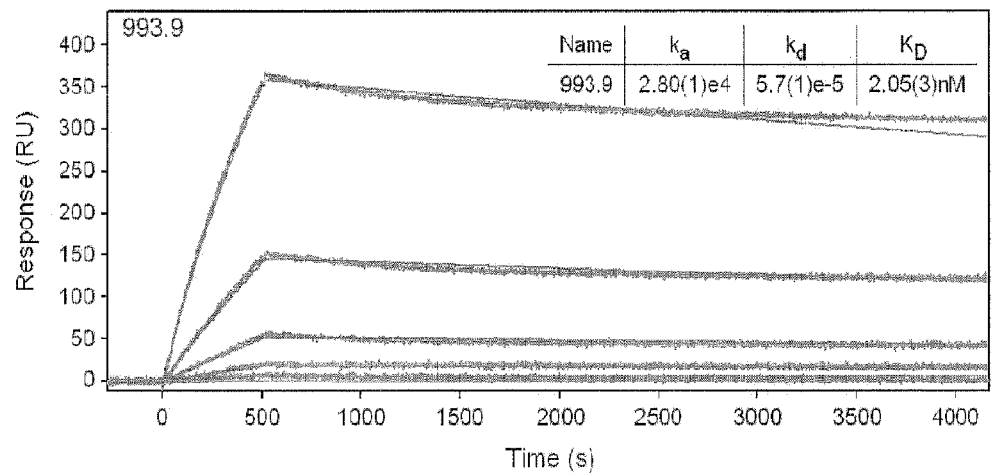
FIGURE 2, cont.

K.
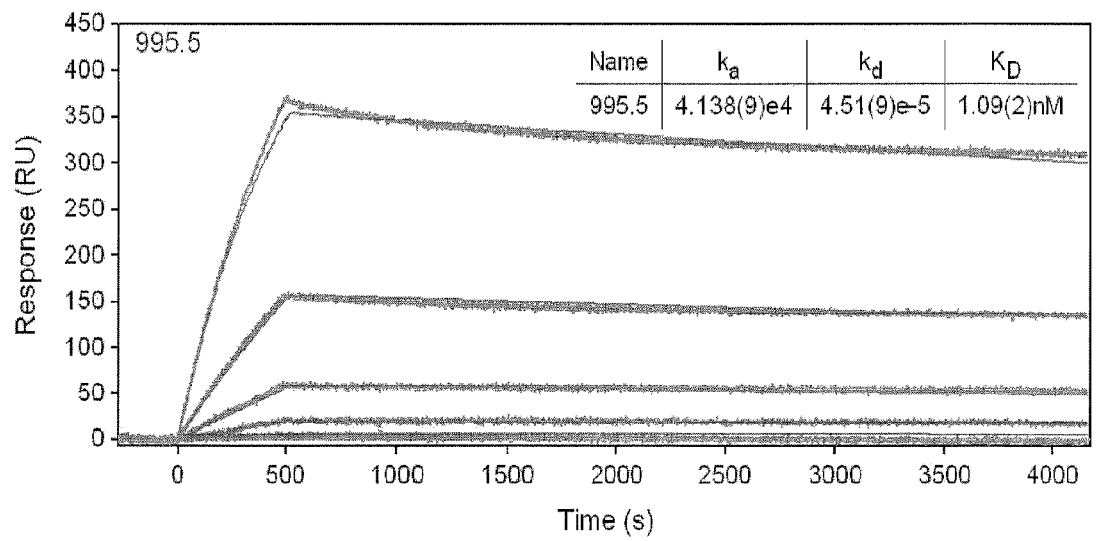
L.
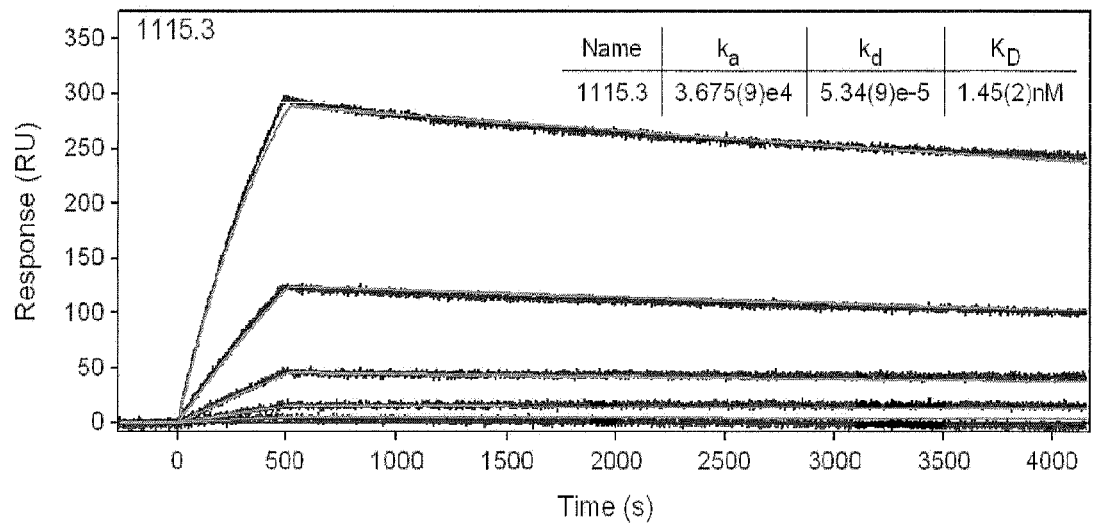
FIGURE 2, cont.

M.
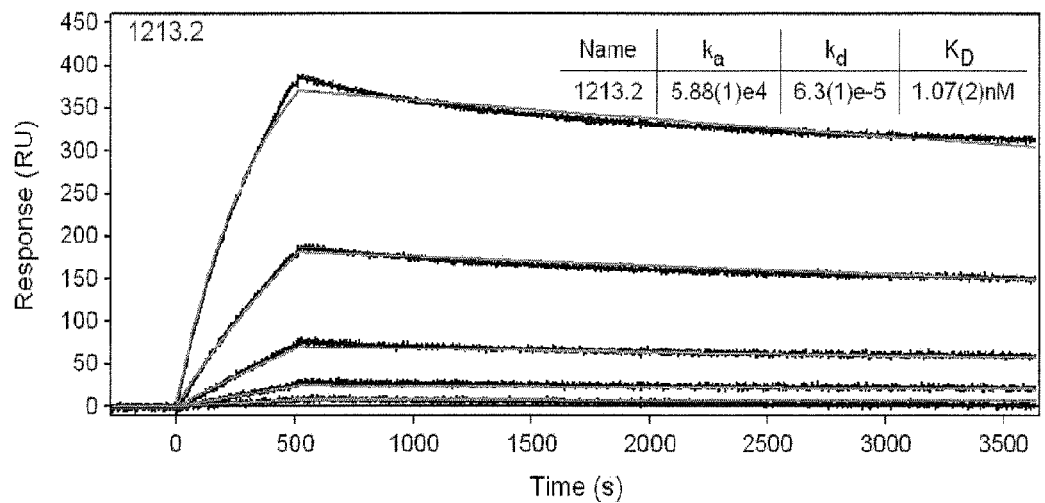
N.
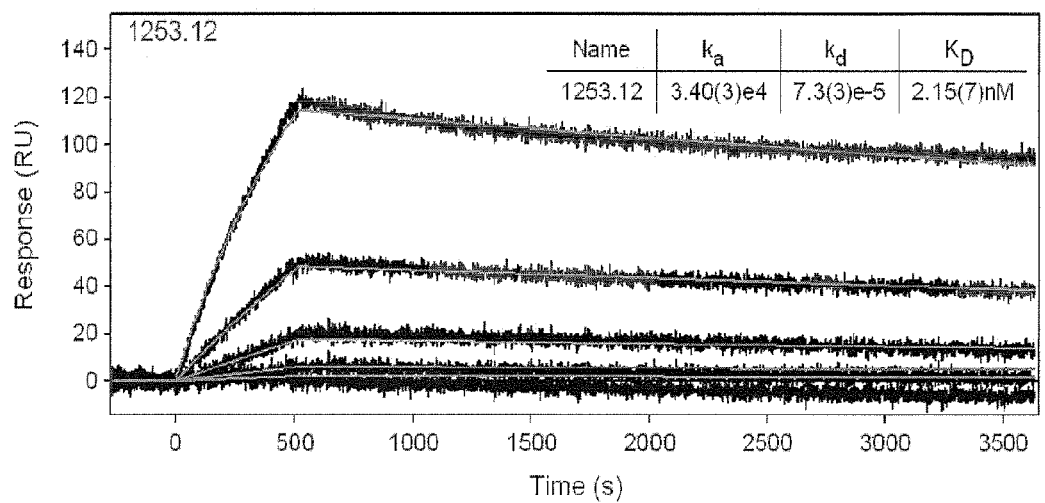
FIGURE 2, cont.

O.
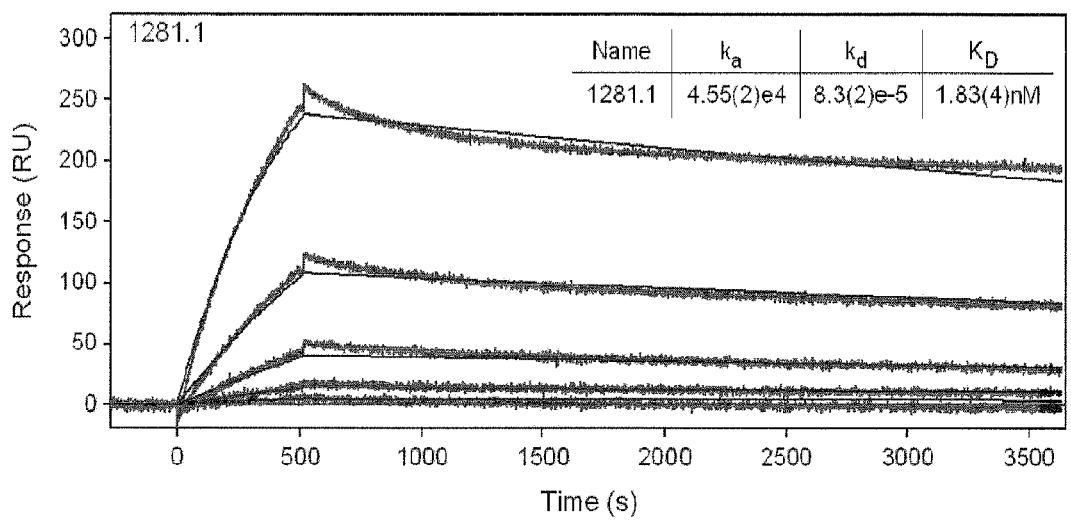
P.
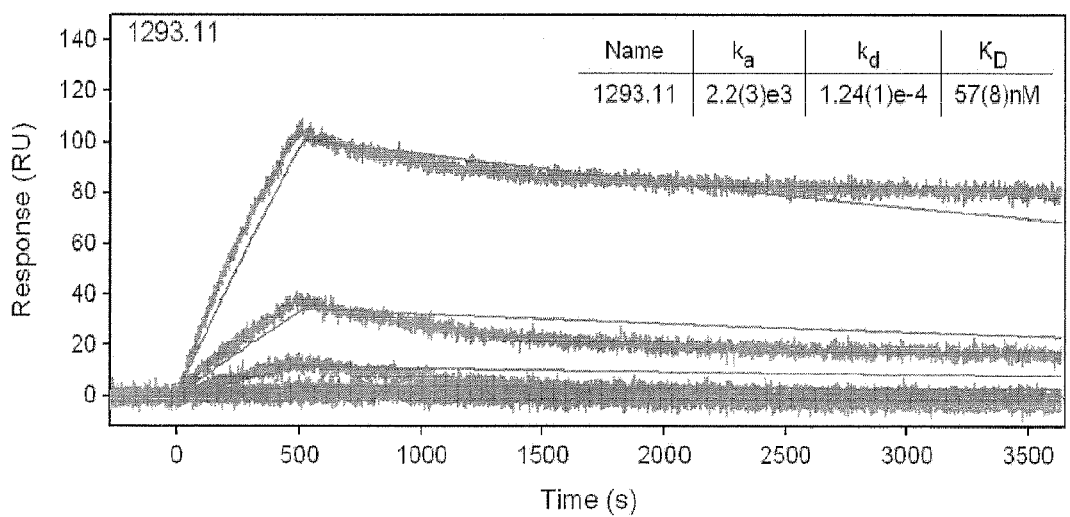
FIGURE 2, cont.

Q.
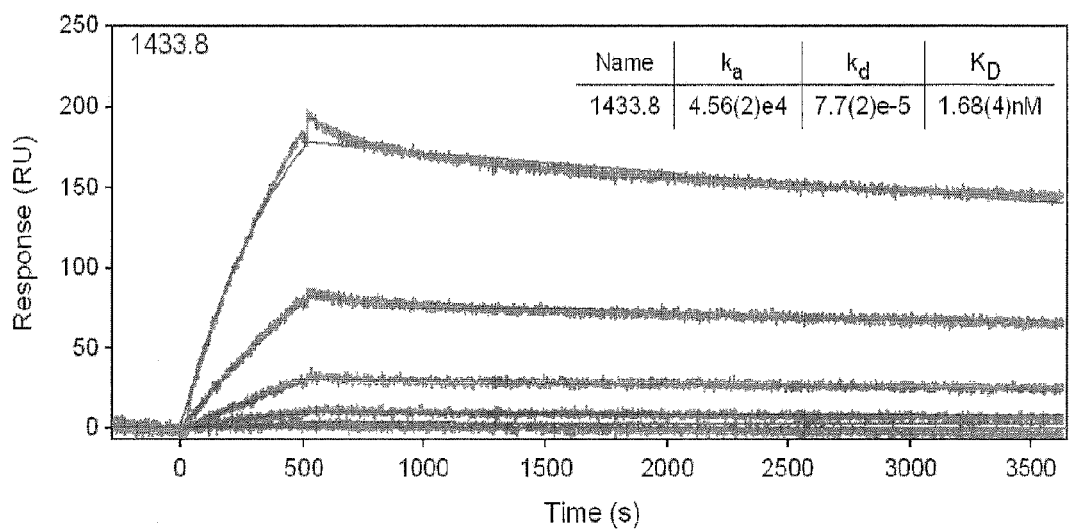
R.
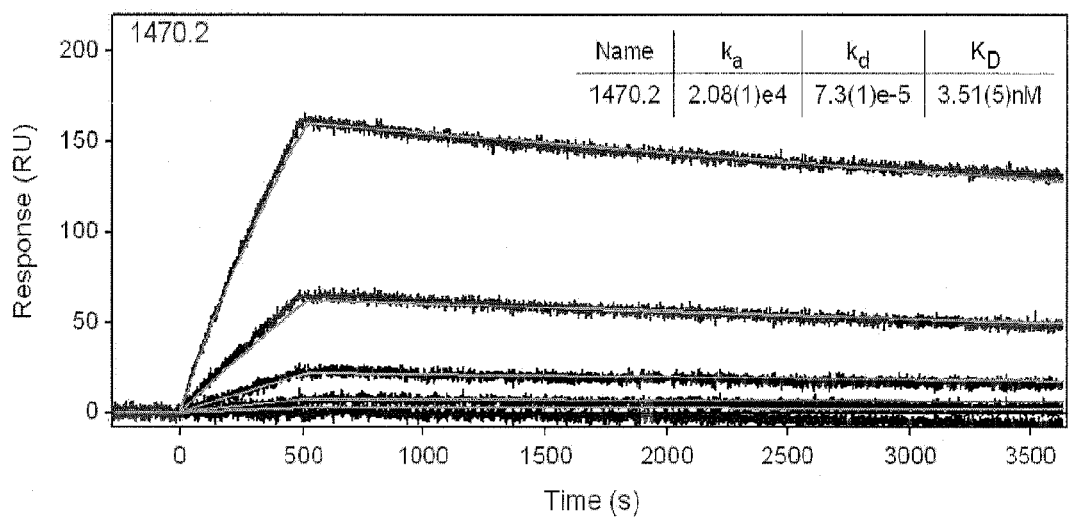
FIGURE 2, cont.

S.
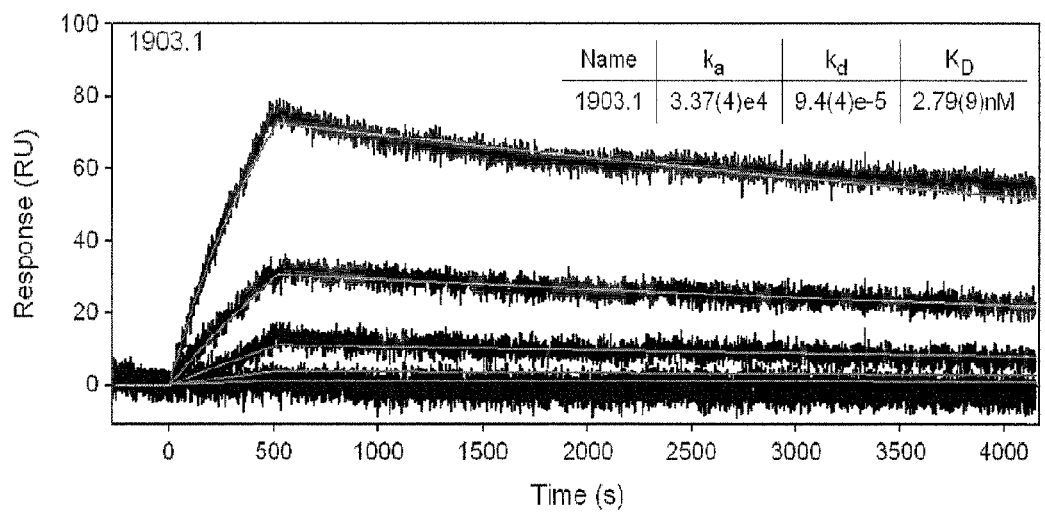
T.
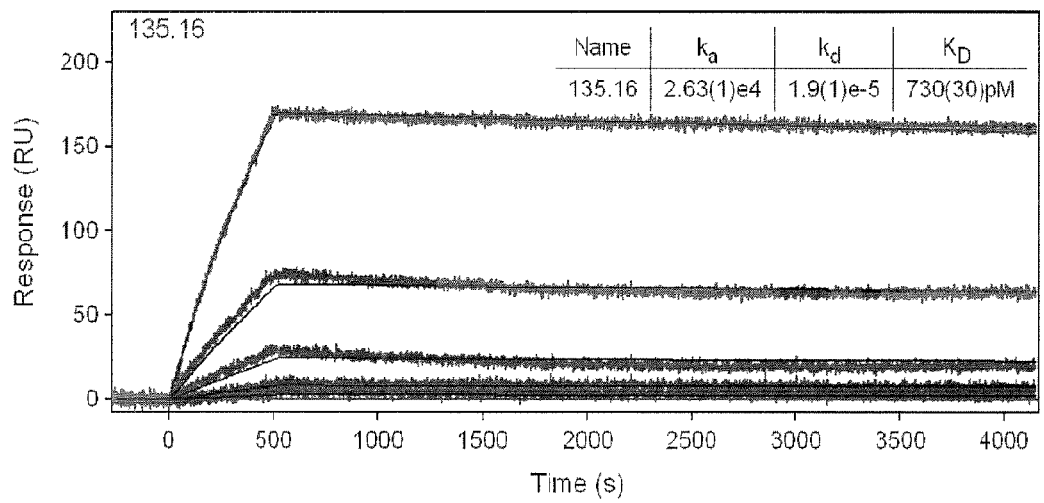
FIGURE 2, cont.

U.
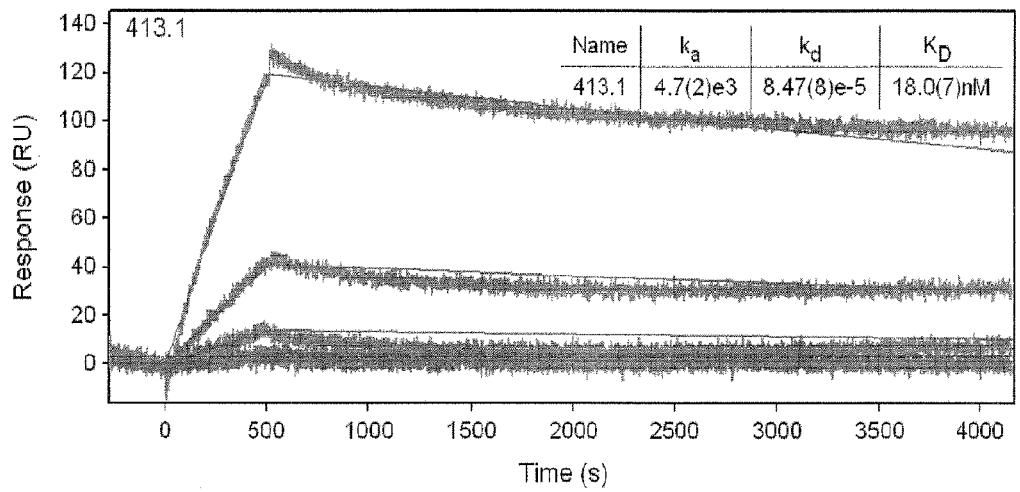
V.
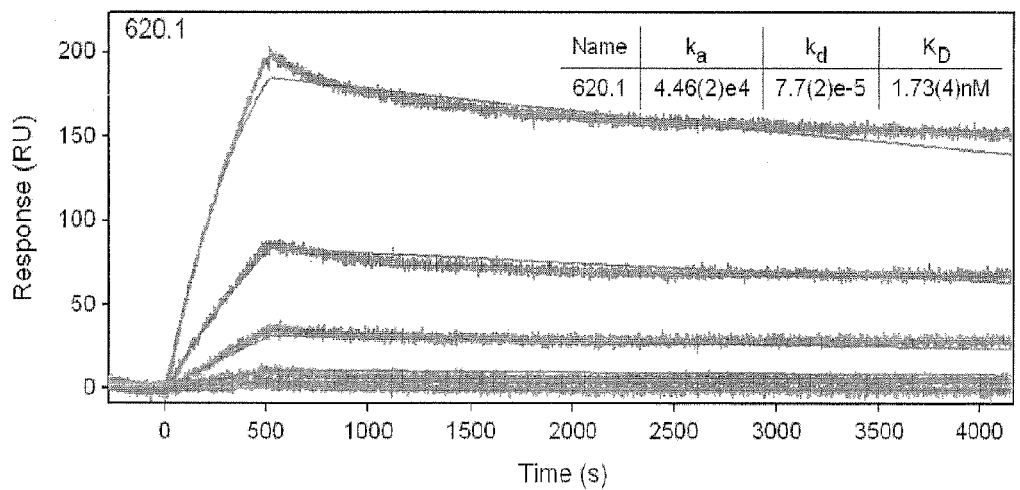
FIGURE 2, cont.

W.
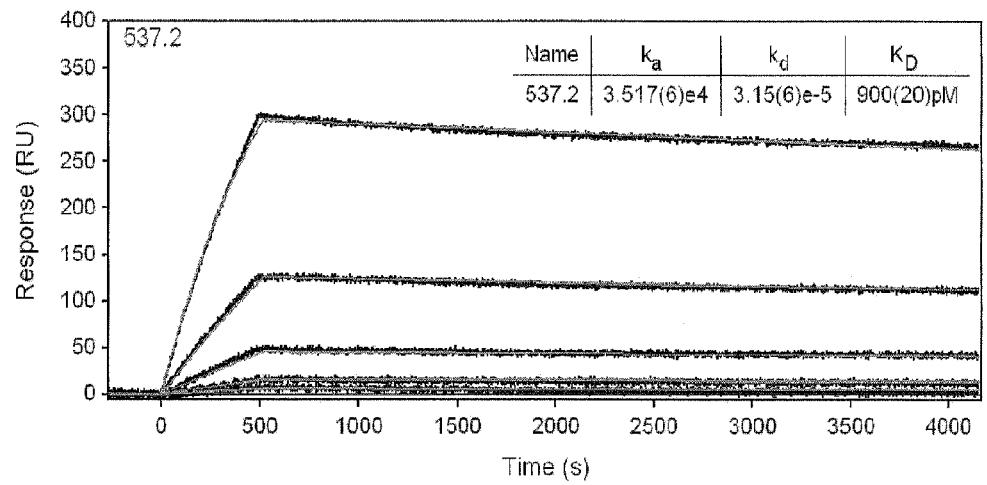
FIGURE 2, cont.

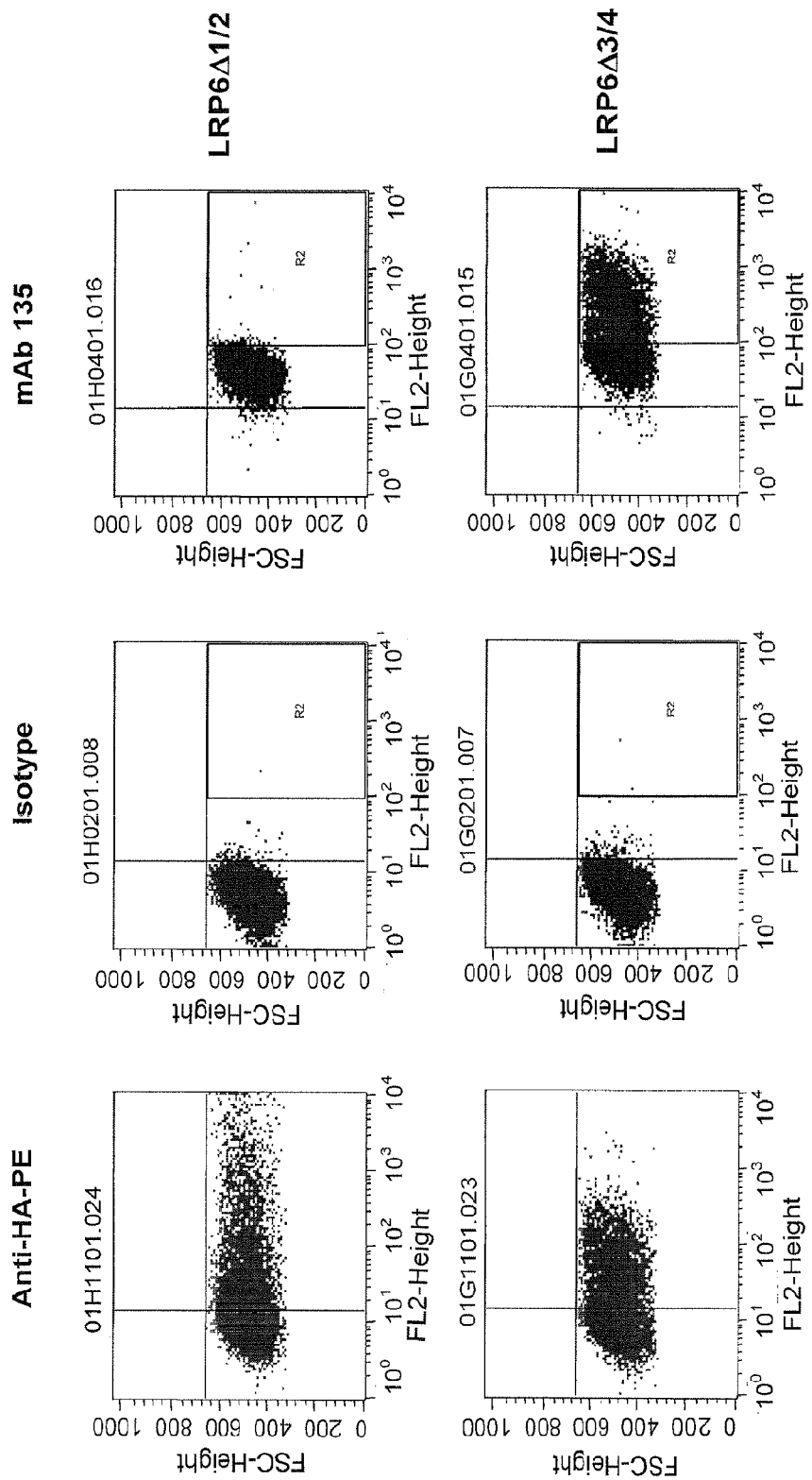
FIGURE 3B, cont.

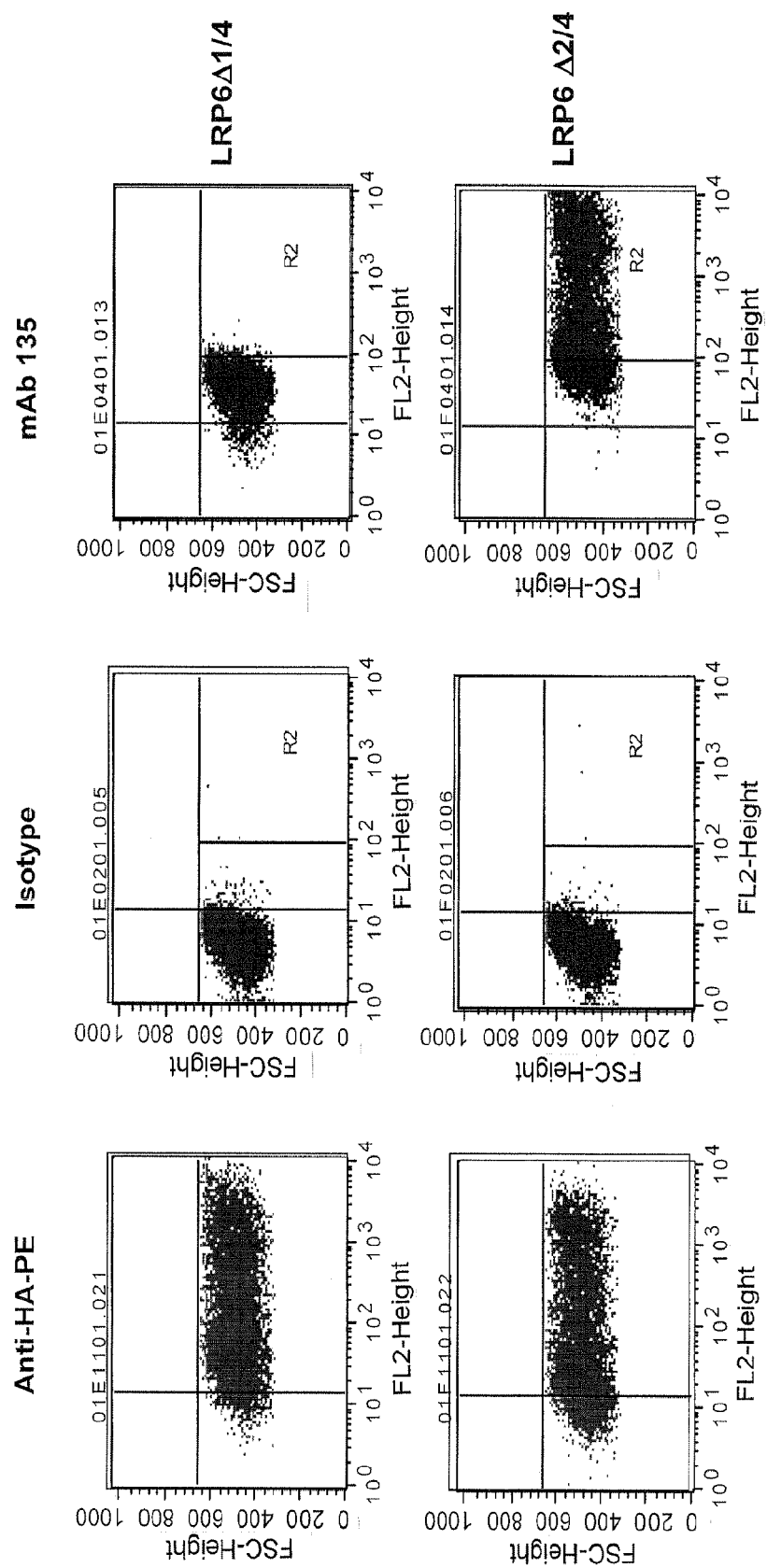
FIGURE 3B, cont.

Alignment of Immunoglobulin Heavy Chain Variable regions for
Activating anti-LRP6 antibodies.

CLUSTAL W (1.83) multiple sequence alignment

```
213.7       ----------------MNFGLRLIFLVLVLKGVLCDVKLVESGGGLVKVGGSLKLSCAAS
606.4       ----------------MNFGLRLTFLVLVLKGVLCDVKLVESGGGLVKVGGSLKLSCAAS
931.1       ----------------MNFGLRLIFLVLVLKGVLCDVNLVESGGGLVKLGGSLKLSCAAS
1213.2      ----------------MNFGLRLIFLVLVLKGVLCDVNLVESGGGLVKLGGSLKLSCAAS
1470.2      ----------------MNFGLRLIFLVLVLKGVLCDVNLVESGGGLVKLGGSLKLSCAAS
1903.1      ----------------MNFGLRLIFLVLVLKGVLCDVNLVESGGGLVKLGGSLKLSCAAS
240.8       ----------------MNFGLRLIFLVLVLKGVLCDVKLVESGGGLVKLGGSLKLSCAAS
923.3       ----------------MNFGLRLIFLVLVLKGVLCDVKLVESGGGLVKVGGSLKLSCAAS
1115.3      ----------------MNFGLRLIFLVLVLKGVLCDVKLVESGGGLVKLGGSLRLSCAAS
498.3       ----------------MNFGLRLIFLVLVLKGVLCDVKLVESGGGLVRLGGSLKLSCAAS
993.9       ----------------MKV-LSLLYLLTAIPGILSDVQVQESGPGLVKPSQSLSLTCSVT
995.5       ---------------RMKV-LSLLYLLTAIPGILSDVQVQESGPGLVKPSQSLSLTCSVT
537.2       ----------------MKV-LSLLYLLTAIPGFLSDVQLQESGPGLVKPSQSLSLTCSVT
77.2        ----------------MERHWIFLFLFSVTAGVHSQVQLQQSGAELAKPGASVKMSCKAS
1433.8      ----------------MERHWIFLFLFSVTAGVHSQVQLQQSGAELAKPGASVKMSCKAS
1281.1      ----------------MERHWIFLFLFSVTAGVHSQVQLQQSGAELAKPGASVKISCKAS
421.1       ----------------MGWSRIFLFLLSIIASVHCQVQLQQSGPELVKPGASVRISCKAS
1293.11     MISVLSTQSLTTLTLTMGWSRIFLFLLSIIASVHCQVQLQQSGPELVKPGASVRISCKAS
856.6       ----------------MGWSRIFLFLLSIIASVHCQVQLQQSGPELVKPGASVRISCKAS
1253.12     MISVLSTQSLTTLTLTMGWSRIFLFLLSIIAGVHCQVQLQQSGPELVMPGASVRISCKAS
413.1       ---MSSPQSLQTLTLSMEWRWIFLFLLSGTTGVHSEIQLQQSGPELVKPGASVKVSCKAS
620.1       ---MSSPQSLQTLTLSMEWRWIFLFLLSGTTGVHSEIQLQQSGPELVKPGASVKVSCKAS
135.16      ----------------MAWISIILFLVATALGVHSQVQLQQSGAELVKPGASVKMSCKAF
                               *     : :*.   .. .:::: :**   *.  . *: ::* .

213.7       GFTFSS-YYMSWVRQTPEKRLELVAVINTNGGSTYYSDTVKGRFTISRDNAKNTLYLQMS
606.4       GFTFSS-YYMSWVRQTPEKRLELVAVINSNGGSTYYSETVKGRFTISRDNAKNTLYLQMS
931.1       GFTFSS-FYMSWVRQTPEKRLDLVATINTNGGSTYYSDTVKGRFTISRDNAKNTLYLQMN
1213.2      GFTFSS-FYMSWVRQTPEKRLDLVATINTNGGSTYYSDTVKGRFTISRDNAKNTLYLQMN
1470.2      GFTFSS-FYMSWVRQTPEKRLDLVAAINTNGGSTYYSDTVKGRFTISRDNAKNTLYLQMS
1903.1      GFTFSR-FYMSWVRQTPEKRLDLVAAINTNGGSTYYSDTVKGRFTISRDNAKNTLYLQMS
240.8       GFTFSS-YYMSWVRQTPEKRLELVAAINSNGGSTYYADTMKGRFTISRDNAKNTLYLQMI
923.3       GFTFSS-YYMSWVRQTPEKRLELVAAININGGSTYYPDTVKGRFTISRDNAKNTLYLQMS
1115.3      GFSFST-SYMSWVRQTPEKRLELVAAINLNGCSTYYSDTVKGRFTISRDNAKNTLYLQMS
498.3       GFTFST-YYMSWVRQTPEKRLELVATINTNGGSTYYPDTLKGRFTISRDNAKNTLYLQMS
993.9       GYSITSGYYWNWIRQFPGNKLEWMGYISYDGRNNYNP-SLKNRISITRDTSKNQFFLKLN
995.5       GYSITSGYYWNWIRQFPGNKLEWMGYISYDGRNNYNP-SLKNRISITRDTSKNQFFLKLN
537.2       GYSITSGYYWNWIRQFPGDKLEWMGHINYDGRDNYNP-SLKNRISITRDTSKNQFFLKLN
77.2        GYTFTS-YWMHWVKQRPGQGLEWIGYINPSTGYTEYNQNFRDKATLTADKSSSTANMQLS
1433.8      GYTFTS-YWMHWVKQRPGQGLEWIGYINPSTGYTEYNQKFRDKATLTADKSSSTANMQLS
1281.1      GYTFTS-YWMHWVKQRPGQGLEWIGYINPNTGYSEYNQKFRDKATLTANKSSSTANMQLS
421.1       GYTFTT-YYIHWLKQRPGQGLEWIGWIFPGNVNTKYNAKFKGKATLTADKSSSTAYMQLS
1293.11     GYTFTT-YYIHWLKQRPGQGLEWIGWIFPGNVNTKYNAKFKGKATLTADKSSSTAYMQLS
856.6       GYTFTT-YYIHWLKQRPGQGLEWIGWIFPGNVNTKYNAKFKGKATLTADKSSSTAYMQLS
1253.12     GYTFTN-YYLHWVKQRPGQGLEWIGWIYPGNVNTKYNEKFKGKASLTADKSSSTAYMQLS
413.1       GYAFTS-YNMYWVKQSHGKGLEWIGYIDPYNGGTDSNQNFKGKATLTVDKSSSTAFMHLN
620.1       GYAFTS-YNMYWVKQSHGKSLEWIGYIDPYNGGTNYNQKFKGKATLTVDKSSSTAYMHLN
135.16      GYTFTS-YPIFWMKQNHGKSLEWIGNFFPYNDNTKYNEKFKGKAKLTVEKSSSTVYLELS
            *::::     *::*   . *: :. :           . ..:.. .:: :.:..  :.:
            |---------|             |----------------|
               CDR-1                       CDR-2
```

FIGURE 4

```
213.7      SLKSEDTALYYCSRQPY------YGNPFDYWGQGTTLTVSSAKT--------
606.4      SLKSEDTALYYCSRQPY------YGNPFDYWGQGTTLTVSSAKT--------
931.1      SLKSEDTALFYCVRQPY------YGGTMDYWGQGTSVTVSSAKT--------
1213.2     SLKSEDTALFYCVRQPY------YGGTMDYWGQGTSVTVSSAKT--------
1470.2     SLKSEDTALFYCARQPY------YGGPMDFWGQGTSVTVSSAKT--------
1903.1     SLKSEDTALFYCARQPY------YGGPMEFWGQGTSVTVSSAKT--------
240.8      SLKSEDTAFYYCASELAG-----YGTPFAYWGHGTLVTVSSAAKT--------
923.3      SLKSEDTAFYYCASELAG-----YGTPFAYWGQGTLVTVSSAAKT--------
1115.3     SLKSEDTAFYYCASELAG-----YGTPFAYWGQGTLVTVSSAAKT--------
498.3      SLRSEDTALYYCARQRN------YGVAVDSWGQGTSVTVSSAKT--------
993.9      SVTTEDTATYYCARENSN-----YPYYYDYWGQGTTLTVSSAKT--------
995.5      SVTTEDTATYYCARENSN-----YPYYYDYWGQGTTLTVSSAKT--------
537.2      SVTTEDTATYYCAREFGN-----FPYYFDYWGQGTTLTVSSAKT--------
77.2       SLTSEDSAVYYCARTAQYYGSPRGYYAMDSWGQGTSVTVSSAKT--------
1433.8     SLTSEDSAVYYCTRTAQYYGSPRGYYAMDSWGQGTSVTVSSAKT--------
1281.1     SLTSDDSAVYYCARTAQYYGSPRGYYAMDSWGQGTSVTVSSAKT--------
421.1      SLTSEDSAVYFCAREEL-------QYYFDYWGQGSTLTVSSAKT--------
1293.11    SLTSEDSAVYFCAREEL-------QYYFDYWGQGSALTVSSAKT--------
856.6      SLTSEDSAVYFCAREGL-------QYYFDYWGQGTTLTVSSAKT--------
1253.12    SLTSEDSAVYFCAREGL-------QYYFDYWAQGTTLTVSSAKT--------
413.1      SLTSEDSAVYYCARGGMGLR----RDHFDYWGQGTSLTVSSAKT--------
620.1      SLTSEDSAVYYCARGGMGLR----RDYFDFWGQGTTLTVSSAKTTPPSVY-
135.16     RSTSDDSAVYYCARGYSGN----YFSAMDYWGQGTSVTVSSAKTTAPSVYP
            ::*:* ::*                *.:*: :***:***
                                 |--------------|
                                       CDR-3
```

FIGURE 4, cont.

Alignment of Immunoglobulin Kappa Light Chain Variable regions for
Activating anti-LRP6 antibodies.

CLUSTAL W (1.83) multiple sequence alignment

```
77.2            ----MRFSAQLLGLLVLWIPG--STADIVMTQAAFSNPVTLGTSASISCRSSKS-LLHSN
1433.8          --------------------------MTQAAFSNPVTLGTSASISCRSSKS-LLHSN
1281.1          ----MRFSAQLLGLLVLWIPG--STADIVMTQAAFSNPVTLGTSASISCRSSKS-LLHSN
931.1           ----MVFTPQILGLMLFWISA--SRGDIVLTQSPATLSVTPGDRVSLSCRASQS-INKN-
1213.2          ----MVFTPQILGLMLFWISA--SRGDIVLTQSPATLSVTPGDRVSLSCRASQS-INKN-
1470.2          ----MVFTPQILGLMLFWISA--SRGDIVLTQSPATLSVTPGDSVSLSCRASQS-INKN-
498.3           ----MVFTPQILGLMLFWISA--SRGDIVLTQSPATLSVTPGDSVSLSCRASQS-ISNN-
213.7           ----MVFTPQILGLMLFWISA--SRSDIVLTQSPATLSVTPGDSVSLSCRASQS-ISNN-
606.4           ----MVFTPQILGLMLFWISA--SRGDIVLTQSPATLSVTPGDSVSLSCRASQS-ISNN-
923.3           ----MVFTPQILGLMLFWISA--SRGDIVLTQSPATLSVTPGDSVSLSCRASQS-ISNN-
240.8           ----MVFTPQILGLMLFWISA--SRGDIVLTQFPATLSVTPGDSVSLSCRASQS-ISSN-
1115.3          ----MVFTPQILGLMLFWISA--SRGDIVLTQSPATLSVTPGDSVSLSCKASQS-ISNN-
135.16          MGIKMEFQTQVFVFVLLWLSG--VDGDIVMTQSQKFMSTSVGDRVSITCKASQ------N
1903.1          MGIKMESQTQVFVYMLLWLSG--VDGDIVMTQSQKFMSTSVGDRVSVTCKASQ------N
620.1           ----MDSQAQVLMLLLLWVSG--TCGDIVMSQSPSSLAVSVGEKVTMSCKSSQSLLYSSN
421.1           ------MHARAAASVMDIYRIRPCRGQIVLTQSPAIMSASPGEKVTISCSANS-------
856.6           ------------------MSRGQIVLTQSPAIMSASPGEKVTISCSANS-------
1253.12         ----MDFQVQIFSFLLISASVIMSRGQIVLTQSPAIMSASPGEKVTISCSANS-------
413.1           ----MDFQVQIFSFLLISASVIMSRGQIVLTQSPAIMSASPGEKVTISCSANS-------
1293.11         ----MDFQVQILSILLISASVIMSRGQIVLTQSPAIMSASPGEKVTISCSANS-------
                        :       ::        ::::*     ..: * .:::* :..  :
                                                                 |----------
                                                                    CDR-1

77.2            GITYLCWFLQKPGQSPQLLIYLMSNLASGVPDRFSSSGSGTDFTLRISRVEAEDVGVYFC
1433.8          GITYLCWFLQKPGQSPQLLIYLMSNLASGVPDRFSSSCSGTDFTLRISRVEAEDVGVYFC
1281.1          GITYLCWFLQKPGQSPQLLIYQMSNLASGVPDRFSSSGSGTDFTLRISRVEAEDVGVYFC
931.1           ----LHWYQQKSHESPRLLIKYASQSISGIPSRFSGSGSGTDFTLSINSVETEDFGMYFC
1213.2          ----LHWYQQKSHESPRLLIKYASQSISGIPSRFSGSGSGTDFTLSINSVETEDFGMYFC
1470.2          ----LHWYQQKSHESPRLLIKYASQSISGIPSRFSGSGSGTDFTLSINSVETEDFGMYFC
498.3           ----LHWYQQKSHESPRLLIKYASQSISGIPSRFSGSGSGTDFTLSINSVETEDFGMYFC
213.7           ----LHWYQQKSHESPRLLIKYVSQSISGIPSRFSGSGSGTDFTLSINSVETEDFGMYFC
606.4           ----LHWYQQKSHESPRLLIKYVSQSISGIPSRFSGSGSGTDFTLSINSVETEDFGMYFC
923.3           ----LHWYQQKSHESPRLLIKYASQSISGIPSRFSGSGSGTDFTLSINSVETEDFGMYFC
240.8           ----LHWYQQTSHESPRLLIKYASQSISGIPSRFSGTGSGTDFTLSINSVETEDFGMYFC
1115.3          ----LHWYQQKSHESPRLLIKYTSQSISGIPSRFSGSGSGTDFTLTINNVETEDFGMYFC
135.16          VRNDVAWYQQKPGQSPKSLIYLASNRHTGVPDRFTGSGSGTDFTLTISNVQSEDLADYFC
1903.1          VGTNVAWYQQKPGQSPKALIYSASYRYSGVPDRFTGSGSGSDFTLTISNVQSEDLAEYFC
620.1           QKNYLAWYQQKPGQSPKVLIYWASTRESGVPDRFTGSGSGTDFTLTISSVKAEDLAVYYC
421.1           SVRFMFWYQQKPGSSPKPLIYRTSNLASGVPARFSGSGSGTSYSLTISSMEAEDAATYYC
856.6           SVRFMFWYQQKPGSSPKPLIYRTSNLASGVPARFSGSGSGTSYSLTISSMEAEDAATYYC
1253.12         SVRYMFWYQQKPGSFPKPWIYRTSNLASGVPARFSGSGSGTSYSLTISSMEAEDVATYYC
413.1           SVRYMFWYQQKPGSFPKPWTYRTSNLASGVPARFSGSGSGTSYSLTISSMEAEDVATYYC
1293.11         SVRFMFWYQQKPGSSPKPLIYRTSNLASGVPARFSGSGSGTSYSLTISSMEAEDAATYYC
                  : *: *.. . *:       *   :*:* **:.:***:.::* *. :::** . *:*
                -----|             |-----|
                                      CDR-2
```

FIGURE 5

```
77.2       AQNLDLPWTFGGGTKLEI--------
1433.8     AQNLDLPWTFGGGTKLEI--------
1281.1     AQNLDLPWTFGGGTKLEI--------
931.1      QQTNNWPLTFGAGTKLEL--------
1213.2     QQTNNWPLTFGAGTKLEL--------
1470.2     QQSNNWPLTFGAGTKLEL--------
498.3      QQTNNWPLTFGAGTKLER--------
213.7      QQSNNWPLTFGAGTKLEL--------
606.4      QQSNNWPLTFGAGTKLEL--------
923.3      QQSNNWPLTFGAGTKLEL--------
240.8      QQSNTWPLTFGAGTKLEL--------
1115.3     QQSNSWPLTFGAGTKLEV--------
135.16     LQHWNYPYTFGGGTKLEIKRADAAP
1903.1     QQYNSYPLTFGAGTKLEL--------
620.1      QQYYSYPYTFGGGTKLEI--------
421.1      QQYHSYPWTFGGGTKLEI--------
856.6      QQYHSYPWTFGGGTKLEI--------
1253.12    QQYHSYPWTFGGGTKLEI--------
413.1      QQYHSYPWTFGGGTKLEI--------
1293.11    QQYHSYPWTFGGGTKLEI--------
           *     *  ***.*****
           |--------|
             CDR-3
```

FIGURE 5, cont.

SEQUENCE LISTING

```
<160> NUMBER OF SEQ ID NOS: 373

<210> SEQ ID NO 1
<211> LENGTH: 10088
<212> TYPE: DNA
<213> ORGANISM: Homo sapiens
<220> FEATURE:
<221> NAME/KEY: CDS
<222> LOCATION: (143)..(4984)

<400> SEQUENCE: 1 gtgcccctttt  ctttcttctc  tcgctgggaa  gctgggaagt  atgagcgtgc  agccctgccg      60
ctgcggcggc  cgccccggct  cctcgcctcc  cccacttctg  gccaccccctc  gccggtgaga    120
```

```
gaagagaacg cgagaaggga ag atg ggg gcc gtc ctg agg agc ctc ctg gcc        172
                        Met Gly Ala Val Leu Arg Ser Leu Leu Ala
                         1               5                  10 tgc agc ttc tgt gtg ctc ctg aga gcg gcc cct ttg ttg ctt tat gca        220
Cys Ser Phe Cys Val Leu Leu Arg Ala Ala Pro Leu Leu Leu Tyr Ala
             15                  20                  25 aac aga cgg gac ttg cga ttg gtt gat gct aca aat ggc aaa gag aat        268
Asn Arg Arg Asp Leu Arg Leu Val Asp Ala Thr Asn Gly Lys Glu Asn
         30                  35                  40 gct acg att gta gtt gga ggc ttg gag gat gca gct gcg gtg gac ttt        316
Ala Thr Ile Val Val Gly Gly Leu Glu Asp Ala Ala Ala Val Asp Phe
             45                  50                  55 gtg ttt agt cat ggc ttg ata tac tgg agt gat gtc agc gaa gaa gcc        364
Val Phe Ser His Gly Leu Ile Tyr Trp Ser Asp Val Ser Glu Glu Ala
         60                  65                  70 att aaa cga aca gaa ttt aac aaa act gag agt gtg cag aat gtt gtt        412
Ile Lys Arg Thr Glu Phe Asn Lys Thr Glu Ser Val Gln Asn Val Val
75                  80                  85                  90 gtt tct gga tta ttg tcc ccc gat ggg ctg gca tgt gat tgg ctt gga        460
Val Ser Gly Leu Leu Ser Pro Asp Gly Leu Ala Cys Asp Trp Leu Gly
                 95                 100                 105 gaa aaa ttg tac tgg aca gat tct gaa act aat cgg att gaa gtt tct        508
Glu Lys Leu Tyr Trp Thr Asp Ser Glu Thr Asn Arg Ile Glu Val Ser
             110                 115                 120 aat tta gat gga tct tta cga aaa gtt tta ttt tgg caa gag ttg gat        556
Asn Leu Asp Gly Ser Leu Arg Lys Val Leu Phe Trp Gln Glu Leu Asp
         125                 130                 135 caa ccc aga gct att gcc tta gat cct tca agt ggg ttc atg tac tgg        604
Gln Pro Arg Ala Ile Ala Leu Asp Pro Ser Ser Gly Phe Met Tyr Trp
     140                 145                 150 aca gac tgg gga gaa gtg cca aag ata gaa cgt gct gga atg gat ggt        652
Thr Asp Trp Gly Glu Val Pro Lys Ile Glu Arg Ala Gly Met Asp Gly
155                 160                 165                 170 tca agt cgc ttc att ata ata aac agt gaa att tac tgg cca aat gga        700
Ser Ser Arg Phe Ile Ile Ile Asn Ser Glu Ile Tyr Trp Pro Asn Gly
                 175                 180                 185 ctg act ttg gat tat gaa gaa caa aag ctt tat tgg gca gat gca aaa        748
Leu Thr Leu Asp Tyr Glu Glu Gln Lys Leu Tyr Trp Ala Asp Ala Lys
             190                 195                 200 ctt aat ttc atc cac aaa tca aat ctg gat gga aca aat cgg cag gca        796
Leu Asn Phe Ile His Lys Ser Asn Leu Asp Gly Thr Asn Arg Gln Ala
         205                 210                 215 gtg gtt aaa ggt tcc ctt cca cat cct ttt gcc ttg acg tta ttt gag        844
Val Val Lys Gly Ser Leu Pro His Pro Phe Ala Leu Thr Leu Phe Glu
     220                 225                 230 gac ata ttg tac tgg act gac tgg agc aca cac tcc att ttg gct tgc        892
Asp Ile Leu Tyr Trp Thr Asp Trp Ser Thr His Ser Ile Leu Ala Cys
235                 240                 245                 250 aac aag tat act ggt gag ggt ctc cgt gaa atc cat tct gac atc ttc        940
Asn Lys Tyr Thr Gly Glu Gly Leu Arg Glu Ile His Ser Asp Ile Phe
                 255                 260                 265 tct ccc atg gat ata cat gcc ttc agc caa cag agg cag cca aat gcc        988
Ser Pro Met Asp Ile His Ala Phe Ser Gln Gln Arg Gln Pro Asn Ala
             270                 275                 280 aca aat cca tgt gga att gac aat ggg ggt tgt tcc cat ttg tgt ttg       1036
Thr Asn Pro Cys Gly Ile Asp Asn Gly Gly Cys Ser His Leu Cys Leu
         285                 290                 295 atg tct cca gtc aag cct ttt tat cag tgt gct tgc ccc act ggg gtc       1084
Met Ser Pro Val Lys Pro Phe Tyr Gln Cys Ala Cys Pro Thr Gly Val
     300                 305                 310
```

```
                                                -continued aaa ctc ctg gag aat gga aaa acc tgc aaa gat ggt gcc aca gaa tta      1132
Lys Leu Leu Glu Asn Gly Lys Thr Cys Lys Asp Gly Ala Thr Glu Leu
315                 320                 325                 330 ttg ctt tta gct cga agg aca gac ttg aga cgc att tct ttg gat aca      1180
Leu Leu Leu Ala Arg Arg Thr Asp Leu Arg Arg Ile Ser Leu Asp Thr
            335                 340                 345 cca gat ttt aca gac att gtt ctg cag tta gaa gac atc cgt cat gcc      1228
Pro Asp Phe Thr Asp Ile Val Leu Gln Leu Glu Asp Ile Arg His Ala
        350                 355                 360 att gcc ata gat tac gat cct gtg gaa ggc tac atc tac tgg act gat      1276
Ile Ala Ile Asp Tyr Asp Pro Val Glu Gly Tyr Ile Tyr Trp Thr Asp
    365                 370                 375 gat gaa gtg agg gcc ata cgc cgt tca ttt ata gat gga tct ggc agt      1324
Asp Glu Val Arg Ala Ile Arg Arg Ser Phe Ile Asp Gly Ser Gly Ser
380                 385                 390 cag ttt gtg gtc act gct caa att gcc cat cct gat ggt att gct gtg      1372
Gln Phe Val Val Thr Ala Gln Ile Ala His Pro Asp Gly Ile Ala Val
395                 400                 405                 410 gac tgg gtt gca cga aat ctt tat tgg aca gac act ggc act gat cga      1420
Asp Trp Val Ala Arg Asn Leu Tyr Trp Thr Asp Thr Gly Thr Asp Arg
            415                 420                 425 ata gaa gtg aca agg ctc aat ggg acc atg agg aag atc ttg att tca      1468
Ile Glu Val Thr Arg Leu Asn Gly Thr Met Arg Lys Ile Leu Ile Ser
        430                 435                 440 gag gac tta gag gaa ccc cgg gct att gtg tta gat ccc atg gtt ggg      1516
Glu Asp Leu Glu Glu Pro Arg Ala Ile Val Leu Asp Pro Met Val Gly
    445                 450                 455 tac atg tat tgg act gac tgg gga gaa att ccg aaa att gag cga gca      1564
Tyr Met Tyr Trp Thr Asp Trp Gly Glu Ile Pro Lys Ile Glu Arg Ala
460                 465                 470 gct ctg gat ggt tct gac cgt gta gta ttg gtt aac act tct ctt ggt      1612
Ala Leu Asp Gly Ser Asp Arg Val Val Leu Val Asn Thr Ser Leu Gly
475                 480                 485                 490 tgg cca aat ggt tta gcc ttg gat tat gat gaa ggc aaa ata tac tgg      1660
Trp Pro Asn Gly Leu Ala Leu Asp Tyr Asp Glu Gly Lys Ile Tyr Trp
            495                 500                 505 gga gat gcc aaa aca gac aag att gag gtt atg aat act gat ggc act      1708
Gly Asp Ala Lys Thr Asp Lys Ile Glu Val Met Asn Thr Asp Gly Thr
        510                 515                 520 ggg aga cga gta cta gtg gaa gac aaa att cct cac ata ttt gga ttt      1756
Gly Arg Arg Val Leu Val Glu Asp Lys Ile Pro His Ile Phe Gly Phe
    525                 530                 535 act ttg ttg ggt gac tat gtt tac tgg act gac tgg cag agg cgt agc      1804
Thr Leu Leu Gly Asp Tyr Val Tyr Trp Thr Asp Trp Gln Arg Arg Ser
540                 545                 550 att gaa aga gtt cat aaa cga agt gca gag agg gaa gtg atc ata gat      1852
Ile Glu Arg Val His Lys Arg Ser Ala Glu Arg Glu Val Ile Ile Asp
555                 560                 565                 570 cag ctg cct gac ctc atg ggc cta aag gct aca aat gtt cat cga gtg      1900
Gln Leu Pro Asp Leu Met Gly Leu Lys Ala Thr Asn Val His Arg Val
            575                 580                 585 att ggt tcc aac ccc tgt gct gag gaa aac ggg gga tgt agc cat ctc      1948
Ile Gly Ser Asn Pro Cys Ala Glu Glu Asn Gly Gly Cys Ser His Leu
        590                 595                 600 tgc ctc tat aga cct cag ggc ctt cgc tgt gct tgc cct att ggc ttt      1996
Cys Leu Tyr Arg Pro Gln Gly Leu Arg Cys Ala Cys Pro Ile Gly Phe
    605                 610                 615 gaa ctc atc agt gac atg aag acc tgc att gtc cca gag gct ttc ctt      2044
Glu Leu Ile Ser Asp Met Lys Thr Cys Ile Val Pro Glu Ala Phe Leu
620                 625                 630
```

| | | |
|---|---|---|
| ttg ttt tca cgg aga gca gat atc aga cga att tct ctg gaa aca aac<br>Leu Phe Ser Arg Arg Ala Asp Ile Arg Arg Ile Ser Leu Glu Thr Asn<br>635                    640                    645                    650 | | 2092 |
| aat aat aat gtg gct att cca ctc act ggt gtc aaa gaa gct tct gct<br>Asn Asn Asn Val Ala Ile Pro Leu Thr Gly Val Lys Glu Ala Ser Ala<br>                   655                    660                    665 | | 2140 |
| ttg gat ttt gat gtg aca gac aac cga att tat tgg act gat ata tca<br>Leu Asp Phe Asp Val Thr Asp Asn Arg Ile Tyr Trp Thr Asp Ile Ser<br>            670                    675                    680 | | 2188 |
| ctc aag acc atc agc aga gcc ttt atg aat ggc agt gca ctg gaa cat<br>Leu Lys Thr Ile Ser Arg Ala Phe Met Asn Gly Ser Ala Leu Glu His<br>                   685                    690                    695 | | 2236 |
| gtg gta gaa ttc ggc tta gat tat cca gaa ggc atg gca gta gac tgg<br>Val Val Glu Phe Gly Leu Asp Tyr Pro Glu Gly Met Ala Val Asp Trp<br>            700                    705                    710 | | 2284 |
| ctt ggg aag aac ttg tac tgg gca gac aca gga acg aat cga att gag<br>Leu Gly Lys Asn Leu Tyr Trp Ala Asp Thr Gly Thr Asn Arg Ile Glu<br>715                    720                    725                    730 | | 2332 |
| gtg tca aag ttg gat ggg cag cac cga caa gtt ttg gtg tgg aaa gac<br>Val Ser Lys Leu Asp Gly Gln His Arg Gln Val Leu Val Trp Lys Asp<br>                   735                    740                    745 | | 2380 |
| cta gat agt ccc aga gct ctc gcg ttg gac cct gcc gaa gga ttt atg<br>Leu Asp Ser Pro Arg Ala Leu Ala Leu Asp Pro Ala Glu Gly Phe Met<br>            750                    755                    760 | | 2428 |
| tat tgg act gaa tgg ggt gga aaa cct aag ata gac aga gct gca atg<br>Tyr Trp Thr Glu Trp Gly Gly Lys Pro Lys Ile Asp Arg Ala Ala Met<br>                   765                    770                    775 | | 2476 |
| gat gga agt gaa cgt act acc tta gtt cca aat gtg ggg cgg gca aac<br>Asp Gly Ser Glu Arg Thr Thr Leu Val Pro Asn Val Gly Arg Ala Asn<br>            780                    785                    790 | | 2524 |
| ggc cta act att gat tat gct aaa agg agg ctt tat tgg aca gac ctg<br>Gly Leu Thr Ile Asp Tyr Ala Lys Arg Arg Leu Tyr Trp Thr Asp Leu<br>795                    800                    805                    810 | | 2572 |
| gac acc aac tta ata gaa tct tca aat atg ctt ggg ctc aac cgt gaa<br>Asp Thr Asn Leu Ile Glu Ser Ser Asn Met Leu Gly Leu Asn Arg Glu<br>                   815                    820                    825 | | 2620 |
| gtt ata gca gat gac ttg cct cat cct ttt ggc tta act cag tac caa<br>Val Ile Ala Asp Asp Leu Pro His Pro Phe Gly Leu Thr Gln Tyr Gln<br>            830                    835                    840 | | 2668 |
| gat tat atc tac tgg acg gac tgg agc cga cgc agc att gag cgt gcc<br>Asp Tyr Ile Tyr Trp Thr Asp Trp Ser Arg Arg Ser Ile Glu Arg Ala<br>                   845                    850                    855 | | 2716 |
| aac aaa acc agt ggc caa aac cgc acc atc att cag ggc cat ttg gat<br>Asn Lys Thr Ser Gly Gln Asn Arg Thr Ile Ile Gln Gly His Leu Asp<br>            860                    865                    870 | | 2764 |
| tat gtg atg gac atc ctc gtc ttt cac tca tct cga cag tca ggg tgg<br>Tyr Val Met Asp Ile Leu Val Phe His Ser Ser Arg Gln Ser Gly Trp<br>875                    880                    885                    890 | | 2812 |
| aat gaa tgt gct tcc agc aat ggg cac tgc tcc cac ctc tgc ttg gct<br>Asn Glu Cys Ala Ser Ser Asn Gly His Cys Ser His Leu Cys Leu Ala<br>                   895                    900                    905 | | 2860 |
| gtg cca gtt ggg ggt ttt gtt tgt gga tgc cct gcc cac tac tct ctt<br>Val Pro Val Gly Gly Phe Val Cys Gly Cys Pro Ala His Tyr Ser Leu<br>            910                    915                    920 | | 2908 |
| aat gct gac aac agg act tgt agt gct cct acg act ttc ctg ctc ttc<br>Asn Ala Asp Asn Arg Thr Cys Ser Ala Pro Thr Thr Phe Leu Leu Phe<br>                   925                    930                    935 | | 2956 |
| agt caa aag agt gcc atc aac cgc atg gtg att gat gaa caa cag agc<br>Ser Gln Lys Ser Ala Ile Asn Arg Met Val Ile Asp Glu Gln Gln Ser<br>            940                    945                    950 | | 3004 |

-continued

| | |
|---|---|
| ccc gac atc atc ctt ccc atc cac agc ctt cgg aat gtc cgg gcc att<br>Pro Asp Ile Ile Leu Pro Ile His Ser Leu Arg Asn Val Arg Ala Ile<br>955                        960                    965                        970 | 3052 |
| gac tat gac cca ctg gac aag caa ctc tat tgg att gac tca cga caa<br>Asp Tyr Asp Pro Leu Asp Lys Gln Leu Tyr Trp Ile Asp Ser Arg Gln<br>                    975                    980                        985 | 3100 |
| aac atg atc cga aag gca caa gaa gat ggc agc cag ggc ttt act gtg<br>Asn Met Ile Arg Lys Ala Gln Glu Asp Gly Ser Gln Gly Phe Thr Val<br>          990                    995                    1000 | 3148 |
| gtt gtg agc tca gtt ccg agt cag aac ctg gaa ata caa ccc tat<br>Val Val Ser Ser Val Pro Ser Gln Asn Leu Glu Ile Gln Pro Tyr<br>1005                  1010                    1015 | 3193 |
| gac ctc agc att gat att tac agc cgc tac atc tac tgg act tgt<br>Asp Leu Ser Ile Asp Ile Tyr Ser Arg Tyr Ile Tyr Trp Thr Cys<br>1020                  1025                    1030 | 3238 |
| gag gct acc aat gtc att aat gtg aca aga tta gat ggg aga tca<br>Glu Ala Thr Asn Val Ile Asn Val Thr Arg Leu Asp Gly Arg Ser<br>1035                  1040                    1045 | 3283 |
| gtt gga gtg gtg ctg aaa ggc gag cag gac aga cct cga gcc gtt<br>Val Gly Val Val Leu Lys Gly Glu Gln Asp Arg Pro Arg Ala Val<br>1050                  1055                    1060 | 3328 |
| gtg gta aac cca gag aaa ggg tat atg tat ttt acc aat ctt cag<br>Val Val Asn Pro Glu Lys Gly Tyr Met Tyr Phe Thr Asn Leu Gln<br>1065                  1070                    1075 | 3373 |
| gaa agg tct cct aaa att gaa cgg gct gct ttg gat ggg aca gaa<br>Glu Arg Ser Pro Lys Ile Glu Arg Ala Ala Leu Asp Gly Thr Glu<br>1080                  1085                    1090 | 3418 |
| cgg gag gtc ctc ttt ttc agt ggc tta agt aaa cca att gct tta<br>Arg Glu Val Leu Phe Phe Ser Gly Leu Ser Lys Pro Ile Ala Leu<br>1095                  1100                    1105 | 3463 |
| gcc ctt gat agc agg ctg ggc aag ctc ttt tgg gct gat tca gat<br>Ala Leu Asp Ser Arg Leu Gly Lys Leu Phe Trp Ala Asp Ser Asp<br>1110                  1115                    1120 | 3508 |
| ctc cgg cga att gaa agc agt gat ctc tca ggt gct aac cgg ata<br>Leu Arg Arg Ile Glu Ser Ser Asp Leu Ser Gly Ala Asn Arg Ile<br>1125                  1130                    1135 | 3553 |
| gta tta gaa gac tcc aat atc ttg cag cct gtg gga ctt act gtg<br>Val Leu Glu Asp Ser Asn Ile Leu Gln Pro Val Gly Leu Thr Val<br>1140                  1145                    1150 | 3598 |
| ttt gaa aac tgg ctc tat tgg att gat aaa cag cag caa atg att<br>Phe Glu Asn Trp Leu Tyr Trp Ile Asp Lys Gln Gln Gln Met Ile<br>1155                  1160                    1165 | 3643 |
| gaa aaa att gac atg aca ggt cga gag ggt aga acc aaa gtc caa<br>Glu Lys Ile Asp Met Thr Gly Arg Glu Gly Arg Thr Lys Val Gln<br>1170                  1175                    1180 | 3688 |
| gct cga att gcc cag ctt agt gac att cat gca gta aag gag ctg<br>Ala Arg Ile Ala Gln Leu Ser Asp Ile His Ala Val Lys Glu Leu<br>1185                  1190                    1195 | 3733 |
| aac ctt caa gaa tac aga cag cac cct tgt gct cag gat aat ggt<br>Asn Leu Gln Glu Tyr Arg Gln His Pro Cys Ala Gln Asp Asn Gly<br>1200                  1205                    1210 | 3778 |
| ggc tgt tca cat att tgt ctt gta aag ggg gat ggt act aca agg<br>Gly Cys Ser His Ile Cys Leu Val Lys Gly Asp Gly Thr Thr Arg<br>1215                  1220                    1225 | 3823 |
| tgt tct tgc ccc atg cac ctg gtt cta ctt caa gat gag cta tca<br>Cys Ser Cys Pro Met His Leu Val Leu Leu Gln Asp Glu Leu Ser<br>1230                  1235                    1240 | 3868 |
| tgt gga gaa cct cca aca tgt tct cct cag cag ttt act tgt ttc<br>Cys Gly Glu Pro Pro Thr Cys Ser Pro Gln Gln Phe Thr Cys Phe<br>1245                  1250                    1255 | 3913 |

| | | | | | | | | | | | | | | |
|---|---|---|---|---|---|---|---|---|---|---|---|---|---|---|
| acg | ggg | gaa | att | gac | tgt | atc | cct | gtg | gct | tgg | cgg | tgc | gat | ggg | 3958 |
| Thr | Gly | Glu | Ile | Asp | Cys | Ile | Pro | Val | Ala | Trp | Arg | Cys | Asp | Gly | |
| | 1260 | | | | 1265 | | | | 1270 | | | | | | |
| ttt | act | gaa | tgt | gaa | gac | cac | agt | gat | gaa | ctc | aat | tgt | cct | gta | 4003 |
| Phe | Thr | Glu | Cys | Glu | Asp | His | Ser | Asp | Glu | Leu | Asn | Cys | Pro | Val | |
| | 1275 | | | | 1280 | | | | 1285 | | | | | | |
| tgc | tca | gag | tcc | cag | ttc | cag | tgt | gcc | agt | ggg | cag | tgt | att | gat | 4048 |
| Cys | Ser | Glu | Ser | Gln | Phe | Gln | Cys | Ala | Ser | Gly | Gln | Cys | Ile | Asp | |
| | 1290 | | | | 1295 | | | | 1300 | | | | | | |
| ggt | gcc | ctc | cga | tgc | aat | gga | gat | gca | aac | tgc | cag | gac | aaa | tca | 4093 |
| Gly | Ala | Leu | Arg | Cys | Asn | Gly | Asp | Ala | Asn | Cys | Gln | Asp | Lys | Ser | |
| | 1305 | | | | 1310 | | | | 1315 | | | | | | |
| gat | gag | aag | aac | tgt | gaa | gtg | ctt | tgt | tta | att | gat | cag | ttc | cgc | 4138 |
| Asp | Glu | Lys | Asn | Cys | Glu | Val | Leu | Cys | Leu | Ile | Asp | Gln | Phe | Arg | |
| | 1320 | | | | 1325 | | | | 1330 | | | | | | |
| tgt | gcc | aat | ggt | cag | tgc | att | gga | aag | cac | aag | aag | tgt | gat | cat | 4183 |
| Cys | Ala | Asn | Gly | Gln | Cys | Ile | Gly | Lys | His | Lys | Lys | Cys | Asp | His | |
| | 1335 | | | | 1340 | | | | 1345 | | | | | | |
| aat | gtg | gat | tgc | agt | gac | aag | tca | gat | gaa | ctg | gat | tgt | tat | ccg | 4228 |
| Asn | Val | Asp | Cys | Ser | Asp | Lys | Ser | Asp | Glu | Leu | Asp | Cys | Tyr | Pro | |
| | 1350 | | | | 1355 | | | | 1360 | | | | | | |
| act | gaa | gaa | cca | gca | cca | cag | gcc | acc | aat | aca | gtt | ggt | tct | gtt | 4273 |
| Thr | Glu | Glu | Pro | Ala | Pro | Gln | Ala | Thr | Asn | Thr | Val | Gly | Ser | Val | |
| | 1365 | | | | 1370 | | | | 1375 | | | | | | |
| att | ggc | gta | att | gtc | acc | att | ttt | gtg | tct | gga | act | gta | tac | ttt | 4318 |
| Ile | Gly | Val | Ile | Val | Thr | Ile | Phe | Val | Ser | Gly | Thr | Val | Tyr | Phe | |
| | 1380 | | | | 1385 | | | | 1390 | | | | | | |
| atc | tgc | cag | agg | atg | ttg | tgt | cca | cgt | atg | aag | gga | gat | ggg | gaa | 4363 |
| Ile | Cys | Gln | Arg | Met | Leu | Cys | Pro | Arg | Met | Lys | Gly | Asp | Gly | Glu | |
| | 1395 | | | | 1400 | | | | 1405 | | | | | | |
| act | atg | act | aat | gac | tat | gta | gtt | cat | gga | cca | gct | tct | gtg | cct | 4408 |
| Thr | Met | Thr | Asn | Asp | Tyr | Val | Val | His | Gly | Pro | Ala | Ser | Val | Pro | |
| | 1410 | | | | 1415 | | | | 1420 | | | | | | |
| ctt | ggt | tat | gtg | cca | cac | cca | agt | tct | ttg | tca | gga | tct | ctt | cca | 4453 |
| Leu | Gly | Tyr | Val | Pro | His | Pro | Ser | Ser | Leu | Ser | Gly | Ser | Leu | Pro | |
| | 1425 | | | | 1430 | | | | 1435 | | | | | | |
| gga | atg | tct | cga | ggt | aaa | tca | atg | atc | agc | tcc | ctc | agt | atc | atg | 4498 |
| Gly | Met | Ser | Arg | Gly | Lys | Ser | Met | Ile | Ser | Ser | Leu | Ser | Ile | Met | |
| | 1440 | | | | 1445 | | | | 1450 | | | | | | |
| ggg | gga | agc | agt | gga | ccc | ccc | tat | gac | cga | gcc | cat | gtt | aca | gga | 4543 |
| Gly | Gly | Ser | Ser | Gly | Pro | Pro | Tyr | Asp | Arg | Ala | His | Val | Thr | Gly | |
| | 1455 | | | | 1460 | | | | 1465 | | | | | | |
| gca | tca | tca | agt | agt | tct | tca | agc | acc | aaa | ggc | act | tac | ttc | cct | 4588 |
| Ala | Ser | Ser | Ser | Ser | Ser | Ser | Ser | Thr | Lys | Gly | Thr | Tyr | Phe | Pro | |
| | 1470 | | | | 1475 | | | | 1480 | | | | | | |
| gca | att | ttg | aac | cct | cca | cca | tcc | cca | gcc | aca | gag | cga | tca | cat | 4633 |
| Ala | Ile | Leu | Asn | Pro | Pro | Pro | Ser | Pro | Ala | Thr | Glu | Arg | Ser | His | |
| | 1485 | | | | 1490 | | | | 1495 | | | | | | |
| tac | act | atg | gaa | ttt | gga | tat | tct | tca | aac | agt | cct | tcc | act | cat | 4678 |
| Tyr | Thr | Met | Glu | Phe | Gly | Tyr | Ser | Ser | Asn | Ser | Pro | Ser | Thr | His | |
| | 1500 | | | | 1505 | | | | 1510 | | | | | | |
| agg | tca | tac | agc | tac | agg | cca | tat | agc | tac | cgg | cac | ttt | gca | ccc | 4723 |
| Arg | Ser | Tyr | Ser | Tyr | Arg | Pro | Tyr | Ser | Tyr | Arg | His | Phe | Ala | Pro | |
| | 1515 | | | | 1520 | | | | 1525 | | | | | | |
| ccc | acc | aca | ccc | tgc | agc | aca | gat | gtt | tgt | gac | agt | gac | tat | gct | 4768 |
| Pro | Thr | Thr | Pro | Cys | Ser | Thr | Asp | Val | Cys | Asp | Ser | Asp | Tyr | Ala | |
| | 1530 | | | | 1535 | | | | 1540 | | | | | | |
| cct | agt | cgg | aga | atg | acc | tca | gtg | gca | aca | gcc | aag | ggc | tat | acc | 4813 |
| Pro | Ser | Arg | Arg | Met | Thr | Ser | Val | Ala | Thr | Ala | Lys | Gly | Tyr | Thr | |
| | 1545 | | | | 1550 | | | | 1555 | | | | | | |

| | | |
|---|---|---|
| agt gac ttg aac tat gat tca gaa cct gtg ccc cca cct ccc aca<br>Ser Asp Leu Asn Tyr Asp Ser Glu Pro Val Pro Pro Pro Pro Thr<br>          1560                     1565                  1570 | 4858 |
| ccc cga agc caa tac ttg tca gca gag gag aac tat gaa agc tgc<br>Pro Arg Ser Gln Tyr Leu Ser Ala Glu Glu Asn Tyr Glu Ser Cys<br>       1575                     1580                    1585 | 4903 |
| cca cct tct cca tac aca gag agg agc tat tct cat cac ctc tac<br>Pro Pro Ser Pro Tyr Thr Glu Arg Ser Tyr Ser His His Leu Tyr<br>       1590                     1595                    1600 | 4948 |
| cca ccg cca ccc tct ccc tgt aca gac tcc tcc tga ggagggccc<br>Pro Pro Pro Pro Ser Pro Cys Thr Asp Ser Ser<br>       1605                     1610 | 4994 |
| tcctcctctg actgcctcca acgtaaaaat gtaaatataa atttggttga gatctggagg | 5054 |
| ggggagggaa gctattagag aaggatgagg cagaccatgt acagttaaaa ttataaaatg | 5114 |
| gggtagggaa tactggagat atttgtacag aagaaaagga tatttatata ttttcttaaa | 5174 |
| acagcagatt tgctgcttgt gccataaaag tttgtataaa aaaaatttgt actaaaagtt | 5234 |
| ttattttttgc aaactaaata cacaaagcat gccttaaacc cagtgaagca actgagtaca | 5294 |
| aaggaaacag gaataataaa ggcatcactg accaggaata tctgggcttt attgatacca | 5354 |
| aaaataaaaa agaggaagaa gaaaaattaa gtccatctca gagcagcaaa ccatagatac | 5414 |
| atggatgtag ccagatagcc ttcagttaac taacatttga gggccaacaa gtaagaaatg | 5474 |
| atgaaaggaa aaaatgcaa ttaatactaa ccttggacga agggctttgt tttctctagg | 5534 |
| aatccaacag tgctagtgag gaaagtgagt atttctaaaa acccattctg ggtgttgctg | 5594 |
| ttgtaggaga gatcagccct ctggtaagat gccatgaagc tgtgtgtgtg tgcaagtctc | 5654 |
| tgtccctacc tttagaatcc atacctctgt caaaatgaat ttttttctct aggtatgttt | 5714 |
| accttgctgc ctcctccagc aacttggtaa gtcattttgc taagatacca tgattttttt | 5774 |
| aagctgaagc attgactaaa tggaattttc taaattaaac ttgattttaa tatttcttct | 5834 |
| agctccattc cccagtaggc ttagctcttc aatttgactg ctgttttgc ataatgatca | 5894 |
| aaagttagac atattattc tcttcttcca agattgtttt aatgctcatt aaaatgtctt | 5954 |
| tttacaacac atatagacaa tgtttaagaa ttaaaaattt aaccattatg ttttgttgt | 6014 |
| aaatctcata tccttgcact actttcagca tatcacag tacgaaatca tttatatata | 6074 |
| tatatatata tatatatata tatatatata tatatatata tatattttgt ttgtttgttt | 6134 |
| gttttctgag taaacatttt aaatatgttc tggttagaga caatctattt aaaaagattt | 6194 |
| ttttcttatt aggattttcc ctatattaac agtttgtgat gttttcatgt tctttagacc | 6254 |
| ggttttctc agaataatgt ctacatacat acctcttcta atgtgtgaca tgaattaat | 6314 |
| atctttctgt tacccactgt gaatgttagg ctgttttcaa attatccaca aattattctt | 6374 |
| gtaatcaccc aatatttta tgtgggtcct ctcttaccca ttatggatta agatagttta | 6434 |
| acaaatttaa caatgaggat taaatgagaa ggcaaactgt taacttctca gctgtcagaa | 6494 |
| tttgggtgga agggaataat ggaagcctct tttgtgatct gcctgacctg ctgtcatgta | 6554 |
| tggtactggg gctgctacat cttgagctat cagggctgac ctgtggaatg attctagcac | 6614 |
| ttgctctgcc accttgccag aagttcgttt cctgcttttt acacatgtgt agcacttctc | 6674 |
| tgctaaaatt gaatggtttt aaactaatgt attttagct taagaggtgt tggtcagtta | 6734 |
| attattgaat tttttttttt tctttttta ttctgtcttg ccaaggcctc tctgggtttc | 6794 |
| agggcccaag agaaacagt ggaagaaagg attcagaatt tgggcaaggg tgaagtaact | 6854 |
| gttcatgcaa gttaaaaata cctaagtaaa gttttgaag ataaaattgt ggtttcagaa | 6914 |

```
taatgctgat tgttggagac tgtaagaatc aggtgcactt gattttgcat ataagcaaat    6974
ggtaaatcta tcagaatcct aaaacagaca agcatgaact cttcccattg ctggaactaa    7034
gtgcccacag tgtcagacaa aatggacatt gaacttggat tctgtgatac acagggcact    7094
tgatgcttaa atgaagatgg aaaggttagc aatacctggg tgtcagttag aatttgagaa    7154
ttctatatgt ttacatattt aaatgtgcat cttgatctgg tgggcttccc atgtggagac    7214
ttgcactcta attaactaag aagaatattg ccttgttgga tctcagtcca cgtgcttgca    7274
ctgcgatggc aatggcctct tcttcaaaat actaatttgt gtgccaattt gtttaaaatt    7334
atttgaaggc agttcagcct aatctcagtg ttctctttct ggggtagatg agatggattc    7394
ttaatatttc tgggagtact ttttaatgag agaattgtca aatttggaaa gatttattga    7454
gccttaggtt acatggacag ttaagcttaa gtaaactgta tattgattat caaacacaag    7514
ctgtaattgg aaaagttgag aggaaaagca tgagatcaca aattaggggg aaaaagaaa     7574
agggattttt aaatttggtg tattaaattc attgtccaag ggggaaaatg aataatgttt    7634
cattagattc cttatatgca aaagtattta ttttgaacat gtgtcctaaa atatatgcac    7694
taactgatgt gattaaaatt gtccaagaaa taaacttgag cataacatac tttgtgtgca    7754
ccacagtaag ctattctgca ttgaagtggt ctttttataac taaggcctgg actttgctcc    7814
aacagagtcg tggtcttctg aatagtgact taaggagttt tgtttgctta agtcagataa    7874
tagcacattc acagggaaac aaagagagtt ggtggataga attttctgac tattaatttt    7934
tcttccatga aattttatta tgcctttggc actttctgcc actcttacag catatcacaa    7994
gatatctgtt tagcagaaga ttatgtagtt actttaattt taatataaaa gtagcttgtg    8054
atacattacc aagagatctc tgattcttta gtaagtttga gaacacctat tctacagaga    8114
tgataggtac ttagaaatga agactttaaa gtacatttta atctaatata ggccagtaat    8174
tggggggaagg ggcttttgagc agtacaattt taagatgatt ttgagggttg tatttcttta    8234
tcatttaaaa atatcctaaa gtcagtaatt tatatgaagg aaactcattc attattgaag    8294
gtattaaaaa tagccatcat ctgtattagg tagcagtttt ggaggatcat cttttctttt    8354
tgctataaag ccctattaat gaagaatact tccagtagag ttaatagctg tagcttacct    8414
agtgtgttaa tgaagtgtgt ttatttatgt gacttgatac cagtagtcat aatagagact    8474
gaagaggtat gcgttaagca cgcctacttc tatgcagtaa acaggctgca gctgcctaga    8534
ttagattctt agaaatgtca tattttgaat tgttttattt cttgtagggg aagctttgtc    8594
ccacttcatt catttgcatg ccataggaat tacatattgg ttatcattac gtatctaaca    8654
agattcagaa acaaaaatct tggacttttc acatccgaaa tatgtcagct cttaataaat    8714
gtgtggtgct taagtctaca tatggcatcc atagttgatt tagagtatgg atatgagtgt    8774
gttgaccagt tatcagtagg tggacaaata tttgggcatc tacagatgag actatgcact    8834
aagtgtggac tgagtcctaa agaagcttat agtcaggtgt tgtttaaaac attatcagaa    8894
ttcttaaacc caaggaattt aattttattt ggtatttctt aagcctaaaa tgaaccaaga    8954
gaaagatgat tttagaaagt acttgtagtg aaagatgatt ttagaaagta cttgtagtgc    9014
atgtgtggct tctgactttt gggatggcac cattttataa tagtttcaaa atttagcttt    9074
tgaaattctc aacattttat ggtagaagac tttggacctc aagtataaaa ttatacgtttt   9134
ataatttttt taaatttaa attataagta ttgtgaattc acactctcag gctattgtct    9194
gacttgatct acgtctcata aagcctgtac ctgagtggag tggaaggtgg agtcttaggt    9254
taatcagtta ctgactctac cctcacccct tttcaattga ggtaaacttt gctgttttc    9314
```

```
ttttcataa agcattctca aattgttgag tttattgctg aaaaaaatct ccatgacttt    9374
acagatagaa ttacaaacta aatgatgtct tgtatttaga agcagagtac agacctaacg    9434
aactgttaga ttctccacca tcacttaggg tttgcccaga agcaacacca gagaattaca    9494
gacaacgcgc ttttgctgaa ctgtccattt tggtggttgt gtttttcagt caaatataag    9554
caggatgggc gatagagata tatttatata tagatacata ttctatatat ctaatgccta    9614
aatatgggta ttaaagggaa aattttaaa gtctgattaa atccaatatg acatgaaatt    9674
aaatatatgg attagtaagg aaaaatgtta aaagtagag aggataccaa gaagattaaa    9734
ctggactagc cttatttgca agtgaaggat ctggtgctgc tttcagatgt ttatctttta    9794 ttttttccc ttaagcttta atcttcgtca ttgtcttaaa gtcaactggt gtttcttgtt    9854
cattgacttt ggtacgatgg tgctttgcaa ggatgtattt atgttataat ggccaacatt    9914
tggtcagccc ttgtccactt attcacttcc ctccttttgt aaaataagtg ctttaattat    9974
aaactgtata aaaataccct tgtaaaccc cttttttgat tattacaata aataagctga   10034
attgtaacaa atgaaatttg attttttgtaa taaaacagtg gaaagtaaaa aaaa   10088
```

<210> SEQ ID NO 2
<211> LENGTH: 1613
<212> TYPE: PRT
<213> ORGANISM: Homo sapiens

<400> SEQUENCE: 2

```
Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
            20                  25                  30

Leu Val Asp Ala Thr Asn Gly Lys Glu Asn Ala Thr Ile Val Val Gly
        35                  40                  45

Gly Leu Glu Asp Ala Ala Ala Val Asp Phe Val Phe Ser His Gly Leu
    50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Ser Gly Leu Leu Ser
                85                  90                  95

Pro Asp Gly Leu Ala Cys Asp Trp Leu Gly Glu Lys Leu Tyr Trp Thr
            100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Ile Leu Tyr Trp Thr
225                 230                 235                 240
```

-continued

Asp Trp Ser Thr His Ser Ile Leu Ala Cys Asn Lys Tyr Thr Gly Glu
            245                 250                 255

Gly Leu Arg Glu Ile His Ser Asp Ile Phe Ser Pro Met Asp Ile His
        260                 265                 270

Ala Phe Ser Gln Gln Arg Gln Pro Asn Ala Thr Asn Pro Cys Gly Ile
    275                 280                 285

Asp Asn Gly Gly Cys Ser His Leu Cys Leu Met Ser Pro Val Lys Pro
290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Ala Arg Arg
            325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
        355                 360                 365

Pro Val Glu Gly Tyr Ile Tyr Trp Thr Asp Asp Glu Val Arg Ala Ile
    370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
        435                 440                 445

Arg Ala Ile Val Leu Asp Pro Met Val Gly Tyr Met Tyr Trp Thr Asp
    450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Lys Ile Tyr Trp Gly Asp Ala Lys Thr Asp
            500                 505                 510

Lys Ile Glu Val Met Asn Thr Asp Gly Thr Gly Arg Arg Val Leu Val
        515                 520                 525

Glu Asp Lys Ile Pro His Ile Phe Gly Phe Thr Leu Leu Gly Asp Tyr
    530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Asn Val His Arg Val Ile Gly Ser Asn Pro Cys
            580                 585                 590

Ala Glu Glu Asn Gly Gly Cys Ser His Leu Cys Leu Tyr Arg Pro Gln
        595                 600                 605

Gly Leu Arg Cys Ala Cys Pro Ile Gly Phe Glu Leu Ile Ser Asp Met
    610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Asn Val Ala Ile
                645                 650                 655

Pro Leu Thr Gly Val Lys Glu Ala Ser Ala Leu Asp Phe Asp Val Thr
            660                 665                 670

Asp Asn Arg Ile Tyr Trp Thr Asp Ile Ser Leu Lys Thr Ile Ser Arg
            675                 680                 685

Ala Phe Met Asn Gly Ser Ala Leu Glu His Val Val Glu Phe Gly Leu
        690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
            740                 745                 750

Leu Ala Leu Asp Pro Ala Glu Gly Phe Met Tyr Trp Thr Glu Trp Gly
        755                 760                 765

Gly Lys Pro Lys Ile Asp Arg Ala Ala Met Asp Gly Ser Glu Arg Thr
    770                 775                 780

Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
                805                 810                 815

Ser Ser Asn Met Leu Gly Leu Asn Arg Glu Val Ile Ala Asp Asp Leu
            820                 825                 830

Pro His Pro Phe Gly Leu Thr Gln Tyr Gln Asp Tyr Ile Tyr Trp Thr
        835                 840                 845

Asp Trp Ser Arg Arg Ser Ile Glu Arg Ala Asn Lys Thr Ser Gly Gln
    850                 855                 860

Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
        915                 920                 925

Cys Ser Ala Pro Thr Thr Phe Leu Leu Phe Ser Gln Lys Ser Ala Ile
    930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
            980                 985                 990

Gln Glu Asp Gly Ser Gln Gly Phe Thr Val Val Val Ser Ser Val Pro
        995                 1000                1005

Ser Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035

Asn Val Thr Arg Leu Asp Gly Arg Ser Val Gly Val Val Leu Lys
    1040                1045                1050

Gly Glu Gln Asp Arg Pro Arg Ala Val Val Val Asn Pro Glu Lys
    1055                1060                1065

Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe

```
              1085                1090                1095
Ser Gly Leu Ser Lys Pro Ile Ala Leu Ala Leu Asp Ser Arg Leu
    1100                1105                1110

Gly Lys Leu Phe Trp Ala Asp Ser Asp Leu Arg Arg Ile Glu Ser
    1115                1120                1125

Ser Asp Leu Ser Gly Ala Asn Arg Ile Val Leu Glu Asp Ser Asn
    1130                1135                1140

Ile Leu Gln Pro Val Gly Leu Thr Val Phe Glu Asn Trp Leu Tyr
    1145                1150                1155

Trp Ile Asp Lys Gln Gln Gln Met Ile Glu Lys Ile Asp Met Thr
    1160                1165                1170

Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
    1190                1195                1200

Gln His Pro Cys Ala Gln Asp Asn Gly Gly Cys Ser His Ile Cys
    1205                1210                1215

Leu Val Lys Gly Asp Gly Thr Thr Arg Cys Ser Cys Pro Met His
    1220                1225                1230

Leu Val Leu Leu Gln Asp Glu Leu Ser Cys Gly Glu Pro Pro Thr
    1235                1240                1245

Cys Ser Pro Gln Gln Phe Thr Cys Phe Thr Gly Glu Ile Asp Cys
    1250                1255                1260

Ile Pro Val Ala Trp Arg Cys Asp Gly Phe Thr Glu Cys Glu Asp
    1265                1270                1275

His Ser Asp Glu Leu Asn Cys Pro Val Cys Ser Glu Ser Gln Phe
    1280                1285                1290

Gln Cys Ala Ser Gly Gln Cys Ile Asp Gly Ala Leu Arg Cys Asn
    1295                1300                1305

Gly Asp Ala Asn Cys Gln Asp Lys Ser Asp Glu Lys Asn Cys Glu
    1310                1315                1320

Val Leu Cys Leu Ile Asp Gln Phe Arg Cys Ala Asn Gly Gln Cys
    1325                1330                1335

Ile Gly Lys His Lys Lys Cys Asp His Asn Val Asp Cys Ser Asp
    1340                1345                1350

Lys Ser Asp Glu Leu Asp Cys Tyr Pro Thr Glu Glu Pro Ala Pro
    1355                1360                1365

Gln Ala Thr Asn Thr Val Gly Ser Val Ile Gly Val Ile Val Thr
    1370                1375                1380

Ile Phe Val Ser Gly Thr Val Tyr Phe Ile Cys Gln Arg Met Leu
    1385                1390                1395

Cys Pro Arg Met Lys Gly Asp Gly Glu Thr Met Thr Asn Asp Tyr
    1400                1405                1410

Val Val His Gly Pro Ala Ser Val Pro Leu Gly Tyr Val Pro His
    1415                1420                1425

Pro Ser Ser Leu Ser Gly Ser Leu Pro Gly Met Ser Arg Gly Lys
    1430                1435                1440

Ser Met Ile Ser Ser Leu Ser Ile Met Gly Gly Ser Ser Gly Pro
    1445                1450                1455

Pro Tyr Asp Arg Ala His Val Thr Gly Ala Ser Ser Ser Ser Ser
    1460                1465                1470

Ser Ser Thr Lys Gly Thr Tyr Phe Pro Ala Ile Leu Asn Pro Pro
    1475                1480                1485
```

-continued

```
Pro Ser Pro Ala Thr Glu Arg Ser His Tyr Thr Met Glu Phe Gly
    1490                1495                1500

Tyr Ser Ser Asn Ser Pro Ser Thr His Arg Ser Tyr Ser Tyr Arg
    1505                1510                1515

Pro Tyr Ser Tyr Arg His Phe Ala Pro Pro Thr Thr Pro Cys Ser
    1520                1525                1530

Thr Asp Val Cys Asp Ser Asp Tyr Ala Pro Ser Arg Arg Met Thr
    1535                1540                1545

Ser Val Ala Thr Ala Lys Gly Tyr Thr Ser Asp Leu Asn Tyr Asp
    1550                1555                1560

Ser Glu Pro Val Pro Pro Pro Thr Pro Arg Ser Gln Tyr Leu
    1565                1570                1575

Ser Ala Glu Glu Asn Tyr Glu Ser Cys Pro Pro Ser Pro Tyr Thr
    1580                1585                1590

Glu Arg Ser Tyr Ser His His Leu Tyr Pro Pro Pro Ser Pro
    1595                1600                1605

Cys Thr Asp Ser Ser
    1610

<210> SEQ ID NO 3
<211> LENGTH: 1354
<212> TYPE: PRT
<213> ORGANISM: Homo sapiens

<400> SEQUENCE: 3

Ala Pro Leu Leu Leu Tyr Ala Asn Arg Arg Asp Leu Arg Leu Val Asp
1                5                  10                 15

Ala Thr Asn Gly Lys Glu Asn Ala Thr Ile Val Val Gly Gly Leu Glu
                20                 25                 30

Asp Ala Ala Ala Val Asp Phe Val Phe Ser His Gly Leu Ile Tyr Trp
            35                 40                 45

Ser Asp Val Ser Glu Glu Ala Ile Lys Arg Thr Glu Phe Asn Lys Thr
        50                 55                 60

Glu Ser Val Gln Asn Val Val Val Ser Gly Leu Leu Ser Pro Asp Gly
65                 70                 75                 80

Leu Ala Cys Asp Trp Leu Gly Glu Lys Leu Tyr Trp Thr Asp Ser Glu
                85                 90                 95

Thr Asn Arg Ile Glu Val Ser Asn Leu Asp Gly Ser Leu Arg Lys Val
                100                105                110

Leu Phe Trp Gln Glu Leu Asp Gln Pro Arg Ala Ile Ala Leu Asp Pro
            115                120                125

Ser Ser Gly Phe Met Tyr Trp Thr Asp Trp Gly Glu Val Pro Lys Ile
        130                135                140

Glu Arg Ala Gly Met Asp Gly Ser Ser Arg Phe Ile Ile Ile Asn Ser
145                150                155                160

Glu Ile Tyr Trp Pro Asn Gly Leu Thr Leu Asp Tyr Glu Glu Gln Lys
                165                170                175

Leu Tyr Trp Ala Asp Ala Lys Leu Asn Phe Ile His Lys Ser Asn Leu
            180                185                190

Asp Gly Thr Asn Arg Gln Ala Val Val Lys Gly Ser Leu Pro His Pro
        195                200                205

Phe Ala Leu Thr Leu Phe Glu Asp Ile Leu Tyr Trp Thr Asp Trp Ser
    210                215                220

Thr His Ser Ile Leu Ala Cys Asn Lys Tyr Thr Gly Glu Gly Leu Arg
225                230                235                240
```

-continued

Glu Ile His Ser Asp Ile Phe Ser Pro Met Asp Ile His Ala Phe Ser
            245                 250                 255

Gln Gln Arg Gln Pro Asn Ala Thr Asn Pro Cys Gly Ile Asp Asn Gly
        260                 265                 270

Gly Cys Ser His Leu Cys Leu Met Ser Pro Val Lys Pro Phe Tyr Gln
    275                 280                 285

Cys Ala Cys Pro Thr Gly Val Lys Leu Leu Glu Asn Gly Lys Thr Cys
290                 295                 300

Lys Asp Gly Ala Thr Glu Leu Leu Leu Ala Arg Arg Thr Asp Leu
305                 310                 315                 320

Arg Arg Ile Ser Leu Asp Thr Pro Asp Phe Thr Asp Ile Val Leu Gln
                325                 330                 335

Leu Glu Asp Ile Arg His Ala Ile Ala Ile Asp Tyr Asp Pro Val Glu
            340                 345                 350

Gly Tyr Ile Tyr Trp Thr Asp Asp Glu Val Arg Ala Ile Arg Arg Ser
        355                 360                 365

Phe Ile Asp Gly Ser Gly Ser Gln Phe Val Val Thr Ala Gln Ile Ala
    370                 375                 380

His Pro Asp Gly Ile Ala Val Asp Trp Val Ala Arg Asn Leu Tyr Trp
385                 390                 395                 400

Thr Asp Thr Gly Thr Asp Arg Ile Glu Val Thr Arg Leu Asn Gly Thr
                405                 410                 415

Met Arg Lys Ile Leu Ile Ser Glu Asp Leu Glu Glu Pro Arg Ala Ile
            420                 425                 430

Val Leu Asp Pro Met Val Gly Tyr Met Tyr Trp Thr Asp Trp Gly Glu
        435                 440                 445

Ile Pro Lys Ile Glu Arg Ala Ala Leu Asp Gly Ser Asp Arg Val Val
    450                 455                 460

Leu Val Asn Thr Ser Leu Gly Trp Pro Asn Gly Leu Ala Leu Asp Tyr
465                 470                 475                 480

Asp Glu Gly Lys Ile Tyr Trp Gly Asp Ala Lys Thr Asp Lys Ile Glu
                485                 490                 495

Val Met Asn Thr Asp Gly Thr Gly Arg Arg Val Leu Val Glu Asp Lys
            500                 505                 510

Ile Pro His Ile Phe Gly Phe Thr Leu Leu Gly Asp Tyr Val Tyr Trp
        515                 520                 525

Thr Asp Trp Gln Arg Arg Ser Ile Glu Arg Val His Lys Arg Ser Ala
530                 535                 540

Glu Arg Glu Val Ile Ile Asp Gln Leu Pro Asp Leu Met Gly Leu Lys
545                 550                 555                 560

Ala Thr Asn Val His Arg Val Ile Gly Ser Asn Pro Cys Ala Glu Glu
                565                 570                 575

Asn Gly Gly Cys Ser His Leu Cys Leu Tyr Arg Pro Gln Gly Leu Arg
            580                 585                 590

Cys Ala Cys Pro Ile Gly Phe Glu Leu Ile Ser Asp Met Lys Thr Cys
        595                 600                 605

Ile Val Pro Glu Ala Phe Leu Leu Phe Ser Arg Ala Asp Ile Arg
    610                 615                 620

Arg Ile Ser Leu Glu Thr Asn Asn Asn Val Ala Ile Pro Leu Thr
625                 630                 635                 640

Gly Val Lys Glu Ala Ser Ala Leu Asp Phe Asp Val Thr Asp Asn Arg
                645                 650                 655

Ile Tyr Trp Thr Asp Ile Ser Leu Lys Thr Ile Ser Arg Ala Phe Met
            660                 665                 670

```
Asn Gly Ser Ala Leu Glu His Val Val Glu Phe Gly Leu Asp Tyr Pro
        675                 680                 685
Glu Gly Met Ala Val Asp Trp Leu Gly Lys Asn Leu Tyr Trp Ala Asp
    690                 695                 700
Thr Gly Thr Asn Arg Ile Glu Val Ser Lys Leu Asp Gly Gln His Arg
705                 710                 715                 720
Gln Val Leu Val Trp Lys Asp Leu Asp Ser Pro Arg Ala Leu Ala Leu
                725                 730                 735
Asp Pro Ala Glu Gly Phe Met Tyr Trp Thr Glu Trp Gly Gly Lys Pro
            740                 745                 750
Lys Ile Asp Arg Ala Ala Met Asp Gly Ser Glu Arg Thr Thr Leu Val
        755                 760                 765
Pro Asn Val Gly Arg Ala Asn Gly Leu Thr Ile Asp Tyr Ala Lys Arg
    770                 775                 780
Arg Leu Tyr Trp Thr Asp Leu Asp Thr Asn Leu Ile Glu Ser Ser Asn
785                 790                 795                 800
Met Leu Gly Leu Asn Arg Glu Val Ile Ala Asp Asp Leu Pro His Pro
                805                 810                 815
Phe Gly Leu Thr Gln Tyr Gln Asp Tyr Ile Tyr Trp Thr Asp Trp Ser
            820                 825                 830
Arg Arg Ser Ile Glu Arg Ala Asn Lys Thr Ser Gly Gln Asn Arg Thr
        835                 840                 845
Ile Ile Gln Gly His Leu Asp Tyr Val Met Asp Ile Leu Val Phe His
    850                 855                 860
Ser Ser Arg Gln Ser Gly Trp Asn Glu Cys Ala Ser Ser Asn Gly His
865                 870                 875                 880
Cys Ser His Leu Cys Leu Ala Val Pro Val Gly Gly Phe Val Cys Gly
                885                 890                 895
Cys Pro Ala His Tyr Ser Leu Asn Ala Asp Asn Arg Thr Cys Ser Ala
            900                 905                 910
Pro Thr Thr Phe Leu Leu Phe Ser Gln Lys Ser Ala Ile Asn Arg Met
        915                 920                 925
Val Ile Asp Glu Gln Gln Ser Pro Asp Ile Ile Leu Pro Ile His Ser
    930                 935                 940
Leu Arg Asn Val Arg Ala Ile Asp Tyr Asp Pro Leu Asp Lys Gln Leu
945                 950                 955                 960
Tyr Trp Ile Asp Ser Arg Gln Asn Met Ile Arg Lys Ala Gln Glu Asp
                965                 970                 975
Gly Ser Gln Gly Phe Thr Val Val Ser Ser Val Pro Ser Gln Asn
            980                 985                 990
Leu Glu Ile Gln Pro Tyr Asp Leu Ser Ile Asp Ile Tyr Ser Arg Tyr
        995                 1000                1005
Ile Tyr Trp Thr Cys Glu Ala Thr Asn Val Ile Asn Val Thr Arg
    1010                1015                1020
Leu Asp Gly Arg Ser Val Gly Val Val Leu Lys Gly Glu Gln Asp
    1025                1030                1035
Arg Pro Arg Ala Ile Val Val Asn Pro Glu Lys Gly Tyr Met Tyr
    1040                1045                1050
Phe Thr Asn Leu Gln Glu Arg Ser Pro Lys Ile Glu Arg Ala Ala
    1055                1060                1065
Leu Asp Gly Thr Glu Arg Glu Val Leu Phe Phe Ser Gly Leu Ser
    1070                1075                1080
Lys Pro Ile Ala Leu Ala Leu Asp Ser Arg Leu Gly Lys Leu Phe
```

```
       1085              1090              1095
Trp Ala Asp Ser Asp Leu Arg Arg Ile Glu Ser Ser Asp Leu Ser
    1100              1105              1110
Gly Ala Asn Arg Ile Val Leu Glu Asp Ser Asn Ile Leu Gln Pro
    1115              1120              1125
Val Gly Leu Thr Val Phe Glu Asn Trp Leu Tyr Trp Ile Asp Lys
    1130              1135              1140
Gln Gln Gln Met Ile Glu Lys Ile Asp Met Thr Gly Arg Glu Gly
    1145              1150              1155
Arg Thr Lys Val Gln Ala Arg Ile Ala Gln Leu Ser Asp Ile His
    1160              1165              1170
Ala Val Lys Glu Leu Asn Leu Gln Glu Tyr Arg Gln His Pro Cys
    1175              1180              1185
Ala Gln Asp Asn Gly Gly Cys Ser His Ile Cys Leu Val Lys Gly
    1190              1195              1200
Asp Gly Thr Thr Arg Cys Ser Cys Pro Met His Leu Val Leu Leu
    1205              1210              1215
Gln Asp Glu Leu Ser Cys Gly Glu Pro Pro Thr Cys Ser Pro Gln
    1220              1225              1230
Gln Phe Thr Cys Phe Thr Gly Glu Ile Asp Cys Ile Pro Val Ala
    1235              1240              1245
Trp Arg Cys Asp Gly Phe Thr Glu Cys Glu Asp His Ser Asp Glu
    1250              1255              1260
Leu Asn Cys Pro Val Cys Ser Glu Ser Gln Phe Gln Cys Ala Ser
    1265              1270              1275
Gly Gln Cys Ile Asp Gly Ala Leu Arg Cys Asn Gly Asp Ala Asn
    1280              1285              1290
Cys Gln Asp Lys Ser Asp Glu Lys Asn Cys Glu Val Leu Cys Leu
    1295              1300              1305
Ile Asp Gln Phe Arg Cys Ala Asn Gly Gln Cys Ile Gly Lys His
    1310              1315              1320
Lys Lys Cys Asp His Asn Val Asp Cys Ser Asp Lys Ser Asp Glu
    1325              1330              1335
Leu Asp Cys Tyr Pro Thr Glu Glu Pro Ala Pro Gln Ala Thr Asn
    1340              1345              1350
Thr

<210> SEQ ID NO 4
<211> LENGTH: 4896
<212> TYPE: DNA
<213> ORGANISM: Artificial
<220> FEATURE:
<223> OTHER INFORMATION: HA-tagged LRP6

<400> SEQUENCE: 4
atggagacag acacactcct gctatgggta ctgctgctct ggttccagg ttccactggt    60 gacgctagat acccatacga tgttccagat tacgctggag gtggcgctag cgccccttg   120 ttgctttatg caaacagacg ggacttgcga ttggttgatg ctacaaatgg caaagagaat   180
gctacgattg tagttggagg cttggaggat gcagctgcgg tggactttgt gtttagtcat   240
ggcttgatat actggagtga tgtcagcgaa gaagccatta acgaacaga atttaacaaa   300 actgagagtg tgcagaatgt tgttgtttct ggattattgt ccccgatgg gctggcatgt   360 gattggcttg gagaaaaatt gtactggaca gattctgaaa ctaatcggat tgaagtttct   420
aatttagatg gatctttacg aaaagttttta ttttggcaag agttggatca acccagagct   480
```

```
attgccttag atccttcaag tgggttcatg tactggacag actggggaga agtgccaaag    540
atagaacgtg ctggaatgga tggttcaagt cgcttcatta taataaacag tgaaatttac    600
tggccaaatg gactgacttt ggattatgaa gaacaaaagc tttattgggc agatgcaaaa    660
cttaatttca tccacaaatc aaatctggat ggaacaaatc ggcaggcagt ggttaaaggt    720
tcccttccac atccttttgc cttgacgtta tttgaggaca tattgtactg gactgactgg    780
agcacacact ccattttggc ttgcaacaag tatactggtg agggtctgcg tgaaatccat    840
tctgacatct tctctcccat ggatatacat gccttcagcc aacagaggca gccaaatgcc    900
acaaatccat gtggaattga caatgggggt tgttcccatt tgtgtttgat gtctccagtc    960
aagccttttt atcagtgtgc ttgccccact ggggtcaaac tcctggagaa tggaaaaacc   1020
tgcaaagatg gtgccacaga attattgctt ttagctcgaa ggacagactt gagacgcatt   1080
tctttggata caccagattt tacagacatt gttctgcagt tagaagacat ccgtcatgcc   1140
attgccatag attacgatcc tgtggaaggc tacatctact ggactgatga tgaagtgagg   1200
gccatacgcc gttcatttat agatggatct ggcagtcagt ttgtggtcac tgctcaaatt   1260
gcccatcctg atggtattgc tgtggactgg gttgcacgaa atctttattg gacagacact   1320
ggcactgatc gaatagaagt gacaaggctc aatgggacca tgaggaagat cttgatttca   1380
gaggacttag aggaacccg ggctattgtg ttagatccca tggttgggta catgtattgg   1440
actgactggg gagaaattcc gaaaattgag cgagcagctc tggatggttc tgaccgtgta   1500
gtattggtta acacttctct tggttggcca aatggtttag ccttggatta tgatgaaggc   1560
aaaatatact ggggagatgc caaaacagac aagattgagg ttatgaatac tgatggcact   1620
gggagacgag tactagtgga agacaaaatt cctcacatat ttggatttac tttgttgggt   1680
gactatgttt actggactga ctggcagagg cgtagcattg aaagagttca taacgaagt    1740
gcagagaggg aagtgatcat agatcagctg cctgacctca tgggcctaaa ggctacaaat   1800
gttcatcgag tgattggttc caaccctgt gctgaggaaa acgggggatg tagccatctc    1860
tgcctctata gacctcaggg ccttcgctgt gcttgcccta ttggctttga actcatcagt   1920
gacatgaaga cctgcattgt cccagaggct ttccttttgt tttcacggag agcagatatc   1980
agacgaattc tctggaaaac aaacaataat aatgtggcta ttccactcac tggtgtcaaa   2040
gaagcttctg ctttggattt tgatgtgaca gacaaccgaa tttattggac tgatatatca   2100
ctcaagacca tcagcagagc ctttatgaat ggcagtgcac tggaacatgt ggtagaattc   2160
ggcttagatt atccagaagg catggcagta gactggcttg gaagaacttt gtactgggca   2220
gacacaggaa cgaatcgaat tgaggtgtca aagttggatg ggcagcaccg acaagttttg   2280
gtgtggaaag acctagatag tcccagagct ctcgcgttgg accctgccga aggatttatg   2340
tattggactg aatggggtgg aaaacctaag atagacagag ctgcaatgga tggaagtgaa   2400
cgtactacct tagttccaaa tgtggggcgg gcaaacggcc taactattga ttatgctaaa   2460
aggaggcttt attggacaga cctgacacc aacttaatag aatcttcaaa tatgcttggg   2520
ctcaaccgtg aagttatagc agatgacttg cctcatcctt ttggcttaac tcagtaccaa   2580
gattatatct actggacgga ctggagccga cgcagcattg agcgtgccaa caaaaccagt   2640
ggccaaaacc gcaccatcat tcagggccat ttggattatg tgatggacat cctcgtcttt   2700
cactcatctc gacagtcagg gtggaatgaa tgtgcttcca gcaatgggca ctgctcccac   2760
ctctgcttgg ctgtgccagt tgggggtttt gtttgtggat gccctgccca ctactctctt   2820
aatgctgaca acaggacttg tagtgctcct acgactttcc tgctcttcag tcaaaagagt   2880
```

```
gccatcaacc gcatggtgat tgatgaacaa cagagccccg acatcatcct tcccatccac     2940
agccttcgga atgtccgggc cattgactat gacccactgg acaagcaact ctattggatt     3000
gactcacgac aaaacatgat ccgaaaggca caagaagatg gcagccaggg ctttactgtg     3060
gttgtgagct cagttccgag tcagaacctg gaaatacaac cctatgacct cagcattgat     3120
atttacagcc gctacatcta ctggacttgt gaggctacca atgtcattaa tgtgacaaga     3180
ttagatggga gatcagttgg agtggtgctg aaaggcgagc aggacagacc tcgagccgtt     3240
gtggtaaacc cagagaaagg gtatatgtat tttaccaatc ttcaggaaag gtctcctaaa     3300
attgaacggg ctgctttgga tgggacagaa cgggaggtcc tcttttcag tggcttaagt      3360 aaaccaattg ctttagccct tgatagcagg ctgggcaagc tcttttgggc tgattcagat     3420
ctccggcgaa ttgaaagcag tgatctctca ggtgctaacc ggatagtatt agaagactcc     3480
aatatcttgc agcctgtggg acttactgtg tttgaaaact ggctctattg gattgataaa     3540
cagcagcaaa tgattgaaaa aattgacatg acaggtcgag agggtagaac caaagtccaa     3600
gctcgaattg cccagcttag tgacattcat gcagtaaagg agctgaacct tcaagaatac     3660
agacagcacc ttgtgctca ggataatggt ggctgttcac atatttgtct tgtaaagggg      3720
gatggtacta caaggtgttc ttgccccatg cacctggttc tacttcaaga tgagctatca     3780 tgtgagaac ctccaacatg ttctcctcag cagtttactt gtttcacggg ggaaattgac       3840
tgtatccctg tggcttggcg gtgcgatggg tttactgaat gtgaagacca cagtgatgaa      3900
ctcaattgtc ctgtatgctc agagtccag ttccagtgtg ccagtgggca gtgtattgat      3960
ggtgccctcc gatgcaatgg agatgcaaac tgccaggaca atcagatga agaactgt        4020 gaagtgcttt gtttaattga tcagttccgc tgtgccaatg gtcagtgcat tggaaagcac    4080
aagaagtgtg atcataatgt ggattgcagt gacaagtcag atgaactgga ttgttatccg     4140
actgaagaac cagcaccaca ggccaccaat acagttggtt ctgttattgg cgtaattgtc     4200
accatttttg tgtctggaac tgtatacttt atctgccaga ggatgttgtg tccacgtatg     4260
aagggagatg gggaaactat gactaatgac tatgtagttc atggaccagc ttctgtgcct    4320
cttggttatg tgccacaccc aagttctttg tcaggatctc ttccaggaat gtctcgaggt     4380
aaatcaatga tcagctccct cagtatcatg gggggaagca gtggaccccc ctatgaccga    4440
gcccatgtta caggagcatc atcaagtagt tcttcaagca ccaaaggcac ttacttccct    4500
gcaattttga accctccacc atccccagcc acagagcgat cacattacac tatggaattt    4560
ggatattctt caaacagtcc ttccactcat aggtcataca gctacaggcc atatagctac    4620
cggcactttg caccccccac cacacccctgc agcacagatg tttgtgacag tgactatgct    4680
cctagtcgga gaatgacctc agtggcaaca gccaagggct ataccagtga cttgaactat    4740
gattcagaac ctgtgccccc acctcccaca ccccgaagcc aatacttgtc agcagaggag    4800
aactatgaaa gctgcccacc ttctccatac acagagagga gctattctca tcacctctac    4860
ccaccgccac cctctcccctg tacagactcc tcctga                             4896
```

<210> SEQ ID NO 5
<211> LENGTH: 1631
<212> TYPE: PRT
<213> ORGANISM: Artificial
<220> FEATURE:
<223> OTHER INFORMATION: HA-tagged LRP6

<400> SEQUENCE: 5

Met Glu Thr Asp Thr Leu Leu Leu Trp Val Leu Leu Leu Trp Val Pro

```
1               5                   10                  15
Gly Ser Thr Gly Asp Ala Arg Tyr Pro Tyr Asp Val Pro Asp Tyr Ala
                20                  25                  30
Gly Gly Gly Ala Ser Ala Pro Leu Leu Leu Tyr Ala Asn Arg Arg Asp
            35                  40                  45
Leu Arg Leu Val Asp Ala Thr Asn Gly Lys Glu Asn Ala Thr Ile Val
50                  55                  60
Val Gly Gly Leu Glu Asp Ala Ala Val Asp Phe Val Phe Ser His
65                  70                  75                  80
Gly Leu Ile Tyr Trp Ser Asp Val Ser Glu Glu Ala Ile Lys Arg Thr
                85                  90                  95
Glu Phe Asn Lys Thr Glu Ser Val Gln Asn Val Val Ser Gly Leu
                100                 105                 110
Leu Ser Pro Asp Gly Leu Ala Cys Asp Trp Leu Gly Glu Lys Leu Tyr
                115                 120                 125
Trp Thr Asp Ser Glu Thr Asn Arg Ile Glu Val Ser Asn Leu Asp Gly
            130                 135                 140
Ser Leu Arg Lys Val Leu Phe Trp Gln Glu Leu Asp Gln Pro Arg Ala
145                 150                 155                 160
Ile Ala Leu Asp Pro Ser Ser Gly Phe Met Tyr Trp Thr Asp Trp Gly
                165                 170                 175
Glu Val Pro Lys Ile Glu Arg Ala Gly Met Asp Gly Ser Ser Arg Phe
                180                 185                 190
Ile Ile Ile Asn Ser Glu Ile Tyr Trp Pro Asn Gly Leu Thr Leu Asp
                195                 200                 205
Tyr Glu Glu Gln Lys Leu Tyr Trp Ala Asp Ala Lys Leu Asn Phe Ile
            210                 215                 220
His Lys Ser Asn Leu Asp Gly Thr Asn Arg Gln Ala Val Val Lys Gly
225                 230                 235                 240
Ser Leu Pro His Pro Phe Ala Leu Thr Leu Phe Glu Asp Ile Leu Tyr
                245                 250                 255
Trp Thr Asp Trp Ser Thr His Ser Ile Leu Ala Cys Asn Lys Tyr Thr
            260                 265                 270
Gly Glu Gly Leu Arg Glu Ile His Ser Asp Ile Phe Ser Pro Met Asp
            275                 280                 285
Ile His Ala Phe Ser Gln Gln Arg Gln Pro Asn Ala Thr Asn Pro Cys
            290                 295                 300
Gly Ile Asp Asn Gly Gly Cys Ser His Leu Cys Leu Met Ser Pro Val
305                 310                 315                 320
Lys Pro Phe Tyr Gln Cys Ala Cys Pro Thr Gly Val Lys Leu Leu Glu
                325                 330                 335
Asn Gly Lys Thr Cys Lys Asp Gly Ala Thr Glu Leu Leu Leu Ala
            340                 345                 350
Arg Arg Thr Asp Leu Arg Arg Ile Ser Leu Asp Thr Pro Asp Phe Thr
            355                 360                 365
Asp Ile Val Leu Gln Leu Glu Asp Ile Arg His Ala Ile Ala Ile Asp
            370                 375                 380
Tyr Asp Pro Val Glu Gly Tyr Ile Tyr Trp Thr Asp Glu Val Arg
385                 390                 395                 400
Ala Ile Arg Arg Ser Phe Ile Asp Gly Ser Gly Ser Gln Phe Val Val
                405                 410                 415
Thr Ala Gln Ile Ala His Pro Asp Gly Ile Ala Val Asp Trp Val Ala
            420                 425                 430
```

-continued

```
Arg Asn Leu Tyr Trp Thr Asp Thr Gly Thr Asp Arg Ile Glu Val Thr
    435                 440                 445

Arg Leu Asn Gly Thr Met Arg Lys Ile Leu Ile Ser Glu Asp Leu Glu
450                 455                 460

Glu Pro Arg Ala Ile Val Leu Asp Pro Met Val Gly Tyr Met Tyr Trp
465                 470                 475                 480

Thr Asp Trp Gly Glu Ile Pro Lys Ile Glu Arg Ala Ala Leu Asp Gly
                485                 490                 495

Ser Asp Arg Val Val Leu Val Asn Thr Ser Leu Gly Trp Pro Asn Gly
                500                 505                 510

Leu Ala Leu Asp Tyr Asp Glu Gly Lys Ile Tyr Trp Gly Asp Ala Lys
            515                 520                 525

Thr Asp Lys Ile Glu Val Met Asn Thr Asp Gly Thr Gly Arg Arg Val
530                 535                 540

Leu Val Glu Asp Lys Ile Pro His Ile Phe Gly Phe Thr Leu Leu Gly
545                 550                 555                 560

Asp Tyr Val Tyr Trp Thr Asp Trp Gln Arg Arg Ser Ile Glu Arg Val
                565                 570                 575

His Lys Arg Ser Ala Glu Arg Glu Val Ile Ile Asp Gln Leu Pro Asp
            580                 585                 590

Leu Met Gly Leu Lys Ala Thr Asn Val His Arg Val Ile Gly Ser Asn
            595                 600                 605

Pro Cys Ala Glu Glu Asn Gly Gly Cys Ser His Leu Cys Leu Tyr Arg
610                 615                 620

Pro Gln Gly Leu Arg Cys Ala Cys Pro Ile Gly Phe Glu Leu Ile Ser
625                 630                 635                 640

Asp Met Lys Thr Cys Ile Val Pro Glu Ala Phe Leu Leu Phe Ser Arg
                645                 650                 655

Arg Ala Asp Ile Arg Arg Ile Ser Leu Glu Thr Asn Asn Asn Asn Val
                660                 665                 670

Ala Ile Pro Leu Thr Gly Val Lys Glu Ala Ser Ala Leu Asp Phe Asp
            675                 680                 685

Val Thr Asp Asn Arg Ile Tyr Trp Thr Asp Ile Ser Leu Lys Thr Ile
690                 695                 700

Ser Arg Ala Phe Met Asn Gly Ser Ala Leu Glu His Val Val Glu Phe
705                 710                 715                 720

Gly Leu Asp Tyr Pro Glu Gly Met Ala Val Asp Trp Leu Gly Lys Asn
                725                 730                 735

Leu Tyr Trp Ala Asp Thr Gly Thr Asn Arg Ile Glu Val Ser Lys Leu
                740                 745                 750

Asp Gly Gln His Arg Gln Val Leu Val Trp Lys Asp Leu Asp Ser Pro
            755                 760                 765

Arg Ala Leu Ala Leu Asp Pro Ala Glu Gly Phe Met Tyr Trp Thr Glu
770                 775                 780

Trp Gly Gly Lys Pro Lys Ile Asp Arg Ala Ala Met Asp Gly Ser Glu
785                 790                 795                 800

Arg Thr Thr Leu Val Pro Asn Val Gly Arg Ala Asn Gly Leu Thr Ile
                805                 810                 815

Asp Tyr Ala Lys Arg Arg Leu Tyr Trp Thr Asp Leu Asp Thr Asn Leu
                820                 825                 830

Ile Glu Ser Ser Asn Met Leu Gly Leu Asn Arg Glu Val Ile Ala Asp
            835                 840                 845

Asp Leu Pro His Pro Phe Gly Leu Thr Gln Tyr Gln Asp Tyr Ile Tyr
850                 855                 860
```

```
Trp Thr Asp Trp Ser Arg Arg Ser Ile Glu Arg Ala Asn Lys Thr Ser
865                 870                 875                 880

Gly Gln Asn Arg Thr Ile Ile Gln Gly His Leu Asp Tyr Val Met Asp
            885                 890                 895

Ile Leu Val Phe His Ser Ser Arg Gln Ser Gly Trp Asn Glu Cys Ala
                900                 905                 910

Ser Ser Asn Gly His Cys Ser His Leu Cys Leu Ala Val Pro Val Gly
            915                 920                 925

Gly Phe Val Cys Gly Cys Pro Ala His Tyr Ser Leu Asn Ala Asp Asn
930                 935                 940

Arg Thr Cys Ser Ala Pro Thr Thr Phe Leu Leu Phe Ser Gln Lys Ser
945                 950                 955                 960

Ala Ile Asn Arg Met Val Ile Asp Glu Gln Gln Ser Pro Asp Ile Ile
                965                 970                 975

Leu Pro Ile His Ser Leu Arg Asn Val Arg Ala Ile Asp Tyr Asp Pro
                980                 985                 990

Leu Asp Lys Gln Leu Tyr Trp Ile Asp Ser Arg Gln Asn Met Ile Arg
            995                 1000                1005

Lys Ala Gln Glu Asp Gly Ser Gln Gly Phe Thr Val Val Val Ser
1010                1015                1020

Ser Val Pro Ser Gln Asn Leu Glu Ile Gln Pro Tyr Asp Leu Ser
1025                1030                1035

Ile Asp Ile Tyr Ser Arg Tyr Ile Tyr Trp Thr Cys Glu Ala Thr
1040                1045                1050

Asn Val Ile Asn Val Thr Arg Leu Asp Gly Arg Ser Val Gly Val
1055                1060                1065

Val Leu Lys Gly Glu Gln Asp Arg Pro Arg Ala Val Val Val Asn
1070                1075                1080

Pro Glu Lys Gly Tyr Met Tyr Phe Thr Asn Leu Gln Glu Arg Ser
1085                1090                1095

Pro Lys Ile Glu Arg Ala Ala Leu Asp Gly Thr Glu Arg Glu Val
1100                1105                1110

Leu Phe Phe Ser Gly Leu Ser Lys Pro Ile Ala Leu Ala Leu Asp
1115                1120                1125

Ser Arg Leu Gly Lys Leu Phe Trp Ala Asp Ser Asp Leu Arg Arg
1130                1135                1140

Ile Glu Ser Ser Asp Leu Ser Gly Ala Asn Arg Ile Val Leu Glu
1145                1150                1155

Asp Ser Asn Ile Leu Gln Pro Val Gly Leu Thr Val Phe Glu Asn
1160                1165                1170

Trp Leu Tyr Trp Ile Asp Lys Gln Gln Gln Met Ile Glu Lys Ile
1175                1180                1185

Asp Met Thr Gly Arg Glu Gly Arg Thr Lys Val Gln Ala Arg Ile
1190                1195                1200

Ala Gln Leu Ser Asp Ile His Ala Val Lys Glu Leu Asn Leu Gln
1205                1210                1215

Glu Tyr Arg Gln His Pro Cys Ala Gln Asp Asn Gly Gly Cys Ser
1220                1225                1230

His Ile Cys Leu Val Lys Gly Asp Gly Thr Thr Arg Cys Ser Cys
1235                1240                1245

Pro Met His Leu Val Leu Leu Gln Asp Glu Leu Ser Cys Gly Glu
1250                1255                1260

Pro Pro Thr Cys Ser Pro Gln Gln Phe Thr Cys Phe Thr Gly Glu
```

```
              1265                1270                1275

Ile Asp Cys Ile Pro Val Ala Trp Arg Cys Asp Gly Phe Thr Glu
    1280                1285                1290

Cys Glu Asp His Ser Asp Glu Leu Asn Cys Pro Val Cys Ser Glu
    1295                1300                1305

Ser Gln Phe Gln Cys Ala Ser Gly Gln Cys Ile Asp Gly Ala Leu
    1310                1315                1320

Arg Cys Asn Gly Asp Ala Asn Cys Gln Asp Lys Ser Asp Glu Lys
    1325                1330                1335

Asn Cys Glu Val Leu Cys Leu Ile Asp Gln Phe Arg Cys Ala Asn
    1340                1345                1350

Gly Gln Cys Ile Gly Lys His Lys Lys Cys Asp His Asn Val Asp
    1355                1360                1365

Cys Ser Asp Lys Ser Asp Glu Leu Asp Cys Tyr Pro Thr Glu Glu
    1370                1375                1380

Pro Ala Pro Gln Ala Thr Asn Thr Val Gly Ser Val Ile Gly Val
    1385                1390                1395

Ile Val Thr Ile Phe Val Ser Gly Thr Val Tyr Phe Ile Cys Gln
    1400                1405                1410

Arg Met Leu Cys Pro Arg Met Lys Gly Asp Gly Glu Thr Met Thr
    1415                1420                1425

Asn Asp Tyr Val Val His Gly Pro Ala Ser Val Pro Leu Gly Tyr
    1430                1435                1440

Val Pro His Pro Ser Ser Leu Ser Gly Ser Leu Pro Gly Met Ser
    1445                1450                1455

Arg Gly Lys Ser Met Ile Ser Ser Leu Ser Ile Met Gly Gly Ser
    1460                1465                1470

Ser Gly Pro Pro Tyr Asp Arg Ala His Val Thr Gly Ala Ser Ser
    1475                1480                1485

Ser Ser Ser Ser Ser Thr Lys Gly Thr Tyr Phe Pro Ala Ile Leu
    1490                1495                1500

Asn Pro Pro Pro Ser Pro Ala Thr Glu Arg Ser His Tyr Thr Met
    1505                1510                1515

Glu Phe Gly Tyr Ser Ser Asn Ser Pro Ser Thr His Arg Ser Tyr
    1520                1525                1530

Ser Tyr Arg Pro Tyr Ser Tyr Arg His Phe Ala Pro Pro Thr Thr
    1535                1540                1545

Pro Cys Ser Thr Asp Val Cys Asp Ser Asp Tyr Ala Pro Ser Arg
    1550                1555                1560

Arg Met Thr Ser Val Ala Thr Ala Lys Gly Tyr Thr Ser Asp Leu
    1565                1570                1575

Asn Tyr Asp Ser Glu Pro Val Pro Pro Pro Thr Pro Arg Ser
    1580                1585                1590

Gln Tyr Leu Ser Ala Glu Glu Asn Tyr Glu Ser Cys Pro Pro Ser
    1595                1600                1605

Pro Tyr Thr Glu Arg Ser Tyr Ser His His Leu Tyr Pro Pro Pro
    1610                1615                1620

Pro Ser Pro Cys Thr Asp Ser Ser
    1625                1630

<210> SEQ ID NO 6
<211> LENGTH: 3069
<212> TYPE: DNA
<213> ORGANISM: Artificial
<220> FEATURE:
```

<223> OTHER INFORMATION: HA-tagged LRP6, deletion of propeller domains 1 and 2.

<400> SEQUENCE: 6

| | |
|---|---|
| atggagacag acacactcct gctatgggta ctgctgctct gggttccagg ttccactggt | 60 |
| gacgctagat acccatacga tgttccagat tacgctggag gtggcgctag cgtcccagag | 120 |
| gctttccttt tgttttcacg gagagcagat atcagacgaa tttctctgga aacaaacaat | 180 |
| aataatgtgg ctattccact cactggtgtc aaagaagctt ctgctttgga ttttgatgtg | 240 |
| acagacaacc gaatttattg gactgatata tcactcaaga ccatcagcag agcctttatg | 300 |
| aatggcagtg cactggaaca tgtggtagaa ttcggcttag attatccaga aggcatggca | 360 |
| gtagactggc ttgggaagaa cttgtactgg gcagacacag gaacgaatcg aattgaggtg | 420 |
| tcaaagttgg atgggcagca ccgacaagtt ttggtgtgga agacctaga tagtcccaga | 480 |
| gctctcgcgt tggaccctgc cgaaggattt atgtattgga ctgaatgggg tggaaaacct | 540 |
| aagatagaca gagctgcaat ggatggaagt gaacgtacta ccttagttcc aaatgtgggg | 600 |
| cgggcaaacg gcctaactat tgattatgct aaaaggaggc tttattggac agacctggac | 660 |
| accaacttaa tagaatcttc aaatatgctt gggctcaacc gtgaagttat agcagatgac | 720 |
| ttgcctcatc cttttggctt aactcagtac caagattata tctactggac ggactggagc | 780 |
| cgacgcagca ttgagcgtgc caacaaaacc agtggccaaa accgcaccat cattcagggc | 840 |
| catttggatt atgtgatgga catcctcgtc tttcactcat ctcgacagtc agggtggaat | 900 |
| gaatgtgctt ccagcaatgg gcactgctcc cacctctgct tggctgtgcc agttgggggt | 960 |
| tttgtttgtg atgccctgc ccactactct cttaatgctg acaacaggac ttgtagtgct | 1020 |
| cctacgactt tcctgctctt cagtcaaaag agtgccatca accgcatggt gattgatgaa | 1080 |
| caacagagcc ccgacatcat cctttcccatc cacagccttc ggaatgtccg ggccattgac | 1140 |
| tatgacccac tggacaagca actctattgg attgactcac gacaaaacat gatccgaaag | 1200 |
| gcacaagaag atggcagcca gggctttact gtggttgtga gctcagttcc gagtcagaac | 1260 |
| ctggaaatac aaccctatga cctcagcatt gatatttaca ccgctacat ctactggact | 1320 |
| tgtgaggcta ccaatgtcat taatgtgaca agattagatg ggagatcagt ggagtggtg | 1380 |
| ctgaaaggcg agcaggacag acctcgagcc gttgtggtaa acccagagaa agggtatatg | 1440 |
| tattttacca atcttcagga aaggtctcct aaaattgaac gggctgcttt ggatgggaca | 1500 |
| gaacgggagg tcctcttttt cagtggctta agtaaaccaa ttgctttagc ccttgatagc | 1560 |
| aggctgggca agctcttttg gctgattca gatctccggc gaattgaaag cagtgatctc | 1620 |
| tcaggtgcta accggatagt attagaagac tccaatatct tgcagcctgt gggacttact | 1680 |
| gtgtttgaaa actggctcta ttggattgat aaacagcagc aaatgattga aaaaattgac | 1740 |
| atgacaggtc gagagggtag aaccaaagtc caagctcgaa ttgcccagct tagtgacatt | 1800 |
| catgcagtaa aggagctgaa ccttcaagaa tacagacagc cccttgtgc tcaggataat | 1860 |
| ggtggctgtt cacatatttg tcttgtaaag ggggatggta ctacaaggtg ttcttgcccc | 1920 |
| atgcacctgg ttctacttca agatgagcta tcatgtggag aacctccaac atgttctcct | 1980 |
| cagcagttta cttgtttcac gggggaaatt gactgtatcc ctgtggcttg gcggtgcgat | 2040 |
| gggtttactg aatgtgaaga ccacagtgat gaactcaatt gtcctgtatg ctcagagtcc | 2100 |
| cagttccagt gtgccagtgg gcagtgtatt gatggtgccc tccgatgcaa tggagatgca | 2160 |
| aactgccagg acaaatcaga tgagaagaac tgtgaagtgc tttgttttaat tgatcagttc | 2220 |
| cgctgtgcca atggtcagtg cattggaaag cacaagaagt gtgatcataa tgtggattgc | 2280 |

```
agtgacaagt cagatgaact ggattgttat ccgactgaag aaccagcacc acaggccacc    2340
aatacagttg gttctgttat tggcgtaatt gtcaccattt ttgtgtctgg aactgtatac    2400
tttatctgcc agaggatgtt gtgtccacgt atgaagggag atggggaaac tatgactaat    2460
gactatgtag ttcatggacc agcttctgtg cctcttggtt atgtgccaca cccaagttct    2520
ttgtcaggat ctcttccagg aatgtctcga ggtaaatcaa tgatcagctc cctcagtatc    2580
atggggggaa gcagtggacc cccctatgac cgagcccatg ttacaggagc atcatcaagt    2640
agttcttcaa gcaccaaagg cacttacttc cctgcaattt tgaaccctcc accatcccca    2700
gccacagagc gatcacatta cactatggaa tttggatatt cttcaaacag tccttccact    2760
cataggtcat acagctacag gccatatagc taccggcact ttgcaccccc caccacaccc    2820
tgcagcacag atgtttgtga cagtgactat gctcctagtc ggagaatgac ctcagtggca    2880
acagccaagg gctataccag tgacttgaac tatgattcag aacctgtgcc cccacctccc    2940
acaccccgaa gccaatactt gtcagcagag gagaactatg aaagctgccc accttctcca    3000
tacacagaga ggagctattc tcatcacctc tacccaccgc caccctctcc ctgtacagac    3060
tcctcctga                                                            3069
```

<210> SEQ ID NO 7
<211> LENGTH: 1022
<212> TYPE: PRT
<213> ORGANISM: Artificial
<220> FEATURE:
<223> OTHER INFORMATION: HA-tagged LRP6, deletion of propeller domains
      1 and 2.

<400> SEQUENCE: 7

```
Met Glu Thr Asp Thr Leu Leu Leu Trp Val Leu Leu Leu Trp Val Pro
1               5                   10                  15

Gly Ser Thr Gly Asp Ala Arg Tyr Pro Tyr Asp Val Pro Asp Tyr Ala
            20                  25                  30

Gly Gly Gly Ala Ser Val Pro Glu Ala Phe Leu Leu Phe Ser Arg Arg
        35                  40                  45

Ala Asp Ile Arg Arg Ile Ser Leu Glu Thr Asn Asn Asn Asn Val Ala
    50                  55                  60

Ile Pro Leu Thr Gly Val Lys Glu Ala Ser Ala Leu Asp Phe Asp Val
65                  70                  75                  80

Thr Asp Asn Arg Ile Tyr Trp Thr Asp Ile Ser Leu Lys Thr Ile Ser
                85                  90                  95

Arg Ala Phe Met Asn Gly Ser Ala Leu Glu His Val Val Glu Phe Gly
            100                 105                 110

Leu Asp Tyr Pro Glu Gly Met Ala Val Asp Trp Leu Gly Lys Asn Leu
        115                 120                 125

Tyr Trp Ala Asp Thr Gly Thr Asn Arg Ile Glu Val Ser Lys Leu Asp
    130                 135                 140

Gly Gln His Arg Gln Val Leu Val Trp Lys Asp Leu Asp Ser Pro Arg
145                 150                 155                 160

Ala Leu Ala Leu Asp Pro Ala Glu Gly Phe Met Tyr Trp Thr Glu Trp
                165                 170                 175

Gly Gly Lys Pro Lys Ile Asp Arg Ala Ala Met Asp Gly Ser Glu Arg
            180                 185                 190

Thr Thr Leu Val Pro Asn Val Gly Arg Ala Asn Gly Leu Thr Ile Asp
        195                 200                 205

Tyr Ala Lys Arg Arg Leu Tyr Trp Thr Asp Leu Asp Thr Asn Leu Ile
```

-continued

```
            210                 215                 220
Glu Ser Ser Asn Met Leu Gly Leu Asn Arg Glu Val Ile Ala Asp Asp
225                 230                 235                 240

Leu Pro His Pro Phe Gly Leu Thr Gln Tyr Gln Asp Tyr Ile Tyr Trp
                    245                 250                 255

Thr Asp Trp Ser Arg Arg Ser Ile Glu Arg Ala Asn Lys Thr Ser Gly
                260                 265                 270

Gln Asn Arg Thr Ile Ile Gln Gly His Leu Asp Tyr Val Met Asp Ile
                275                 280                 285

Leu Val Phe His Ser Ser Arg Gln Ser Gly Trp Asn Glu Cys Ala Ser
290                 295                 300

Ser Asn Gly His Cys Ser His Leu Cys Leu Ala Val Pro Val Gly Gly
305                 310                 315                 320

Phe Val Cys Gly Cys Pro Ala His Tyr Ser Leu Asn Ala Asp Asn Arg
                325                 330                 335

Thr Cys Ser Ala Pro Thr Thr Phe Leu Leu Phe Ser Gln Lys Ser Ala
                340                 345                 350

Ile Asn Arg Met Val Ile Asp Glu Gln Gln Ser Pro Asp Ile Ile Leu
                355                 360                 365

Pro Ile His Ser Leu Arg Asn Val Arg Ala Ile Asp Tyr Asp Pro Leu
370                 375                 380

Asp Lys Gln Leu Tyr Trp Ile Asp Ser Arg Gln Asn Met Ile Arg Lys
385                 390                 395                 400

Ala Gln Glu Asp Gly Ser Gln Gly Phe Thr Val Val Ser Ser Val
                405                 410                 415

Pro Ser Gln Asn Leu Glu Ile Gln Pro Tyr Asp Leu Ser Ile Asp Ile
                420                 425                 430

Tyr Ser Arg Tyr Ile Tyr Trp Thr Cys Glu Ala Thr Asn Val Ile Asn
                435                 440                 445

Val Thr Arg Leu Asp Gly Arg Ser Val Gly Val Leu Lys Gly Glu
                450                 455                 460

Gln Asp Arg Pro Arg Ala Val Val Val Asn Pro Glu Lys Gly Tyr Met
465                 470                 475                 480

Tyr Phe Thr Asn Leu Gln Glu Arg Ser Pro Lys Ile Glu Arg Ala Ala
                485                 490                 495

Leu Asp Gly Thr Glu Arg Glu Val Leu Phe Phe Ser Gly Leu Ser Lys
                500                 505                 510

Pro Ile Ala Leu Ala Leu Asp Ser Arg Leu Gly Lys Leu Phe Trp Ala
                515                 520                 525

Asp Ser Asp Leu Arg Arg Ile Glu Ser Ser Asp Leu Ser Gly Ala Asn
                530                 535                 540

Arg Ile Val Leu Glu Asp Ser Asn Ile Leu Gln Pro Val Gly Leu Thr
545                 550                 555                 560

Val Phe Glu Asn Trp Leu Tyr Trp Ile Asp Lys Gln Gln Gln Met Ile
                565                 570                 575

Glu Lys Ile Asp Met Thr Gly Arg Glu Gly Arg Thr Lys Val Gln Ala
                580                 585                 590

Arg Ile Ala Gln Leu Ser Asp Ile His Ala Val Lys Glu Leu Asn Leu
                595                 600                 605

Gln Glu Tyr Arg Gln His Pro Cys Ala Gln Asp Asn Gly Gly Cys Ser
                610                 615                 620

His Ile Cys Leu Val Lys Gly Asp Gly Thr Thr Arg Cys Ser Cys Pro
625                 630                 635                 640
```

-continued

```
Met His Leu Val Leu Leu Gln Asp Glu Leu Ser Cys Gly Glu Pro Pro
                645                 650                 655

Thr Cys Ser Pro Gln Gln Phe Thr Cys Phe Thr Gly Glu Ile Asp Cys
            660                 665                 670

Ile Pro Val Ala Trp Arg Cys Asp Gly Phe Thr Glu Cys Glu Asp His
        675                 680                 685

Ser Asp Glu Leu Asn Cys Pro Val Cys Ser Glu Ser Gln Phe Gln Cys
    690                 695                 700

Ala Ser Gly Gln Cys Ile Asp Gly Ala Leu Arg Cys Asn Gly Asp Ala
705                 710                 715                 720

Asn Cys Gln Asp Lys Ser Asp Glu Lys Asn Cys Glu Val Leu Cys Leu
                725                 730                 735

Ile Asp Gln Phe Arg Cys Ala Asn Gly Gln Cys Ile Gly Lys His Lys
            740                 745                 750

Lys Cys Asp His Asn Val Asp Cys Ser Asp Lys Ser Asp Glu Leu Asp
        755                 760                 765

Cys Tyr Pro Thr Glu Glu Pro Ala Pro Gln Ala Thr Asn Thr Val Gly
    770                 775                 780

Ser Val Ile Gly Val Ile Val Thr Ile Phe Val Ser Gly Thr Val Tyr
785                 790                 795                 800

Phe Ile Cys Gln Arg Met Leu Cys Pro Arg Met Lys Gly Asp Gly Glu
                805                 810                 815

Thr Met Thr Asn Asp Tyr Val Val His Gly Pro Ala Ser Val Pro Leu
            820                 825                 830

Gly Tyr Val Pro His Pro Ser Ser Leu Ser Gly Ser Leu Pro Gly Met
        835                 840                 845

Ser Arg Gly Lys Ser Met Ile Ser Ser Leu Ser Ile Met Gly Gly Ser
    850                 855                 860

Ser Gly Pro Pro Tyr Asp Arg Ala His Val Thr Gly Ala Ser Ser Ser
865                 870                 875                 880

Ser Ser Ser Ser Thr Lys Gly Thr Tyr Phe Pro Ala Ile Leu Asn Pro
                885                 890                 895

Pro Pro Ser Pro Ala Thr Glu Arg Ser His Tyr Thr Met Glu Phe Gly
            900                 905                 910

Tyr Ser Ser Asn Ser Pro Ser Thr His Arg Ser Tyr Ser Tyr Arg Pro
        915                 920                 925

Tyr Ser Tyr Arg His Phe Ala Pro Pro Thr Thr Pro Cys Ser Thr Asp
    930                 935                 940

Val Cys Asp Ser Asp Tyr Ala Pro Ser Arg Arg Met Thr Ser Val Ala
945                 950                 955                 960

Thr Ala Lys Gly Tyr Thr Ser Asp Leu Asn Tyr Asp Ser Glu Pro Val
                965                 970                 975

Pro Pro Pro Pro Thr Pro Arg Ser Gln Tyr Leu Ser Ala Glu Glu Asn
            980                 985                 990

Tyr Glu Ser Cys Pro Pro Ser Pro  Tyr Thr Glu Arg Ser  Tyr Ser His
        995                 1000                1005

His Leu  Tyr Pro Pro Pro Pro  Ser Pro Cys Thr Asp  Ser Ser
    1010                1015                1020

<210> SEQ ID NO 8
<211> LENGTH: 2160
<212> TYPE: DNA
<213> ORGANISM: Artificial
<220> FEATURE:
<223> OTHER INFORMATION: HA-tagged LRP6, deletion of propeller domains
      1, 2 and 3.
```

<400> SEQUENCE: 8

```
atggagacag acacactcct gctatgggta ctgctgctct gggttccagg ttccactggt    60
gacgctagat acccatacga tgttccagat tacgctggag gtggcgctag ccctacgact   120
ttcctgctct tcagtcaaaa gagtgccatc aaccgcatgg tgattgatga acaacagagc   180
cccgacatca tccttcccat ccacagcctt cggaatgtcc gggccattga ctatgaccca   240
ctggacaagc aactctattg gattgactca cgacaaaaca tgatccgaaa ggcacaagaa   300
gatggcagcc agggctttac gtggttgtg agctcagttc cgagtcagaa cctggaaata    360
caaccctatg acctcagcat tgatatttac agccgctaca tctactggac ttgtgaggct   420
accaatgtca ttaatgtgac aagattagat gggagatcag ttggagtggt gctgaaaggc   480
gagcaggaca gacctcgagc cgttgtggta acccagaga aagggtatat gtattttacc    540
aatcttcagg aaaggtctcc taaaattgaa cgggctgctt tggatgggac agaacgggag   600
gtcctctttt tcagtggctt aagtaaacca attgctttag cccttgatag caggctgggc   660
aagctctttt gggctgattc agatctccgg cgaattgaaa gcagtgatct ctcaggtgct   720
aaccggatag tattagaaga ctccaatatc ttgcagcctg tgggacttac tgtgtttgaa   780
aactggctct attggattga taaacagcag caaatgattg aaaaaattga catgacaggt   840
cgagagggta gaaccaaagt ccaagctcga attgcccagc ttagtgacat tcatgcagta   900
aaggagctga accttcaaga atacagacag caccttgtg ctcaggataa tggtggctgt    960
tcacatattt gtcttgtaaa gggggatggt actacaaggt gttcttgccc catgcacctg  1020
gttctacttc aagatgagct atcatgtgga gaacctccaa catgttctcc tcagcagttt  1080
acttgtttca cggggaaat tgactgtatc cctgtggctt ggcggtgcga tgggtttact  1140
gaatgtgaag accacagtga tgaactcaat tgtcctgtat gctcagagtc ccagttccag  1200
tgtgccagtg gcagtgtat tgatggtgcc ctccgatgca atggagatgc aaactgccag  1260
gacaaatcag atgagaagaa ctgtgaagtg ctttgtttaa ttgatcagtt ccgctgtgcc  1320
aatggtcagt gcattggaaa gcacaagaag tgtgatcata atgtggattg cagtgacaag  1380
tcagatgaac tggattgtta tccgactgaa gaaccagcac acaggccac caatacagtt   1440
ggttctgtta ttggcgtaat tgtcaccatt tttgtgtctg gaactgtata ctttatctgc  1500
cagaggatgt tgtgtccacg tatgaaggga gatggggaaa ctatgactaa tgactatgta  1560
gttcatggac cagcttctgt gcctcttggt tatgtgccac acccaagttc tttgtcagga  1620
tctcttccag gaatgtctcg aggtaaatca atgatcagct ccctcagtat catgggggga  1680
agcagtggac cccccatgaa ccgagcccat gttacaggag catcatcaag tagttcttca  1740
agcaccaaag gcacttactt ccctgcaatt ttgaaccctc accatccccc agccacagag  1800
cgatcacatt acactatgga atttggatat tcttcaaaca gtcctccac tcataggtca   1860
tacagctaca ggccatatag ctaccggcac tttgcacccc ccaccacacc ctgcagcaca  1920
gatgtttgtg acagtgacta tgctcctagt cggagaatga cctcagtggc aacagccaag  1980
ggctatacca gtgacttgaa ctatgattca gaacctgtgc ccccacctcc cacacccga   2040
agccaatact tgtcagcaga ggagaactat gaaagctgcc accttctcc atacacagag  2100
aggagctatt ctcatcacct ctacccaccg ccaccctctc cctgtacaga ctcctcctga  2160
```

<210> SEQ ID NO 9
<211> LENGTH: 719
<212> TYPE: PRT
<213> ORGANISM: Artificial

-continued

```
<220> FEATURE:
<223> OTHER INFORMATION: HA-tagged LRP6, deletion of propeller domains
      1, 2 and 3.

<400> SEQUENCE: 9

Met Glu Thr Asp Thr Leu Leu Leu Trp Val Leu Leu Leu Trp Val Pro
1               5                   10                  15

Gly Ser Thr Gly Asp Ala Arg Tyr Pro Tyr Asp Val Pro Asp Tyr Ala
            20                  25                  30

Gly Gly Gly Ala Ser Pro Thr Thr Phe Leu Leu Phe Ser Gln Lys Ser
        35                  40                  45

Ala Ile Asn Arg Met Val Ile Asp Glu Gln Ser Pro Asp Ile Ile
50                  55                  60

Leu Pro Ile His Ser Leu Arg Asn Val Arg Ala Ile Asp Tyr Asp Pro
65                  70                  75                  80

Leu Asp Lys Gln Leu Tyr Trp Ile Asp Ser Arg Gln Asn Met Ile Arg
                85                  90                  95

Lys Ala Gln Glu Asp Gly Ser Gln Gly Phe Thr Val Val Ser Ser
                100                 105                 110

Val Pro Ser Gln Asn Leu Glu Ile Gln Pro Tyr Asp Leu Ser Ile Asp
            115                 120                 125

Ile Tyr Ser Arg Tyr Ile Tyr Trp Thr Cys Glu Ala Thr Asn Val Ile
        130                 135                 140

Asn Val Thr Arg Leu Asp Gly Arg Ser Val Gly Val Val Leu Lys Gly
145                 150                 155                 160

Glu Gln Asp Arg Pro Arg Ala Val Val Asn Pro Glu Lys Gly Tyr
                165                 170                 175

Met Tyr Phe Thr Asn Leu Gln Glu Arg Ser Pro Lys Ile Glu Arg Ala
            180                 185                 190

Ala Leu Asp Gly Thr Glu Arg Glu Val Leu Phe Phe Ser Gly Leu Ser
        195                 200                 205

Lys Pro Ile Ala Leu Ala Leu Asp Ser Arg Leu Gly Lys Leu Phe Trp
210                 215                 220

Ala Asp Ser Asp Leu Arg Arg Ile Glu Ser Ser Asp Leu Ser Gly Ala
225                 230                 235                 240

Asn Arg Ile Val Leu Glu Asp Ser Asn Ile Leu Gln Pro Val Gly Leu
                245                 250                 255

Thr Val Phe Glu Asn Trp Leu Tyr Trp Ile Asp Lys Gln Gln Gln Met
            260                 265                 270

Ile Glu Lys Ile Asp Met Thr Gly Arg Glu Gly Arg Thr Lys Val Gln
        275                 280                 285

Ala Arg Ile Ala Gln Leu Ser Asp Ile His Ala Val Lys Glu Leu Asn
290                 295                 300

Leu Gln Glu Tyr Arg Gln His Pro Cys Ala Gln Asp Asn Gly Gly Cys
305                 310                 315                 320

Ser His Ile Cys Leu Val Lys Gly Asp Gly Thr Thr Arg Cys Ser Cys
                325                 330                 335

Pro Met His Leu Val Leu Leu Gln Asp Glu Leu Ser Cys Gly Glu Pro
            340                 345                 350

Pro Thr Cys Ser Pro Gln Gln Phe Thr Cys Phe Thr Gly Glu Ile Asp
        355                 360                 365

Cys Ile Pro Val Ala Trp Arg Cys Asp Gly Phe Thr Glu Cys Glu Asp
370                 375                 380

His Ser Asp Glu Leu Asn Cys Pro Val Cys Ser Glu Ser Gln Phe Gln
385                 390                 395                 400
```

```
Cys Ala Ser Gly Gln Cys Ile Asp Gly Ala Leu Arg Cys Asn Gly Asp
            405                 410                 415
Ala Asn Cys Gln Asp Lys Ser Asp Glu Lys Asn Cys Glu Val Leu Cys
        420                 425                 430
Leu Ile Asp Gln Phe Arg Cys Ala Asn Gly Gln Cys Ile Gly Lys His
            435                 440                 445
Lys Lys Cys Asp His Asn Val Asp Cys Ser Asp Lys Ser Asp Glu Leu
450                 455                 460
Asp Cys Tyr Pro Thr Glu Glu Pro Ala Pro Gln Ala Thr Asn Thr Val
465                 470                 475                 480
Gly Ser Val Ile Gly Val Ile Val Thr Ile Phe Val Ser Gly Thr Val
                485                 490                 495
Tyr Phe Ile Cys Gln Arg Met Leu Cys Pro Arg Met Lys Gly Asp Gly
                500                 505                 510
Glu Thr Met Thr Asn Asp Tyr Val Val His Gly Pro Ala Ser Val Pro
            515                 520                 525
Leu Gly Tyr Val Pro His Pro Ser Ser Leu Ser Gly Ser Leu Pro Gly
        530                 535                 540
Met Ser Arg Gly Lys Ser Met Ile Ser Ser Leu Ser Ile Met Gly Gly
545                 550                 555                 560
Ser Ser Gly Pro Pro Tyr Asp Arg Ala His Val Thr Gly Ala Ser Ser
                565                 570                 575
Ser Ser Ser Ser Ser Thr Lys Gly Thr Tyr Phe Pro Ala Ile Leu Asn
            580                 585                 590
Pro Pro Pro Ser Pro Ala Thr Glu Arg Ser His Tyr Thr Met Glu Phe
        595                 600                 605
Gly Tyr Ser Ser Asn Ser Pro Ser Thr His Arg Ser Tyr Ser Tyr Arg
            610                 615                 620
Pro Tyr Ser Tyr Arg His Phe Ala Pro Pro Thr Thr Pro Cys Ser Thr
625                 630                 635                 640
Asp Val Cys Asp Ser Asp Tyr Ala Pro Ser Arg Arg Met Thr Ser Val
                645                 650                 655
Ala Thr Ala Lys Gly Tyr Thr Ser Asp Leu Asn Tyr Asp Ser Glu Pro
            660                 665                 670
Val Pro Pro Pro Pro Thr Pro Arg Ser Gln Tyr Leu Ser Ala Glu Glu
        675                 680                 685
Asn Tyr Glu Ser Cys Pro Pro Ser Pro Tyr Thr Glu Arg Ser Tyr Ser
        690                 695                 700
His His Leu Tyr Pro Pro Pro Ser Pro Cys Thr Asp Ser Ser
705                 710                 715

<210> SEQ ID NO 10
<211> LENGTH: 1224
<212> TYPE: DNA
<213> ORGANISM: Artificial
<220> FEATURE:
<223> OTHER INFORMATION: HA-tagged LRP6, deletion of propeller domains
      1-4.

<400> SEQUENCE: 10
atggagacag acacactcct gctatgggta ctgctgctct gggttccagg ttccactggt      60
gacgctagat acccatacga tgttccagat tacgctggag gtggcgctag cggagaacct     120
ccaacatgtt ctcctcagca gtttacttgt ttcacggggg aaattgactg tatccctgtg     180
gcttggcggt gcgatgggtt tactgaatgt gaagaccaca gtgatgaact caattgtcct     240
```

```
gtatgctcag agtcccagtt ccagtgtgcc agtgggcagt gtattgatgg tgccctccga    300
tgcaatggag atgcaaactg ccaggacaaa tcagatgaga agaactgtga agtgctttgt    360
ttaattgatc agttccgctg tgccaatggt cagtgcattg aaagcacaa gaagtgtgat     420
cataatgtgg attgcagtga caagtcagat gaactggatt gttatccgac tgaagaacca    480
gcaccacagg ccaccaatac agttggttct gttattggcg taattgtcac cattttgtg    540
tctggaactg tatactttat ctgccagagg atgttgtgtc cacgtatgaa gggagatggg    600
gaaactatga ctaatgacta tgtagttcat ggaccagctt ctgtgcctct tggttatgtg    660
ccacacccaa gttctttgtc aggatctctt ccaggaatgt ctcgaggtaa atcaatgatc    720
agctccctca gtatcatggg gggaagcagt ggacccccct atgaccgagc ccatgttaca    780
ggagcatcat caagtagttc ttcaagcacc aaaggcactt acttccctgc aattttgaac    840
cctccaccat ccccagccac agagcgatca cattaacta tggaatttgg atattcttca    900
aacagtcctt ccactcatag gtcatacagc tacaggccat atagctaccg gcactttgca    960
cccccaccac acccctgcag cacagatgtt tgtgacagtg actatgctcc tagtcggaga   1020
atgacctcag tggcaacagc caagggctat accagtgact tgaactatga ttcagaacct   1080
gtgccccac ctcccacacc ccgaagccaa tacttgtcag cagaggagaa ctatgaaagc    1140
tgccacctt ctccatacac agagaggagc tattctcatc acctctaccc accgccaccc    1200
tctccctgta cagactcctc ctga                                          1224
```

<210> SEQ ID NO 11
<211> LENGTH: 407
<212> TYPE: PRT
<213> ORGANISM: Artificial
<220> FEATURE:
<223> OTHER INFORMATION: HA-tagged LRP6, deletion of propeller domains
      1-4.

<400> SEQUENCE: 11

Met Glu Thr Asp Thr Leu Leu Leu Trp Val Leu Leu Leu Trp Val Pro
1               5                   10                  15

Gly Ser Thr Gly Asp Ala Arg Tyr Pro Tyr Asp Val Pro Asp Tyr Ala
            20                  25                  30

Gly Gly Gly Ala Ser Gly Glu Pro Pro Thr Cys Ser Pro Gln Gln Phe
        35                  40                  45

Thr Cys Phe Thr Gly Glu Ile Asp Cys Ile Pro Val Ala Trp Arg Cys
    50                  55                  60

Asp Gly Phe Thr Glu Cys Glu Asp His Ser Asp Glu Leu Asn Cys Pro
65                  70                  75                  80

Val Cys Ser Glu Ser Gln Phe Gln Cys Ala Ser Gly Gln Cys Ile Asp
                85                  90                  95

Gly Ala Leu Arg Cys Asn Gly Asp Ala Asn Cys Gln Asp Lys Ser Asp
            100                 105                 110

Glu Lys Asn Cys Glu Val Leu Cys Leu Ile Asp Gln Phe Arg Cys Ala
        115                 120                 125

Asn Gly Gln Cys Ile Gly Lys His Lys Lys Cys Asp His Asn Val Asp
    130                 135                 140

Cys Ser Asp Lys Ser Asp Glu Leu Asp Cys Tyr Pro Thr Glu Glu Pro
145                 150                 155                 160

Ala Pro Gln Ala Thr Asn Thr Val Gly Ser Val Ile Gly Val Ile Val
                165                 170                 175

Thr Ile Phe Val Ser Gly Thr Val Tyr Phe Ile Cys Gln Arg Met Leu
            180                 185                 190

```
Cys Pro Arg Met Lys Gly Asp Gly Glu Thr Met Thr Asn Asp Tyr Val
            195                 200                 205

Val His Gly Pro Ala Ser Val Pro Leu Gly Tyr Val Pro His Pro Ser
        210                 215                 220

Ser Leu Ser Gly Ser Leu Pro Gly Met Ser Arg Gly Lys Ser Met Ile
225                 230                 235                 240

Ser Ser Leu Ser Ile Met Gly Gly Ser Gly Pro Pro Tyr Asp Arg
                245                 250                 255

Ala His Val Thr Gly Ala Ser Ser Ser Ser Ser Ser Thr Lys Gly
            260                 265                 270

Thr Tyr Phe Pro Ala Ile Leu Asn Pro Pro Ser Pro Ala Thr Glu
        275                 280                 285

Arg Ser His Tyr Thr Met Glu Phe Gly Tyr Ser Ser Asn Ser Pro Ser
        290                 295                 300

Thr His Arg Ser Tyr Ser Tyr Arg Pro Tyr Ser Tyr Arg His Phe Ala
305                 310                 315                 320

Pro Pro Thr Thr Pro Cys Ser Thr Asp Val Cys Asp Ser Asp Tyr Ala
                325                 330                 335

Pro Ser Arg Arg Met Thr Ser Val Ala Thr Ala Lys Gly Tyr Thr Ser
                340                 345                 350

Asp Leu Asn Tyr Asp Ser Glu Pro Val Pro Pro Pro Thr Pro Arg
            355                 360                 365

Ser Gln Tyr Leu Ser Ala Glu Glu Asn Tyr Glu Ser Cys Pro Pro Ser
        370                 375                 380

Pro Tyr Thr Glu Arg Ser Tyr Ser His His Leu Tyr Pro Pro Pro Pro
385                 390                 395                 400

Ser Pro Cys Thr Asp Ser Ser
                405

<210> SEQ ID NO 12
<211> LENGTH: 2148
<212> TYPE: DNA
<213> ORGANISM: Artificial
<220> FEATURE:
<223> OTHER INFORMATION: HA-tagged LRP6, deletion of propeller domains
      2-4

<400> SEQUENCE: 12
atggagacag acacactcct gctatgggta ctgctgctct gggttccagg ttccactggt     60
gacgctagat acccatacga tgttccagat tacgctggag gtggcgctag cgcccctttg    120
ttgctttatg caaacagacg ggacttgcga ttggttgatg ctacaaatgg caaagagaat    180
gctacgattg tagttggagg cttggaggat gcagctgcgg tggactttgt gtttagtcat    240
ggcttgatat actggagtga tgtcagcgaa gaagccatta acgaacaga atttaacaaa    300 actgagagtg tgcagaatgt tgttgtttct ggattattgt cccccgatgg gctggcatgt    360
gattggcttg agaaaaaatt gtactggaca gattctgaaa ctaatcggat tgaagtttct    420
aatttagatg atctttacg aaaagtttta ttttggcaag agttggatca acccagagct    480
attgccttag atccttcaag tgggttcatg tactggacag actggggaga agtgccaaag    540
atagaacgtg ctggaatgga tggttcaagt cgcttcatta taataaacag tgaaattac    600 tggccaaatg gactgacttt ggattatgaa gaacaaaagc tttattgggc agatgcaaaa    660
cttaatttca tccacaaatc aaatctggat ggaacaaatc ggcaggcagt ggttaaggt    720 tccctttcca tcctttttgc cttgacgtta tttgaggaca tattgtactg gactgactgg    780
```

-continued

```
agcacacact ccattttggc ttgcaacaag tatactggtg agggtctgcg tgaaatccat    840
tctgacatct tctctcccat ggatatacat gccttcagcc aacagaggca gccaaatgcc    900
acaaatccat gtggaattga caatgggggt tgttcccatt tgtgtttgat gtctccagtc    960 aagcctttt atcagtgtgc ttgccccact ggggtcaaac tcctggagaa tggaaaaacc    1020
tgcaaagatg gtgccggaga acctccaaca tgttctcctc agcagtttac ttgtttcacg    1080
ggggaaattg actgtatccc gtggcttgg cggtgcgatg ggtttactga atgtgaagac    1140
cacagtgatg aactcaattg tcctgtatgc tcagagtccc agttccagtg tgccagtggg    1200
cagtgtattg atggtgccct ccgatgcaat ggagatgcaa actgccagga caaatcagat    1260
gagaagaact gtgaagtgct ttgtttaatt gatcagttcc gctgtgccaa tggtcagtgc    1320
attggaaagc acaagaagtg tgatcataat gtggattgca gtgacaagtc agatgaactg    1380
gattgttatc cgactgaaga accagcacca caggccacca atacagttgg ttctgttatt    1440
ggcgtaattg tcaccatttt tgtgtctgga actgtatact ttatctgcca gaggatgttg    1500
tgtccacgta tgaagggaga tggggaaact atgactaatg actatgtagt tcatggacca    1560
gcttctgtgc ctcttggtta tgtgccacac ccaagttctt tgtcaggatc tcttccagga    1620
atgtctcgag gtaaatcaat gatcagctcc ctcagtatca tgggggaag cagtggaccc    1680 ccctatgacc gagcccatgt tacaggagca tcatcaagta gttcttcaag caccaaaggc    1740
acttacttcc ctgcaatttt gaaccctcca ccatccccag ccacagagcg atcacattac    1800
actatggaat ttggatattc ttcaaacagt ccttccactc ataggtcata cagctacagg    1860
ccatatagct accggcactt tgcaccccca accacaccct gcagcacaga tgtttgtgac    1920
agtgactatg ctcctagtcg gagaatgacc tcagtggcaa cagccaaggg ctataccagt    1980
gacttgaact atgattcaga acctgtgccc ccacctccca caccccgaag ccaatacttg    2040
tcagcagagg agaactatga aagctgccca ccttctccat acacagagag gagctattct    2100
catcacctct acccaccgcc accctctccc tgtacagact cctcctga    2148
```

<210> SEQ ID NO 13
<211> LENGTH: 715
<212> TYPE: PRT
<213> ORGANISM: Artificial
<220> FEATURE:
<223> OTHER INFORMATION: HA-tagged LRP6, deletion of propeller domains 2-4

<400> SEQUENCE: 13

```
Met Glu Thr Asp Thr Leu Leu Leu Trp Val Leu Leu Leu Trp Val Pro
1               5                   10                  15

Gly Ser Thr Gly Asp Ala Arg Tyr Pro Tyr Asp Val Pro Asp Tyr Ala
            20                  25                  30

Gly Gly Gly Ala Ser Ala Pro Leu Leu Leu Tyr Ala Asn Arg Arg Asp
        35                  40                  45

Leu Arg Leu Val Asp Ala Thr Asn Gly Lys Glu Asn Ala Thr Ile Val
    50                  55                  60

Val Gly Gly Leu Glu Asp Ala Ala Ala Val Asp Phe Val Phe Ser His
65                  70                  75                  80

Gly Leu Ile Tyr Trp Ser Asp Val Ser Glu Glu Ala Ile Lys Arg Thr
                85                  90                  95

Glu Phe Asn Lys Thr Glu Ser Val Gln Asn Val Val Val Ser Gly Leu
            100                 105                 110

Leu Ser Pro Asp Gly Leu Ala Cys Asp Trp Leu Gly Glu Lys Leu Tyr
        115                 120                 125
```

-continued

```
Trp Thr Asp Ser Glu Thr Asn Arg Ile Glu Val Ser Asn Leu Asp Gly
        130                 135                 140

Ser Leu Arg Lys Val Leu Phe Trp Gln Glu Leu Asp Gln Pro Arg Ala
145                 150                 155                 160

Ile Ala Leu Asp Pro Ser Ser Gly Phe Met Tyr Trp Thr Asp Trp Gly
                    165                 170                 175

Glu Val Pro Lys Ile Glu Arg Ala Gly Met Asp Gly Ser Ser Arg Phe
                180                 185                 190

Ile Ile Ile Asn Ser Glu Ile Tyr Trp Pro Asn Gly Leu Thr Leu Asp
            195                 200                 205

Tyr Glu Glu Gln Lys Leu Tyr Trp Ala Asp Ala Lys Leu Asn Phe Ile
        210                 215                 220

His Lys Ser Asn Leu Asp Gly Thr Asn Arg Gln Ala Val Val Lys Gly
225                 230                 235                 240

Ser Leu Pro His Pro Phe Ala Leu Thr Leu Phe Glu Asp Ile Leu Tyr
                    245                 250                 255

Trp Thr Asp Trp Ser Thr His Ser Ile Leu Ala Cys Asn Lys Tyr Thr
                260                 265                 270

Gly Glu Gly Leu Arg Glu Ile His Ser Asp Ile Phe Ser Pro Met Asp
            275                 280                 285

Ile His Ala Phe Ser Gln Gln Arg Gln Pro Asn Ala Thr Asn Pro Cys
        290                 295                 300

Gly Ile Asp Asn Gly Gly Cys Ser His Leu Cys Leu Met Ser Pro Val
305                 310                 315                 320

Lys Pro Phe Tyr Gln Cys Ala Cys Pro Thr Gly Val Lys Leu Leu Glu
                    325                 330                 335

Asn Gly Lys Thr Cys Lys Asp Gly Ala Gly Glu Pro Pro Thr Cys Ser
                340                 345                 350

Pro Gln Gln Phe Thr Cys Phe Thr Gly Glu Ile Asp Cys Ile Pro Val
            355                 360                 365

Ala Trp Arg Cys Asp Gly Phe Thr Glu Cys Glu Asp His Ser Asp Glu
        370                 375                 380

Leu Asn Cys Pro Val Cys Ser Glu Ser Gln Phe Gln Cys Ala Ser Gly
385                 390                 395                 400

Gln Cys Ile Asp Gly Ala Leu Arg Cys Asn Gly Asp Ala Asn Cys Gln
                    405                 410                 415

Asp Lys Ser Asp Glu Lys Asn Cys Glu Val Leu Cys Leu Ile Asp Gln
                420                 425                 430

Phe Arg Cys Ala Asn Gly Gln Cys Ile Gly Lys His Lys Lys Cys Asp
            435                 440                 445

His Asn Val Asp Cys Ser Asp Lys Ser Asp Glu Leu Asp Cys Tyr Pro
        450                 455                 460

Thr Glu Glu Pro Ala Pro Gln Ala Thr Asn Thr Val Gly Ser Val Ile
465                 470                 475                 480

Gly Val Ile Val Thr Ile Phe Val Ser Gly Thr Val Tyr Phe Ile Cys
                    485                 490                 495

Gln Arg Met Leu Cys Pro Arg Met Lys Gly Asp Gly Glu Thr Met Thr
                500                 505                 510

Asn Asp Tyr Val Val His Gly Pro Ala Ser Val Pro Leu Gly Tyr Val
            515                 520                 525

Pro His Pro Ser Ser Leu Ser Gly Ser Leu Pro Gly Met Ser Arg Gly
        530                 535                 540

Lys Ser Met Ile Ser Ser Leu Ser Ile Met Gly Gly Ser Ser Gly Pro
```

```
545                 550                 555                 560
Pro Tyr Asp Arg Ala His Val Thr Gly Ala Ser Ser Ser Ser Ser
                565                 570                 575

Ser Thr Lys Gly Thr Tyr Phe Pro Ala Ile Leu Asn Pro Pro Ser
            580                 585                 590

Pro Ala Thr Glu Arg Ser His Tyr Thr Met Glu Phe Gly Tyr Ser Ser
        595                 600                 605

Asn Ser Pro Ser Thr His Arg Ser Tyr Ser Tyr Arg Pro Tyr Ser Tyr
    610                 615                 620

Arg His Phe Ala Pro Pro Thr Thr Pro Cys Ser Thr Asp Val Cys Asp
625                 630                 635                 640

Ser Asp Tyr Ala Pro Ser Arg Arg Met Thr Ser Val Ala Thr Ala Lys
                645                 650                 655

Gly Tyr Thr Ser Asp Leu Asn Tyr Asp Ser Glu Pro Val Pro Pro Pro
            660                 665                 670

Pro Thr Pro Arg Ser Gln Tyr Leu Ser Ala Glu Glu Asn Tyr Glu Ser
        675                 680                 685

Cys Pro Pro Ser Pro Tyr Thr Glu Arg Ser Tyr Ser His His Leu Tyr
    690                 695                 700

Pro Pro Pro Pro Ser Pro Cys Thr Asp Ser Ser
705                 710                 715
```

<210> SEQ ID NO 14
<211> LENGTH: 3057
<212> TYPE: DNA
<213> ORGANISM: Artificial
<220> FEATURE:
<223> OTHER INFORMATION: HA-tagged LRP6, deletion of propeller domains 3-4

<400> SEQUENCE: 14

```
atggagacag acacactcct gctatgggta ctgctgctct ggttccagg ttccactggt    60
gacgctagat acccatacga tgttccagat tacgctggag gtggcgctag cgccccttg   120
ttgctttatg caaacagacg ggacttgcga ttggttgatg ctacaaatgg caaagagaat   180
gctacgattg tagttggagg cttggaggat gcagctgcgg tggactttgt gtttagtcat   240
ggcttgatat actggagtga tgtcagcgaa gaagccatta acgaacaga atttaacaaa   300
actgagagtg tgcagaatgt tgttgttttct ggattattgt cccccgatgg gctggcatgt   360
gattggcttg agaaaaaatt gtactggaca gattctgaaa ctaatcggat tgaagtttct   420
aatttagatg gatctttacg aaaagttttta ttttggcaag agttggatca acccagagct   480
attgccttag atccttcaag tgggttcatg tactggacag actggggaga agtgccaaag   540
atagaacgtg ctggaatgga tggttcaagt cgcttcatta ataaaacag tgaaatttac   600
tggccaaatg gactgacttt ggattatgaa gaacaaaagc tttattggc agatgcaaaa   660
cttaatttca tccacaaatc aaatctggat ggaacaaatc ggcaggcagt ggttaaaggt   720
tcccttccac atccttttgc cttgacgtta tttgaggaca tatttgtactg gactgactgg   780
agcacacact ccattttggc ttgcaacaag tatactggtg agggtctgcg tgaaatccat   840
tctgacatct ctctcccat ggatatacat gccttcagcc aacagaggca gccaaatgcc   900
acaaatccat gtggaattga caatggggt tgttcccatt tgtgtttgat gtctccagtc   960
aagccttttt atcagtgtgc ttgccccact ggggtcaaac tcctggagaa tggaaaaacc  1020
tgcaaagatg tgccacaga attattgctt ttagctcgaa ggacagactt gagacgcatt  1080
tcttttggata caccagattt tacagacatt gttctgcagt tagaagacat ccgtcatgcc  1140
```

```
attgccatag attacgatcc tgtggaaggc tacatctact ggactgatga tgaagtgagg    1200
gccatacgcc gttcatttat agatggatct ggcagtcagt ttgtggtcac tgctcaaatt    1260
gcccatcctg atggtattgc tgtggactgg gttgcacgaa atctttattg acagacact     1320 ggcactgatc gaatagaagt gacaaggctc aatgggacca tgaggaagat cttgatttca    1380
gaggacttag aggaaccccg ggctattgtg ttagatccca tggttgggta catgtattgg    1440
actgactggg gagaaattcc gaaaattgag cgagcagctc tggatggttc tgaccgtgta    1500
gtattggtta acacttctct tggttggcca aatggtttag ccttggatta tgatgaaggc    1560
aaaatatact ggggagatgc caaaacagac aagattgagg ttatgaatac tgatggcact    1620
gggagacgag tactagtgga agacaaaatt cctcacatat ttggatttac tttgttgggt    1680
gactatgttt actggactga ctggcagagg cgtagcattg aaagagttca taaacgaagt    1740
gcagagaggg aagtgatcat agatcagctg cctgacctca tgggcctaaa ggctacaaat    1800
gttcatcgag tgattggttc caaccctgt gctgaggaaa acgggggatg tagccatctc    1860
tgcctctata gacctcaggg ccttcgctgt gcttgcccta ttggctttga actcatcagt    1920
gacatgaaga cctgcattgt cccaggagaa cctccaacat gttctcctca gcagtttact    1980
tgtttcacgg gggaaattga ctgtatccct gtggcttggc ggtgcgatgg gtttactgaa    2040
tgtgaagacc acagtgatga actcaattgt cctgtatgct cagagtccca gttccagtgt    2100
gccagtgggc agtgtattga tggtgccctc cgatgcaatg gagatgcaaa ctgccaggac    2160
aaatcagatg agaagaactg tgaagtgctt tgtttaattg atcagttccg ctgtgccaat    2220
ggtcagtgca ttggaaagca caagaagtgt gatcataatg tggattgcag tgacaagtca    2280
gatgaactgg attgttatcc gactgaagaa ccagcaccac aggccaccaa tacagttggt    2340
tctgttattg gcgtaattgt caccattttt gtgtctggaa ctgtatactt tatctgccag    2400
aggatgttgt gtccacgtat gaagggagat ggggaaacta tgactaatga ctatgtagtt    2460
catggaccag cttctgtgcc tcttggttat gtgccacacc caagttcttt gtcaggatct    2520
cttccaggaa tgtctcgagg taaatcaatg atcagctccc tcagtatcat gggggaaagc    2580
agtggacccc cctatgaccg agcccatgtt acaggagcat catcaagtag ttcttcaagc    2640
accaaaggca cttacttccc tgcaattttg aaccctccac catccccagc cacagagcga    2700
tcacattaca ctatggaatt tggatattct tcaaacagtc cttccactca taggtcatac    2760
agctacaggc catatagcta ccggcacttt gcaccccca ccacaccctg cagcacagat    2820
gtttgtgaca gtgactatgc tcctagtcgg agaatgacct cagtggcaac agccaagggc    2880
tataccagtg acttgaacta tgattcagaa cctgtgcccc cacctccac accccgaagc    2940 caatacttgt cagcagagga gaactatgaa agctgcccac cttctccata cacagagagg    3000
agctattctc atcacctcta cccaccgcca ccctctccct gtacagactc ctcctga      3057
```

<210> SEQ ID NO 15
<211> LENGTH: 1018
<212> TYPE: PRT
<213> ORGANISM: Artificial
<220> FEATURE:
<223> OTHER INFORMATION: HA-tagged LRP6, deletion of propeller domains
      3-4

<400> SEQUENCE: 15

```
Met Glu Thr Asp Thr Leu Leu Leu Trp Val Leu Leu Leu Trp Val Pro
1               5                   10                  15

Gly Ser Thr Gly Asp Ala Arg Tyr Pro Tyr Asp Val Pro Asp Tyr Ala
```

```
                    20                  25                  30
Gly Gly Gly Ala Ser Ala Pro Leu Leu Tyr Ala Asn Arg Arg Asp
            35                  40                  45

Leu Arg Leu Val Asp Ala Thr Asn Gly Lys Glu Asn Ala Thr Ile Val
50                  55                  60

Val Gly Gly Leu Glu Asp Ala Ala Val Asp Phe Val Phe Ser His
65              70                  75                  80

Gly Leu Ile Tyr Trp Ser Asp Val Ser Glu Ala Ile Lys Arg Thr
                    85                  90                  95

Glu Phe Asn Lys Thr Glu Ser Val Gln Asn Val Val Ser Gly Leu
                100                 105                 110

Leu Ser Pro Asp Gly Leu Ala Cys Asp Trp Leu Gly Glu Lys Leu Tyr
            115                 120                 125

Trp Thr Asp Ser Glu Thr Asn Arg Ile Glu Val Ser Asn Leu Asp Gly
        130                 135                 140

Ser Leu Arg Lys Val Leu Phe Trp Gln Glu Leu Asp Gln Pro Arg Ala
145                 150                 155                 160

Ile Ala Leu Asp Pro Ser Ser Gly Phe Met Tyr Trp Thr Asp Trp
                165                 170                 175

Glu Val Pro Lys Ile Glu Arg Ala Gly Met Asp Gly Ser Ser Arg Phe
            180                 185                 190

Ile Ile Ile Asn Ser Glu Ile Tyr Trp Pro Asn Gly Leu Thr Leu Asp
        195                 200                 205

Tyr Glu Glu Gln Lys Leu Tyr Trp Ala Asp Ala Lys Leu Asn Phe Ile
210                 215                 220

His Lys Ser Asn Leu Asp Gly Thr Asn Arg Gln Ala Val Val Lys Gly
225                 230                 235                 240

Ser Leu Pro His Pro Phe Ala Leu Thr Leu Phe Glu Asp Ile Leu Tyr
                245                 250                 255

Trp Thr Asp Trp Ser Thr His Ser Ile Leu Ala Cys Asn Lys Tyr Thr
            260                 265                 270

Gly Glu Gly Leu Arg Glu Ile His Ser Asp Ile Phe Ser Pro Met Asp
        275                 280                 285

Ile His Ala Phe Ser Gln Gln Arg Gln Pro Asn Ala Thr Asn Pro Cys
    290                 295                 300

Gly Ile Asp Asn Gly Gly Cys Ser His Leu Cys Leu Met Ser Pro Val
305                 310                 315                 320

Lys Pro Phe Tyr Gln Cys Ala Cys Pro Thr Gly Val Lys Leu Leu Glu
                325                 330                 335

Asn Gly Lys Thr Cys Lys Asp Gly Ala Thr Glu Leu Leu Leu Leu Ala
            340                 345                 350

Arg Arg Thr Asp Leu Arg Arg Ile Ser Leu Asp Thr Pro Asp Phe Thr
        355                 360                 365

Asp Ile Val Leu Gln Leu Glu Asp Ile Arg His Ala Ile Ala Ile Asp
    370                 375                 380

Tyr Asp Pro Val Glu Gly Tyr Ile Tyr Trp Thr Asp Asp Glu Val Arg
385                 390                 395                 400

Ala Ile Arg Arg Ser Phe Ile Asp Gly Ser Gly Ser Gln Phe Val Val
                405                 410                 415

Thr Ala Gln Ile Ala His Pro Asp Gly Ile Ala Val Asp Trp Val Ala
            420                 425                 430

Arg Asn Leu Tyr Trp Thr Asp Thr Gly Thr Asp Arg Ile Glu Val Thr
        435                 440                 445
```

```
Arg Leu Asn Gly Thr Met Arg Lys Ile Leu Ile Ser Glu Asp Leu Glu
450                 455                 460

Glu Pro Arg Ala Ile Val Leu Asp Pro Met Val Gly Tyr Met Tyr Trp
465                 470                 475                 480

Thr Asp Trp Gly Glu Ile Pro Lys Ile Glu Arg Ala Ala Leu Asp Gly
                485                 490                 495

Ser Asp Arg Val Val Leu Val Asn Thr Ser Leu Gly Trp Pro Asn Gly
            500                 505                 510

Leu Ala Leu Asp Tyr Asp Glu Gly Lys Ile Tyr Trp Gly Asp Ala Lys
        515                 520                 525

Thr Asp Lys Ile Glu Val Met Asn Thr Asp Gly Thr Gly Arg Arg Val
530                 535                 540

Leu Val Glu Asp Lys Ile Pro His Ile Phe Gly Phe Thr Leu Leu Gly
545                 550                 555                 560

Asp Tyr Val Tyr Trp Thr Asp Trp Gln Arg Arg Ser Ile Glu Arg Val
                565                 570                 575

His Lys Arg Ser Ala Glu Arg Glu Val Ile Ile Asp Gln Leu Pro Asp
            580                 585                 590

Leu Met Gly Leu Lys Ala Thr Asn Val His Arg Val Ile Gly Ser Asn
        595                 600                 605

Pro Cys Ala Glu Glu Asn Gly Gly Cys Ser His Leu Cys Leu Tyr Arg
610                 615                 620

Pro Gln Gly Leu Arg Cys Ala Cys Pro Ile Gly Phe Glu Leu Ile Ser
625                 630                 635                 640

Asp Met Lys Thr Cys Ile Val Pro Gly Glu Pro Pro Thr Cys Ser Pro
                645                 650                 655

Gln Gln Phe Thr Cys Phe Thr Gly Glu Ile Asp Cys Ile Pro Val Ala
            660                 665                 670

Trp Arg Cys Asp Gly Phe Thr Glu Cys Glu Asp His Ser Asp Glu Leu
        675                 680                 685

Asn Cys Pro Val Cys Ser Glu Ser Gln Phe Gln Cys Ala Ser Gly Gln
690                 695                 700

Cys Ile Asp Gly Ala Leu Arg Cys Asn Gly Asp Ala Asn Cys Gln Asp
705                 710                 715                 720

Lys Ser Asp Glu Lys Asn Cys Glu Val Leu Cys Leu Ile Asp Gln Phe
                725                 730                 735

Arg Cys Ala Asn Gly Gln Cys Ile Gly Lys His Lys Lys Cys Asp His
            740                 745                 750

Asn Val Asp Cys Ser Asp Lys Ser Asp Glu Leu Asp Cys Tyr Pro Thr
        755                 760                 765

Glu Glu Pro Ala Pro Gln Ala Thr Asn Thr Val Gly Ser Val Ile Gly
770                 775                 780

Val Ile Val Thr Ile Phe Val Ser Gly Thr Val Tyr Phe Ile Cys Gln
785                 790                 795                 800

Arg Met Leu Cys Pro Arg Met Lys Gly Asp Gly Glu Thr Met Thr Asn
                805                 810                 815

Asp Tyr Val Val His Gly Pro Ala Ser Val Pro Leu Gly Tyr Val Pro
            820                 825                 830

His Pro Ser Ser Leu Ser Gly Ser Leu Pro Gly Met Ser Arg Gly Lys
        835                 840                 845

Ser Met Ile Ser Ser Leu Ser Ile Met Gly Gly Ser Ser Gly Pro Pro
850                 855                 860

Tyr Asp Arg Ala His Val Thr Gly Ala Ser Ser Ser Ser Ser Ser Ser
865                 870                 875                 880
```

-continued

```
Thr Lys Gly Thr Tyr Phe Pro Ala Ile Leu Asn Pro Pro Ser Pro
            885                 890                 895

Ala Thr Glu Arg Ser His Tyr Thr Met Glu Phe Gly Tyr Ser Ser Asn
        900                 905                 910

Ser Pro Ser Thr His Arg Ser Tyr Ser Tyr Arg Pro Tyr Ser Tyr Arg
            915                 920                 925

His Phe Ala Pro Pro Thr Thr Pro Cys Ser Thr Asp Val Cys Asp Ser
        930                 935                 940

Asp Tyr Ala Pro Ser Arg Arg Met Thr Ser Val Ala Thr Ala Lys Gly
945                 950                 955                 960

Tyr Thr Ser Asp Leu Asn Tyr Asp Ser Glu Pro Val Pro Pro Pro
            965                 970                 975

Thr Pro Arg Ser Gln Tyr Leu Ser Ala Glu Glu Asn Tyr Glu Ser Cys
            980                 985                 990

Pro Pro Ser Pro Tyr Thr Glu Arg  Ser Tyr Ser His His  Leu Tyr Pro
            995                 1000                1005

Pro Pro  Pro Ser Pro Cys Thr  Asp Ser Ser
    1010                1015
```

```
<210> SEQ ID NO 16
<211> LENGTH: 282
<212> TYPE: PRT
<213> ORGANISM: Homo sapiens

<400> SEQUENCE: 16
```

```
Ala Thr Ile Val Val Gly Gly Leu Glu Asp Ala Ala Val Asp Phe
1               5                   10                  15

Val Phe Ser His Gly Leu Ile Tyr Trp Ser Asp Val Ser Glu Glu Ala
            20                  25                  30

Ile Lys Arg Thr Glu Phe Asn Lys Thr Glu Ser Val Gln Asn Val Val
        35                  40                  45

Val Ser Gly Leu Leu Ser Pro Asp Gly Leu Ala Cys Asp Trp Leu Gly
    50                  55                  60

Glu Lys Leu Tyr Trp Thr Asp Ser Glu Thr Asn Arg Ile Glu Val Ser
65                  70                  75                  80

Asn Leu Asp Gly Ser Leu Arg Lys Val Leu Phe Trp Gln Glu Leu Asp
                85                  90                  95

Gln Pro Arg Ala Ile Ala Leu Asp Pro Ser Ser Gly Phe Met Tyr Trp
            100                 105                 110

Thr Asp Trp Gly Glu Val Pro Lys Ile Glu Arg Ala Gly Met Asp Gly
        115                 120                 125

Ser Ser Arg Phe Ile Ile Ile Asn Ser Glu Ile Tyr Trp Pro Asn Gly
    130                 135                 140

Leu Thr Leu Asp Tyr Glu Glu Gln Lys Leu Tyr Trp Ala Asp Ala Lys
145                 150                 155                 160

Leu Asn Phe Ile His Lys Ser Asn Leu Asp Gly Thr Asn Arg Gln Ala
                165                 170                 175

Val Val Lys Gly Ser Leu Pro His Pro Phe Ala Leu Thr Leu Phe Glu
            180                 185                 190

Asp Ile Leu Tyr Trp Thr Asp Trp Ser Thr His Ser Ile Leu Ala Cys
        195                 200                 205

Asn Lys Tyr Thr Gly Glu Gly Leu Arg Glu Ile His Ser Asp Ile Phe
    210                 215                 220

Ser Pro Met Asp Ile His Ala Phe Ser Gln Gln Arg Gln Pro Asn Ala
225                 230                 235                 240
```

```
Thr Asn Pro Cys Gly Ile Asp Asn Gly Gly Cys Ser His Leu Cys Leu
                245                 250                 255
Met Ser Pro Val Lys Pro Phe Tyr Gln Cys Ala Cys Pro Thr Gly Val
            260                 265                 270
Lys Leu Leu Glu Asn Gly Lys Thr Cys Lys
        275                 280
```

<210> SEQ ID NO 17
<211> LENGTH: 441
<212> TYPE: DNA
<213> ORGANISM: Mus musculus

<400> SEQUENCE: 17

```
atggaaaggc actggatctt tctcttcctg ttttcagtaa ctgcaggtgt ccactcccag      60
gtccaacttc agcagtctgg ggctgaactg gcaaaacctg gggcctcagt gaagatgtcc    120
tgcaaggctt ctggctacac ctttactagc tactggatgc actgggtaaa acagaggcct    180
ggacagggtc tggaatggat tggatacatt aatcctagca ctggttatac tgagtacaat    240
cagaacttca gggacaaggc cacattgact gcagacaaat cctccagcac agccaacatg    300
caactgagca gcctgacatc tgaggactct gcagtctatt actgtgcaag aactgcgcaa    360
tactacggta gtcctagggg ttactatgct atggactcct ggggtcaagg aacctcagtc    420
accgtctcct cagccaaaac a                                              441
```

<210> SEQ ID NO 18
<211> LENGTH: 147
<212> TYPE: PRT
<213> ORGANISM: Mus musculus

<400> SEQUENCE: 18

```
Met Glu Arg His Trp Ile Phe Leu Phe Leu Phe Ser Val Thr Ala Gly
1               5                   10                  15
Val His Ser Gln Val Gln Leu Gln Gln Ser Gly Ala Glu Leu Ala Lys
            20                  25                  30
Pro Gly Ala Ser Val Lys Met Ser Cys Lys Ala Ser Gly Tyr Thr Phe
        35                  40                  45
Thr Ser Tyr Trp Met His Trp Val Lys Gln Arg Pro Gly Gln Gly Leu
    50                  55                  60
Glu Trp Ile Gly Tyr Ile Asn Pro Ser Thr Gly Tyr Thr Glu Tyr Asn
65                  70                  75                  80
Gln Asn Phe Arg Asp Lys Ala Thr Leu Thr Ala Asp Lys Ser Ser Ser
                85                  90                  95
Thr Ala Asn Met Gln Leu Ser Ser Leu Thr Ser Glu Asp Ser Ala Val
            100                 105                 110
Tyr Tyr Cys Ala Arg Thr Ala Gln Tyr Tyr Gly Ser Pro Arg Gly Tyr
        115                 120                 125
Tyr Ala Met Asp Ser Trp Gly Gln Gly Thr Ser Val Thr Val Ser Ser
    130                 135                 140
Ala Lys Thr
145
```

<210> SEQ ID NO 19
<211> LENGTH: 393
<212> TYPE: DNA
<213> ORGANISM: Mus musculus

<400> SEQUENCE: 19

```
atgaggttct ctgctcagct tctggggctg cttgtgctct ggatccctgg atccactgca      60
gatattgtga tgacgcaggc tgcattctcc aatccagtca ctcttggaac atcagcttcc     120
atctcctgca ggtctagtaa gagtctccta catagtaacg gcatcactta tttgtgttgg     180
tttctgcaga agccaggcca gtctcctcag ctcctgattt atctgatgtc caaccttgcc     240
tcaggagtcc cagacaggtt cagtagcagt gggtcaggaa ctgatttcac actgagaatc     300
agcagagtgg aggctgagga tgtgggtgtt tatttctgtg ctcaaaatct agatcttccg     360
tggacgttcg gtgggggcac caagctggaa atc                                  393
```

<210> SEQ ID NO 20
<211> LENGTH: 131
<212> TYPE: PRT
<213> ORGANISM: Mus musculus

<400> SEQUENCE: 20

```
Met Arg Phe Ser Ala Gln Leu Leu Gly Leu Leu Val Leu Trp Ile Pro
  1               5                  10                  15

Gly Ser Thr Ala Asp Ile Val Met Thr Gln Ala Ala Phe Ser Asn Pro
             20                  25                  30

Val Thr Leu Gly Thr Ser Ala Ser Ile Ser Cys Arg Ser Ser Lys Ser
         35                  40                  45

Leu Leu His Ser Asn Gly Ile Thr Tyr Leu Cys Trp Phe Leu Gln Lys
     50                  55                  60

Pro Gly Gln Ser Pro Gln Leu Leu Ile Tyr Leu Met Ser Asn Leu Ala
 65                  70                  75                  80

Ser Gly Val Pro Asp Arg Phe Ser Ser Ser Gly Ser Gly Thr Asp Phe
                 85                  90                  95

Thr Leu Arg Ile Ser Arg Val Glu Ala Glu Asp Val Gly Val Tyr Phe
            100                 105                 110

Cys Ala Gln Asn Leu Asp Leu Pro Trp Thr Phe Gly Gly Gly Thr Lys
        115                 120                 125

Leu Glu Ile
    130
```

<210> SEQ ID NO 21
<211> LENGTH: 449
<212> TYPE: DNA
<213> ORGANISM: Mus musculus

<400> SEQUENCE: 21

```
atggcgtgga tctctatcat cctcttccta gtggcaacag ctttaggtgt ccactcccag      60
gttcaactgc agcagtctgg ggctgagctg gtgaagcctg gggcctcagt gaagatgtcc     120
tgcaaggctt ttggctacac cttcacttcc tatccaatag agtggatgaa acagaatcat     180
gggaagagcc tagagtggat tggaaatttt catccttaca tgataatac taagtacaat     240 gaaaaattca agggcaaggc caaattgact gttgaaaaat cctctagcac agtctacttg     300
gagctcagcc gatcaacatc tgatgactct gctgtttatt actgtgcaag ggggtactct     360
ggtaactact tctctgctat ggactactgg ggtcaaggaa cctcagtcac cgtctcctca     420
gccaaaacaa cagccccatc ggtctatcc                                       449
```

<210> SEQ ID NO 22
<211> LENGTH: 150
<212> TYPE: PRT
<213> ORGANISM: Mus musculus

<400> SEQUENCE: 22

```
Met Ala Trp Ile Ser Ile Ile Leu Phe Leu Val Ala Thr Ala Leu Gly
1               5                   10                  15

Val His Ser Gln Val Gln Leu Gln Gln Ser Gly Ala Glu Leu Val Lys
            20                  25                  30

Pro Gly Ala Ser Val Lys Met Ser Cys Lys Ala Phe Gly Tyr Thr Phe
        35                  40                  45

Thr Ser Tyr Pro Ile Glu Trp Met Lys Gln Asn His Gly Lys Ser Leu
    50                  55                  60

Glu Trp Ile Gly Asn Phe His Pro Tyr Asn Asp Asn Thr Lys Tyr Asn
65                  70                  75                  80

Glu Lys Phe Lys Gly Lys Ala Lys Leu Thr Val Glu Lys Ser Ser Ser
                85                  90                  95

Thr Val Tyr Leu Glu Leu Ser Arg Ser Thr Ser Asp Asp Ser Ala Val
            100                 105                 110

Tyr Tyr Cys Ala Arg Gly Tyr Ser Gly Asn Tyr Phe Ser Ala Met Asp
        115                 120                 125

Tyr Trp Gly Gln Gly Thr Ser Val Thr Val Ser Ser Ala Lys Thr Thr
    130                 135                 140

Ala Pro Ser Val Tyr Pro
145             150
```

<210> SEQ ID NO 23
<211> LENGTH: 411
<212> TYPE: DNA
<213> ORGANISM: Mus musculus

<400> SEQUENCE: 23

```
atgggcatca agatggagtt tcagacccag gtctttgtat tcgtgttgct ctggttgtct    60
ggtgttgatg gagacattgt gatgacccag tctcaaaaat tcatgtccac atcagtagga   120
gacagggtca gcatcacctg caaggccagt cagaatgttc gtaatgatgt agcctggtat   180
caacagaaac cagggcagtc tcctaaatca ctgatttact ggcatccaac cggcacact    240 ggagtccctg atcgcttcac aggcagtgga tctgggacag atttcactct caccattagc   300
aatgtgcaat ctgaagacct ggcagattat ttctgtctgc aacattggaa ttatccgtac   360
acgttcggag gggggaccaa gctggaaata aaacgggctg atgctgcacc g            411
```

<210> SEQ ID NO 24
<211> LENGTH: 137
<212> TYPE: PRT
<213> ORGANISM: Mus musculus

<400> SEQUENCE: 24

```
Met Gly Ile Lys Met Glu Phe Gln Thr Gln Val Phe Val Phe Val Leu
1               5                   10                  15

Leu Trp Leu Ser Gly Val Asp Gly Asp Ile Val Met Thr Gln Ser Gln
            20                  25                  30

Lys Phe Met Ser Thr Ser Val Gly Asp Arg Val Ser Ile Thr Cys Lys
        35                  40                  45

Ala Ser Gln Asn Val Arg Asn Asp Val Ala Trp Tyr Gln Gln Lys Pro
    50                  55                  60

Gly Gln Ser Pro Lys Ser Leu Ile Tyr Leu Ala Ser Asn Arg His Thr
65                  70                  75                  80

Gly Val Pro Asp Arg Phe Thr Gly Ser Gly Ser Gly Thr Asp Phe Thr
                85                  90                  95

Leu Thr Ile Ser Asn Val Gln Ser Glu Asp Leu Ala Asp Tyr Phe Cys
```

```
                  100                 105                 110
Leu Gln His Trp Asn Tyr Pro Tyr Thr Phe Gly Gly Gly Thr Lys Leu
    115                 120                 125

Glu Ile Lys Arg Ala Asp Ala Ala Pro
    130                 135

<210> SEQ ID NO 25
<211> LENGTH: 423
<212> TYPE: DNA
<213> ORGANISM: Mus musculus

<400> SEQUENCE: 25
atgaacttcg ggctcagatt gattttcctt gtccttgttt taaaaggtgt cctgtgtgac      60
gtgaagctcg tggagtctgg gggaggctta gtgaaggttg gcgggtccct gaaactctcc     120
tgtgcagcct ctggattcac tttcagtagt tattacatgt cttgggttcg ccagactcca     180
gagaagaggc tggagttggt cgcagtcatt aatactaatg gtggtagcac ctactattca     240
gacactgtga agggccgatt caccatctcc agagacaatg ccaagaacac cctgtacctg     300
caaatgagca gtctgaagtc tgaggacaca gccttgtatt actgttcaag acaaccctat     360
tatggtaacc cttttgacta ctggggccaa ggcaccactc tcacagtctc ctcagccaaa     420
aca                                                                  423

<210> SEQ ID NO 26
<211> LENGTH: 141
<212> TYPE: PRT
<213> ORGANISM: Mus musculus

<400> SEQUENCE: 26

Met Asn Phe Gly Leu Arg Leu Ile Phe Leu Val Leu Val Leu Lys Gly
1               5                   10                  15

Val Leu Cys Asp Val Lys Leu Val Glu Ser Gly Gly Gly Leu Val Lys
            20                  25                  30

Val Gly Gly Ser Leu Lys Leu Ser Cys Ala Ala Ser Gly Phe Thr Phe
        35                  40                  45

Ser Ser Tyr Tyr Met Ser Trp Val Arg Gln Thr Pro Glu Lys Arg Leu
    50                  55                  60

Glu Leu Val Ala Val Ile Asn Thr Asn Gly Gly Ser Thr Tyr Tyr Ser
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Leu
            100                 105                 110

Tyr Tyr Cys Ser Arg Gln Pro Tyr Tyr Gly Asn Pro Phe Asp Tyr Trp
        115                 120                 125

Gly Gln Gly Thr Thr Leu Thr Val Ser Ser Ala Lys Thr
    130                 135                 140

<210> SEQ ID NO 27
<211> LENGTH: 378
<212> TYPE: DNA
<213> ORGANISM: Mus musculus

<400> SEQUENCE: 27
atggttttca cacctcagat acttggactt atgcttttt ggatttcagc ctccagaagt       60
gatattgtgc taactcagtc tccagccacc ctgtctgtga ctccaggaga tagcgtcagt     120
ctttcctgca gggccagcca agtattagc aacaacctac actggtatca acaaaaatca     180
```

```
catgagtctc caaggcttct catcaagtat gtttcccagt ccatctctgg gatcccctcc    240
aggttcagtg gcagtggatc agggacagat ttcactctca gtatcaacag tgtggagact    300
gaagattttg gaatgtattt ctgtcaacag agtaacaact ggccgctcac gttcggtgct    360
gggaccaagc tggagctg                                                  378
```

```
<210> SEQ ID NO 28
<211> LENGTH: 126
<212> TYPE: PRT
<213> ORGANISM: Mus musculus

<400> SEQUENCE: 28
```

```
Met Val Phe Thr Pro Gln Ile Leu Gly Leu Met Leu Phe Trp Ile Ser
1               5                   10                  15

Ala Ser Arg Ser Asp Ile Val Leu Thr Gln Ser Pro Ala Thr Leu Ser
            20                  25                  30

Val Thr Pro Gly Asp Ser Val Ser Leu Ser Cys Arg Ala Ser Gln Ser
        35                  40                  45

Ile Ser Asn Asn Leu His Trp Tyr Gln Gln Lys Ser His Glu Ser Pro
    50                  55                  60

Arg Leu Leu Ile Lys Tyr Val Ser Gln Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Thr Glu Asp Phe Gly Met Tyr Phe Cys Gln Gln Ser Asn
            100                 105                 110

Asn Trp Pro Leu Thr Phe Gly Ala Gly Thr Lys Leu Glu Leu
        115                 120                 125
```

```
<210> SEQ ID NO 29
<211> LENGTH: 426
<212> TYPE: DNA
<213> ORGANISM: Mus musculus

<400> SEQUENCE: 29
```

```
atgaacttcg ggctcagatt gattttcctt gtccttgttt taaaaggtgt cctgtgtgac    60
gtgaagctcg tggagtctgg gggaggctta gtgaagcttg agggtccct aaaactctcc    120 tgtgcagcct ctggattcac tttcagtagc tattacatgt cttgggttcg ccagactcca    180
gagaagaggc tggagttggt cgcagccatt aatagtaatg gtggtagtac ctactatgca    240
gacactatga agggccgatt caccatctcc agagacaatg ccaagaacac cctttacctg    300
caaatgatca gtctgaagtc tgaggacaca gccttctatt actgtgcaag cgagttggcc    360
gggtatggta ccccgtttgc ttactggggc cacgggactc tggtcactgt ctctgcagcc    420
aaaacg                                                                426
```

```
<210> SEQ ID NO 30
<211> LENGTH: 142
<212> TYPE: PRT
<213> ORGANISM: Mus musculus

<400> SEQUENCE: 30
```

```
Met Asn Phe Gly Leu Arg Leu Ile Phe Leu Val Leu Val Leu Lys Gly
1               5                   10                  15

Val Leu Cys Asp Val Lys Leu Val Glu Ser Gly Gly Gly Leu Val Lys
            20                  25                  30

Leu Gly Gly Ser Leu Lys Leu Ser Cys Ala Ala Ser Gly Phe Thr Phe
```

```
                35                  40                  45
Ser Ser Tyr Tyr Met Ser Trp Val Arg Gln Thr Pro Glu Lys Arg Leu
 50                  55                  60

Glu Leu Val Ala Ala Ile Asn Ser Asn Gly Gly Ser Thr Tyr Tyr Ala
 65                  70                  75                  80

Asp Thr Met Lys Gly Arg Phe Thr Ile Ser Arg Asp Asn Ala Lys Asn
                 85                  90                  95

Thr Leu Tyr Leu Gln Met Ile Ser Leu Lys Ser Glu Asp Thr Ala Phe
                100                 105                 110

Tyr Tyr Cys Ala Ser Glu Leu Ala Gly Tyr Gly Thr Pro Phe Ala Tyr
                115                 120                 125

Trp Gly His Gly Thr Leu Val Thr Val Ser Ala Ala Lys Thr
130                 135                 140

<210> SEQ ID NO 31
<211> LENGTH: 378
<212> TYPE: DNA
<213> ORGANISM: Mus musculus

<400> SEQUENCE: 31
atggttttca cacctcagat acttggactt atgcttttt  ggatttcagc ctccagaggt      60
gatattgtgc tcactcagtt tccagccacc ctgtctgtga ctccaggaga tagcgtcagt     120
ctttcctgca gggccagcca agtattagc  agcaacctac actggtatca acaaacatca     180
catgagtctc caaggcttct catcaagtat gcttcccagt ccatctctgg catcccctcc     240
aggttcagtg gcactggatc aggacagat  ttcactctca gtatcaacag tgtggagact     300
gaagattttg gaatgtattt ctgtcaacag agtaacacct ggccgctcac gttcggtgct     360
gggaccaagc tggagctg                                                   378

<210> SEQ ID NO 32
<211> LENGTH: 126
<212> TYPE: PRT
<213> ORGANISM: Mus musculus

<400> SEQUENCE: 32

Met Val Phe Thr Pro Gln Ile Leu Gly Leu Met Leu Phe Trp Ile Ser
  1               5                  10                  15

Ala Ser Arg Gly Asp Ile Val Leu Thr Gln Phe Pro Ala Thr Leu Ser
                 20                  25                  30

Val Thr Pro Gly Asp Ser Val Ser Leu Ser Cys Arg Ala Ser Gln Ser
             35                  40                  45

Ile Ser Ser Asn Leu His Trp Tyr Gln Gln Thr Ser His Glu Ser Pro
 50                  55                  60

Arg Leu Leu Ile Lys Tyr Ala Ser Gln Ser Ile Ser Gly Ile Pro Ser
 65                  70                  75                  80

Arg Phe Ser Gly Thr Gly Ser Gly Thr Asp Phe Thr Leu Ser Ile Asn
                 85                  90                  95

Ser Val Glu Thr Glu Asp Phe Gly Met Tyr Phe Cys Gln Gln Ser Asn
                100                 105                 110

Thr Trp Pro Leu Thr Phe Gly Ala Gly Thr Lys Leu Glu Leu
            115                 120                 125

<210> SEQ ID NO 33
<211> LENGTH: 468
<212> TYPE: DNA
<213> ORGANISM: Mus musculus
```

<400> SEQUENCE: 33

```
atgtcctctc cacagtccct gcagacactg accctaagca tggaatggag atggatcttt      60
ctcttcctcc tgtcaggaac tacaggtgtc cactctgaga tccagctgca gcagtctgga     120
cctgagctgg tgaagcctgg ggcttcagtg aaggtatcct gcaaggcttc tggttatgca     180
ttcactagct acaacatgta ctgggtgaaa cagagccatg gaaagggcct tgagtggatt     240
ggatatattg atccttacaa tggcggtact gactccaacc agaacttcaa gggcaaggcc     300
acattgactg ttgacaagtc ctccagcaca gccttcatgc atctcaacag cctgacatct     360
gaggactctg cagtctatta ctgtgcaaga ggggggatgg gattacgacg ggaccacttt     420
gactactggg gccaaggcac cagtctcacg gtctcctcag ccaaaaca                  468
```

<210> SEQ ID NO 34
<211> LENGTH: 156
<212> TYPE: PRT
<213> ORGANISM: Mus musculus

<400> SEQUENCE: 34

```
Met Ser Ser Pro Gln Ser Leu Gln Thr Leu Thr Leu Ser Met Glu Trp
1               5                   10                  15
Arg Trp Ile Phe Leu Phe Leu Leu Ser Gly Thr Thr Gly Val His Ser
            20                  25                  30
Glu Ile Gln Leu Gln Gln Ser Gly Pro Glu Leu Val Lys Pro Gly Ala
        35                  40                  45
Ser Val Lys Val Ser Cys Lys Ala Ser Gly Tyr Ala Phe Thr Ser Tyr
    50                  55                  60
Asn Met Tyr Trp Val Lys Gln Ser His Gly Lys Gly Leu Glu Trp Ile
65                  70                  75                  80
Gly Tyr Ile Asp Pro Tyr Asn Gly Gly Thr Asp Ser Asn Gln Asn Phe
                85                  90                  95
Lys Gly Lys Ala Thr Leu Thr Val Asp Lys Ser Ser Ser Thr Ala Phe
            100                 105                 110
Met His Leu Asn Ser Leu Thr Ser Glu Asp Ser Ala Val Tyr Tyr Cys
        115                 120                 125
Ala Arg Gly Gly Met Gly Leu Arg Arg Asp His Phe Asp Tyr Trp Gly
    130                 135                 140
Gln Gly Thr Ser Leu Thr Val Ser Ser Ala Lys Thr
145                 150                 155
```

<210> SEQ ID NO 35
<211> LENGTH: 381
<212> TYPE: DNA
<213> ORGANISM: Mus musculus

<400> SEQUENCE: 35

```
atggatttc aggtgcagat tttcagcttc ctgctaatca gtgcctcagt cataatgtcc      60
agaggacaaa ttgttctcac ccagtctcca gcaatcatgt ctgcatctcc aggggagaag     120
gtcaccatat cctgcagtgc caactcaagt gtacgttaca tgttctggta ccagcagaag     180
ccaggatcct cccccaaacc ctggacttat cgcacatcca acctggcttc tggagtccct     240
gctcgcttca gtggcagtgg gtctgggacc tcttactctc tcacaatcag cagtatggag     300
gctgaagatg ttgccactta ttactgccag cagtatcata gttacccgtg gacgttcggt     360
ggaggcacca agctggaaat c                                               381
```

<210> SEQ ID NO 36

```
<211> LENGTH: 127
<212> TYPE: PRT
<213> ORGANISM: Mus musculus

<400> SEQUENCE: 36

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Ser Cys Ser Ala Asn
        35                  40                  45

Ser Ser Val Arg Tyr Met Phe Trp Tyr Gln Gln Lys Pro Gly Ser Phe
    50                  55                  60

Pro Lys Pro Trp Thr Tyr Arg Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Val Ala Thr Tyr Tyr Cys Gln Gln Tyr
            100                 105                 110

His Ser Tyr Pro Trp Thr Phe Gly Gly Gly Thr Lys Leu Glu Ile
        115                 120                 125

<210> SEQ ID NO 37
<211> LENGTH: 420
<212> TYPE: DNA
<213> ORGANISM: Mus musculus

<400> SEQUENCE: 37
atgggatgga gccggatctt tctcttcctc ctgtcaataa ttgcaagtgt ccattgccag      60
gtccagctgc agcagtctgg acctgagctg gtgaagcctg ggcttcagt gaggatatcc     120
tgcaaggctt ctggctacac cttcacaacc tactatatac actggttgaa acagaggcct    180
ggacagggac ttgagtggat tggatggatt tttcctggaa atgttaatac taagtacaat    240
gcgaagttca aggcaaggc cacactgact gcagacaagt cctccagcac agcctacatg    300
cagctcagca gcctgacctc tgaggactct gcggtctatt tctgtgcaag agaggaatta    360
cagtactact ttgactactg gggccaaggc tccactctca cagtctcctc agccaaaaca    420

<210> SEQ ID NO 38
<211> LENGTH: 80
<212> TYPE: PRT
<213> ORGANISM: Mus musculus

<400> SEQUENCE: 38

Met Gly Trp Ser Arg Ile Phe Leu Phe Leu Leu Ser Ile Ile Ala Ser
1               5                   10                  15

Val His Cys Gln Val Gln Leu Gln Gln Ser Gly Pro Glu Leu Val Lys
            20                  25                  30

Pro Gly Ala Ser Val Arg Ile Ser Cys Lys Ala Ser Gly Tyr Thr Phe
        35                  40                  45

Thr Thr Tyr Tyr Ile His Trp Leu Lys Gln Arg Pro Gly Gln Gly Leu
    50                  55                  60

Glu Trp Ile Gly Trp Ile Phe Pro Gly Asn Val Asn Thr Lys Tyr Asn
65                  70                  75                  80

<210> SEQ ID NO 39
<211> LENGTH: 327
<212> TYPE: DNA
<213> ORGANISM: Mus musculus
```

<400> SEQUENCE: 39

```
atgtccagag acaaattgt tctcacccag tctccagcaa tcatgtctgc atctccaggg    60
gagaaggtca ccatatcctg cagtgccaac tcaagtgtac gtttcatgtt ctggtaccag   120
cagaagccag atcctcccc caaacccttg atttatcgca catccaacct ggcctctgga   180
gtccctgctc gcttcagtgg ctgtgggtct gggacctctt actctctcac aatcagcagc   240
atggaggctg aagatgccgc cacttattac tgccagcagt atcatagtta cccgtggacg   300
ttcggtggag gcaccaagtt ggaaatc                                      327
```

<210> SEQ ID NO 40
<211> LENGTH: 109
<212> TYPE: PRT
<213> ORGANISM: Mus musculus

<400> SEQUENCE: 40

```
Met Ser Arg Gly Gln Ile Val Leu Thr Gln Ser Pro Ala Ile Met Ser
1               5                   10                  15

Ala Ser Pro Gly Glu Lys Val Thr Ile Ser Cys Ser Ala Asn Ser Ser
            20                  25                  30

Val Arg Phe Met Phe Trp Tyr Gln Gln Lys Pro Gly Ser Ser Pro Lys
        35                  40                  45

Pro Leu Ile Tyr Arg Thr Ser Asn Leu Ala Ser Gly Val Pro Ala Arg
    50                  55                  60

Phe Ser Gly Cys Gly Ser Gly Thr Ser Tyr Ser Leu Thr Ile Ser Ser
65                  70                  75                  80

Met Glu Ala Glu Asp Ala Ala Thr Tyr Tyr Cys Gln Gln Tyr His Ser
                85                  90                  95

Tyr Pro Trp Thr Phe Gly Gly Gly Thr Lys Leu Glu Ile
            100                 105
```

<210> SEQ ID NO 41
<211> LENGTH: 423
<212> TYPE: DNA
<213> ORGANISM: Mus musculus

<400> SEQUENCE: 41

```
atgaacttcg ggctcagatt gattttcctt gtccttgttt taaaaggtgt cctgtgtgac    60
gtgaagctcg tggagtctgg gggaggctta gtgaggcttg agggtccct gaaactctcc   120
tgtgcagcct ctggattcac tttcagtacc tattacatgt cttgggttcg ccagactcca   180
gagaagaggc tggagttggt cgcaaccatt aatactaatg gtggtagcac ctactatcca   240
gacactttga aggccgatt caccatctcc agagacaatg ccaagaacac cctgtacctg   300
caaatgagca gtctgaggtc tgaggacaca gccttgtatt actgtgcgag acagcgtaac   360
tacggagtgg ctgtggactc ctggggtcaa ggaacctcag tcaccgtctc ctcagccaaa   420
acg                                                                423
```

<210> SEQ ID NO 42
<211> LENGTH: 141
<212> TYPE: PRT
<213> ORGANISM: Mus musculus

<400> SEQUENCE: 42

```
Met Asn Phe Gly Leu Arg Leu Ile Phe Leu Val Leu Val Leu Lys Gly
1               5                   10                  15

Val Leu Cys Asp Val Lys Leu Val Glu Ser Gly Gly Gly Leu Val Arg
```

```
                    20                   25                  30
Leu Gly Gly Ser Leu Lys Leu Ser Cys Ala Ala Ser Gly Phe Thr Phe
            35                  40                  45

Ser Thr Tyr Tyr Met Ser Trp Val Arg Gln Thr Pro Glu Lys Arg Leu
50                  55                  60

Glu Leu Val Ala Thr Ile Asn Thr Asn Gly Gly Ser Thr Tyr Tyr Pro
65                  70                  75                  80

Asp Thr Leu Lys Gly Arg Phe Thr Ile Ser Arg Asp Asn Ala Lys Asn
            85                  90                  95

Thr Leu Tyr Leu Gln Met Ser Ser Leu Arg Ser Glu Asp Thr Ala Leu
            100                 105                 110

Tyr Tyr Cys Ala Arg Gln Arg Asn Tyr Gly Val Ala Val Asp Ser Trp
            115                 120                 125

Gly Gln Gly Thr Ser Val Thr Val Ser Ser Ala Lys Thr
            130                 135                 140

<210> SEQ ID NO 43
<211> LENGTH: 378
<212> TYPE: DNA
<213> ORGANISM: Mus musculus

<400> SEQUENCE: 43
atggttttca cacctcagat acttggactt atgcttttt  ggatttcagc ctccagaggt     60
gatattgtgc tgactcagtc tccagccacc ctgtctgtga ctccaggaga tagcgtcagt    120
ctttcctgca gggccagcca aagtattagc aacaacctac actggtatca acaaaaatca    180
catgagtctc caaggcttct catcaagtat gcttcccagt ccatctctgg gatcccctcc    240
aggttcagtg gcagtggatc agggacagat ttcactctca gtatcaacag tgtggagact    300
gaagattttg gaatgtattt ctgtcaacag actaacaact ggcctctcac gttcggtgct    360
gggaccaagc tggagcgg                                                  378

<210> SEQ ID NO 44
<211> LENGTH: 126
<212> TYPE: PRT
<213> ORGANISM: Mus musculus

<400> SEQUENCE: 44

Met Val Phe Thr Pro Gln Ile Leu Gly Leu Met Leu Phe Trp Ile Ser
1               5                   10                  15

Ala Ser Arg Gly Asp Ile Val Leu Thr Gln Ser Pro Ala Thr Leu Ser
            20                  25                  30

Val Thr Pro Gly Asp Ser Val Ser Leu Ser Cys Arg Ala Ser Gln Ser
            35                  40                  45

Ile Ser Asn Asn Leu His Trp Tyr Gln Gln Lys Ser His Glu Ser Pro
50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Thr Asp Phe Thr Leu Ser Ile Asn
            85                  90                  95

Ser Val Glu Thr Glu Asp Phe Gly Met Tyr Phe Cys Gln Gln Thr Asn
            100                 105                 110

Asn Trp Pro Leu Thr Phe Gly Ala Gly Thr Lys Leu Glu Arg
            115                 120                 125

<210> SEQ ID NO 45
<211> LENGTH: 423
```

-continued

```
<212> TYPE: DNA
<213> ORGANISM: Mus musculus

<400> SEQUENCE: 45
atgaaagtgt tgagtctgtt gtacctgttg acagccattc ctggtttcct gtctgatgta      60
cagcttcagg agtcaggacc tggcctcgtg aaaccttctc agtctctgtc tctcacctgc     120
tctgtcactg gctactccat caccagtggt tattactgga actggatccg gcaatttcca     180
ggagacaaac tggaatggat gggccacata aactacgacg gtagagataa ctacaaccca     240
tctctcaaaa atcgaatctc catcactcgt gacacatcta agaaccagtt tttcctgaag     300
ttgaattctg tgactactga ggacacagct acatattact gtgcaagaga gtttggtaac     360
ttcccttact actttgacta ctggggccaa ggcaccactc tcacagtctc ctcagccaaa     420
aca                                                                   423

<210> SEQ ID NO 46
<211> LENGTH: 141
<212> TYPE: PRT
<213> ORGANISM: Mus musculus

<400> SEQUENCE: 46

Met Lys Val Leu Ser Leu Leu Tyr Leu Leu Thr Ala Ile Pro Gly Phe
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Ser Val Thr Gly Tyr Ser Ile Thr
            35                  40                  45

Ser Gly Tyr Tyr Trp Asn Trp Ile Arg Gln Phe Pro Gly Asp Lys Leu
        50                  55                  60

Glu Trp Met Gly His Ile Asn Tyr Asp Gly Arg Asp Asn Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Thr Glu Asp Thr Ala Thr Tyr
            100                 105                 110

Tyr Cys Ala Arg Glu Phe Gly Asn Phe Pro Tyr Tyr Phe Asp Tyr Trp
        115                 120                 125

Gly Gln Gly Thr Thr Leu Thr Val Ser Ser Ala Lys Thr
    130                 135                 140

<210> SEQ ID NO 47
<211> LENGTH: 381
<212> TYPE: DNA
<213> ORGANISM: Mus musculus

<400> SEQUENCE: 47 atggatttc aggtgcagat tctcagcatc ctgctaatca gtgcctcagt cataatgtcc      60
agaggacaaa ttgttctcac ccagtctcca gcaatcatgt ctgcatctcc aggggagaag     120
gtcaccatat cctgcagtgc ctactcaagt gtacgtttca tgttctgtta ccagcagaag     180
ccaggatcct cccccaaacc cttgatttat cgcacatcca acctggcttc tggagtctct     240
gctcgcttca gtggcagtgg gtctgggacc tcttactctc tcacaatcag cagcatggag     300
gctgaagatg ctgccactta ttactgccag cagtatcata gttacccgtg gacgttcggt     360
ggaggcacca agttggaaat c                                                381

<210> SEQ ID NO 48
```

```
<211> LENGTH: 127
<212> TYPE: PRT
<213> ORGANISM: Mus musculus

<400> SEQUENCE: 48

Met Asp Phe Gln Val Gln Ile Leu Ser Ile Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Ser Cys Ser Ala Tyr
        35                  40                  45

Ser Ser Val Arg Phe Met Phe Trp Tyr Gln Gln Lys Pro Gly Ser Ser
    50                  55                  60

Pro Lys Pro Leu Ile Tyr Arg Thr Ser Asn Leu Ala Ser Gly Val Ser
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Tyr
            100                 105                 110

His Ser Tyr Pro Trp Thr Phe Gly Gly Gly Thr Lys Leu Glu Ile
        115                 120                 125

<210> SEQ ID NO 49
<211> LENGTH: 423
<212> TYPE: DNA
<213> ORGANISM: Mus musculus

<400> SEQUENCE: 49
atgaacttcg ggctcagatt gactttcctt gtccttgttt taaaaggtgt cctgtgtgac      60
gtgaagctcg tggagtcggg gggaggctta gtgaaggttg agggtccct gaaactctcc     120 tgtgcagcct ctggattcac tttcagtagt tattacatgt cttgggttcg ccagactcca     180
gagaagaggc tggagttggt cgcagtcatt aatagtaatg gtggtagcac ctactattca     240
gagactgtga agggccgatt caccatctcc agagacaatg ccaagaacac cctgtacctg     300
caaatgagca gtctgaagtc tgaggacaca gccttgtatt actgttcaag acaacccat     360 tatggtaacc ttttgactac tggggccaa ggcaccactc tcacagtctc ctcagccaaa     420
aca                                                                   423

<210> SEQ ID NO 50
<211> LENGTH: 141
<212> TYPE: PRT
<213> ORGANISM: Mus musculus

<400> SEQUENCE: 50

Met Asn Phe Gly Leu Arg Leu Thr Phe Leu Val Leu Val Leu Lys Gly
1               5                   10                  15

Val Leu Cys Asp Val Lys Leu Val Glu Ser Gly Gly Gly Leu Val Lys
            20                  25                  30

Val Gly Gly Ser Leu Lys Leu Ser Cys Ala Ala Ser Gly Phe Thr Phe
        35                  40                  45

Ser Ser Tyr Tyr Met Ser Trp Val Arg Gln Thr Pro Glu Lys Arg Leu
    50                  55                  60

Glu Leu Val Ala Val Ile Asn Ser Asn Gly Gly Ser Thr Tyr Tyr Ser
65                  70                  75                  80

Glu Thr Val Lys Gly Arg Phe Thr Ile Ser Arg Asp Asn Ala Lys Asn
                85                  90                  95
```

```
Thr Leu Tyr Leu Gln Met Ser Ser Leu Lys Ser Glu Asp Thr Ala Leu
            100                 105                 110
Tyr Tyr Cys Ser Arg Gln Pro Tyr Gly Asn Pro Phe Asp Tyr Trp
            115                 120                 125
Gly Gln Gly Thr Thr Leu Thr Val Ser Ser Ala Lys Thr
    130                 135                 140

<210> SEQ ID NO 51
<211> LENGTH: 378
<212> TYPE: DNA
<213> ORGANISM: Mus musculus

<400> SEQUENCE: 51
atggttttca cacctcagat acttggactt atgcttttt  ggatttcagc ctccagaggt   60
gatattgtgc taactcagtc tccagccacc ctgtctgtga ctccaggaga tagcgtcagt  120
ctttcctgca gggccagcca aagtattagc aacaacctac actggtatca acaaaaatca  180
catgagtctc caaggcttct catcaagtat gtttcccagt ccatctctgg gatcccctcc  240
aggttcagtg gcagtggatc aggacagat ttcactctca gtatcaacag tgtggagact  300
gaagattttg gaatgtattt ctgtcaacag agtaacaact ggccgctcac gttcggtgct  360
gggaccaagc tggagctg                                                 378

<210> SEQ ID NO 52
<211> LENGTH: 126
<212> TYPE: PRT
<213> ORGANISM: Mus musculus

<400> SEQUENCE: 52

Met Val Phe Thr Pro Gln Ile Leu Gly Leu Met Leu Phe Trp Ile Ser
1               5                   10                  15

Ala Ser Arg Gly Asp Ile Val Leu Thr Gln Ser Pro Ala Thr Leu Ser
            20                  25                  30

Val Thr Pro Gly Asp Ser Val Ser Leu Ser Cys Arg Ala Ser Gln Ser
        35                  40                  45

Ile Ser Asn Asn Leu His Trp Tyr Gln Gln Lys Ser His Glu Ser Pro
    50                  55                  60

Arg Leu Leu Ile Lys Tyr Val Ser Gln Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Thr Glu Asp Phe Gly Met Tyr Phe Cys Gln Gln Ser Asn
            100                 105                 110

Asn Trp Pro Leu Thr Phe Gly Ala Gly Thr Lys Leu Glu Leu
        115                 120                 125

<210> SEQ ID NO 53
<211> LENGTH: 487
<212> TYPE: DNA
<213> ORGANISM: Mus musculus

<400> SEQUENCE: 53
atgtcctctc cacagtccct gcagacactg accctaagca tggaatggag atggatcttt   60
ctcttcctcc tgtcaggaac tacaggtgtc cactctgaga tccagctgca gcagtctgga  120
cctgagctgg tgaagcctgg ggcttcagtg aaggtatcct gcaaggcttc tggttatgca  180
ttcactagct acaacatgta ctgggtgaag cagagccatg gaaagagcct tgagtggatt  240
ggatatattg atccttacaa tggtggtact aactacaacc agaagttcaa gggcaaggcc  300
```

| | | |
|---|---|---|
| acattgactg ttgacaagtc ctccagcaca gcctacatgc atctcaacag cctgacatct | 360 | |
| gaggactctg cagtctatta ctgtgcaaga ggggggatgg gattacgacg ggactacttt | 420 | |
| gacttctggg gccaaggcac cactctcaca gtctcctcag ccaaaacgac accccatct | 480 | |
| gtctatc | 487 | |

```
<210> SEQ ID NO 54
<211> LENGTH: 162
<212> TYPE: PRT
<213> ORGANISM: Mus musculus

<400> SEQUENCE: 54
```

Met Ser Ser Pro Gln Ser Leu Gln Thr Leu Thr Leu Ser Met Glu Trp
1               5                   10                  15

Arg Trp Ile Phe Leu Phe Leu Leu Ser Gly Thr Thr Gly Val His Ser
            20                  25                  30

Glu Ile Gln Leu Gln Gln Ser Gly Pro Glu Leu Val Lys Pro Gly Ala
        35                  40                  45

Ser Val Lys Val Ser Cys Lys Ala Ser Gly Tyr Ala Phe Thr Ser Tyr
    50                  55                  60

Asn Met Tyr Trp Val Lys Gln Ser His Gly Lys Ser Leu Glu Trp Ile
65                  70                  75                  80

Gly Tyr Ile Asp Pro Tyr Asn Gly Gly Thr Asn Tyr Asn Gln Lys Phe
                85                  90                  95

Lys Gly Lys Ala Thr Leu Thr Val Asp Lys Ser Ser Thr Ala Tyr
            100                 105                 110

Met His Leu Asn Ser Leu Thr Ser Glu Asp Ser Ala Val Tyr Tyr Cys
        115                 120                 125

Ala Arg Gly Gly Met Gly Leu Arg Arg Asp Tyr Phe Asp Phe Trp Gly
    130                 135                 140

Gln Gly Thr Thr Leu Thr Val Ser Ser Ala Lys Thr Thr Pro Pro Ser
145                 150                 155                 160

Val Tyr

```
<210> SEQ ID NO 55
<211> LENGTH: 396
<212> TYPE: DNA
<213> ORGANISM: Mus musculus

<400> SEQUENCE: 55
```

| | | |
|---|---|---|
| atggattcac aggcccaggt tcttatgtta ctgctgctat gggtatctgg tacctgtggg | 60 | |
| gacattgtga tgtcacagtc tccatcctcc ctagctgtgt cagttggaga gaaggttact | 120 | |
| atgagctgca agtccagtca gagccttttta tatagtagca atcaaaagaa ctacttggcc | 180 | |
| tggtaccagc agaaaccagg gcagtctcct aaagtgctga tttactgggc atccactagg | 240 | |
| gaatctgggg tccctgatcg cttcacaggc agtggatctg gacagatttt cactctcacc | 300 | |
| atcagcagtg tgaaggctga agacctggca gtttattact gtcagcaata ttatagctat | 360 | |
| ccgtacacgt tcggaggggg gaccaagctg gaaata | 396 | |

```
<210> SEQ ID NO 56
<211> LENGTH: 132
<212> TYPE: PRT
<213> ORGANISM: Mus musculus

<400> SEQUENCE: 56
```

Met Asp Ser Gln Ala Gln Val Leu Met Leu Leu Leu Leu Trp Val Ser

```
              1               5              10              15
        Gly Thr Cys Gly Asp Ile Val Met Ser Gln Ser Pro Ser Ser Leu Ala
                        20                  25                  30

Val Ser Val Gly Glu Lys Val Thr Met Ser Cys Lys Ser Ser Gln Ser
                        35                  40                  45

Leu Leu Tyr Ser Ser Asn Gln Lys Asn Tyr Leu Ala Trp Tyr Gln Gln
                    50                  55                  60

Lys Pro Gly Gln Ser Pro Lys Val Leu Ile Tyr Trp Ala Ser Thr Arg
         65                  70                  75                  80

Glu Ser Gly Val Pro Asp Arg Phe Thr Gly Ser Gly Ser Gly Thr Asp
                        85                  90                  95

Phe Thr Leu Thr Ile Ser Ser Val Lys Ala Glu Asp Leu Ala Val Tyr
                       100                 105                 110

Tyr Cys Gln Gln Tyr Tyr Ser Tyr Pro Tyr Thr Phe Gly Gly Gly Thr
                       115                 120                 125

Lys Leu Glu Ile
                130

<210> SEQ ID NO 57
<211> LENGTH: 420
<212> TYPE: DNA
<213> ORGANISM: Mus musculus

<400> SEQUENCE: 57
atgggatgga gccggatctt tctcttcctc ctgtcaataa ttgcaagtgt ccattgccag    60
gtccagctgc agcagtctgg acctgagctg gtgaagcctg ggcttcagt gaggatatcc    120 tgcaaggctt ctggctacac cttcacaacc tactatatac actggttgaa acagaggcct    180
ggacagggac ttgagtggat tggatggatt tttcctggaa atgttaatac taagtacaat    240
gcgaagttca aggcaaggc cacactgact gcagacaaat cctccagcac agcctacatg    300
cagctcagca gcctgacctc tgaggactct gcggtctatt tctgtgcaag agagggatta    360
cagtactact ttgactactg gggccaaggc accactctca cagtctcctc agccaaaaca    420

<210> SEQ ID NO 58
<211> LENGTH: 140
<212> TYPE: PRT
<213> ORGANISM: Mus musculus

<400> SEQUENCE: 58

Met Gly Trp Ser Arg Ile Phe Leu Phe Leu Leu Ser Ile Ile Ala Ser
         1               5                  10                  15

Val His Cys Gln Val Gln Leu Gln Gln Ser Gly Pro Glu Leu Val Lys
                        20                  25                  30

Pro Gly Ala Ser Val Arg Ile Ser Cys Lys Ala Ser Gly Tyr Thr Phe
                        35                  40                  45

Thr Thr Tyr Tyr Ile His Trp Leu Lys Gln Arg Pro Gly Gln Gly Leu
                    50                  55                  60

Glu Trp Ile Gly Trp Ile Phe Pro Gly Asn Val Asn Thr Lys Tyr Asn
         65                  70                  75                  80

Ala Lys Phe Lys Gly Lys Ala Thr Leu Thr Ala Asp Lys Ser Ser Ser
                        85                  90                  95

Thr Ala Tyr Met Gln Leu Ser Ser Leu Thr Ser Glu Asp Ser Ala Val
                       100                 105                 110

Tyr Phe Cys Ala Arg Glu Gly Leu Gln Tyr Tyr Phe Asp Tyr Trp Gly
                       115                 120                 125
```

Gln Gly Thr Thr Leu Thr Val Ser Ser Ala Lys Thr
        130                 135                 140

<210> SEQ ID NO 59
<211> LENGTH: 327
<212> TYPE: DNA
<213> ORGANISM: Mus musculus

<400> SEQUENCE: 59
atgtccagag acaaattgt tctcacccag tctccagcaa tcatgtctgc atctccaggg      60
gagaaggtca ccatatcctg cagtgccaac tcaagtgtac gtttcatgtt ctggtaccag    120
cagaagccag atcctccccc caaacccttg atttatcgca catccaacct ggcttctgga    180
gtccctgctc gcttcagtgg cagtgggtct gggacctctt actctctcac aatcagcagc    240
atggaggctg aagatgctgc cacttattac tgccagcagt atcatagtta cccgtggacg    300
ttcggtggag gcaccaagtt ggaaatc                                         327

<210> SEQ ID NO 60
<211> LENGTH: 109
<212> TYPE: PRT
<213> ORGANISM: Mus musculus

<400> SEQUENCE: 60

Met Ser Arg Gly Gln Ile Val Leu Thr Gln Ser Pro Ala Ile Met Ser
1               5                   10                  15

Ala Ser Pro Gly Glu Lys Val Thr Ile Ser Cys Ser Ala Asn Ser Ser
            20                  25                  30

Val Arg Phe Met Phe Trp Tyr Gln Gln Lys Pro Gly Ser Ser Pro Lys
        35                  40                  45

Pro Leu Ile Tyr Arg Thr Ser Asn Leu Ala Ser Gly Val Pro Ala Arg
    50                  55                  60

Phe Ser Gly Ser Gly Ser Gly Thr Ser Tyr Ser Leu Thr Ile Ser Ser
65                  70                  75                  80

Met Glu Ala Glu Asp Ala Ala Thr Tyr Tyr Cys Gln Gln Tyr His Ser
                85                  90                  95

Tyr Pro Trp Thr Phe Gly Gly Gly Thr Lys Leu Glu Ile
            100                 105

<210> SEQ ID NO 61
<211> LENGTH: 426
<212> TYPE: DNA
<213> ORGANISM: Mus musculus

<400> SEQUENCE: 61
atgaacttcg ggctcagatt gattttcctt gtccttgttt taaaaggtgt cctgtgtgac      60
gtgaaactcg tggagtctgg gggaggctta gtgaaggttg agggtccct gaaactctcc     120 tgtgcagcct ctggattcac tttcagtagc tattatatgt cttgggttcg ccagactcca    180
gagaagaggc tggagttggt cgcagccatt aatattaatg gtggtagcac ctactatcca    240
gacactgtga aggccgatt caccatctcc agagacaatg ccaagaacac cctgtacctg     300
caaatgagca gtctgaagtc tgaggacaca gccttctatt actgtgcaag cgagttggcc    360
ggctatggta ccccgtttgc ttactggggc caagggactc tggtcactgt ctctgcagcc    420
aaaacg                                                                426

<210> SEQ ID NO 62
<211> LENGTH: 142
<212> TYPE: PRT

<213> ORGANISM: Mus musculus

<400> SEQUENCE: 62

```
Met Asn Phe Gly Leu Arg Leu Ile Phe Leu Val Leu Val Leu Lys Gly
1               5                   10                  15
Val Leu Cys Asp Val Lys Leu Val Glu Ser Gly Gly Gly Leu Val Lys
            20                  25                  30
Val Gly Gly Ser Leu Lys Leu Ser Cys Ala Ala Ser Gly Phe Thr Phe
        35                  40                  45
Ser Ser Tyr Tyr Met Ser Trp Val Arg Gln Thr Pro Glu Lys Arg Leu
    50                  55                  60
Glu Leu Val Ala Ala Ile Asn Ile Asn Gly Gly Ser Thr Tyr Tyr Pro
65                  70                  75                  80
Asp Thr Val Lys Gly Arg Phe Thr Ile Ser Arg Asp Asn Ala Lys Asn
                85                  90                  95
Thr Leu Tyr Leu Gln Met Ser Ser Leu Lys Ser Glu Asp Thr Ala Phe
            100                 105                 110
Tyr Tyr Cys Ala Ser Glu Leu Ala Gly Tyr Gly Thr Pro Phe Ala Tyr
        115                 120                 125
Trp Gly Gln Gly Thr Leu Val Thr Val Ser Ala Ala Lys Thr
    130                 135                 140
```

<210> SEQ ID NO 63
<211> LENGTH: 378
<212> TYPE: DNA
<213> ORGANISM: Mus musculus

<400> SEQUENCE: 63

```
atggttttca cacctcagat acttggactt atgctttttt ggatttcagc ctccagaggt      60
gatattgtgc taactcagtc tccagccacc ctgtctgtga ctccaggaga tagcgtcagt     120
ctttcctgca gggccagcca aagtattagc aacaacctac actggtatca acaaaaatca     180
catgagtctc caaggcttct catcaagtat gcttcccagt ccatctctgg atcccctcc      240
aggttcagtg gcagtggatc aggacagat tcactctca gtatcaacag tgtggagact       300
gaagattttg gaatgtattt ctgtcaacag agtaacaact ggccgctcac gttcggtgct     360
gggaccaagc tggagctg                                                   378
```

<210> SEQ ID NO 64
<211> LENGTH: 126
<212> TYPE: PRT
<213> ORGANISM: Mus musculus

<400> SEQUENCE: 64

```
Met Val Phe Thr Pro Gln Ile Leu Gly Leu Met Leu Phe Trp Ile Ser
1               5                   10                  15
Ala Ser Arg Gly Asp Ile Val Leu Thr Gln Ser Pro Ala Thr Leu Ser
            20                  25                  30
Val Thr Pro Gly Asp Ser Val Ser Leu Ser Cys Arg Ala Ser Gln Ser
        35                  40                  45
Ile Ser Asn Asn Leu His Trp Tyr Gln Gln Lys Ser His Glu Ser Pro
    50                  55                  60
Arg Leu Leu Ile Lys Tyr Ala Ser Gln Ser Ile Ser Gly Ile Pro Ser
65                  70                  75                  80
Arg Phe Ser Gly Ser Gly Ser Gly Thr Asp Phe Thr Leu Ser Ile Asn
                85                  90                  95
Ser Val Glu Thr Glu Asp Phe Gly Met Tyr Phe Cys Gln Gln Ser Asn
```

```
               100                 105                 110
Asn Trp Pro Leu Thr Phe Gly Ala Gly Thr Lys Leu Glu Leu
        115                 120                 125

<210> SEQ ID NO 65
<211> LENGTH: 423
<212> TYPE: DNA
<213> ORGANISM: Mus musculus

<400> SEQUENCE: 65
atgaacttcg ggctcagatt gatttttcctt gtccttgttt taaaaggtgt cctgtgtgac    60
gtgaacctcg tggagtctgg gggaggctta gtgaagcttg agggtccct gaaactctcc    120 tgtgcagcct ctggattcac tttcagtagc ttttacatgt cttgggttcg ccagactcca    180
gagaagaggc tggacttggt cgcaaccatt aatactaatg gtggtagcac ctactattca    240
gacactgtga agggccgatt caccatctcc agagacaatg ccaaaaacac cctgtacctg    300
caaatgaaca gtctgaagtc tgaggacaca gccttgtttt attgtgtaag acagccttac    360
tacggaggga ctatggacta ctggggtcaa ggaacctcag tcaccgtctc ctcagccaaa    420
acg                                                                  423

<210> SEQ ID NO 66
<211> LENGTH: 141
<212> TYPE: PRT
<213> ORGANISM: Mus musculus

<400> SEQUENCE: 66

Met Asn Phe Gly Leu Arg Leu Ile Phe Leu Val Leu Val Leu Lys Gly
1               5                   10                  15

Val Leu Cys Asp Val Asn Leu Val Glu Ser Gly Gly Gly Leu Val Lys
            20                  25                  30

Leu Gly Gly Ser Leu Lys Leu Ser Cys Ala Ala Ser Gly Phe Thr Phe
        35                  40                  45

Ser Ser Phe Tyr Met Ser Trp Val Arg Gln Thr Pro Glu Lys Arg Leu
    50                  55                  60

Asp Leu Val Ala Thr Ile Asn Thr Asn Gly Gly Ser Thr Tyr Tyr Ser
65                  70                  75                  80

Asp Thr Val Lys Gly Arg Phe Thr Ile Ser Arg Asp Asn Ala Lys Asn
                85                  90                  95

Thr Leu Tyr Leu Gln Met Asn Ser Leu Lys Ser Glu Asp Thr Ala Leu
            100                 105                 110

Phe Tyr Cys Val Arg Gln Pro Tyr Tyr Gly Gly Thr Met Asp Tyr Trp
        115                 120                 125

Gly Gln Gly Thr Ser Val Thr Val Ser Ser Ala Lys Thr
    130                 135                 140

<210> SEQ ID NO 67
<211> LENGTH: 378
<212> TYPE: DNA
<213> ORGANISM: Mus musculus

<400> SEQUENCE: 67
atggttttca cacctcagat acttggactt atgcttttttt ggatttcagc ctccagaggt    60
gatattgtgc tgactcagtc tccagccacc ctgtctgtga ctccgggaga tcgcgtcagt    120
ctttcctgca gggccagcca agtattaac aacaatctac actggtatca acaaaagtca    180
catgagtctc caaggcttct catcaaatat gcttcccagt ccatctctgg gatcccctcc    240
```

```
aggttcagtg gcagtggatc agggacagat ttcactctca gtatcaacag tgtggagact      300
gaagattttg gaatgtattt ctgtcaacag actaacaact ggcctctcac gttcggtgct      360
gggaccaagc tggagctg                                                    378
```

<210> SEQ ID NO 68
<211> LENGTH: 126
<212> TYPE: PRT
<213> ORGANISM: Mus musculus

<400> SEQUENCE: 68

```
Met Val Phe Thr Pro Gln Ile Leu Gly Leu Met Leu Phe Trp Ile Ser
1               5                   10                  15

Ala Ser Arg Gly Asp Ile Val Leu Thr Gln Ser Pro Ala Thr Leu Ser
            20                  25                  30

Val Thr Pro Gly Asp Arg Val Ser Leu Ser Cys Arg Ala Ser Gln Ser
        35                  40                  45

Ile Asn Asn Asn Leu His Trp Tyr Gln Gln Lys Ser His Glu Ser Pro
    50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Thr Glu Asp Phe Gly Met Tyr Phe Cys Gln Gln Thr Asn
            100                 105                 110

Asn Trp Pro Leu Thr Phe Gly Ala Gly Thr Lys Leu Glu Leu
        115                 120                 125
```

<210> SEQ ID NO 69
<211> LENGTH: 423
<212> TYPE: DNA
<213> ORGANISM: Mus musculus

<400> SEQUENCE: 69

```
atgaaagtgt tgagtctgtt gtacctgttg acagccattc ctggaatcct gtctgatgta       60
caggttcagg agtcaggacc tggcctcgtg aaaccttctc agtctctgtc tctcacctgc      120
tctgtcactg gctactccat caccagtggt tattactgga actggatccg cagtttcca       180 ggaaacaaac tggaatggat gggctacata agctacgacg tagaaataa ctacaaccca       240 tctctcaaaa atcgaatctc catcactcgt gacacatcta agaaccagtt tttcctgaag      300
ttgaattctg tgactactga ggacacagct acatattact gtgcaagaga aaatagtaac      360
tacccttact actatgacta ctggggccaa ggcaccactc tcacagtctc ctcagccaaa      420
acg                                                                    423
```

<210> SEQ ID NO 70
<211> LENGTH: 141
<212> TYPE: PRT
<213> ORGANISM: Mus musculus

<400> SEQUENCE: 70

```
Met Lys Val Leu Ser Leu Leu Tyr Leu Leu Thr Ala Ile Pro Gly Ile
1               5                   10                  15

Leu Ser Asp Val Gln Val Gln Glu Ser Gly Pro Gly Leu Val Lys Pro
            20                  25                  30

Ser Gln Ser Leu Ser Leu Thr Cys Ser Val Thr Gly Tyr Ser Ile Thr
        35                  40                  45

Ser Gly Tyr Tyr Trp Asn Trp Ile Arg Gln Phe Pro Gly Asn Lys Leu
```

```
                50                  55                  60
Glu Trp Met Gly Tyr Ile Ser Tyr Asp Gly Arg Asn Asn Tyr Asn Pro
 65                  70                  75                  80

Ser Leu Lys Asn Arg Ile Ser Ile Thr Arg Asp Thr Ser Lys Asn Gln
                 85                  90                  95

Phe Phe Leu Lys Leu Asn Ser Val Thr Thr Glu Asp Thr Ala Thr Tyr
                100                 105                 110

Tyr Cys Ala Arg Glu Asn Ser Asn Tyr Pro Tyr Tyr Tyr Asp Tyr Trp
                115                 120                 125

Gly Gln Gly Thr Thr Leu Thr Val Ser Ser Ala Lys Thr
130                 135                 140

<210> SEQ ID NO 71
<211> LENGTH: 426
<212> TYPE: DNA
<213> ORGANISM: Mus musculus

<400> SEQUENCE: 71
aggatgaaag tgttgagtct gttgtacctg ttgacagcca ttcctggaat cctgtctgat    60
gtacaggttc aggagtcagg acctggcctc gtgaaacctt ctcagtctct gtctctcacc   120
tgctctgtca ctggctactc catcaccagt ggttattact ggaactggat ccggcagttt   180
ccaggaaaca aactggaatg gatgggctac ataagctacg acggtagaaa taactacaac   240
ccatctctca aaatcgaatc tccatcact cgtgacacat ctaagaacca gttttcctg    300 aagttgaatt ctgtgactac tgaggacaca gctacatatt actgtgcaag agaaaatagt   360 aactacccctt actactatga ctactggggc caaggcacca ctctcacagt ctcctcagcc   420
aaaacg                                                              426

<210> SEQ ID NO 72
<211> LENGTH: 142
<212> TYPE: PRT
<213> ORGANISM: Mus musculus

<400> SEQUENCE: 72

Arg Met Lys Val Leu Ser Leu Leu Tyr Leu Leu Thr Ala Ile Pro Gly
 1               5                  10                  15

Ile Leu Ser Asp Val Gln Val Gln Glu Ser Gly Pro Gly Leu Val Lys
                20                  25                  30

Pro Ser Gln Ser Leu Ser Leu Thr Cys Ser Val Thr Gly Tyr Ser Ile
             35                  40                  45

Thr Ser Gly Tyr Tyr Trp Asn Trp Ile Arg Gln Phe Pro Gly Asn Lys
 50                  55                  60

Leu Glu Trp Met Gly Tyr Ile Ser Tyr Asp Gly Arg Asn Asn Tyr Asn
 65                  70                  75                  80

Pro Ser Leu Lys Asn Arg Ile Ser Ile Thr Arg Asp Thr Ser Lys Asn
                 85                  90                  95

Gln Phe Phe Leu Lys Leu Asn Ser Val Thr Thr Glu Asp Thr Ala Thr
                100                 105                 110

Tyr Tyr Cys Ala Arg Glu Asn Ser Asn Tyr Pro Tyr Tyr Tyr Asp Tyr
             115                 120                 125

Trp Gly Gln Gly Thr Thr Leu Thr Val Ser Ser Ala Lys Thr
        130                 135                 140

<210> SEQ ID NO 73
<211> LENGTH: 426
<212> TYPE: DNA
```

<213> ORGANISM: Mus musculus

<400> SEQUENCE: 73

```
atgaacttcg ggctcagatt gattttcctt gtccttgttt taaaaggtgt cctgtgtgac      60
gtgaagctcg tggagtctgg gggaggctta gtgaagcttg agggtccct gagactctcc      120
tgtgcagcct ctggattcag tttcagtacc tcttacatgt cttgggttcg ccagactcca    180
gagaagaggc tggagttggt cgcagccatt aatcttaatg gtggtagtac ctactattca   240
gacactgtga agggccgatt caccatctcc agagacaatg ccaagaacac cctgtacctg    300
caaatgagca gtctgaagtc tgaggacaca gccttctatt actgtgcaag cgagttggcc    360
gggtatggta cccgtttgc ttactggggc caagggactc tggtcactgt ctctgcagcc    420
aaaacg                                                                426
```

<210> SEQ ID NO 74
<211> LENGTH: 142
<212> TYPE: PRT
<213> ORGANISM: Mus musculus

<400> SEQUENCE: 74

```
Met Asn Phe Gly Leu Arg Leu Ile Phe Leu Val Leu Val Leu Lys Gly
1               5                   10                  15
Val Leu Cys Asp Val Lys Leu Val Glu Ser Gly Gly Gly Leu Val Lys
            20                  25                  30
Leu Gly Gly Ser Leu Arg Leu Ser Cys Ala Ala Ser Gly Phe Ser Phe
        35                  40                  45
Ser Thr Ser Tyr Met Ser Trp Val Arg Gln Thr Pro Glu Lys Arg Leu
    50                  55                  60
Glu Leu Val Ala Ala Ile Asn Leu Asn Gly Gly Ser Thr Tyr Tyr Ser
65                  70                  75                  80
Asp Thr Val Lys Gly Arg Phe Thr Ile Ser Arg Asp Asn Ala Lys Asn
                85                  90                  95
Thr Leu Tyr Leu Gln Met Ser Ser Leu Lys Ser Glu Asp Thr Ala Phe
            100                 105                 110
Tyr Tyr Cys Ala Ser Glu Leu Ala Gly Tyr Gly Thr Pro Phe Ala Tyr
        115                 120                 125
Trp Gly Gln Gly Thr Leu Val Thr Val Ser Ala Ala Lys Thr
    130                 135                 140
```

<210> SEQ ID NO 75
<211> LENGTH: 378
<212> TYPE: DNA
<213> ORGANISM: Mus musculus

<400> SEQUENCE: 75

```
atggttttca cacctcagat acttggactt atgcttttt ggatttcagc ctccagaggt      60
gatattgtgc taactcagtc tccagccacc ctgtctgtga ctccaggaga tagcgtcagt    120
ctttcctgta aggccagcca agtattagc aacaacctac actggtatca acaaaaatca    180
catgagtctc caaggcttct catcaagtat acttcccagt ccatctctgg gatcccctcc    240
aggttcagtg gcagtggatc agggacagat tcactctca ctatcaacaa tgtggagact    300
gaagattttg gaatgtattt ctgtcaacag agtaacagtt ggccgctcac gttcggtgct    360
gggaccaagc tggaggtg                                                  378
```

<210> SEQ ID NO 76
<211> LENGTH: 126

```
<212> TYPE: PRT
<213> ORGANISM: Mus musculus

<400> SEQUENCE: 76

Met Val Phe Thr Pro Gln Ile Leu Gly Leu Met Leu Phe Trp Ile Ser
1               5                   10                  15

Ala Ser Arg Gly Asp Ile Val Leu Thr Gln Ser Pro Ala Thr Leu Ser
                20                  25                  30

Val Thr Pro Gly Asp Ser Val Ser Leu Ser Cys Lys Ala Ser Gln Ser
            35                  40                  45

Ile Ser Asn Asn Leu His Trp Tyr Gln Gln Lys Ser His Glu Ser Pro
        50                  55                  60

Arg Leu Leu Ile Lys Tyr Thr Ser Gln Ser Ile Ser Gly Ile Pro Ser
65                  70                  75                  80

Arg Phe Ser Gly Ser Gly Ser Gly Thr Asp Phe Thr Leu Thr Ile Asn
                85                  90                  95

Asn Val Glu Thr Glu Asp Phe Gly Met Tyr Phe Cys Gln Gln Ser Asn
                100                 105                 110

Ser Trp Pro Leu Thr Phe Gly Ala Gly Thr Lys Leu Glu Val
            115                 120                 125

<210> SEQ ID NO 77
<211> LENGTH: 423
<212> TYPE: DNA
<213> ORGANISM: Mus musculus

<400> SEQUENCE: 77
atgaacttcg ggctcagatt gatttttcctt gtccttgttt taaaaggtgt cctgtgtgac     60
gtgaacctcg tggagtctgg gggaggctta gtgaagcttg agggtccct gaaactctcc      120 tgtgcagcct ctggattcac tttcagtagc ttttacatgt cttgggttcg ccagactcca     180
gagaagaggc tggacttggt cgcaaccatt aatactaatg gtggtagcac ctactattca     240
gacactgtga agggccgatt caccatctcc agagacaatg ccaaaaacac cctgtacctg     300
caaatgaaca gtctgaagtc tgaggacaca gccttgtttt attgtgtaag acagccttac     360
tacggaggga ctatggacta ctggggtcaa ggaacctcag tcaccgtctc ctcagccaaa     420
acg                                                                  423

<210> SEQ ID NO 78
<211> LENGTH: 141
<212> TYPE: PRT
<213> ORGANISM: Mus musculus

<400> SEQUENCE: 78

Met Asn Phe Gly Leu Arg Leu Ile Phe Leu Val Leu Val Leu Lys Gly
1               5                   10                  15

Val Leu Cys Asp Val Asn Leu Val Glu Ser Gly Gly Gly Leu Val Lys
                20                  25                  30

Leu Gly Gly Ser Leu Lys Leu Ser Cys Ala Ala Ser Gly Phe Thr Phe
            35                  40                  45

Ser Ser Phe Tyr Met Ser Trp Val Arg Gln Thr Pro Glu Lys Arg Leu
        50                  55                  60

Asp Leu Val Ala Thr Ile Asn Thr Asn Gly Gly Ser Thr Tyr Tyr Ser
65                  70                  75                  80

Asp Thr Val Lys Gly Arg Phe Thr Ile Ser Arg Asp Asn Ala Lys Asn
                85                  90                  95

Thr Leu Tyr Leu Gln Met Asn Ser Leu Lys Ser Glu Asp Thr Ala Leu
```

```
                100             105             110
Phe Tyr Cys Val Arg Gln Pro Tyr Tyr Gly Gly Thr Met Asp Tyr Trp
        115                 120                 125

Gly Gln Gly Thr Ser Val Thr Val Ser Ser Ala Lys Thr
        130                 135                 140

<210> SEQ ID NO 79
<211> LENGTH: 378
<212> TYPE: DNA
<213> ORGANISM: Mus musculus

<400> SEQUENCE: 79
atggttttca cacctcagat acttggactt atgcttttt  ggatttcagc ctccagaggt     60
gatattgtgc tgactcagtc tccagccacc ctgtctgtga ctccgggaga tcgcgtcagt    120
ctttcctgca gggccagcca agtattaac  aacaatctac actggtatca acaaaagtca    180
catgagtctc caaggcttct catcaaatat gcttcccagt ccatctctgg gatcccctcc    240
aggttcagtg gcagtggatc aggacagat  ttcactctca gtatcaacag tgtggagact    300
gaagattttg gaatgtattt ctgtcaacag actaacaact ggcctctcac gttcggtgct    360
gggaccaagc tggagctg                                                  378

<210> SEQ ID NO 80
<211> LENGTH: 126
<212> TYPE: PRT
<213> ORGANISM: Mus musculus

<400> SEQUENCE: 80

Met Val Phe Thr Pro Gln Ile Leu Gly Leu Met Leu Phe Trp Ile Ser
1               5                   10                  15

Ala Ser Arg Gly Asp Ile Val Leu Thr Gln Ser Pro Ala Thr Leu Ser
                20                  25                  30

Val Thr Pro Gly Asp Arg Val Ser Leu Ser Cys Arg Ala Ser Gln Ser
            35                  40                  45

Ile Asn Asn Asn Leu His Trp Tyr Gln Gln Lys Ser His Glu Ser Pro
        50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Thr Glu Asp Phe Gly Met Tyr Phe Cys Gln Gln Thr Asn
                100                 105                 110

Asn Trp Pro Leu Thr Phe Gly Ala Gly Thr Lys Leu Glu Leu
        115                 120                 125

<210> SEQ ID NO 81
<211> LENGTH: 468
<212> TYPE: DNA
<213> ORGANISM: Mus musculus

<400> SEQUENCE: 81
atgatcagtg tcctctctac acagtccctg acaacactga ctctaaccat gggatggagc     60
cggatctttc tcttcctcct gtcaataatt gcaggtgtcc attgccaggt ccagctgcag    120
cagtctggac ctgagctggt gatgcctggg gcttcagtga ggatatcctg caaggcttct    180
ggctacacct tcacaaacta ctatttacac tgggttaagc agaggcctgg acagggactt    240
gaatggattg gatggattta tcctggaaat gttaatacta gtacaatgaa gaagttcaag    300
```

```
ggcaaggcct cactgactgc agacaaatcc tccagcacag cctacatgca gctcagcagc    360
ctgacctctg aggactctgc ggtctatttc tgtgcaagag agggattaca gtactacttt    420
gactactggg cccaaggcac cactctcaca gtctcctcag ccaaaaca                 468
```

<210> SEQ ID NO 82
<211> LENGTH: 156
<212> TYPE: PRT
<213> ORGANISM: Mus musculus

<400> SEQUENCE: 82

```
Met Ile Ser Val Leu Ser Thr Gln Ser Leu Thr Thr Leu Thr Leu Thr
1               5                   10                  15

Met Gly Trp Ser Arg Ile Phe Leu Phe Leu Leu Ser Ile Ile Ala Gly
            20                  25                  30

Val His Cys Gln Val Gln Leu Gln Gln Ser Gly Pro Glu Leu Val Met
        35                  40                  45

Pro Gly Ala Ser Val Arg Ile Ser Cys Lys Ala Ser Gly Tyr Thr Phe
    50                  55                  60

Thr Asn Tyr Tyr Leu His Trp Val Lys Gln Arg Pro Gly Gln Gly Leu
65                  70                  75                  80

Glu Trp Ile Gly Trp Ile Tyr Pro Gly Asn Val Asn Thr Lys Tyr Asn
                85                  90                  95

Glu Lys Phe Lys Gly Lys Ala Ser Leu Thr Ala Asp Lys Ser Ser Ser
            100                 105                 110

Thr Ala Tyr Met Gln Leu Ser Ser Leu Thr Ser Glu Asp Ser Ala Val
        115                 120                 125

Tyr Phe Cys Ala Arg Glu Gly Leu Gln Tyr Tyr Phe Asp Tyr Trp Ala
    130                 135                 140

Gln Gly Thr Thr Leu Thr Val Ser Ser Ala Lys Thr
145                 150                 155
```

<210> SEQ ID NO 83
<211> LENGTH: 381
<212> TYPE: DNA
<213> ORGANISM: Mus musculus

<400> SEQUENCE: 83

```
atggattttc aggtgcagat tttcagcttc ctgctaatca gtgcctcagt cataatgtcc    60
agaggacaaa ttgttctcac ccagtctcca gcaatcatgt ctgcatctcc aggggagaag    120
gtcaccatat cctgcagtgc caactcaagt gtacgttaca tgttctggta ccagcagaag    180
ccaggatcct cccccaaacc ctggatttat cgcacatcca acctggcttc tggagtccct    240
gctcgcttca gtggcagtgg gtctgggacc tcttactctc tcacaatcag cagtatggag    300
gctgaagatg ttgccactta ttactgccag cagtatcata gttacccgtg gacgttcggt    360
ggaggcacca agctggaaat c                                              381
```

<210> SEQ ID NO 84
<211> LENGTH: 127
<212> TYPE: PRT
<213> ORGANISM: Mus musculus

<400> SEQUENCE: 84

```
Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30
```

```
Met Ser Ala Ser Pro Gly Glu Lys Val Thr Ile Ser Cys Ser Ala Asn
        35                  40                  45

Ser Ser Val Arg Tyr Met Phe Trp Tyr Gln Gln Lys Pro Gly Ser Phe
    50                  55                  60

Pro Lys Pro Trp Ile Tyr Arg Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Val Ala Thr Tyr Tyr Cys Gln Gln Tyr
            100                 105                 110

His Ser Tyr Pro Trp Thr Phe Gly Gly Gly Thr Lys Leu Glu Ile
        115                 120                 125
```

<210> SEQ ID NO 85
<211> LENGTH: 441
<212> TYPE: DNA
<213> ORGANISM: Mus musculus

<400> SEQUENCE: 85

```
atggaaaggc actggatctt tctcttcctg ttttcagtaa ctgcaggtgt ccactcccag      60
gtccaacttc agcaatctgg ggctgaactg gcaaaacctg gggcctcagt gaaaatctcc     120
tgcaaggctt ctggctacac ctttactagc tactggatgc actgggtaaa acagaggcct     180
ggacagggtc tggaatggat tggatacatt aatcctaaca ctggttatag tgagtacaat     240
caaaagttca gggacaaggc cacattgact gcaaacaaat cctccagcac agccaacatg     300
caactgagca gcctgacatc tgacgactct gcagtctatt actgtgcaag aactgcacaa     360
tactacggta gtcctagggg ttactatgct atggactcct ggggtcaagg aacctcagtc     420
accgtctcct cagccaaaac g                                               441
```

<210> SEQ ID NO 86
<211> LENGTH: 147
<212> TYPE: PRT
<213> ORGANISM: Mus musculus

<400> SEQUENCE: 86

```
Met Glu Arg His Trp Ile Phe Leu Phe Leu Phe Ser Val Thr Ala Gly
1               5                   10                  15

Val His Ser Gln Val Gln Leu Gln Gln Ser Gly Ala Glu Leu Ala Lys
            20                  25                  30

Pro Gly Ala Ser Val Lys Ile Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Tyr Ile Asn Pro Asn Thr Gly Tyr Ser Glu Tyr Asn
65                  70                  75                  80

Gln Lys Phe Arg Asp Lys Ala Thr Leu Thr Ala Asn Lys Ser Ser Ser
                85                  90                  95

Thr Ala Asn Met Gln Leu Ser Ser Leu Thr Ser Asp Asp Ser Ala Val
            100                 105                 110

Tyr Tyr Cys Ala Arg Thr Ala Gln Tyr Tyr Gly Ser Pro Arg Gly Tyr
        115                 120                 125

Tyr Ala Met Asp Ser Trp Gly Gln Gly Thr Ser Val Thr Val Ser Ser
    130                 135                 140

Ala Lys Thr
145
```

<210> SEQ ID NO 87
<211> LENGTH: 393
<212> TYPE: DNA
<213> ORGANISM: Mus musculus

<400> SEQUENCE: 87

```
atgaggttct ctgctcagct tctggggctg cttgtgctct ggatccctgg atccactgca      60
gatattgtga tgacgcaggc tgcattctcc aatccagtca ctcttggaac atcagcttcc     120
atctcctgca ggtctagtaa gagtctccta catagtaacg gcatcactta tttgtgttgg     180
tttctgcaga agccaggcca gtctcctcag ctcctgattt atcagatgtc caaccttgcc     240
tcaggagtcc cagacaggtt cagtagcagt gggtcaggaa ctgatttcac actgagaatc     300
agcagagtgg aggctgagga tgtgggtgtt tatttctgtg ctcaaaatct agatctgccg     360
tggacgttcg gtgggggcac caagctggaa atc                                  393
```

<210> SEQ ID NO 88
<211> LENGTH: 131
<212> TYPE: PRT
<213> ORGANISM: Mus musculus

<400> SEQUENCE: 88

```
Met Arg Phe Ser Ala Gln Leu Leu Gly Leu Leu Val Leu Trp Ile Pro
1               5                   10                  15
Gly Ser Thr Ala Asp Ile Val Met Thr Gln Ala Ala Phe Ser Asn Pro
            20                  25                  30
Val Thr Leu Gly Thr Ser Ala Ser Ile Ser Cys Arg Ser Ser Lys Ser
        35                  40                  45
Leu Leu His Ser Asn Gly Ile Thr Tyr Leu Cys Trp Phe Leu Gln Lys
    50                  55                  60
Pro Gly Gln Ser Pro Gln Leu Leu Ile Tyr Gln Met Ser Asn Leu Ala
65                  70                  75                  80
Ser Gly Val Pro Asp Arg Phe Ser Ser Ser Gly Ser Gly Thr Asp Phe
                85                  90                  95
Thr Leu Arg Ile Ser Arg Val Glu Ala Glu Asp Val Gly Val Tyr Phe
            100                 105                 110
Cys Ala Gln Asn Leu Asp Leu Pro Trp Thr Phe Gly Gly Gly Thr Lys
        115                 120                 125
Leu Glu Ile
    130
```

<210> SEQ ID NO 89
<211> LENGTH: 468
<212> TYPE: DNA
<213> ORGANISM: Mus musculus

<400> SEQUENCE: 89

```
atgatcagtg tcctctctac acagtccctg acaacactga ctctaaccat gggatggagc      60
cggatctttc tcttcctcct gtcaataatt gcaagtgtcc attgccaggt ccagctgcag     120
cagtctggac ctgaactggt gaagcctggg gcttcagtga ggatatcctg caaggcttct     180
ggctacacct tcacaaccta ctatatacac tggttgaaac agaggcctgg acagggactt     240
gagtggattg atggattttt cctggaaatg ttaatacta gtacaatgc gaagttcaag     300
ggcaaggcca cactgactgc agacaaatcc tccagcacag cctacatgca gctcagcagc     360
ctgacctctg aggactctgc ggtctatttc tgtgcaagag gaattaca gtactacttt     420
gactactggg gccaaggctc cgctctcaca gtctcctcag ccaaaaca                 468
```

<210> SEQ ID NO 90
<211> LENGTH: 156
<212> TYPE: PRT
<213> ORGANISM: Mus musculus

<400> SEQUENCE: 90

Met Ile Ser Val Leu Ser Thr Gln Ser Leu Thr Thr Leu Thr Leu Thr
1               5                   10                  15

Met Gly Trp Ser Arg Ile Phe Leu Phe Leu Leu Ser Ile Ile Ala Ser
            20                  25                  30

Val His Cys Gln Val Gln Leu Gln Gln Ser Gly Pro Glu Leu Val Lys
        35                  40                  45

Pro Gly Ala Ser Val Arg Ile Ser Cys Lys Ala Ser Gly Tyr Thr Phe
    50                  55                  60

Thr Thr Tyr Tyr Ile His Trp Leu Lys Gln Arg Pro Gly Gln Gly Leu
65                  70                  75                  80

Glu Trp Ile Gly Trp Ile Phe Pro Gly Asn Val Asn Thr Lys Tyr Asn
                85                  90                  95

Ala Lys Phe Lys Gly Lys Ala Thr Leu Thr Ala Asp Lys Ser Ser Ser
            100                 105                 110

Thr Ala Tyr Met Gln Leu Ser Ser Leu Thr Ser Glu Asp Ser Ala Val
        115                 120                 125

Tyr Phe Cys Ala Arg Glu Glu Leu Gln Tyr Tyr Phe Asp Tyr Trp Gly
    130                 135                 140

Gln Gly Ser Ala Leu Thr Val Ser Ser Ala Lys Thr
145                 150                 155

<210> SEQ ID NO 91
<211> LENGTH: 381
<212> TYPE: DNA
<213> ORGANISM: Mus musculus

<400> SEQUENCE: 91 atggatttc aggtgcagat tctcagcatc ctgctaatca gtgcctcagt cataatgtcc      60
agaggacaaa ttgttctcac ccagtctcca gcaatcatgt ctgcatctcc aggggagaag    120
gtcaccatat cctgcagtgc caactcaagt gtacgtttca tgttctggta ccagcagaag    180
ccaggatcct cccccaaacc cttgatttat cgcacatcca acctggcttc tggagtccct    240
gctcgcttca gtggcagtgg gtctgggacc tcttactctc tcacaatcag cagcatggag    300
gctgaagatg ctgccactta ttactgccag cagtatcata gttacccgtg gacgttcggt    360
ggaggcacca agttggaaat c                                               381

<210> SEQ ID NO 92
<211> LENGTH: 127
<212> TYPE: PRT
<213> ORGANISM: Mus musculus

<400> SEQUENCE: 92

Met Asp Phe Gln Val Gln Ile Leu Ser Ile Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Ser Cys Ser Ala Asn
        35                  40                  45

Ser Ser Val Arg Phe Met Phe Trp Tyr Gln Gln Lys Pro Gly Ser Ser
    50                  55                  60

```
Pro Lys Pro Leu Ile Tyr Arg Thr Ser Asn Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Ser Met Glu Ala Glu Asp Ala Ala Thr Tyr Tyr Cys Gln Gln Tyr
            100                 105                 110

His Ser Tyr Pro Trp Thr Phe Gly Gly Gly Thr Lys Leu Glu Ile
        115                 120                 125

<210> SEQ ID NO 93
<211> LENGTH: 441
<212> TYPE: DNA
<213> ORGANISM: Mus musculus

<400> SEQUENCE: 93
atggaaaggc actggatctt tctcttcctg ttttcagtaa ctgcaggtgt ccactcccag    60
gtccaacttc agcagtctgg ggctgaactg gcaaaacctg gggcctcagt gaagatgtcc   120
tgcaaggctt ctggctacac ctttactagc tactggatgc actgggtaaa cagaggcct   180 ggacagggtc tggaatggat tggatacatt aatcctagta ctggttatac tgagtacaat   240
cagaagttca gggacaaggc cacattgact gcagacaaat cctccagcac agccaacatg   300
caactgagca gcctgacatc tgaggactct gcagtctatt actgtacaag aactgcgcaa   360
tactacggta gtcctagggg ttactatgct atggactcct ggggtcaagg aacctcagtc   420
accgtctcct cggccaaaac g                                             441

<210> SEQ ID NO 94
<211> LENGTH: 147
<212> TYPE: PRT
<213> ORGANISM: Mus musculus

<400> SEQUENCE: 94

Met Glu Arg His Trp Ile Phe Leu Phe Leu Phe Ser Val Thr Ala Gly
  1               5                  10                  15

Val His Ser Gln Val Gln Leu Gln Gln Ser Gly Ala Glu Leu Ala Lys
             20                  25                  30

Pro Gly Ala Ser Val Lys Met Ser Cys Lys Ala Ser Gly Tyr Thr Phe
         35                  40                  45

Thr Ser Tyr Trp Met His Trp Val Lys Gln Arg Pro Gly Gln Gly Leu
     50                  55                  60

Glu Trp Ile Gly Tyr Ile Asn Pro Ser Thr Gly Tyr Thr Glu Tyr Asn
 65                  70                  75                  80

Gln Lys Phe Arg Asp Lys Ala Thr Leu Thr Ala Asp Lys Ser Ser Ser
                 85                  90                  95

Thr Ala Asn Met Gln Leu Ser Ser Leu Thr Ser Glu Asp Ser Ala Val
            100                 105                 110

Tyr Tyr Cys Thr Arg Thr Ala Gln Tyr Tyr Gly Ser Pro Arg Gly Tyr
        115                 120                 125

Tyr Ala Met Asp Ser Trp Gly Gln Gly Thr Ser Val Thr Val Ser Ser
    130                 135                 140

Ala Lys Thr
145

<210> SEQ ID NO 95
<211> LENGTH: 324
<212> TYPE: DNA
<213> ORGANISM: Mus musculus
```

<400> SEQUENCE: 95

```
atgacgcagg ctgcattctc caatccagtc actcttggaa catcagcttc catctcctgc      60
aggtctagta agagtctcct acatagtaac ggcatcactt atttgtgttg gtttctgcag     120
aagccaggcc agtctcctca gctcctgatt tatctgatgt ccaaccttgc ctcaggagtc     180
ccagacaggt tcagtagcag tgggtcagga actgatttta cactgagaat cagcagagtg     240
gaggctgagg atgtgggtgt ttatttctgt gctcaaaatc tagatcttcc gtggacgttc     300
ggtgggggca ccaagctgga aatc                                             324
```

<210> SEQ ID NO 96
<211> LENGTH: 108
<212> TYPE: PRT
<213> ORGANISM: Mus musculus

<400> SEQUENCE: 96

```
Met Thr Gln Ala Ala Phe Ser Asn Pro Val Thr Leu Gly Thr Ser Ala
1               5                   10                  15

Ser Ile Ser Cys Arg Ser Ser Lys Ser Leu Leu His Ser Asn Gly Ile
            20                  25                  30

Thr Tyr Leu Cys Trp Phe Leu Gln Lys Pro Gly Gln Ser Pro Gln Leu
        35                  40                  45

Leu Ile Tyr Leu Met Ser Asn Leu Ala Ser Gly Val Pro Asp Arg Phe
    50                  55                  60

Ser Ser Ser Gly Ser Gly Thr Asp Phe Thr Leu Arg Ile Ser Arg Val
65                  70                  75                  80

Glu Ala Glu Asp Val Gly Val Tyr Phe Cys Ala Gln Asn Leu Asp Leu
                85                  90                  95

Pro Trp Thr Phe Gly Gly Gly Thr Lys Leu Glu Ile
            100                 105
```

<210> SEQ ID NO 97
<211> LENGTH: 423
<212> TYPE: DNA
<213> ORGANISM: Mus musculus

<400> SEQUENCE: 97

```
atgaacttcg ggctcagatt gattttcctt gtccttgttt taaaaggtgt cctgtgtgac      60
gtgaacctcg tggagtctgg gggaggctta gtgaagcttg agggtccct gaaactctcc     120
tgtgcagcct ctggattcac tttcagtagc ttttacatgt cttgggttcg ccagactcca     180
gagaagaggc tggacttggt cgcagccatt aatactaatg gtggtagcac ctactattca     240
gacactgtga aggccgatt caccatctcc agagacaatg ccaagaacac cctgtacctg     300
caaatgagca gtctgaagtc tgaggacaca gccttgtttt actgtgcaag acagccttac     360
tacgagggc tatggacttt ctggggtcaa ggaacctcag tcaccgtctc ctcagccaaa     420
acg                                                                    423
```

<210> SEQ ID NO 98
<211> LENGTH: 141
<212> TYPE: PRT
<213> ORGANISM: Mus musculus

<400> SEQUENCE: 98

```
Met Asn Phe Gly Leu Arg Leu Ile Phe Leu Val Leu Val Leu Lys Gly
1               5                   10                  15

Val Leu Cys Asp Val Asn Leu Val Glu Ser Gly Gly Gly Leu Val Lys
```

|     |     |     | 20  |     |     |     | 25  |     |     |     | 30  |     |     |
| --- | --- | --- | --- | --- | --- | --- | --- | --- | --- | --- | --- | --- | --- |

Leu Gly Gly Ser Leu Lys Leu Ser Cys Ala Ala Ser Gly Phe Thr Phe
          35                    40                    45

Ser Ser Phe Tyr Met Ser Trp Val Arg Gln Thr Pro Glu Lys Arg Leu
 50                       55                  60

Asp Leu Val Ala Ala Ile Asn Thr Asn Gly Gly Ser Thr Tyr Tyr Ser
65                    70                  75                  80

Asp Thr Val Lys Gly Arg Phe Thr Ile Ser Arg Asp Asn Ala Lys Asn
                 85                    90                  95

Thr Leu Tyr Leu Gln Met Ser Ser Leu Lys Ser Glu Asp Thr Ala Leu
            100                  105              110

Phe Tyr Cys Ala Arg Gln Pro Tyr Tyr Gly Gly Pro Met Asp Phe Trp
            115                  120              125

Gly Gln Gly Thr Ser Val Thr Val Ser Ser Ala Lys Thr
            130                  135              140

```
<210> SEQ ID NO 99
<211> LENGTH: 378
<212> TYPE: DNA
<213> ORGANISM: Mus musculus

<400> SEQUENCE: 99
atggttttca cacctcagat acttggactt atgcttttt ggatttcagc ctccagaggt     60
gatattgtgc taactcagtc tccagccacc ctgtctgtga ctccaggaga tagcgtcagt    120
ctttcctgca gggccagcca aagtattaac aacaacctac actggtatca acaaaaatca    180
catgagtctc caaggcttct catcaagtat gcttcccagt ccatctctgg atcccctcc     240
aggttcagtg gcagtggatc agggacagat ttcactctca gtatcaacag tgtggagact    300
gaagattttg gaatgtattt ctgtcaacag agtaacaact ggcctctcac gttcggtgct    360
gggaccaagc tggagctg                                                 378

<210> SEQ ID NO 100
<211> LENGTH: 126
<212> TYPE: PRT
<213> ORGANISM: Mus musculus

<400> SEQUENCE: 100
```

Met Val Phe Thr Pro Gln Ile Leu Gly Leu Met Leu Phe Trp Ile Ser
1                  5                  10                  15

Ala Ser Arg Gly Asp Ile Val Leu Thr Gln Ser Pro Ala Thr Leu Ser
            20                  25              30

Val Thr Pro Gly Asp Ser Val Ser Leu Ser Cys Arg Ala Ser Gln Ser
            35                  40              45

Ile Asn Asn Asn Leu His Trp Tyr Gln Gln Lys Ser His Glu Ser Pro
 50                      55                  60

Arg Leu Leu Ile Lys Tyr Ala Ser Gln Ser Ile Ser Gly Ile Pro Ser
65                    70                  75                  80

Arg Phe Ser Gly Ser Gly Ser Gly Thr Asp Phe Thr Leu Ser Ile Asn
                 85                    90                  95

Ser Val Glu Thr Glu Asp Phe Gly Met Tyr Phe Cys Gln Gln Ser Asn
            100                  105              110

Asn Trp Pro Leu Thr Phe Gly Ala Gly Thr Lys Leu Glu Leu
            115                  120              125

```
<210> SEQ ID NO 101
<211> LENGTH: 423
```

<212> TYPE: DNA
<213> ORGANISM: Mus musculus

<400> SEQUENCE: 101

```
atgaacttcg ggctcagatt gattttcctt gtccttgttt taaaaggtgt cctgtgtgac    60
gtgaacctcg tggagtctgg gggaggctta gtgaagcttg agggtccct gaaactctcc    120
tgtgcagcct ctggattcac tttcagtaga ttttacatgt cttgggttcg ccagactcca    180
gagaagaggc tggacttggt cgcagccatt aatactaatg gtggtagcac ctattattca    240
gacactgtga agggccgatt caccatctcc agagacaatg ccaagaacac cctgtacctg    300
caaatgagca gtctgaagtc tgaggacaca gccttgtttt actgtgcaag acagccttac    360
tacggagggc ctatggagtt ctggggtcaa ggaacctcag tcaccgtctc ctcagccaaa    420
acg                                                                 423
```

<210> SEQ ID NO 102
<211> LENGTH: 141
<212> TYPE: PRT
<213> ORGANISM: Mus musculus

<400> SEQUENCE: 102

```
Met Asn Phe Gly Leu Arg Leu Ile Phe Leu Val Leu Val Leu Lys Gly
1               5                   10                  15
Val Leu Cys Asp Val Asn Leu Val Glu Ser Gly Gly Gly Leu Val Lys
            20                  25                  30
Leu Gly Gly Ser Leu Lys Leu Ser Cys Ala Ala Ser Gly Phe Thr Phe
        35                  40                  45
Ser Arg Phe Tyr Met Ser Trp Val Arg Gln Thr Pro Glu Lys Arg Leu
    50                  55                  60
Asp Leu Val Ala Ala Ile Asn Thr Asn Gly Gly Ser Thr Tyr Tyr Ser
65                  70                  75                  80
Asp Thr Val Lys Gly Arg Phe Thr Ile Ser Arg Asp Asn Ala Lys Asn
                85                  90                  95
Thr Leu Tyr Leu Gln Met Ser Ser Leu Lys Ser Glu Asp Thr Ala Leu
            100                 105                 110
Phe Tyr Cys Ala Arg Gln Pro Tyr Tyr Gly Gly Pro Met Glu Phe Trp
        115                 120                 125
Gly Gln Gly Thr Ser Val Thr Val Ser Ser Ala Lys Thr
    130                 135                 140
```

<210> SEQ ID NO 103
<211> LENGTH: 390
<212> TYPE: DNA
<213> ORGANISM: Mus musculus

<400> SEQUENCE: 103

```
atgggcatca agatggagtc acagactcag gtctttgtat acatgttgct gtggttgtct    60
ggtgttgatg gagacattgt gatgacccag tctcaaaaat tcatgtccac atcagtagga    120
gacagggtca gcgtcacctg caaggccagt cagaatgtgg gtactaatgt agcctggtat    180
caacagaaac cagggcaatc tcctaaagca ctgatttact cggcatccta ccggtacagt    240
ggagtccctg atcgcttcac aggcagtgga tctgggtcag atttcactct caccatcagc    300
aatgtgcagt ctgaagactt ggcagagtat ttctgtcagc aatataacag ctatcctctc    360
acgttcggtg ctgggaccaa gctggagctg                                    390
```

<210> SEQ ID NO 104

```
<211> LENGTH: 130
<212> TYPE: PRT
<213> ORGANISM: Mus musculus

<400> SEQUENCE: 104

Met Gly Ile Lys Met Glu Ser Gln Thr Gln Val Phe Val Tyr Met Leu
1               5                   10                  15

Leu Trp Leu Ser Gly Val Asp Gly Asp Ile Val Met Thr Gln Ser Gln
            20                  25                  30

Lys Phe Met Ser Thr Ser Val Gly Asp Arg Val Ser Val Thr Cys Lys
        35                  40                  45

Ala Ser Gln Asn Val Gly Thr Asn Val Ala Trp Tyr Gln Gln Lys Pro
    50                  55                  60

Gly Gln Ser Pro Lys Ala Leu Ile Tyr Ser Ala Ser Tyr Arg Tyr Ser
65                  70                  75                  80

Gly Val Pro Asp Arg Phe Thr Gly Ser Gly Ser Gly Ser Asp Phe Thr
                85                  90                  95

Leu Thr Ile Ser Asn Val Gln Ser Glu Asp Leu Ala Glu Tyr Phe Cys
            100                 105                 110

Gln Gln Tyr Asn Ser Tyr Pro Leu Thr Phe Gly Ala Gly Thr Lys Leu
        115                 120                 125

Glu Leu
    130

<210> SEQ ID NO 105
<211> LENGTH: 31
<212> TYPE: DNA
<213> ORGANISM: Mus musculus

<400> SEQUENCE: 105
ggctacacct ttactagcta ctggatgcac t                              31

<210> SEQ ID NO 106
<211> LENGTH: 52
<212> TYPE: DNA
<213> ORGANISM: Mus musculus

<400> SEQUENCE: 106
tacattaatc ctagcactgg ttatactgag tacaatcaga acttcaggga ca        52

<210> SEQ ID NO 107
<211> LENGTH: 49
<212> TYPE: DNA
<213> ORGANISM: Mus musculus

<400> SEQUENCE: 107
actgcgcaat actacggtag tcctagggt tactatgcta tggactcct            49

<210> SEQ ID NO 108
<211> LENGTH: 10
<212> TYPE: PRT
<213> ORGANISM: Mus musculus

<400> SEQUENCE: 108

Gly Tyr Thr Phe Thr Ser Tyr Trp Met His
1               5                   10

<210> SEQ ID NO 109
<211> LENGTH: 17
<212> TYPE: PRT
<213> ORGANISM: Mus musculus
```

```
<400> SEQUENCE: 109

Tyr Ile Asn Pro Ser Thr Gly Tyr Thr Glu Tyr Asn Gln Asn Phe Arg
1               5                   10                  15

Asp

<210> SEQ ID NO 110
<211> LENGTH: 16
<212> TYPE: PRT
<213> ORGANISM: Mus musculus

<400> SEQUENCE: 110

Thr Ala Gln Tyr Tyr Gly Ser Pro Arg Gly Tyr Tyr Ala Met Asp Ser
1               5                   10                  15

<210> SEQ ID NO 111
<211> LENGTH: 49
<212> TYPE: DNA
<213> ORGANISM: Mus musculus

<400> SEQUENCE: 111
aggtctagta agagtctcct acatagtaac ggcatcactt atttgtgtt            49

<210> SEQ ID NO 112
<211> LENGTH: 22
<212> TYPE: DNA
<213> ORGANISM: Mus musculus

<400> SEQUENCE: 112
ctgatgtcca accttgcctc ag                                         22

<210> SEQ ID NO 113
<211> LENGTH: 28
<212> TYPE: DNA
<213> ORGANISM: Mus musculus

<400> SEQUENCE: 113
gctcaaaatc tagatcttcc gtggacgt                                   28

<210> SEQ ID NO 114
<211> LENGTH: 16
<212> TYPE: PRT
<213> ORGANISM: Mus musculus

<400> SEQUENCE: 114

Arg Ser Ser Lys Ser Leu Leu His Ser Asn Gly Ile Thr Tyr Leu Cys
1               5                   10                  15

<210> SEQ ID NO 115
<211> LENGTH: 7
<212> TYPE: PRT
<213> ORGANISM: Mus musculus

<400> SEQUENCE: 115

Leu Met Ser Asn Leu Ala Ser
1               5

<210> SEQ ID NO 116
<211> LENGTH: 9
<212> TYPE: PRT
<213> ORGANISM: Mus musculus

<400> SEQUENCE: 116

Ala Gln Asn Leu Asp Leu Pro Trp Thr
1               5
```

<210> SEQ ID NO 117
<211> LENGTH: 30
<212> TYPE: DNA
<213> ORGANISM: Mus musculus

<400> SEQUENCE: 117
ggctacacct tcacttccta tccaatagag                                30

<210> SEQ ID NO 118
<211> LENGTH: 51
<212> TYPE: DNA
<213> ORGANISM: Mus musculus

<400> SEQUENCE: 118
aattttcatc cttacaatga taatactaag tacaatgaaa aattcaaggg c         51

<210> SEQ ID NO 119
<211> LENGTH: 36
<212> TYPE: DNA
<213> ORGANISM: Mus musculus

<400> SEQUENCE: 119
gggtactctg gtaactactt ctctgctatg gactac                         36

<210> SEQ ID NO 120
<211> LENGTH: 10
<212> TYPE: PRT
<213> ORGANISM: Mus musculus

<400> SEQUENCE: 120

Gly Tyr Thr Phe Thr Ser Tyr Pro Ile Glu
1               5                   10

<210> SEQ ID NO 121
<211> LENGTH: 17
<212> TYPE: PRT
<213> ORGANISM: Mus musculus

<400> SEQUENCE: 121

Asn Phe His Pro Tyr Asn Asp Asn Thr Lys Tyr Asn Glu Lys Phe Lys
1               5                   10                  15
Gly

<210> SEQ ID NO 122
<211> LENGTH: 12
<212> TYPE: PRT
<213> ORGANISM: Mus musculus

<400> SEQUENCE: 122

Gly Tyr Ser Gly Asn Tyr Phe Ser Ala Met Asp Tyr
1               5                   10

<210> SEQ ID NO 123
<211> LENGTH: 33
<212> TYPE: DNA
<213> ORGANISM: Mus musculus

<400> SEQUENCE: 123
aaggccagtc agaatgttcg taatgatgta gcc                            33

<210> SEQ ID NO 124
<211> LENGTH: 21
<212> TYPE: DNA

-continued

```
<213> ORGANISM: Mus musculus

<400> SEQUENCE: 124
ttggcatcca accggcacac t                                               21

<210> SEQ ID NO 125
<211> LENGTH: 27
<212> TYPE: DNA
<213> ORGANISM: Mus musculus

<400> SEQUENCE: 125
ctgcaacatt ggaattatcc gtacacg                                         27

<210> SEQ ID NO 126
<211> LENGTH: 11
<212> TYPE: PRT
<213> ORGANISM: Mus musculus

<400> SEQUENCE: 126
```

Lys Ala Ser Gln Asn Val Arg Asn Asp Val Ala
1               5                   10

```
<210> SEQ ID NO 127
<211> LENGTH: 7
<212> TYPE: PRT
<213> ORGANISM: Mus musculus

<400> SEQUENCE: 127
```

Leu Ala Ser Asn Arg His Thr
1               5

```
<210> SEQ ID NO 128
<211> LENGTH: 9
<212> TYPE: PRT
<213> ORGANISM: Mus musculus

<400> SEQUENCE: 128
```

Leu Gln His Trp Asn Tyr Pro Tyr Thr
1               5

```
<210> SEQ ID NO 129
<211> LENGTH: 31
<212> TYPE: DNA
<213> ORGANISM: Mus musculus

<400> SEQUENCE: 129
ggattcactt tcagtagtta ttacatgtct t                                    31

<210> SEQ ID NO 130
<211> LENGTH: 51
<212> TYPE: DNA
<213> ORGANISM: Mus musculus

<400> SEQUENCE: 130
gtcattaata ctaatggtgg tagcacctac tattcagaca ctgtgaaggg c               51

<210> SEQ ID NO 131
<211> LENGTH: 31
<212> TYPE: DNA
<213> ORGANISM: Mus musculus

<400> SEQUENCE: 131
caaccctatt atggtaaccc ttttgactac t                                    31
```

```
<210> SEQ ID NO 132
<211> LENGTH: 10
<212> TYPE: PRT
<213> ORGANISM: Mus musculus

<400> SEQUENCE: 132

Gly Phe Thr Phe Ser Ser Tyr Tyr Met Ser
1               5                   10

<210> SEQ ID NO 133
<211> LENGTH: 17
<212> TYPE: PRT
<213> ORGANISM: Mus musculus

<400> SEQUENCE: 133

Val Ile Asn Thr Asn Gly Gly Ser Thr Tyr Tyr Ser Asp Thr Val Lys
1               5                   10                  15

Gly

<210> SEQ ID NO 134
<211> LENGTH: 10
<212> TYPE: PRT
<213> ORGANISM: Mus musculus

<400> SEQUENCE: 134

Gln Pro Tyr Tyr Gly Asn Pro Phe Asp Tyr
1               5                   10

<210> SEQ ID NO 135
<211> LENGTH: 34
<212> TYPE: DNA
<213> ORGANISM: Mus musculus

<400> SEQUENCE: 135
agggccagcc aaagtattag caacaaccta cact                              34

<210> SEQ ID NO 136
<211> LENGTH: 22
<212> TYPE: DNA
<213> ORGANISM: Mus musculus

<400> SEQUENCE: 136
tatgtttccc agtccatctc tg                                          22

<210> SEQ ID NO 137
<211> LENGTH: 28
<212> TYPE: DNA
<213> ORGANISM: Mus musculus

<400> SEQUENCE: 137
caacagagta acaactggcc gctcacgt                                    28

<210> SEQ ID NO 138
<211> LENGTH: 11
<212> TYPE: PRT
<213> ORGANISM: Mus musculus

<400> SEQUENCE: 138

Arg Ala Ser Gln Ser Ile Ser Asn Asn Leu His
1               5                   10

<210> SEQ ID NO 139
<211> LENGTH: 7
<212> TYPE: PRT
<213> ORGANISM: Mus musculus
```

```
<400> SEQUENCE: 139

Tyr Val Ser Gln Ser Ile Ser
1               5

<210> SEQ ID NO 140
<211> LENGTH: 9
<212> TYPE: PRT
<213> ORGANISM: Mus musculus

<400> SEQUENCE: 140

Gln Gln Ser Asn Asn Trp Pro Leu Thr
1               5

<210> SEQ ID NO 141
<211> LENGTH: 31
<212> TYPE: DNA
<213> ORGANISM: Mus musculus

<400> SEQUENCE: 141
ggattcactt tcagtagcta ttacatgtct t                              31

<210> SEQ ID NO 142
<211> LENGTH: 52
<212> TYPE: DNA
<213> ORGANISM: Mus musculus

<400> SEQUENCE: 142
gccattaata gtaatggtgg tagtacctac tatgcagaca ctatgaaggg cc        52

<210> SEQ ID NO 143
<211> LENGTH: 34
<212> TYPE: DNA
<213> ORGANISM: Mus musculus

<400> SEQUENCE: 143
gagttggccg ggtatggtac cccgtttgct tact                           34

<210> SEQ ID NO 144
<211> LENGTH: 10
<212> TYPE: PRT
<213> ORGANISM: Mus musculus

<400> SEQUENCE: 144

Gly Phe Thr Phe Ser Ser Tyr Tyr Met Ser
1               5                   10

<210> SEQ ID NO 145
<211> LENGTH: 17
<212> TYPE: PRT
<213> ORGANISM: Mus musculus

<400> SEQUENCE: 145

Ala Ile Asn Ser Asn Gly Gly Ser Thr Tyr Tyr Ala Asp Thr Met Lys
1               5                   10                  15

Gly

<210> SEQ ID NO 146
<211> LENGTH: 11
<212> TYPE: PRT
<213> ORGANISM: Mus musculus

<400> SEQUENCE: 146

Glu Leu Ala Gly Tyr Gly Thr Pro Phe Ala Tyr
```

```
<210> SEQ ID NO 147
<211> LENGTH: 34
<212> TYPE: DNA
<213> ORGANISM: Mus musculus

<400> SEQUENCE: 147
agggccagcc aaagtattag cagcaaccta cact                          34

<210> SEQ ID NO 148
<211> LENGTH: 22
<212> TYPE: DNA
<213> ORGANISM: Mus musculus

<400> SEQUENCE: 148
tatgcttccc agtccatctc tg                                       22

<210> SEQ ID NO 149
<211> LENGTH: 28
<212> TYPE: DNA
<213> ORGANISM: Mus musculus

<400> SEQUENCE: 149
caacagagta acacctggcc gctcacgt                                 28

<210> SEQ ID NO 150
<211> LENGTH: 11
<212> TYPE: PRT
<213> ORGANISM: Mus musculus

<400> SEQUENCE: 150

Arg Ala Ser Gln Ser Ile Ser Ser Asn Leu His
1               5                   10

<210> SEQ ID NO 151
<211> LENGTH: 7
<212> TYPE: PRT
<213> ORGANISM: Mus musculus

<400> SEQUENCE: 151

Tyr Ala Ser Gln Ser Ile Ser
1               5

<210> SEQ ID NO 152
<211> LENGTH: 9
<212> TYPE: PRT
<213> ORGANISM: Mus musculus

<400> SEQUENCE: 152

Gln Gln Ser Asn Thr Trp Pro Leu Thr
1               5

<210> SEQ ID NO 153
<211> LENGTH: 31
<212> TYPE: DNA
<213> ORGANISM: Mus musculus

<400> SEQUENCE: 153
ggttatgcat tcactagcta caacatgtac t                             31

<210> SEQ ID NO 154
<211> LENGTH: 52
<212> TYPE: DNA
<213> ORGANISM: Mus musculus
```

```
<400> SEQUENCE: 154
tatattgatc cttacaatgg cggtactgac tccaaccaga acttcaaggg ca        52

<210> SEQ ID NO 155
<211> LENGTH: 37
<212> TYPE: DNA
<213> ORGANISM: Mus musculus

<400> SEQUENCE: 155 gggggatgg gattacgacg ggaccacttt gactact                          37

<210> SEQ ID NO 156
<211> LENGTH: 10
<212> TYPE: PRT
<213> ORGANISM: Mus musculus

<400> SEQUENCE: 156

Gly Tyr Ala Phe Thr Ser Tyr Asn Met Tyr
1               5                   10

<210> SEQ ID NO 157
<211> LENGTH: 17
<212> TYPE: PRT
<213> ORGANISM: Mus musculus

<400> SEQUENCE: 157

Tyr Ile Asp Pro Tyr Asn Gly Gly Thr Asp Ser Asn Gln Asn Phe Lys
1               5                   10                  15

Gly

<210> SEQ ID NO 158
<211> LENGTH: 12
<212> TYPE: PRT
<213> ORGANISM: Mus musculus

<400> SEQUENCE: 158

Gly Gly Met Gly Leu Arg Arg Asp His Phe Asp Tyr
1               5                   10

<210> SEQ ID NO 159
<211> LENGTH: 30
<212> TYPE: DNA
<213> ORGANISM: Mus musculus

<400> SEQUENCE: 159
agtgccaact caagtgtacg ttacatgttc                                 30

<210> SEQ ID NO 160
<211> LENGTH: 21
<212> TYPE: DNA
<213> ORGANISM: Mus musculus

<400> SEQUENCE: 160
cgcacatcca acctggcttc t                                          21

<210> SEQ ID NO 161
<211> LENGTH: 27
<212> TYPE: DNA
<213> ORGANISM: Mus musculus

<400> SEQUENCE: 161
cagcagtatc atagttaccc gtggacg                                    27
```

<210> SEQ ID NO 162
<211> LENGTH: 10
<212> TYPE: PRT
<213> ORGANISM: Mus musculus

<400> SEQUENCE: 162

Ser Ala Asn Ser Ser Val Arg Tyr Met Phe
1               5                   10

<210> SEQ ID NO 163
<211> LENGTH: 7
<212> TYPE: PRT
<213> ORGANISM: Mus musculus

<400> SEQUENCE: 163

Arg Thr Ser Asn Leu Ala Ser
1               5

<210> SEQ ID NO 164
<211> LENGTH: 9
<212> TYPE: PRT
<213> ORGANISM: Mus musculus

<400> SEQUENCE: 164

Gln Gln Tyr His Ser Tyr Pro Trp Thr
1               5

<210> SEQ ID NO 165
<211> LENGTH: 31
<212> TYPE: DNA
<213> ORGANISM: Mus musculus

<400> SEQUENCE: 165
ggctacacct tcacaaccta ctatatacac t                            31

<210> SEQ ID NO 166
<211> LENGTH: 52
<212> TYPE: DNA
<213> ORGANISM: Mus musculus

<400> SEQUENCE: 166
tggatttttc ctggaaatgt taatactaag tacaatgcga agttcaaggg ca      52

<210> SEQ ID NO 167
<211> LENGTH: 28
<212> TYPE: DNA
<213> ORGANISM: Mus musculus

<400> SEQUENCE: 167
gaggaattac agtactactt tgactact                                28

<210> SEQ ID NO 168
<211> LENGTH: 10
<212> TYPE: PRT
<213> ORGANISM: Mus musculus

<400> SEQUENCE: 168

Gly Tyr Thr Phe Thr Thr Tyr Tyr Ile His
1               5                   10

<210> SEQ ID NO 169
<211> LENGTH: 17
<212> TYPE: PRT
<213> ORGANISM: Mus musculus -continued

```
<400> SEQUENCE: 169

Trp Ile Phe Pro Gly Asn Val Asn Thr Lys Tyr Asn Ala Lys Phe Lys
1               5                   10                  15

Gly

<210> SEQ ID NO 170
<211> LENGTH: 9
<212> TYPE: PRT
<213> ORGANISM: Mus musculus

<400> SEQUENCE: 170

Glu Glu Leu Gln Tyr Tyr Phe Asp Tyr
1               5

<210> SEQ ID NO 171
<211> LENGTH: 31
<212> TYPE: DNA
<213> ORGANISM: Mus musculus

<400> SEQUENCE: 171
agtgccaact caagtgtacg tttcatgttc t                              31

<210> SEQ ID NO 172
<211> LENGTH: 22
<212> TYPE: DNA
<213> ORGANISM: Mus musculus

<400> SEQUENCE: 172
cgcacatcca acctggcctc tg                                        22

<210> SEQ ID NO 173
<211> LENGTH: 28
<212> TYPE: DNA
<213> ORGANISM: Mus musculus

<400> SEQUENCE: 173
cagcagtatc atagttaccc gtggacgt                                  28

<210> SEQ ID NO 174
<211> LENGTH: 10
<212> TYPE: PRT
<213> ORGANISM: Mus musculus

<400> SEQUENCE: 174

Ser Ala Asn Ser Ser Val Arg Phe Met Phe
1               5                   10

<210> SEQ ID NO 175
<211> LENGTH: 7
<212> TYPE: PRT
<213> ORGANISM: Mus musculus

<400> SEQUENCE: 175

Arg Thr Ser Asn Leu Ala Ser
1               5

<210> SEQ ID NO 176
<211> LENGTH: 9
<212> TYPE: PRT
<213> ORGANISM: Mus musculus

<400> SEQUENCE: 176

Gln Gln Tyr His Ser Tyr Pro Trp Thr
1               5
```

<210> SEQ ID NO 177
<211> LENGTH: 31
<212> TYPE: DNA
<213> ORGANISM: Mus musculus

<400> SEQUENCE: 177
ggattcactt tcagtaccta ttacatgtct t                              31

<210> SEQ ID NO 178
<211> LENGTH: 52
<212> TYPE: DNA
<213> ORGANISM: Mus musculus

<400> SEQUENCE: 178
accattaata ctaatggtgg tagcacctac tatccagaca ctttgaaggg cc        52

<210> SEQ ID NO 179
<211> LENGTH: 31
<212> TYPE: DNA
<213> ORGANISM: Mus musculus

<400> SEQUENCE: 179
cagcgtaact acggagtggc tgtggactcc t                              31

<210> SEQ ID NO 180
<211> LENGTH: 10
<212> TYPE: PRT
<213> ORGANISM: Mus musculus

<400> SEQUENCE: 180

Gly Phe Thr Phe Ser Thr Tyr Tyr Met Ser
1               5                   10

<210> SEQ ID NO 181
<211> LENGTH: 17
<212> TYPE: PRT
<213> ORGANISM: Mus musculus

<400> SEQUENCE: 181

Thr Ile Asn Thr Asn Gly Gly Ser Thr Tyr Tyr Pro Asp Thr Leu Lys
1               5                   10                  15
Gly

<210> SEQ ID NO 182
<211> LENGTH: 10
<212> TYPE: PRT
<213> ORGANISM: Mus musculus

<400> SEQUENCE: 182

Gln Arg Asn Tyr Gly Val Ala Val Asp Ser
1               5                   10

<210> SEQ ID NO 183
<211> LENGTH: 34
<212> TYPE: DNA
<213> ORGANISM: Mus musculus

<400> SEQUENCE: 183
agggccagcc aaagtattag caacaaccta cact                           34

<210> SEQ ID NO 184
<211> LENGTH: 22
<212> TYPE: DNA

-continued

```
<213> ORGANISM: Mus musculus

<400> SEQUENCE: 184
tatgcttccc agtccatctc tg                                              22

<210> SEQ ID NO 185
<211> LENGTH: 28
<212> TYPE: DNA
<213> ORGANISM: Mus musculus

<400> SEQUENCE: 185
caacagacta caactggcc tctcacgt                                         28

<210> SEQ ID NO 186
<211> LENGTH: 11
<212> TYPE: PRT
<213> ORGANISM: Mus musculus

<400> SEQUENCE: 186

Arg Ala Ser Gln Ser Ile Ser Asn Asn Leu His
1               5                   10

<210> SEQ ID NO 187
<211> LENGTH: 7
<212> TYPE: PRT
<213> ORGANISM: Mus musculus

<400> SEQUENCE: 187

Tyr Ala Ser Gln Ser Ile Ser
1               5

<210> SEQ ID NO 188
<211> LENGTH: 9
<212> TYPE: PRT
<213> ORGANISM: Mus musculus

<400> SEQUENCE: 188

Gln Gln Thr Asn Asn Trp Pro Leu Thr
1               5

<210> SEQ ID NO 189
<211> LENGTH: 34
<212> TYPE: DNA
<213> ORGANISM: Mus musculus

<400> SEQUENCE: 189
ggctactcca tcaccagtgg ttattactgg aact                                 34

<210> SEQ ID NO 190
<211> LENGTH: 49
<212> TYPE: DNA
<213> ORGANISM: Mus musculus

<400> SEQUENCE: 190
cacataaact acgacggtag agataactac aacccatctc tcaaaaatc                 49

<210> SEQ ID NO 191
<211> LENGTH: 34
<212> TYPE: DNA
<213> ORGANISM: Mus musculus

<400> SEQUENCE: 191
gagtttggta acttccctta ctactttgac tact                                 34
```

```
<210> SEQ ID NO 192
<211> LENGTH: 11
<212> TYPE: PRT
<213> ORGANISM: Mus musculus

<400> SEQUENCE: 192

Gly Tyr Ser Ile Thr Ser Gly Tyr Tyr Trp Asn
1               5                   10

<210> SEQ ID NO 193
<211> LENGTH: 16
<212> TYPE: PRT
<213> ORGANISM: Mus musculus

<400> SEQUENCE: 193

His Ile Asn Tyr Asp Gly Arg Asp Asn Tyr Asn Pro Ser Leu Lys Asn
1               5                   10                  15

<210> SEQ ID NO 194
<211> LENGTH: 11
<212> TYPE: PRT
<213> ORGANISM: Mus musculus

<400> SEQUENCE: 194

Glu Phe Gly Asn Phe Pro Tyr Tyr Phe Asp Tyr
1               5                   10

<210> SEQ ID NO 195
<211> LENGTH: 31
<212> TYPE: DNA
<213> ORGANISM: Mus musculus

<400> SEQUENCE: 195
agtgcctact caagtgtacg tttcatgttc t                              31

<210> SEQ ID NO 196
<211> LENGTH: 22
<212> TYPE: DNA
<213> ORGANISM: Mus musculus

<400> SEQUENCE: 196
cgcacatcca acctggcttc tg                                        22

<210> SEQ ID NO 197
<211> LENGTH: 28
<212> TYPE: DNA
<213> ORGANISM: Mus musculus

<400> SEQUENCE: 197
cagcagtatc atagttaccc gtggacgt                                  28

<210> SEQ ID NO 198
<211> LENGTH: 10
<212> TYPE: PRT
<213> ORGANISM: Mus musculus

<400> SEQUENCE: 198

Ser Ala Tyr Ser Ser Val Arg Phe Met Phe
1               5                   10

<210> SEQ ID NO 199
<211> LENGTH: 7
<212> TYPE: PRT
<213> ORGANISM: Mus musculus

<400> SEQUENCE: 199
```

```
Arg Thr Ser Asn Leu Ala Ser
1               5

<210> SEQ ID NO 200
<211> LENGTH: 9
<212> TYPE: PRT
<213> ORGANISM: Mus musculus

<400> SEQUENCE: 200

Gln Gln Tyr His Ser Tyr Pro Trp Thr
1               5

<210> SEQ ID NO 201
<211> LENGTH: 31
<212> TYPE: DNA
<213> ORGANISM: Mus musculus

<400> SEQUENCE: 201
ggattcactt tcagtagtta ttacatgtct t                              31

<210> SEQ ID NO 202
<211> LENGTH: 52
<212> TYPE: DNA
<213> ORGANISM: Mus musculus

<400> SEQUENCE: 202
gtcattaata gtaatggtgg tagcacctac tattcagaga ctgtgaaggg cc       52

<210> SEQ ID NO 203
<211> LENGTH: 31
<212> TYPE: DNA
<213> ORGANISM: Mus musculus

<400> SEQUENCE: 203
caaccctatt atggtaaccc ttttgactac t                              31

<210> SEQ ID NO 204
<211> LENGTH: 10
<212> TYPE: PRT
<213> ORGANISM: Mus musculus

<400> SEQUENCE: 204

Gly Phe Thr Phe Ser Ser Tyr Tyr Met Ser
1               5                   10

<210> SEQ ID NO 205
<211> LENGTH: 17
<212> TYPE: PRT
<213> ORGANISM: Mus musculus

<400> SEQUENCE: 205

Val Ile Asn Ser Asn Gly Gly Ser Thr Tyr Tyr Ser Glu Thr Val Lys
1               5                   10                  15
Gly

<210> SEQ ID NO 206
<211> LENGTH: 10
<212> TYPE: PRT
<213> ORGANISM: Mus musculus

<400> SEQUENCE: 206

Gln Pro Tyr Tyr Gly Asn Pro Phe Asp Tyr
1               5                   10
```

<210> SEQ ID NO 207
<211> LENGTH: 34
<212> TYPE: DNA
<213> ORGANISM: Mus musculus

<400> SEQUENCE: 207
agggccagcc aaagtattag caacaaccta cact                          34

<210> SEQ ID NO 208
<211> LENGTH: 22
<212> TYPE: DNA
<213> ORGANISM: Mus musculus

<400> SEQUENCE: 208
tatgtttccc agtccatctc tg                                       22

<210> SEQ ID NO 209
<211> LENGTH: 28
<212> TYPE: DNA
<213> ORGANISM: Mus musculus

<400> SEQUENCE: 209
caacagagta acaactggcc gctcacgt                                 28

<210> SEQ ID NO 210
<211> LENGTH: 11
<212> TYPE: PRT
<213> ORGANISM: Mus musculus

<400> SEQUENCE: 210

Arg Ala Ser Gln Ser Ile Ser Asn Asn Leu His
1               5                   10

<210> SEQ ID NO 211
<211> LENGTH: 7
<212> TYPE: PRT
<213> ORGANISM: Mus musculus

<400> SEQUENCE: 211

Tyr Val Ser Gln Ser Ile Ser
1               5

<210> SEQ ID NO 212
<211> LENGTH: 9
<212> TYPE: PRT
<213> ORGANISM: Mus musculus

<400> SEQUENCE: 212

Gln Gln Ser Asn Asn Trp Pro Leu Thr
1               5

<210> SEQ ID NO 213
<211> LENGTH: 31
<212> TYPE: DNA
<213> ORGANISM: Mus musculus

<400> SEQUENCE: 213
ggttatgcat tcactagcta caacatgtac t                             31

<210> SEQ ID NO 214
<211> LENGTH: 52
<212> TYPE: DNA
<213> ORGANISM: Mus musculus

<400> SEQUENCE: 214

```
tatattgatc cttacaatgg tggtactaac tacaaccaga agttcaaggg ca          52
```

<210> SEQ ID NO 215
<211> LENGTH: 37
<212> TYPE: DNA
<213> ORGANISM: Mus musculus
<400> SEQUENCE: 215

```
gggggatgg gattacgacg ggactacttt gacttct                            37
```

<210> SEQ ID NO 216
<211> LENGTH: 10
<212> TYPE: PRT
<213> ORGANISM: Mus musculus
<400> SEQUENCE: 216

Gly Tyr Ala Phe Thr Ser Tyr Asn Met Tyr
1               5                   10

<210> SEQ ID NO 217
<211> LENGTH: 17
<212> TYPE: PRT
<213> ORGANISM: Mus musculus
<400> SEQUENCE: 217

Tyr Ile Asp Pro Tyr Asn Gly Gly Thr Asn Tyr Asn Gln Lys Phe Lys
1               5                   10                  15
Gly

<210> SEQ ID NO 218
<211> LENGTH: 12
<212> TYPE: PRT
<213> ORGANISM: Mus musculus
<400> SEQUENCE: 218

Gly Gly Met Gly Leu Arg Arg Asp Tyr Phe Asp Phe
1               5                   10

<210> SEQ ID NO 219
<211> LENGTH: 52
<212> TYPE: DNA
<213> ORGANISM: Mus musculus
<400> SEQUENCE: 219

```
aagtccagtc agagcctttt atatagtagc aatcaaaaga actacttggc ct          52
```

<210> SEQ ID NO 220
<211> LENGTH: 22
<212> TYPE: DNA
<213> ORGANISM: Mus musculus
<400> SEQUENCE: 220

```
tgggcatcca ctagggaatc tg                                           22
```

<210> SEQ ID NO 221
<211> LENGTH: 28
<212> TYPE: DNA
<213> ORGANISM: Mus musculus
<400> SEQUENCE: 221

```
cagcaatatt atagctatcc gtacacgt                                     28
```

<210> SEQ ID NO 222

```
<211> LENGTH: 17
<212> TYPE: PRT
<213> ORGANISM: Mus musculus

<400> SEQUENCE: 222

Lys Ser Ser Gln Ser Leu Leu Tyr Ser Ser Asn Gln Lys Asn Tyr Leu
1               5                   10                  15

Ala

<210> SEQ ID NO 223
<211> LENGTH: 7
<212> TYPE: PRT
<213> ORGANISM: Mus musculus

<400> SEQUENCE: 223

Trp Ala Ser Thr Arg Glu Ser
1               5

<210> SEQ ID NO 224
<211> LENGTH: 9
<212> TYPE: PRT
<213> ORGANISM: Mus musculus

<400> SEQUENCE: 224

Gln Gln Tyr Tyr Ser Tyr Pro Tyr Thr
1               5

<210> SEQ ID NO 225
<211> LENGTH: 31
<212> TYPE: DNA
<213> ORGANISM: Mus musculus

<400> SEQUENCE: 225
ggctacacct tcacaaccta ctatatacac t                              31

<210> SEQ ID NO 226
<211> LENGTH: 52
<212> TYPE: DNA
<213> ORGANISM: Mus musculus

<400> SEQUENCE: 226 tggattttc ctggaaatgt taatactaag tacaatgcga agttcaaggg ca         52

<210> SEQ ID NO 227
<211> LENGTH: 28
<212> TYPE: DNA
<213> ORGANISM: Mus musculus

<400> SEQUENCE: 227
gagggattac agtactactt tgactact                                   28

<210> SEQ ID NO 228
<211> LENGTH: 10
<212> TYPE: PRT
<213> ORGANISM: Mus musculus

<400> SEQUENCE: 228

Gly Tyr Thr Phe Thr Thr Tyr Tyr Ile His
1               5                   10

<210> SEQ ID NO 229
<211> LENGTH: 17
<212> TYPE: PRT
<213> ORGANISM: Mus musculus
```

```
<400> SEQUENCE: 229

Trp Ile Phe Pro Gly Asn Val Asn Thr Lys Tyr Asn Ala Lys Phe Lys
1               5                   10                  15

Gly

<210> SEQ ID NO 230
<211> LENGTH: 9
<212> TYPE: PRT
<213> ORGANISM: Mus musculus

<400> SEQUENCE: 230

Glu Gly Leu Gln Tyr Tyr Phe Asp Tyr
1               5

<210> SEQ ID NO 231
<211> LENGTH: 31
<212> TYPE: DNA
<213> ORGANISM: Mus musculus

<400> SEQUENCE: 231
agtgccaact caagtgtacg tttcatgttc t                              31

<210> SEQ ID NO 232
<211> LENGTH: 22
<212> TYPE: DNA
<213> ORGANISM: Mus musculus

<400> SEQUENCE: 232
cgcacatcca acctggcttc tg                                        22

<210> SEQ ID NO 233
<211> LENGTH: 28
<212> TYPE: DNA
<213> ORGANISM: Mus musculus

<400> SEQUENCE: 233
cagcagtatc atagttaccc gtggacgt                                  28

<210> SEQ ID NO 234
<211> LENGTH: 10
<212> TYPE: PRT
<213> ORGANISM: Mus musculus

<400> SEQUENCE: 234

Ser Ala Asn Ser Ser Val Arg Phe Met Phe
1               5                   10

<210> SEQ ID NO 235
<211> LENGTH: 7
<212> TYPE: PRT
<213> ORGANISM: Mus musculus

<400> SEQUENCE: 235

Arg Thr Ser Asn Leu Ala Ser
1               5

<210> SEQ ID NO 236
<211> LENGTH: 9
<212> TYPE: PRT
<213> ORGANISM: Mus musculus

<400> SEQUENCE: 236

Gln Gln Tyr His Ser Tyr Pro Trp Thr
1               5
```

<210> SEQ ID NO 237
<211> LENGTH: 31
<212> TYPE: DNA
<213> ORGANISM: Mus musculus

<400> SEQUENCE: 237
ggattcactt tcagtagcta ttatatgtct t                                    31

<210> SEQ ID NO 238
<211> LENGTH: 52
<212> TYPE: PRT
<213> ORGANISM: Mus musculus

<400> SEQUENCE: 238

Gly Cys Cys Ala Thr Thr Ala Ala Thr Ala Thr Ala Ala Thr Gly
1               5                   10                  15

Gly Thr Gly Gly Thr Ala Gly Cys Ala Cys Cys Thr Ala Cys Thr Ala
            20                  25                  30

Thr Cys Cys Ala Gly Ala Cys Ala Cys Thr Gly Thr Gly Ala Ala Gly
        35                  40                  45

Gly Gly Cys Cys
    50

<210> SEQ ID NO 239
<211> LENGTH: 34
<212> TYPE: DNA
<213> ORGANISM: Mus musculus

<400> SEQUENCE: 239
gagttggccg gctatggtac cccgtttgct tact                                 34

<210> SEQ ID NO 240
<211> LENGTH: 10
<212> TYPE: PRT
<213> ORGANISM: Mus musculus

<400> SEQUENCE: 240

Gly Phe Thr Phe Ser Ser Tyr Tyr Met Ser
1               5                   10

<210> SEQ ID NO 241
<211> LENGTH: 17
<212> TYPE: PRT
<213> ORGANISM: Mus musculus

<400> SEQUENCE: 241

Ala Ile Asn Ile Asn Gly Gly Ser Thr Tyr Tyr Pro Asp Thr Val Lys
1               5                   10                  15

Gly

<210> SEQ ID NO 242
<211> LENGTH: 11
<212> TYPE: PRT
<213> ORGANISM: Mus musculus

<400> SEQUENCE: 242

Glu Leu Ala Gly Tyr Gly Thr Pro Phe Ala Tyr
1               5                   10

<210> SEQ ID NO 243
<211> LENGTH: 34
<212> TYPE: DNA

```
<213> ORGANISM: Mus musculus

<400> SEQUENCE: 243
agggccagcc aaagtattag caacaaccta cact                                   34

<210> SEQ ID NO 244
<211> LENGTH: 22
<212> TYPE: DNA
<213> ORGANISM: Mus musculus

<400> SEQUENCE: 244
tatgcttccc agtccatctc tg                                                22

<210> SEQ ID NO 245
<211> LENGTH: 28
<212> TYPE: DNA
<213> ORGANISM: Mus musculus

<400> SEQUENCE: 245
caacagagta acaactggcc gctcacgt                                          28

<210> SEQ ID NO 246
<211> LENGTH: 11
<212> TYPE: PRT
<213> ORGANISM: Mus musculus

<400> SEQUENCE: 246

Arg Ala Ser Gln Ser Ile Ser Asn Asn Leu His
1               5                   10

<210> SEQ ID NO 247
<211> LENGTH: 7
<212> TYPE: PRT
<213> ORGANISM: Mus musculus

<400> SEQUENCE: 247

Tyr Ala Ser Gln Ser Ile Ser
1               5

<210> SEQ ID NO 248
<211> LENGTH: 9
<212> TYPE: PRT
<213> ORGANISM: Mus musculus

<400> SEQUENCE: 248

Gln Gln Ser Asn Asn Trp Pro Leu Thr
1               5

<210> SEQ ID NO 249
<211> LENGTH: 31
<212> TYPE: DNA
<213> ORGANISM: Mus musculus

<400> SEQUENCE: 249
ggattcactt tcagtagctt ttacatgtct t                                      31

<210> SEQ ID NO 250
<211> LENGTH: 52
<212> TYPE: DNA
<213> ORGANISM: Mus musculus

<400> SEQUENCE: 250
accattaata ctaatggtgg tagcacctac tattcagaca ctgtgaaggg cc               52
```

-continued

```
<210> SEQ ID NO 251
<211> LENGTH: 31
<212> TYPE: DNA
<213> ORGANISM: Mus musculus

<400> SEQUENCE: 251
cagccttact acggagggac tatggactac t                              31

<210> SEQ ID NO 252
<211> LENGTH: 10
<212> TYPE: PRT
<213> ORGANISM: Mus musculus

<400> SEQUENCE: 252

Gly Phe Thr Phe Ser Ser Phe Tyr Met Ser
1               5                   10

<210> SEQ ID NO 253
<211> LENGTH: 17
<212> TYPE: PRT
<213> ORGANISM: Mus musculus

<400> SEQUENCE: 253

Thr Ile Asn Thr Asn Gly Gly Ser Thr Tyr Tyr Ser Asp Thr Val Lys
1               5                   10                  15

Gly

<210> SEQ ID NO 254
<211> LENGTH: 10
<212> TYPE: PRT
<213> ORGANISM: Mus musculus

<400> SEQUENCE: 254

Gln Pro Tyr Tyr Gly Gly Thr Met Asp Tyr
1               5                   10

<210> SEQ ID NO 255
<211> LENGTH: 34
<212> TYPE: DNA
<213> ORGANISM: Mus musculus

<400> SEQUENCE: 255
agggccagcc aaagtattaa caacaatcta cact                           34

<210> SEQ ID NO 256
<211> LENGTH: 22
<212> TYPE: DNA
<213> ORGANISM: Mus musculus

<400> SEQUENCE: 256
tatgcttccc agtccatctc tg                                        22

<210> SEQ ID NO 257
<211> LENGTH: 28
<212> TYPE: DNA
<213> ORGANISM: Mus musculus

<400> SEQUENCE: 257
caacagacta caactggcc tctcacgt                                   28

<210> SEQ ID NO 258
<211> LENGTH: 11
<212> TYPE: PRT
<213> ORGANISM: Mus musculus
```

-continued

<400> SEQUENCE: 258

Arg Ala Ser Gln Ser Ile Asn Asn Asn Leu His
1               5                   10

<210> SEQ ID NO 259
<211> LENGTH: 7
<212> TYPE: PRT
<213> ORGANISM: Mus musculus

<400> SEQUENCE: 259

Tyr Ala Ser Gln Ser Ile Ser
1               5

<210> SEQ ID NO 260
<211> LENGTH: 9
<212> TYPE: PRT
<213> ORGANISM: Mus musculus

<400> SEQUENCE: 260

Gln Gln Thr Asn Asn Trp Pro Leu Thr
1               5

<210> SEQ ID NO 261
<211> LENGTH: 34
<212> TYPE: DNA
<213> ORGANISM: Mus musculus

<400> SEQUENCE: 261
ggctactcca tcaccagtgg ttattactgg aact                              34

<210> SEQ ID NO 262
<211> LENGTH: 49
<212> TYPE: DNA
<213> ORGANISM: Mus musculus

<400> SEQUENCE: 262
tacataagct acgacggtag aaataactac aacccatctc tcaaaaatc              49

<210> SEQ ID NO 263
<211> LENGTH: 34
<212> TYPE: DNA
<213> ORGANISM: Mus musculus

<400> SEQUENCE: 263
gaaaatagta actaccctta ctactatgac tact                              34

<210> SEQ ID NO 264
<211> LENGTH: 11
<212> TYPE: PRT
<213> ORGANISM: Mus musculus

<400> SEQUENCE: 264

Gly Tyr Ser Ile Thr Ser Gly Tyr Tyr Trp Asn
1               5                   10

<210> SEQ ID NO 265
<211> LENGTH: 16
<212> TYPE: PRT
<213> ORGANISM: Mus musculus

<400> SEQUENCE: 265

Tyr Ile Ser Tyr Asp Gly Arg Asn Asn Tyr Asn Pro Ser Leu Lys Asn
1               5                   10                  15

<210> SEQ ID NO 266
<211> LENGTH: 11
<212> TYPE: PRT
<213> ORGANISM: Mus musculus

<400> SEQUENCE: 266

Glu Asn Ser Asn Tyr Pro Tyr Tyr Tyr Asp Tyr
1               5                   10

<210> SEQ ID NO 267
<211> LENGTH: 34
<212> TYPE: DNA
<213> ORGANISM: Mus musculus

<400> SEQUENCE: 267
ggctactcca tcaccagtgg ttattactgg aact                                   34

<210> SEQ ID NO 268
<211> LENGTH: 49
<212> TYPE: DNA
<213> ORGANISM: Mus musculus

<400> SEQUENCE: 268
tacataagct acgacggtag aaataactac aacccatctc tcaaaaatc                   49

<210> SEQ ID NO 269
<211> LENGTH: 34
<212> TYPE: DNA
<213> ORGANISM: Mus musculus

<400> SEQUENCE: 269
gaaaatagta actacccttα ctactatgac tact                                   34

<210> SEQ ID NO 270
<211> LENGTH: 11
<212> TYPE: PRT
<213> ORGANISM: Mus musculus

<400> SEQUENCE: 270

Gly Tyr Ser Ile Thr Ser Gly Tyr Tyr Trp Asn
1               5                   10

<210> SEQ ID NO 271
<211> LENGTH: 16
<212> TYPE: PRT
<213> ORGANISM: Mus musculus

<400> SEQUENCE: 271

Tyr Ile Ser Tyr Asp Gly Arg Asn Asn Tyr Asn Pro Ser Leu Lys Asn
1               5                   10                  15

<210> SEQ ID NO 272
<211> LENGTH: 11
<212> TYPE: PRT
<213> ORGANISM: Mus musculus

<400> SEQUENCE: 272

Glu Asn Ser Asn Tyr Pro Tyr Tyr Tyr Asp Tyr
1               5                   10

<210> SEQ ID NO 273
<211> LENGTH: 31
<212> TYPE: DNA
<213> ORGANISM: Mus musculus

<400> SEQUENCE: 273

```
ggattcagtt tcagtacctc ttacatgtct t                                    31

<210> SEQ ID NO 274
<211> LENGTH: 52
<212> TYPE: DNA
<213> ORGANISM: Mus musculus

<400> SEQUENCE: 274
gccattaatc ttaatggtgg tagtacctac tattcagaca ctgtgaaggg cc             52

<210> SEQ ID NO 275
<211> LENGTH: 34
<212> TYPE: DNA
<213> ORGANISM: Mus musculus

<400> SEQUENCE: 275
gagttggccg ggtatggtac cccgtttgct tact                                 34

<210> SEQ ID NO 276
<211> LENGTH: 10
<212> TYPE: PRT
<213> ORGANISM: Mus musculus

<400> SEQUENCE: 276

Gly Phe Ser Phe Ser Thr Ser Tyr Met Ser
1               5                   10

<210> SEQ ID NO 277
<211> LENGTH: 17
<212> TYPE: PRT
<213> ORGANISM: Mus musculus

<400> SEQUENCE: 277

Ala Ile Asn Leu Asn Gly Gly Ser Thr Tyr Tyr Ser Asp Thr Val Lys
1               5                   10                  15

Gly

<210> SEQ ID NO 278
<211> LENGTH: 11
<212> TYPE: PRT
<213> ORGANISM: Mus musculus

<400> SEQUENCE: 278

Glu Leu Ala Gly Tyr Gly Thr Pro Phe Ala Tyr
1               5                   10

<210> SEQ ID NO 279
<211> LENGTH: 34
<212> TYPE: DNA
<213> ORGANISM: Mus musculus

<400> SEQUENCE: 279
aaggccagcc aaagtattag caacaaccta cact                                 34

<210> SEQ ID NO 280
<211> LENGTH: 22
<212> TYPE: DNA
<213> ORGANISM: Mus musculus

<400> SEQUENCE: 280
tatacttccc agtccatctc tg                                              22

<210> SEQ ID NO 281
```

-continued

```
<211> LENGTH: 28
<212> TYPE: DNA
<213> ORGANISM: Mus musculus

<400> SEQUENCE: 281
caacagagta acagttggcc gctcacgt                                          28

<210> SEQ ID NO 282
<211> LENGTH: 11
<212> TYPE: PRT
<213> ORGANISM: Mus musculus

<400> SEQUENCE: 282

Lys Ala Ser Gln Ser Ile Ser Asn Asn Leu His
1               5                   10

<210> SEQ ID NO 283
<211> LENGTH: 7
<212> TYPE: PRT
<213> ORGANISM: Mus musculus

<400> SEQUENCE: 283

Tyr Thr Ser Gln Ser Ile Ser
1               5

<210> SEQ ID NO 284
<211> LENGTH: 9
<212> TYPE: PRT
<213> ORGANISM: Mus musculus

<400> SEQUENCE: 284

Gln Gln Ser Asn Ser Trp Pro Leu Thr
1               5

<210> SEQ ID NO 285
<211> LENGTH: 31
<212> TYPE: DNA
<213> ORGANISM: Mus musculus

<400> SEQUENCE: 285
ggattcactt tcagtagctt ttacatgtct t                                      31

<210> SEQ ID NO 286
<211> LENGTH: 52
<212> TYPE: DNA
<213> ORGANISM: Mus musculus

<400> SEQUENCE: 286
accattaata ctaatggtgg tagcacctac tattcagaca ctgtgaaggg cc               52

<210> SEQ ID NO 287
<211> LENGTH: 31
<212> TYPE: DNA
<213> ORGANISM: Mus musculus

<400> SEQUENCE: 287
cagccttact acggagggac tatggactac t                                      31

<210> SEQ ID NO 288
<211> LENGTH: 10
<212> TYPE: PRT
<213> ORGANISM: Mus musculus

<400> SEQUENCE: 288

Gly Phe Thr Phe Ser Ser Phe Tyr Met Ser
```

```
<210> SEQ ID NO 289
<211> LENGTH: 17
<212> TYPE: PRT
<213> ORGANISM: Mus musculus

<400> SEQUENCE: 289

Thr Ile Asn Thr Asn Gly Gly Ser Thr Tyr Tyr Ser Asp Thr Val Lys
1               5                   10                  15
Gly

<210> SEQ ID NO 290
<211> LENGTH: 10
<212> TYPE: PRT
<213> ORGANISM: Mus musculus

<400> SEQUENCE: 290

Gln Pro Tyr Tyr Gly Gly Thr Met Asp Tyr
1               5                   10

<210> SEQ ID NO 291
<211> LENGTH: 34
<212> TYPE: DNA
<213> ORGANISM: Mus musculus

<400> SEQUENCE: 291
agggccagcc aaagtattaa caacaatcta cact                              34

<210> SEQ ID NO 292
<211> LENGTH: 22
<212> TYPE: DNA
<213> ORGANISM: Mus musculus

<400> SEQUENCE: 292
tatgcttccc agtccatctc tg                                           22

<210> SEQ ID NO 293
<211> LENGTH: 28
<212> TYPE: DNA
<213> ORGANISM: Mus musculus

<400> SEQUENCE: 293
caacagacta acaactggcc tctcacgt                                     28

<210> SEQ ID NO 294
<211> LENGTH: 11
<212> TYPE: PRT
<213> ORGANISM: Mus musculus

<400> SEQUENCE: 294

Arg Ala Ser Gln Ser Ile Asn Asn Asn Leu His
1               5                   10

<210> SEQ ID NO 295
<211> LENGTH: 7
<212> TYPE: PRT
<213> ORGANISM: Mus musculus

<400> SEQUENCE: 295

Tyr Ala Ser Gln Ser Ile Ser
1               5

<210> SEQ ID NO 296
```

```
<211> LENGTH: 9
<212> TYPE: PRT
<213> ORGANISM: Mus musculus

<400> SEQUENCE: 296

Gln Gln Thr Asn Asn Trp Pro Leu Thr
1               5

<210> SEQ ID NO 297
<211> LENGTH: 30
<212> TYPE: DNA
<213> ORGANISM: Mus musculus

<400> SEQUENCE: 297
ggctacacct tcacaaacta ctatttacac                              30

<210> SEQ ID NO 298
<211> LENGTH: 51
<212> TYPE: DNA
<213> ORGANISM: Mus musculus

<400> SEQUENCE: 298
tggatttatc ctggaaatgt taatactaag tacaatgaga agttcaaggg c       51

<210> SEQ ID NO 299
<211> LENGTH: 27
<212> TYPE: DNA
<213> ORGANISM: Mus musculus

<400> SEQUENCE: 299
gagggattac agtactactt tgactac                                 27

<210> SEQ ID NO 300
<211> LENGTH: 10
<212> TYPE: PRT
<213> ORGANISM: Mus musculus

<400> SEQUENCE: 300

Gly Tyr Thr Phe Thr Asn Tyr Tyr Leu His
1               5                   10

<210> SEQ ID NO 301
<211> LENGTH: 17
<212> TYPE: PRT
<213> ORGANISM: Mus musculus

<400> SEQUENCE: 301

Trp Ile Tyr Pro Gly Asn Val Asn Thr Lys Tyr Asn Glu Lys Phe Lys
1               5                   10                  15

Gly

<210> SEQ ID NO 302
<211> LENGTH: 9
<212> TYPE: PRT
<213> ORGANISM: Mus musculus

<400> SEQUENCE: 302

Glu Gly Leu Gln Tyr Tyr Phe Asp Tyr
1               5

<210> SEQ ID NO 303
<211> LENGTH: 31
<212> TYPE: DNA
<213> ORGANISM: Mus musculus
```

```
<400> SEQUENCE: 303
agtgccaact caagtgtacg ttacatgttc t                              31

<210> SEQ ID NO 304
<211> LENGTH: 22
<212> TYPE: DNA
<213> ORGANISM: Mus musculus

<400> SEQUENCE: 304
cgcacatcca acctggcttc tg                                        22

<210> SEQ ID NO 305
<211> LENGTH: 28
<212> TYPE: DNA
<213> ORGANISM: Mus musculus

<400> SEQUENCE: 305
cagcagtatc atagttaccc gtggacgt                                  28

<210> SEQ ID NO 306
<211> LENGTH: 10
<212> TYPE: PRT
<213> ORGANISM: Mus musculus

<400> SEQUENCE: 306

Ser Ala Asn Ser Ser Val Arg Tyr Met Phe
1               5                   10

<210> SEQ ID NO 307
<211> LENGTH: 7
<212> TYPE: PRT
<213> ORGANISM: Mus musculus

<400> SEQUENCE: 307

Arg Thr Ser Asn Leu Ala Ser
1               5

<210> SEQ ID NO 308
<211> LENGTH: 9
<212> TYPE: PRT
<213> ORGANISM: Mus musculus

<400> SEQUENCE: 308

Gln Gln Tyr His Ser Tyr Pro Trp Thr
1               5

<210> SEQ ID NO 309
<211> LENGTH: 31
<212> TYPE: DNA
<213> ORGANISM: Mus musculus

<400> SEQUENCE: 309
ggctacacct ttactagcta ctggatgcac t                              31

<210> SEQ ID NO 310
<211> LENGTH: 52
<212> TYPE: DNA
<213> ORGANISM: Mus musculus

<400> SEQUENCE: 310
tacattaatc ctaacactgg ttatagtgag tacaatcaaa agttcaggga ca        52

<210> SEQ ID NO 311
<211> LENGTH: 49
```

<212> TYPE: DNA
<213> ORGANISM: Mus musculus

<400> SEQUENCE: 311
actgcacaat actacggtag tcctagggdt tactatgcta tggactcct        49

<210> SEQ ID NO 312
<211> LENGTH: 10
<212> TYPE: PRT
<213> ORGANISM: Mus musculus

<400> SEQUENCE: 312

Gly Tyr Thr Phe Thr Ser Tyr Trp Met His
1               5                   10

<210> SEQ ID NO 313
<211> LENGTH: 17
<212> TYPE: PRT
<213> ORGANISM: Mus musculus

<400> SEQUENCE: 313

Tyr Ile Asn Pro Asn Thr Gly Tyr Ser Glu Tyr Asn Gln Lys Phe Arg
1               5                   10                  15

Asp

<210> SEQ ID NO 314
<211> LENGTH: 16
<212> TYPE: PRT
<213> ORGANISM: Mus musculus

<400> SEQUENCE: 314

Thr Ala Gln Tyr Tyr Gly Ser Pro Arg Gly Tyr Tyr Ala Met Asp Ser
1               5                   10                  15

<210> SEQ ID NO 315
<211> LENGTH: 49
<212> TYPE: DNA
<213> ORGANISM: Mus musculus

<400> SEQUENCE: 315
aggtctagta agagtctcct acatagtaac ggcatcactt atttgtgtt         49

<210> SEQ ID NO 316
<211> LENGTH: 22
<212> TYPE: DNA
<213> ORGANISM: Mus musculus

<400> SEQUENCE: 316
cagatgtcca accttgcctc ag                                      22

<210> SEQ ID NO 317
<211> LENGTH: 28
<212> TYPE: DNA
<213> ORGANISM: Mus musculus

<400> SEQUENCE: 317
gctcaaaatc tagatctgcc gtggacgt                                28

<210> SEQ ID NO 318
<211> LENGTH: 16
<212> TYPE: PRT
<213> ORGANISM: Mus musculus

<400> SEQUENCE: 318

-continued

Arg Ser Ser Lys Ser Leu Leu His Ser Asn Gly Ile Thr Tyr Leu Cys
1               5                   10                  15

<210> SEQ ID NO 319
<211> LENGTH: 7
<212> TYPE: PRT
<213> ORGANISM: Mus musculus

<400> SEQUENCE: 319

Gln Met Ser Asn Leu Ala Ser
1               5

<210> SEQ ID NO 320
<211> LENGTH: 9
<212> TYPE: PRT
<213> ORGANISM: Mus musculus

<400> SEQUENCE: 320

Ala Gln Asn Leu Asp Leu Pro Trp Thr
1               5

<210> SEQ ID NO 321
<211> LENGTH: 31
<212> TYPE: DNA
<213> ORGANISM: Mus musculus

<400> SEQUENCE: 321
ggctacacct tcacaaccta ctatatacac t                                      31

<210> SEQ ID NO 322
<211> LENGTH: 52
<212> TYPE: DNA
<213> ORGANISM: Mus musculus

<400> SEQUENCE: 322 tggattttc ctggaaatgt taatactaag tacaatgcga agttcaaggg ca                52

<210> SEQ ID NO 323
<211> LENGTH: 28
<212> TYPE: DNA
<213> ORGANISM: Mus musculus

<400> SEQUENCE: 323
gaggaattac agtactactt tgactact                                          28

<210> SEQ ID NO 324
<211> LENGTH: 10
<212> TYPE: PRT
<213> ORGANISM: Mus musculus

<400> SEQUENCE: 324

Gly Tyr Thr Phe Thr Thr Tyr Tyr Ile His
1               5                   10

<210> SEQ ID NO 325
<211> LENGTH: 17
<212> TYPE: PRT
<213> ORGANISM: Mus musculus

<400> SEQUENCE: 325

Trp Ile Phe Pro Gly Asn Val Asn Thr Lys Tyr Asn Ala Lys Phe Lys
1               5                   10                  15
Gly

<210> SEQ ID NO 326
<211> LENGTH: 9
<212> TYPE: PRT
<213> ORGANISM: Mus musculus

<400> SEQUENCE: 326

Glu Glu Leu Gln Tyr Tyr Phe Asp Tyr
1               5

<210> SEQ ID NO 327
<211> LENGTH: 31
<212> TYPE: DNA
<213> ORGANISM: Mus musculus

<400> SEQUENCE: 327
agtgccaact caagtgtacg tttcatgttc t                              31

<210> SEQ ID NO 328
<211> LENGTH: 22
<212> TYPE: DNA
<213> ORGANISM: Mus musculus

<400> SEQUENCE: 328
cgcacatcca acctggcttc tg                                        22

<210> SEQ ID NO 329
<211> LENGTH: 28
<212> TYPE: DNA
<213> ORGANISM: Mus musculus

<400> SEQUENCE: 329
cagcagtatc atagttaccc gtggacgt                                  28

<210> SEQ ID NO 330
<211> LENGTH: 10
<212> TYPE: PRT
<213> ORGANISM: Mus musculus

<400> SEQUENCE: 330

Ser Ala Asn Ser Ser Val Arg Phe Met Phe
1               5                   10

<210> SEQ ID NO 331
<211> LENGTH: 7
<212> TYPE: PRT
<213> ORGANISM: Mus musculus

<400> SEQUENCE: 331

Arg Thr Ser Asn Leu Ala Ser
1               5

<210> SEQ ID NO 332
<211> LENGTH: 9
<212> TYPE: PRT
<213> ORGANISM: Mus musculus

<400> SEQUENCE: 332

Gln Gln Tyr His Ser Tyr Pro Trp Thr
1               5

<210> SEQ ID NO 333
<211> LENGTH: 31
<212> TYPE: DNA
<213> ORGANISM: Mus musculus

<400> SEQUENCE: 333

```
ggctacacct ttactagcta ctggatgcac t                              31

<210> SEQ ID NO 334
<211> LENGTH: 52
<212> TYPE: DNA
<213> ORGANISM: Mus musculus

<400> SEQUENCE: 334
tacattaatc ctagtactgg ttatactgag tacaatcaga agttcaggga ca        52

<210> SEQ ID NO 335
<211> LENGTH: 49
<212> TYPE: DNA
<213> ORGANISM: Mus musculus

<400> SEQUENCE: 335
actgcgcaat actacggtag tcctaggggt tactatgcta tggactcct           49

<210> SEQ ID NO 336
<211> LENGTH: 10
<212> TYPE: PRT
<213> ORGANISM: Mus musculus

<400> SEQUENCE: 336

Gly Tyr Thr Phe Thr Ser Tyr Trp Met His
1               5                   10

<210> SEQ ID NO 337
<211> LENGTH: 17
<212> TYPE: PRT
<213> ORGANISM: Mus musculus

<400> SEQUENCE: 337

Tyr Ile Asn Pro Ser Thr Gly Tyr Thr Glu Tyr Asn Gln Lys Phe Arg
1               5                   10                  15

Asp

<210> SEQ ID NO 338
<211> LENGTH: 16
<212> TYPE: PRT
<213> ORGANISM: Mus musculus

<400> SEQUENCE: 338

Thr Ala Gln Tyr Tyr Gly Ser Pro Arg Gly Tyr Tyr Ala Met Asp Ser
1               5                   10                  15

<210> SEQ ID NO 339
<211> LENGTH: 49
<212> TYPE: DNA
<213> ORGANISM: Mus musculus

<400> SEQUENCE: 339
aggtctagta agagtctcct acatagtaac ggcatcactt atttgtgtt           49

<210> SEQ ID NO 340
<211> LENGTH: 22
<212> TYPE: DNA
<213> ORGANISM: Mus musculus

<400> SEQUENCE: 340
ctgatgtcca accttgcctc ag                                        22

<210> SEQ ID NO 341
```

```
<211> LENGTH: 28
<212> TYPE: DNA
<213> ORGANISM: Mus musculus

<400> SEQUENCE: 341
gctcaaaatc tagatcttcc gtggacgt                                            28

<210> SEQ ID NO 342
<211> LENGTH: 16
<212> TYPE: PRT
<213> ORGANISM: Mus musculus

<400> SEQUENCE: 342

Arg Ser Ser Lys Ser Leu Leu His Ser Asn Gly Ile Thr Tyr Leu Cys
1               5                   10                  15

<210> SEQ ID NO 343
<211> LENGTH: 7
<212> TYPE: PRT
<213> ORGANISM: Mus musculus

<400> SEQUENCE: 343

Leu Met Ser Asn Leu Ala Ser
1               5

<210> SEQ ID NO 344
<211> LENGTH: 9
<212> TYPE: PRT
<213> ORGANISM: Mus musculus

<400> SEQUENCE: 344

Ala Gln Asn Leu Asp Leu Pro Trp Thr
1               5

<210> SEQ ID NO 345
<211> LENGTH: 31
<212> TYPE: DNA
<213> ORGANISM: Mus musculus

<400> SEQUENCE: 345
ggattcactt tcagtagctt ttacatgtct t                                        31

<210> SEQ ID NO 346
<211> LENGTH: 52
<212> TYPE: DNA
<213> ORGANISM: Mus musculus

<400> SEQUENCE: 346
gccattaata ctaatggtgg tagcacctac tattcagaca ctgtgaaggg cc                 52

<210> SEQ ID NO 347
<211> LENGTH: 31
<212> TYPE: DNA
<213> ORGANISM: Mus musculus

<400> SEQUENCE: 347
cagccttact acggagggcc tatggacttc t                                        31

<210> SEQ ID NO 348
<211> LENGTH: 10
<212> TYPE: PRT
<213> ORGANISM: Mus musculus

<400> SEQUENCE: 348

Gly Phe Thr Phe Ser Ser Phe Tyr Met Ser
```

```
1               5                   10
```

<210> SEQ ID NO 349
<211> LENGTH: 17
<212> TYPE: PRT
<213> ORGANISM: Mus musculus

<400> SEQUENCE: 349

```
Ala Ile Asn Thr Asn Gly Gly Ser Thr Tyr Tyr Ser Asp Thr Val Lys
1               5                   10                  15

Gly
```

<210> SEQ ID NO 350
<211> LENGTH: 10
<212> TYPE: PRT
<213> ORGANISM: Mus musculus

<400> SEQUENCE: 350

```
Gln Pro Tyr Tyr Gly Gly Pro Met Asp Phe
1               5                   10
```

<210> SEQ ID NO 351
<211> LENGTH: 34
<212> TYPE: DNA
<213> ORGANISM: Mus musculus

<400> SEQUENCE: 351

```
agggccagcc aaagtattaa caacaaccta cact                              34
```

<210> SEQ ID NO 352
<211> LENGTH: 22
<212> TYPE: DNA
<213> ORGANISM: Mus musculus

<400> SEQUENCE: 352

```
tatgcttccc agtccatctc tg                                          22
```

<210> SEQ ID NO 353
<211> LENGTH: 28
<212> TYPE: DNA
<213> ORGANISM: Mus musculus

<400> SEQUENCE: 353

```
caacagagta acaactggcc tctcacgt                                    28
```

<210> SEQ ID NO 354
<211> LENGTH: 11
<212> TYPE: PRT
<213> ORGANISM: Mus musculus

<400> SEQUENCE: 354

```
Arg Ala Ser Gln Ser Ile Asn Asn Asn Leu His
1               5                   10
```

<210> SEQ ID NO 355
<211> LENGTH: 7
<212> TYPE: PRT
<213> ORGANISM: Mus musculus

<400> SEQUENCE: 355

```
Tyr Ala Ser Gln Ser Ile Ser
1               5
```

<210> SEQ ID NO 356

```
<211> LENGTH: 9
<212> TYPE: PRT
<213> ORGANISM: Mus musculus

<400> SEQUENCE: 356

Gln Gln Ser Asn Asn Trp Pro Leu Thr
1               5

<210> SEQ ID NO 357
<211> LENGTH: 30
<212> TYPE: DNA
<213> ORGANISM: Mus musculus

<400> SEQUENCE: 357
ggattcactt tcagtagatt ttacatgtct                               30

<210> SEQ ID NO 358
<211> LENGTH: 51
<212> TYPE: DNA
<213> ORGANISM: Mus musculus

<400> SEQUENCE: 358
gccattaata ctaatggtgg tagcacctat tattcagaca ctgtgaaggg c         51

<210> SEQ ID NO 359
<211> LENGTH: 30
<212> TYPE: DNA
<213> ORGANISM: Mus musculus

<400> SEQUENCE: 359
cagccttact acggagggcc tatggagttc                               30

<210> SEQ ID NO 360
<211> LENGTH: 10
<212> TYPE: PRT
<213> ORGANISM: Mus musculus

<400> SEQUENCE: 360

Gly Phe Thr Phe Ser Arg Phe Tyr Met Ser
1               5                   10

<210> SEQ ID NO 361
<211> LENGTH: 17
<212> TYPE: PRT
<213> ORGANISM: Mus musculus

<400> SEQUENCE: 361

Ala Ile Asn Thr Asn Gly Gly Ser Thr Tyr Tyr Ser Asp Thr Val Lys
1               5                   10                  15

Gly

<210> SEQ ID NO 362
<211> LENGTH: 10
<212> TYPE: PRT
<213> ORGANISM: Mus musculus

<400> SEQUENCE: 362

Gln Pro Tyr Tyr Gly Gly Pro Met Glu Phe
1               5                   10

<210> SEQ ID NO 363
<211> LENGTH: 34
<212> TYPE: DNA
```

-continued

```
<400> SEQUENCE: 363
aaggccagtc agaatgtggg tactaatgta gcct                                    34

<210> SEQ ID NO 364
<211> LENGTH: 22
<212> TYPE: DNA
<213> ORGANISM: Mus musculus

<400> SEQUENCE: 364
tcggcatcct accggtacag tg                                                 22

<210> SEQ ID NO 365
<211> LENGTH: 28
<212> TYPE: DNA
<213> ORGANISM: Mus musculus

<400> SEQUENCE: 365
cagcaatata acagctatcc tctcacgt                                           28

<210> SEQ ID NO 366
<211> LENGTH: 11
<212> TYPE: PRT
<213> ORGANISM: Mus musculus

<400> SEQUENCE: 366

Lys Ala Ser Gln Asn Val Gly Thr Asn Val Ala
1               5                   10

<210> SEQ ID NO 367
<211> LENGTH: 7
<212> TYPE: PRT
<213> ORGANISM: Mus musculus

<400> SEQUENCE: 367

Ser Ala Ser Tyr Arg Tyr Ser
1               5

<210> SEQ ID NO 368
<211> LENGTH: 9
<212> TYPE: PRT
<213> ORGANISM: Mus musculus

<400> SEQUENCE: 368

Gln Gln Tyr Asn Ser Tyr Pro Leu Thr
1               5

<210> SEQ ID NO 369
<211> LENGTH: 10
<212> TYPE: DNA
<213> ORGANISM: Artificial
<220> FEATURE:
<223> OTHER INFORMATION: TCF Consensus sequence

<400> SEQUENCE: 369
agatcaaagg                                                               10

<210> SEQ ID NO 370
<211> LENGTH: 276
<212> TYPE: PRT
<213> ORGANISM: Homo sapiens

<400> SEQUENCE: 370

Ile Val Leu Gln Leu Glu Asp Ile Arg His Ala Ile Ala Ile Asp Tyr
1               5                   10                  15
```

```
Asp Pro Val Glu Gly Tyr Ile Tyr Trp Thr Asp Glu Val Arg Ala
                20                  25                  30

Ile Arg Arg Ser Phe Ile Asp Gly Ser Gly Ser Gln Phe Val Val Thr
         35                  40                  45

Ala Gln Ile Ala His Pro Asp Gly Ile Ala Val Asp Trp Val Ala Arg
 50                  55                  60

Asn Leu Tyr Trp Thr Asp Thr Gly Thr Asp Arg Ile Glu Val Thr Arg
 65                  70                  75                  80

Leu Asn Gly Thr Met Arg Lys Ile Leu Ile Ser Glu Asp Leu Glu Glu
                 85                  90                  95

Pro Arg Ala Ile Val Leu Asp Pro Met Val Gly Tyr Met Tyr Trp Thr
                100                 105                 110

Asp Trp Gly Glu Ile Pro Lys Ile Glu Arg Ala Ala Leu Asp Gly Ser
            115                 120                 125

Asp Arg Val Val Leu Val Asn Thr Ser Leu Gly Trp Pro Asn Gly Leu
130                 135                 140

Ala Leu Asp Tyr Asp Glu Gly Lys Ile Tyr Trp Gly Asp Ala Lys Thr
145                 150                 155                 160

Asp Lys Ile Glu Val Met Asn Thr Asp Gly Thr Gly Arg Arg Val Leu
                165                 170                 175

Val Glu Asp Lys Ile Pro His Ile Phe Gly Phe Thr Leu Leu Gly Asp
                180                 185                 190

Tyr Val Tyr Trp Thr Asp Trp Gln Arg Arg Ser Ile Glu Arg Val His
            195                 200                 205

Lys Arg Ser Ala Glu Arg Glu Val Ile Ile Asp Gln Leu Pro Asp Leu
210                 215                 220

Met Gly Leu Lys Ala Thr Asn Val His Arg Val Ile Gly Ser Asn Pro
225                 230                 235                 240

Cys Ala Glu Glu Asn Gly Gly Cys Ser His Leu Cys Leu Tyr Arg Pro
                245                 250                 255

Gln Gly Leu Arg Cys Ala Cys Pro Ile Gly Phe Glu Leu Ile Ser Asp
            260                 265                 270

Met Lys Thr Cys
        275

<210> SEQ ID NO 371
<211> LENGTH: 48
<212> TYPE: PRT
<213> ORGANISM: Homo sapiens

<400> SEQUENCE: 371

Ile Leu Tyr Trp Thr Asp Trp Ser Thr His Ser Ile Leu Ala Cys Asn
1               5                   10                  15

Lys Tyr Thr Gly Glu Gly Leu Arg Glu Ile His Ser Asp Ile Phe Ser
            20                  25                  30

Pro Met Asp Ile His Ala Phe Ser Gln Gln Arg Gln Pro Asn Ala Thr
        35                  40                  45

<210> SEQ ID NO 372
<211> LENGTH: 48
<212> TYPE: PRT
<213> ORGANISM: Mus musculus

<400> SEQUENCE: 372

Thr Leu Tyr Trp Thr Asp Trp Asn Thr His Ser Ile Leu Ala Cys Asn
1               5                   10                  15

Lys Tyr Thr Gly Glu Gly Leu Arg Glu Ile His Ser Asn Ile Phe Ser
```

-continued

```
                20                  25                  30
Pro Met Asp Ile His Ala Phe Ser Gln Gln Arg Gln Pro Asn Ala Thr
            35                  40                  45

<210> SEQ ID NO 373
<211> LENGTH: 1613
<212> TYPE: PRT
<213> ORGANISM: Mus musculus

<400> SEQUENCE: 373

Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
                20                  25                  30

Leu Val Asp Ala Thr Asn Gly Lys Glu Asn Ala Thr Ile Val Val Gly
            35                  40                  45

Gly Leu Glu Asp Ala Ala Val Asp Phe Val Phe Gly His Gly Leu
        50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Ser Gly Leu Leu Ser
                85                  90                  95

Pro Asp Gly Leu Ala Cys Asp Trp Leu Gly Glu Lys Leu Tyr Trp Thr
            100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Val Ile
                165                 170                 175

Ile Asn Thr Glu Ile Tyr Trp Pro Asn Gly Leu Thr Leu Asp Tyr Gln
            180                 185                 190

Glu Arg Lys Leu Tyr Trp Ala Asp Ala Lys Leu Asn Phe Ile His Lys
        195                 200                 205

Ser Asn Leu Asp Gly Thr Asn Arg Gln Ala Val Val Lys Gly Ser Leu
    210                 215                 220

Pro His Pro Phe Ala Leu Thr Leu Phe Glu Asp Thr Leu Tyr Trp Thr
225                 230                 235                 240

Asp Trp Asn Thr His Ser Ile Leu Ala Cys Asn Lys Tyr Thr Gly Glu
                245                 250                 255

Gly Leu Arg Glu Ile His Ser Asn Ile Phe Ser Pro Met Asp Ile His
            260                 265                 270

Ala Phe Ser Gln Gln Arg Gln Pro Asn Ala Thr Asn Pro Cys Gly Ile
        275                 280                 285

Asp Asn Gly Gly Cys Ser His Leu Cys Leu Met Ser Pro Val Lys Pro
    290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
```

```
                355                 360                 365
Pro Val Glu Gly Tyr Ile Tyr Trp Thr Asp Asp Glu Val Arg Ala Ile
370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
                420                 425                 430

Asn Gly Thr Met Arg Lys Ile Leu Ile Ser Glu Asp Leu Glu Glu Pro
                435                 440                 445

Arg Ala Ile Val Leu Asp Pro Met Val Gly Tyr Met Tyr Trp Thr Asp
450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Thr Ile Tyr Trp Gly Asp Ala Lys Thr Asp
                500                 505                 510

Lys Ile Glu Val Met Asn Thr Asp Gly Thr Gly Arg Arg Val Leu Val
                515                 520                 525

Glu Asp Lys Ile Pro His Ile Phe Gly Phe Thr Leu Leu Gly Asp Tyr
530                 535                 540

Val Tyr Trp Thr Asp Trp Gln Arg Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Ser Val His Arg Ile Ile Gly Ser Asn Pro Cys
                580                 585                 590

Ala Glu Asp Asn Gly Gly Cys Ser His Leu Cys Leu Tyr Arg Pro Gln
                595                 600                 605

Gly Leu Arg Cys Ala Cys Pro Ile Gly Phe Glu Leu Ile Ser Asp Met
610                 615                 620

Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Val Ala Ile
                645                 650                 655

Pro Leu Thr Gly Val Lys Glu Ala Ser Ala Leu Asp Phe Asp Val Thr
                660                 665                 670

Asp Asn Arg Ile Tyr Trp Thr Asp Ile Ser Leu Lys Thr Ile Ser Arg
                675                 680                 685

Ala Phe Met Asn Gly Ser Ala Leu Glu His Val Val Glu Phe Gly Leu
690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
                740                 745                 750

Leu Ala Leu Asp Pro Ala Glu Gly Phe Met Tyr Trp Thr Glu Trp Gly
                755                 760                 765

Gly Lys Pro Lys Ile Asp Arg Ala Ala Met Asp Gly Ser Glu Arg Thr
770                 775                 780
```

-continued

Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
            805                 810                 815

Ser Ser Asp Met Leu Gly Leu Asn Arg Glu Val Ile Ala Asp Asp Leu
            820                 825                 830

Pro His Pro Phe Gly Leu Thr Gln Tyr Gln Asp Tyr Ile Tyr Trp Thr
            835                 840                 845

Asp Trp Ser Arg Arg Ser Ile Glu Arg Ala Asn Lys Thr Ser Gly Gln
            850                 855                 860

Asn Arg Thr Ile Ile Gln Gly His Leu Asp Tyr Val Met Asp Ile Leu
865                 870                 875                 880

Val Phe His Ser Ser Arg Gln Ala Gly Trp Asn Glu Cys Ala Ser Ser
            885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
            915                 920                 925

Cys Ser Ala Pro Thr Thr Phe Leu Leu Phe Ser Gln Lys Ser Ala Ile
930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
            965                 970                 975

Lys Gln Leu Tyr Trp Ile Asp Ser Arg Gln Asn Ser Ile Arg Lys Ala
            980                 985                 990

His Glu Asp Gly Gly Gln Gly Phe Asn Val Val Ala Asn Ser Val Ala
            995                 1000                1005

Asn Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035

Asp Val Thr Arg Leu Asp Gly Arg Ser Val Gly Val Val Leu Lys
    1040                1045                1050

Gly Glu Gln Asp Arg Pro Arg Ala Ile Val Val Asn Pro Glu Lys
    1055                1060                1065

Gly Tyr Met Tyr Phe Thr Asn Leu Gln Glu Arg Ser Pro Lys Ile
    1070                1075                1080

Glu Arg Ala Ala Leu Asp Gly Thr Glu Arg Glu Val Leu Phe Phe
    1085                1090                1095

Ser Gly Leu Ser Lys Pro Ile Ala Leu Ala Leu Asp Ser Lys Leu
    1100                1105                1110

Gly Lys Leu Phe Trp Ala Asp Ser Asp Leu Arg Arg Ile Glu Ser
    1115                1120                1125

Ser Asp Leu Ser Gly Ala Asn Arg Ile Val Leu Glu Asp Ser Asn
    1130                1135                1140

Ile Leu Gln Pro Val Gly Leu Thr Val Phe Glu Asn Trp Leu Tyr
    1145                1150                1155

Trp Ile Asp Lys Gln Gln Gln Met Ile Glu Lys Ile Asp Met Thr
    1160                1165                1170

Gly Arg Glu Gly Arg Thr Lys Val Gln Ala Arg Ile Ala Gln Leu
    1175                1180                1185

Ser Asp Ile His Ala Val Lys Glu Leu Asn Leu Gln Glu Tyr Arg
    1190                1195                1200

-continued

```
Gln His Pro Cys Ala Gln Asp Asn Gly Gly Cys Ser His Ile Cys
    1205                1210                1215
Leu Val Lys Gly Asp Gly Thr Thr Arg Cys Ser Cys Pro Met His
    1220                1225                1230
Leu Val Leu Leu Gln Asp Glu Leu Ser Cys Gly Glu Pro Pro Thr
    1235                1240                1245
Cys Ser Pro Gln Gln Phe Thr Cys Phe Thr Gly Asp Ile Asp Cys
    1250                1255                1260
Ile Pro Val Ala Trp Arg Cys Asp Gly Phe Thr Glu Cys Glu Asp
    1265                1270                1275
His Ser Asp Glu Leu Asn Cys Pro Val Cys Ser Glu Ser Gln Phe
    1280                1285                1290
Gln Cys Ala Ser Gly Gln Cys Ile Asp Gly Ala Leu Arg Cys Asn
    1295                1300                1305
Gly Asp Ala Asn Cys Gln Asp Lys Ser Asp Glu Lys Asn Cys Glu
    1310                1315                1320
Val Leu Cys Leu Ile Asp Gln Phe Arg Cys Ala Asn Gly Gln Cys
    1325                1330                1335
Val Gly Lys His Lys Lys Cys Asp His Ser Val Asp Cys Ser Asp
    1340                1345                1350
Arg Ser Asp Glu Leu Asp Cys Tyr Pro Thr Glu Glu Pro Ala Pro
    1355                1360                1365
Gln Ala Thr Asn Thr Val Gly Ser Val Ile Gly Val Ile Val Thr
    1370                1375                1380
Ile Phe Val Ser Gly Thr Ile Tyr Phe Ile Cys Gln Arg Met Leu
    1385                1390                1395
Cys Pro Arg Met Lys Gly Asp Gly Glu Thr Met Thr Asn Asp Tyr
    1400                1405                1410
Val Val His Ser Pro Ala Ser Val Pro Leu Gly Tyr Val Pro His
    1415                1420                1425
Pro Ser Ser Leu Ser Gly Ser Leu Pro Gly Met Ser Arg Gly Lys
    1430                1435                1440
Ser Met Ile Ser Ser Leu Ser Ile Met Gly Gly Ser Ser Gly Pro
    1445                1450                1455
Pro Tyr Asp Arg Ala His Val Thr Gly Ala Ser Ser Ser Ser Ser
    1460                1465                1470
Ser Ser Thr Lys Gly Thr Tyr Phe Pro Ala Ile Leu Asn Pro Pro
    1475                1480                1485
Pro Ser Pro Ala Thr Glu Arg Ser His Tyr Thr Met Glu Phe Gly
    1490                1495                1500
Tyr Ser Ser Asn Ser Pro Ser Thr His Arg Ser Tyr Ser Tyr Arg
    1505                1510                1515
Pro Tyr Ser Tyr Arg His Phe Ala Pro Pro Thr Thr Pro Cys Ser
    1520                1525                1530
Thr Asp Val Cys Asp Ser Asp Tyr Ala Pro Ser Arg Arg Met Thr
    1535                1540                1545
Ser Val Ala Thr Ala Lys Gly Tyr Thr Ser Asp Val Asn Tyr Asp
    1550                1555                1560
Ser Glu Pro Val Pro Pro Pro Thr Pro Arg Ser Gln Tyr Leu
    1565                1570                1575
Ser Ala Glu Glu Asn Tyr Glu Ser Cys Pro Pro Ser Pro Tyr Thr
    1580                1585                1590
Glu Arg Ser Tyr Ser His His Leu Tyr Pro Pro Pro Pro Ser Pro
```

```
                1595                1600              1605
Cys Thr  Asp Ser Ser
    1610
```

ANTIBODIES TO LRP6

CROSS-REFERENCE TO PRIOR APPLICATIONS

This application is a national phase application under 35 U.S.C. §371 of International Application No. PCT/US2008/083486 filed Nov. 14, 2008, which claims the benefit of priority under 35 U. S. C. §1 19(e)(1) of provisional application serial no. 60/988,647, filed Nov. 16, 2007 which applications are hereby incorporated by reference in their entirety.

TECHNICAL FIELD OF THE INVENTION

The present invention relates to anti-LRP6 antibodies and to binding epitopes of LRP6 used to produce such antibodies. The invention also relates to methods of using such antibodies to diagnose and treat Wnt-associated diseases, such as bone disorders.

SEQUENCE LISTING

The sequences of the polynucleotides and polypeptides of the invention are listed in the Sequence Listing and are submitted electronically in the file labeled "NUVO-31PCT_ST25.txt"—263 KB (269,747 bytes) which was created on an IBM PC, Windows 2000 operating system on Oct. 8, 2008 at 9:06:02 AM. The Sequence Listing entitled "NUVO-31PCT_ST25.txt" is herein incorporated by reference in its entirety.

BACKGROUND OF THE INVENTION

The Wnt/β-catenin cell signaling pathway is implicated in a variety of developmental processes including stem cell maintenance and growth, cellular differentiation, cell growth, oncogenesis and disease pathogenesis (Kirikoshi et al, *Int. J. Oncol.* 19:767-771 (2001); Munroe et al, *Proc. Natl. Acad. Sci. USA* 96:1569-1573 (1999); Reya and Clevers, *Nature* 434:843-850 (2005); Sher et al, *FEBS Lett.* 522:150-154 (2003)). The activation and regulation of the Wnt/β-catenin pathway therefore appears to be critical for tissue homeostasis, regeneration and repair. The "canonical" Wnt cell signaling pathway has as its central player, the cytosolic protein β-catenin (FIG. 1). When Wnt receptors are not engaged, the level of cytosolic β-catenin is kept low through the action of an intracellular complex, known as the "destruction complex," composed of the tumor suppressor proteins axin and adenomatous polyposis coli (APC) and the serine kinase protein glycogen synthase 3β (GSK3β). The constitutive kinase activity of the destruction complex on β-catenin results in the targeted proteosomal degradation of phosphorylated β-catenin. Binding of Wnt to the receptor proteins LRP5 and/or LRP6, members of the LDL receptor family, and Frizzled (FZD), a serpentine receptor, induces phorphorylation-dependent binding of Axin to the LRP6 cytoplasmic tail and recruitment of the cytoplasmic protein Dishevelled (Dvl) to the cytoplasmic tail of FZD, which together lead to the inactivation of the β-catenin destruction complex. As a consequence, β-catenin accumulates in the cytoplasm and translocates to the nucleus where it is thought to interact with members of the lymphoid enhancer factor (LEF)/T-cell factor (TCF) family of transcription factors and activate target gene expression.

The Wnt coreceptors LRP5/6 are modulated by the secreted ligands Dkk1, Dkk2 and SOST/Sclerostin, a ligand for LRP5/6 and a Wnt signaling inhibitor. Interaction of SOST or Dkk1/2 wth LRP5/6 antagonizes Wnt/β-catenin signaling. Dkk1 is a high affinity ligand for LRP5/6 and disrupts the formation of the FZD-LRP complex. Dkk1 also binds Kremen-1 and -2 which are single-pass transmembrane proteins that cooperate with Dkk1 to inhibit Wnt-FZD-LRP6 function. Upon binding of Dkk1 to LRP6 and Kremen-1, receptor complex internalization occurs thereby dampening the Wnt signal due to a decrease of the Wnt coreceptors available for signaling indicating that the cell surface levels of LRP5/6 may limit cellular responses to Wnt ligands (reviewed in He et al, *Development* 131:1663-1677 (2004) and Semënov et al, *J. Biol. Chem.* 283:21427-21432 (2008)).

An area in which Wnt signaling has been implicated is the regulation of bone mass in homeostasis and bone disease. Bone mass appears to be influenced by the balance achieved between bone forming cells (osteoblasts) and bone resorbing cells (osteoclasts). Mutations in LRP5 and LRP6 receptors have been reported that either decrease or increase bone density, indicating that the level of Wnt and/or LRP5/6 signaling is critical for maintaining normal bone homeostasis. Consistant with these findings, it has been reported that elevated levels of the LRP5/6 inhibitor Dkk1 in diseases such as rheumatoid arthritis and multiple myeloma, result in osteolytic bone lesions, which can be reversed by Dkk1 antagonists, indicating that Dkk1 may be a regulator of bone density (reviewed in Krishnan et al, *J Clin Invest* 116:1202-1209 (2006)).

Several studies have also implicated the Wnt signaling pathway in tissue homeostasis and repair in a variety of systems including intestinal, epidermal, and hematopoietic systems. In the intestine, continuous renewal of absorptive epithelium is driven by proliferation of stem cells residing in the intestinal crypts. Current evidence suggests that the Wnt signaling cascade is important in controlling stem cell function in the intestinal crypt since deletion of the β-catenin-dependent transcription factor TCF4 in mice results in depletion of intestinal crypts and loss of intestinal function (Korinek et al., *Nat Genet.* 19:379-83 (1998); Barker and Clevers, *Nature Rev.* 5:997 (2006)). Similarly, overexpression of Dkk1 in the intestine in transgenic mice or in mice injected with adenovirus expressing Dkk1, resulted in a complete loss of crypts in adult mice (Kormek et al, *Nature Gen.* 19:1-5 (1998); Kuhnert et al., *Proc Natl Acad Sci USA.* 101:266-71 (2004)). Intestinal diseases, such as inflammatory bowel disease, ulcerative colitis and radiation- or chemotherapy-induced mucositis, are associated with intestinal lesions and loss of intestinal absorptive epithelium, suggesting that modulation of Wnt signaling in intestinal crypts could have therapeutic benefit in treating such diseases.

A similar mechanism of Wnt signaling regulating stem cell function, tissue homeostasis and repair is found in the skin. Hair follicle density and the hair cycle are regulated by Wnt-dependent hair follicle epithelial stem cells (van Genderen et al, *Genes Dev.* 8:2691-2703 (1994); Lo Celso et al, *Development* 131:1787-1799 (2004)). Interestingly, the LRP5/6 inhibitor Dkk1 is expressed adjacent to hair follicle buds and over-expression of Dkk1 reduces hair follicle density, indicating that the level of LRP/Wnt signaling is important for regulation of hair follicle density and that Dkk1 may be a regulator of this process (Sick et al., *Science.* 314:1447-50 (2006)). Recently it was shown that hair follicle stem cells contribute to re-epithelialization during wound healing (Ito et al, *Nat. Med.* 11:1351-4 (2005)), indicating that modulation of Wnt signaling in hair follicle stem cells could be beneficial for wound repair.

In addition to the examples described above, Wnt signaling has also been shown to be important for regulation of stem cells in other tissues and organs, including hematopoietic stem cells (Reya et al, *Nature* 423:409-414 (2003); Xu et al., *Nature Immunol.* 4:1177-1182 (2003)), neuronal progenitor stem cells (Zecher et al, *Dev. Biol.* 258:406-418 (2003)), and even embryonic stem cells (Sato et al, *Nature Med.* 10:55-63 (2004)) suggesting that modulation of Wnt signaling could also have therapeutic benefits in these systems.

Thus, molecules that modulate Wnt signaling can be useful targets for a broad range of conditions where proliferation, differentiation, tissue regeneration and repair are important to disease processes. The present invention provides anti-LRP6 antibodies that enhance LRP6 activity and antagonize Dkk1 activity for treatment of diseases such as, but not limited to bone disorders such as osteoporosis and osteolytic lesions caused by osteoarthritis and multiple myeloma as well as gastrointestinal disease and wound healing.

SUMMARY OF THE INVENTION

The present invention provides isolated antibodies or immunologically functional antibody fragments (i.e. antigen-binding fragments) thereof that bind LRP6 epitopes with high affinity and can be used to enhance Wnt signaling and/or antagonize DKK1 activity. These antibodies can be used for treating a variety of diseases in which Wnt signaling is implicated, such as bone diseases and disorders and other cell proliferative-related disorders including wound healing and gastrointestinal diseases such as inflammatory bowel disease, ulcerative colitis and radiation- or chemotherapy-induced mucositis. Preferably the antibodies or antibody fragments thereof bind to primate and human LRP6. More preferably, the antibodies and antigen-binding fragments bind with high affinity to human LRP6. In particular embodiments, the antibodies or antigen-binding fragments thereof are chimeric, humanized, or human antibodies or antigen-binding fragments thereof. In other embodiments, the antibodies or antigen-binding fragments thereof are selected from the group consisting of scFv, Fab, Fab', F(ab')$_2$, Fv, and single chain antibodies. In another particular embodiment, the antibody or antigen-binding fragment thereof is an IgG isotype. Preferably the antibodies or antibody fragments enhance LRP6 activity. In one embodiment, the antibodies or antibody fragments enhance Wnt activity. In another embodiment, the antibodies or antibody fragments antagonize Dkk1 activity. In yet another embodiment, the antibodies or antibody fragments enhance LRP6 activity and antagonize Dkk1 activity.

One aspect of the present invention provides antibodies or antibody fragments thereof comprising a heavy chain variable region ($V_H$) and/or a light chain variable region ($V_L$) of anti-LRP6 antibodies 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1. In a particular embodiment, the antibodies comprise a heavy chain variable region of SEQ ID NO: 18, 22, 26, 30, 34, 38, 42, 46, 50, 54, 58, 62, 66, 70, 72, 74, 78, 82, 86, 90, 94, 98, 102 and/or a light chain variable region of SEQ ID NO: 20, 24, 28, 32, 36, 40, 44, 48, 52, 56, 60, 64, 68, 76, 80, 84, 88, 92, 96, 100, or 104. In another embodiment, the antibodies comprise a heavy chain variable region comprising a sequence that has at least 90%, at least 95%, at least 96%, at least 97%, at least 98% or at least 99% identity to the amino acid sequence set forth in SEQ ID NO: 18, 22, 26, 30, 34, 38, 42, 46, 50, 54, 58, 62, 66, 70, 72, 74, 78, 82, 86, 90, 94, 98, or 102 and/or a light chain variable region comprising a sequence that has at least 90%, at least 95%, at least 96%, at least 97%, at least 98% or at least 99% identity to the amino acid sequence set forth in SEQ ID NO: 20, 24, 28, 32, 36, 40, 44, 48, 52, 56, 60, 64, 68, 76, 80, 84, 88, 92, 96, 100, or 104.

Some of the antibodies and antigen-binding fragments that are provided include (a) one or more light chain (LC) complementarity determining regions (CDRs) selected from the group consisting of:
(i) a LC CDR1 with at least 80% sequence identity to SEQ ID NO: 114, 126, 138, 150, 162, 174, 186, 198, 210, 222, 234, 246, 258, 282, 294, 306, 318, 330, 342, 354, or 366;
(ii) a LC CDR2 with at least 80% sequence identity to SEQ ID NO: 115, 127, 139, 151, 163, 175, 187, 199, 211, 223, 235, 247, 259, 283, 295, 307, 319, 331, 343, 355, or 367; and
(iii) a LC CDR3 with at least 80% sequence identity to SEQ ID NO: 116, 128, 140, 152, 164, 176, 188, 200, 212, 224, 236, 248, 260, 284, 296, 308, 320, 332, 344, 356, or 368;
(b) one or more heavy chain (HC) CDRs selected from the group consisting of:
(i) a HC CDR1 with at least 80% sequence identity to SEQ ID NO: 108, 120, 132, 144, 156, 168, 180, 192, 204, 216, 228, 240, 252, 264, 270, 276, 288, 300, 312, 324, 336, 348, or 360;
(ii) a HC CDR2 with at least 80% sequence identity to SEQ ID NO: 109, 121, 133, 145, 157, 169, 181, 193, 205, 217, 229, 241, 253, 265, 271, 277, 289, 301, 313, 325, 337, 349, or 361; and
(iii) a HC CDR3 with at least 80% sequence identity to SEQ ID NO: 110, 122, 134, 146, 158, 170, 182, 194, 206, 218, 230, 242, 254, 266, 272, 278, 290, 302, 314, 326, 338, 350, or 362; or
(c) one or more LC CDRs of (a) and one or more HC CDRs of (b).

Such antibodies or antigen-binding fragments thereof can specifically bind an LRP6 polypeptide. Certain antibodies or antigen-binding fragments thereof include one, two, three, four, five or six of the foregoing CDRs in any combination thereof.

The light chain and heavy chains of other antibodies or antigen-binding fragments thereof are as described above but have at least 90% sequence identity to the foregoing sequences. Still other antibodies or antigen-binding fragments thereof have a light chain in which CDR1 has the amino acid sequence as set forth in SEQ ID NO: 114, 126, 138, 150, 162, 174, 186, 198, 210, 222, 234, 246, 258, 282, 294, 306, 318, 330, 342, 354, or 366, CDR2 has the amino acid sequence as set forth in SEQ ID NO: 115, 127, 139, 151, 163, 175, 187, 199, 211, 223, 235, 247, 259, 283, 295, 307, 319, 331, 343, 355, or 367, and/or CDR3 has the amino acid sequence as set forth in SEQ ID NO: 116, 128, 140, 152, 164, 176, 188, 200, 212, 224, 236, 248, 260, 284, 296, 308, 320, 332, 344, 356 or 368. Some antibodies or antigen-binding fragments thereof may also have a heavy chain in which CDR1 has the amino acid sequence as set forth in SEQ ID NO: 108, 120, 132, 144, 156, 168, 180, 192, 204, 216, 228, 240, 252, 264, 270, 276, 288, 300, 312, 324, 336, 348, or 360, CDR2 has the amino acid sequence as set forth in SEQ ID NO: 109, 121, 133, 145, 157, 169, 181, 193, 205, 217, 229, 241, 253, 265, 271, 277, 289, 301, 313, 325, 337, 349, or 361, and/or CDR3 has the amino acid sequence as set forth in SEQ ID NO: 110, 122, 134, 146, 158, 170, 182, 194, 206, 218, 230, 242, 254, 266, 272, 278, 290, 302, 314, 326, 338, 350, or 362.

Another aspect of the present invention provides isolated antibodies or antigen-binding fragments thereof that bind to LRP6 or an LRP6 epitope. In a particular embodiment, the antibodies include isolated antibodies or antigen-binding fragments thereof bind with high affinity to a human LRP6 epitope defined by amino acids 43-324 of SEQ ID NO: 2 (i.e., SEQ ID NO: 13 or 16). In another embodiment, the antibodies include isolated antibodies or antigen-binding fragments thereof that bind with high affinity to a human LRP6 epitope defined by amino acids 43-627 of SEQ ID NO: 2 (i.e., SEQ ID NO: 15) or as defined by amino acids 352-627 of SEQ ID NO: 2 (i.e. SEQ ID NO: 370). In yet another embodiment, the antibodies include isolated antibodies or antigen-binding fragments thereof that bind with high affinity to a human LRP6 epitope defined by amino acids 236-283 of SEQ ID NO: 2 (i.e. SEQ ID NO: 371). Examples of such antibodies include monoclonal antibodies 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1.

The invention provides a pharmaceutical composition comprising the antibody and a pharmaceutically acceptable carrier. The pharmaceutical composition may further comprise another pharmaceutically active ingredient, such as an anti-tumor agent or an imaging reagent. A particular embodiment provides an antibody or antigen-binding fragment thereof present in a therapeutically effective amount, such as in a concentration of at least about 10 µg/ml.

Another aspect of the invention provides LRP6 epitopes, which epitopes include isolated polypeptides comprising amino acids 43-324 of SEQ ID NO: 2 (i.e., SEQ ID NO: 16), or amino acids 236-283 of SEQ ID NO: 2 (i.e., SEQ ID NO: 371), or any fragment thereof that binds to an anti-LRP6 antibody or antigen-binding fragment thereof.

Another aspect of the invention provides LRP6 epitopes, which epitopes include isolated polypeptides comprising amino acids 352-627 of SEQ ID NO: 2 (i.e., SEQ ID NO: 370), or any fragment thereof that binds to an anti-LRP6 antibody or antigen-binding fragment thereof.

Diagnostic and therapeutic methods are also provided by the invention. A particular embodiment provides a method for diagnosing the presence or location of an LRP6-expressing tissue or cells using an anti-LRP6 antibody. In yet another embodiment, a therapeutic method comprises administering the antibody to a subject in need thereof. In yet a further embodiment, a therapeutic method comprises administering the antibody to a subject in need thereof in conjunction with administration of another therapeutic agent.

The invention provides isolated cell lines, such as hybridoma cells and/or host cells that have been transfected to express LRP6 antibodies or antigen-binding fragments thereof, that produce the anti-LRP6 antibody or antigen-binding fragment thereof, and antibodies or antigen-binding fragments thereof produced by such cell lines. A hybridoma may include B cells obtained from a transgenic non-human animal having a genome comprising a human heavy chain transgene and a human light chain transgene fused to an immortalized cell. In another aspect, a hybridoma may include B cells obtained from a non-transgenic, non-human animal. Such transformed host cells may include nucleic acids encoding a human heavy chain and a human light chain.

Another aspect of the present invention provides a method of producing an antibody or antigen-binding fragment thereof that binds with high affinity to a human LRP6 epitope defined by amino acids 43-324 of SEQ ID NO: 2 (i.e. SEQ ID NO: 16), comprising immunizing a non-human animal with a human LRP6 epitope defined by amino acids 43-324 of SEQ ID NO: 2, such that antibodies are produced by B cells of the animal; isolating the B cells of the animal; and fusing the B cells with myeloma cells to form immortal, hybridoma cells that secrete the antibody or antigen binding region thereof.

Another aspect of the present invention provides a method of producing an antibody or antigen-binding fragment thereof that binds with high affinity to a human LRP6 epitope defined by amino acids 263-283 of SEQ ID NO: 2 (i.e. SEQ ID NO: 371), comprising immunizing a non-human animal with a human LRP6 epitope defined by amino acids 263-283 of SEQ ID NO: 2, such that antibodies are produced by B cells of the animal; isolating the B cells of the animal; and fusing the B cells with myeloma cells to form immortal, hybridoma cells that secrete the antibody or antigen binding region thereof.

Yet another aspect of the present invention provides a method of producing an antibody or antigen-binding fragment thereof that binds with high affinity to a human LRP6 epitope defined by amino acids 352-627 of SEQ ID NO: 2 (i.e. SEQ ID NO: 370), comprising immunizing a non-human animal with a human LRP6 epitope defined by amino acids 352-627 of SEQ ID NO: 2, such that antibodies are produced by B cells of the animal; isolating the B cells of the animal; and fusing the B cells with myeloma cells to form immortal, hybridoma cells that secrete the anti-LRP6 antibody or antigen binding region thereof.

The invention also provides nucleic acid molecules encoding the heavy and/or light chain or antigen-binding portions thereof of an anti-LRP6 antibody.

The invention provides vectors and host cells comprising the nucleic acid molecules, as well as methods of recombinantly producing the polypeptides encoded by the nucleic acid molecules.

BRIEF DESCRIPTION OF THE DRAWINGS

FIG. 2: Affinity measurements and KD determination for anti-LRP6 mAbs: A) 77.2, B) 213.7, C) 240.8, D) 421.1, E) 498.3, F) 606.4, G) 856.6, H) 923.3, I) 931.1, J) 993.9, K) 995.5, L) 21115.3, M) 1213.2, N) 1253, 12, O) 1281.1, P) 1293.11, Q) 1433.8, R) 1470.2, S) 1903.1, T) 135.16, U) 413.1, V) 620.1, W) 537.2.

FIG. 4: Multiple amino acid sequence alignment of the heavy chain variable regions for anti-LRP6 mAbs (77.2 (SEQ ID NO: 18), 135.16 (SEQ ID NO: 22), 213.7 (SEQ ID NO: 26), 240.8 (SEQ ID NO: 30), 413.1 (SEQ ID NO: 34), 421.1 (SEQ ID NO: 38), 498.3 (SEQ ID NO: 42), 537.2 (SEQ ID NO: 46), 606.4 (SEQ ID NO: 50), 620.1 (SEQ ID NO: 54), 856.6 (SEQ ID NO: 58), 923.3 (SEQ ID NO: 62), 931.1 (SEQ ID NO: 66), 993.9 (SEQ ID NO: 70), 995.5 (SEQ ID NO: 72), 1115.3 (SEQ ID NO: 74), 1213.2 (SEQ ID NO: 78), 1253.12 (SEQ ID NO: 82), 1281.1 (SEQ ID NO: 86), 1293.11 (SEQ ID NO: 90), 1433.8 (SEQ ID NO: 94), 1470.2 (SEQ ID NO: 98), and 1903.1 (SEQ ID NO: 102)).

FIG. 5: Multiple amino acid sequence alignment of the light chain variable regions for anti-LRP6 mAbs (77.2 (SEQ ID NO: 20), 135.16 (SEQ ID NO: 24), 213.7 (SEQ ID NO: 28), 240.8 (SEQ ID NO: 32), 413.1 (SEQ ID NO: 36), 421.1 (SEQ ID NO: 40), 498.3 (SEQ ID NO: 44), 537.2 (SEQ ID NO: 48), 606.4 (SEQ ID NO: 52), 620.1 (SEQ ID NO: 56), 856.6 (SEQ ID NO: 60), 923.3 (SEQ ID NO: 64), 931.1 (SEQ ID NO: 68), 1115.3 (SEQ ID NO: 76), 1213.2 (SEQ ID NO: 80), 1253.12 (SEQ ID NO: 84), 1281.1 (SEQ ID NO: 88), 1293.11 (SEQ ID NO: 92), 1433.8 (SEQ ID NO: 96), 1470.2 (SEQ ID NO: 100), and 1903.1 (SEQ ID NO: 104)).

DETAILED DESCRIPTION OF THE INVENTION

Figure 1A:
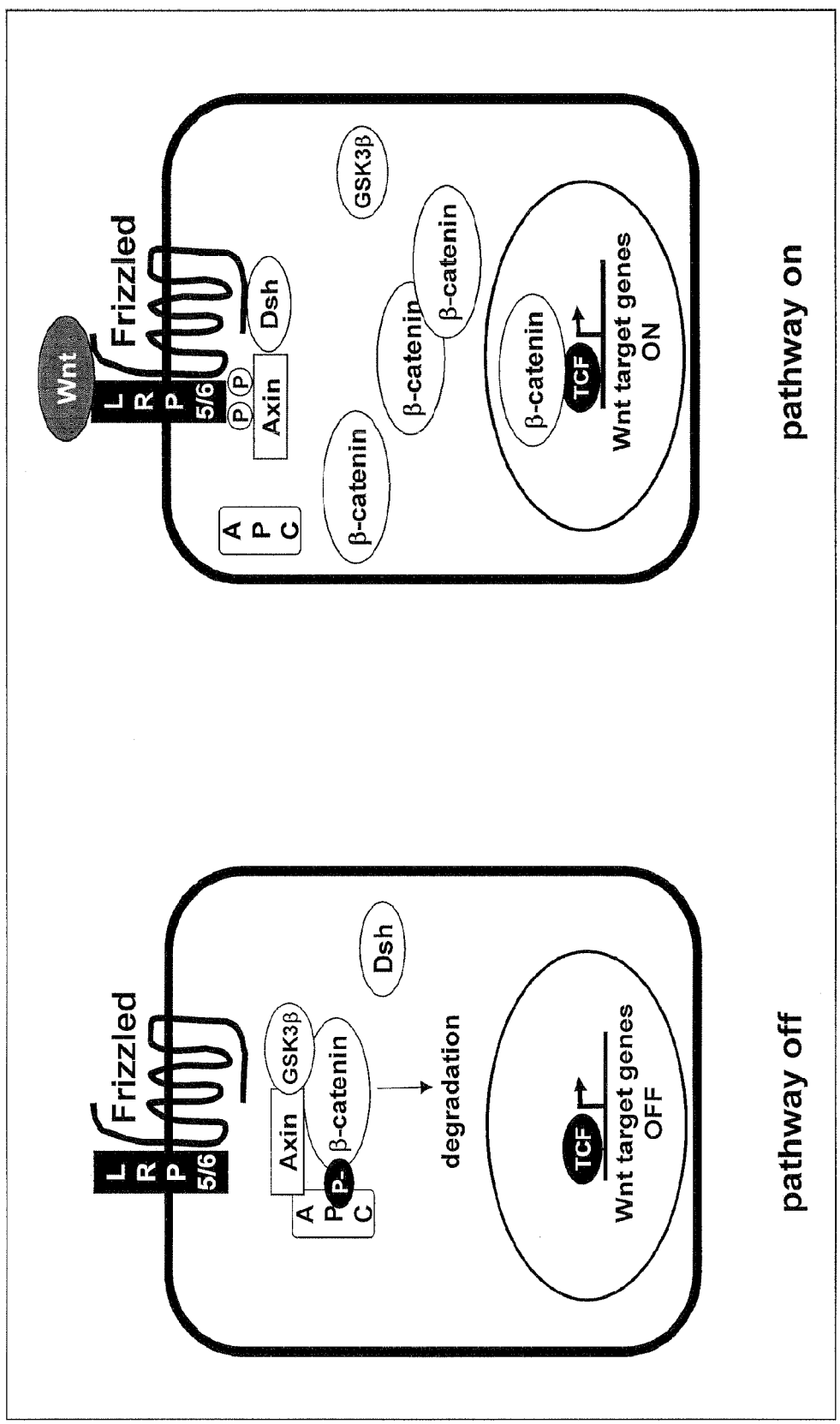
FIG. 1: A model of the Wnt signaling pathway. A) In the absence of Wnt signaling, beta-catenin is targeted for degradation by a beta-catenin destruction complex consisting of GSK3β, Axin and APC. Upon binding of a canonical Wnt ligand to frizzled (FZD) and LRP5/6 receptors, recruitment of axin to the phosphorylated cytoplasmic tail of LRP5/6 and Dishevelled (Dsh) to the cytoplasmic tail of frizzled, lead to inactivation of the beta-catenin destruction complex, allowing beta-catenin to accumulate and initiate TCF mediated transcription. B) Wnt signaling is limited by the amount of LRP6 on the cell surface, which is kept low by the LRP6 inhibitor Dkk1. Dkk1 inhibits binding of Wnt ligands to the LRP6 receptor and targets LRP6 for internalization through formation of a ternary complex with Kremen1/2 receptors.
Figure 1B:
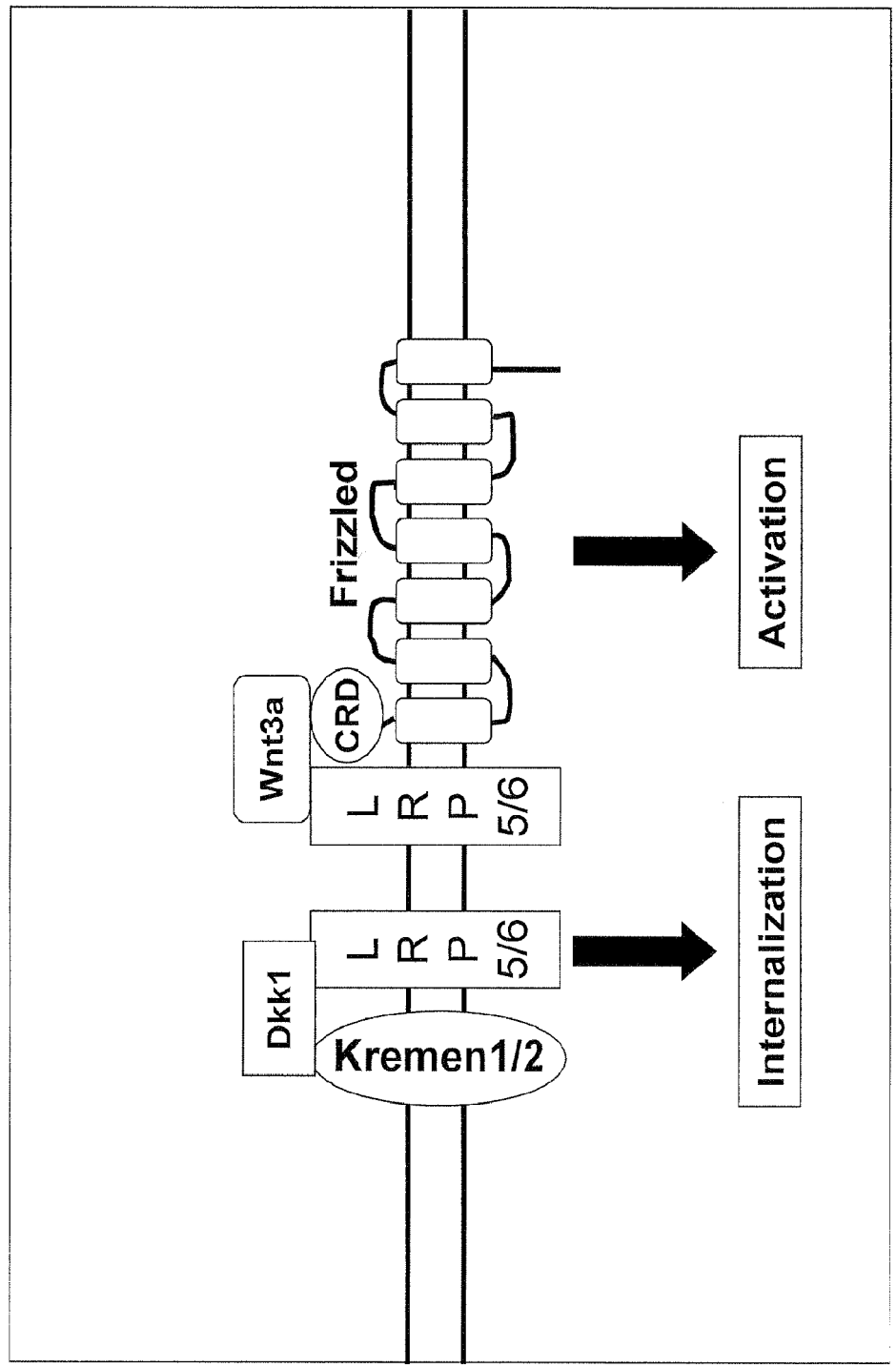

Section titles are used herein for convenience purposes only and are not to be construed in any way as limiting the invention.

I. Definitions

Unless otherwise defined herein, scientific and technical terms used in connection with the present invention have the meanings that are commonly understood by those of ordinary skill in the art. Further, unless otherwise required by context, singular terms shall include pluralities and plural terms shall include the singular. Unless otherwise indicated, nucleic acids are written left to right in 5' to 3' orientation; amino acid sequences are written left to right in amino to carboxy orientation.

Standard techniques are used for recombinant DNA, oligonucleotide synthesis, and tissue culture and transformation (e.g. electroporation, lipofection). Enzymatic reactions and purification techniques are performed according to manufacturer's specifications or as commonly accomplished in the art or as described herein. The foregoing techniques and procedures are as generally performed according to conventional methods well known in the art and as described in various general and more specific references that are cited and discussed throughout the present specification. See Sambrook et al., *Molecular Cloning: A Laboratory Manual*, 2d ed., Cold Spring Harbor Laboratory Press, Cold Spring Harbor, N.Y. (1989), Ausubel et al., *Current Protocols in Molecular Biology*, Greene Publishing Associates (1992), and Harlow and Lane, *Antibodies: A Laboratory Manual*, Cold Spring Harbor Laboratory Press, Cold Spring Harbor, N.Y. (1990), which are incorporated herein by reference in their entirety for all purposes. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The terms "a," "an," and "the" mean one or more and include the plural unless the context is inappropriate.

The term "polynucleotide" as referred to herein means a polymeric form of nucleotides of at least 10 bases in length, either ribonucleotides or deoxyribonucleotides or a modified form of either type of nucleotide. The term includes single and double stranded forms of DNA.

The term "oligonucleotide" referred to herein includes naturally occurring, and modified nucleotides linked together by naturally occurring and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides may be double stranded, e.g., for use in the construction of a gene mutant. Oligonucleotides of the invention can be either sense or anti-sense oligonucleotides.

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., Kozak consensus sequence); sequences that enhance protein stability; and when desired, sequences that enhance protein secretion. The nature of such control sequences differs depending upon the host organism; in prokaryotes, such control sequences generally include promoters and transcription termination sequence. The term "control sequences" as referred to herein includes, at a minimum, all components whose presence is essential for expression and processing, and can also include additional components whose presence is advantageous, for example, leader sequences and fusion partner sequences.

The term "vector" as used herein, refers to a nucleic acid molecule capable of transporting another nucleic acid to which it has been linked. One type of vector is a "plasmid", which refers to a circular double stranded loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors).

Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors (e.g., replication defective retroviruses, adenoviruses and adeno-associated viruses), which serve equivalent functions.

The term "recombinant host cell" (or simply "host cell"), as used herein, refers to a cell that has been transformed, or is capable of being transformed, with a nucleic acid sequence and thereby expresses a gene of interest. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Host cells may be prokaryotic or eukaryotic cells that are capable of expressing exogenous nucleic acid sequences. Examples of host cells include bacteria such as *E. coli*, yeast, plant cells, Chinese hamster ovary (CHO) cells, human embryonic kidney (HEK)-293 cells and insect cells.

The term "transduction" means the transfer of genes from one bacterium to another, usually by bacteriophage. "Transduction" also refers to the acquisition and transfer of eukaryotic cellular sequences by retroviruses.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., *Virology* 52:456 (1973); Sambrook et al., *Molecular Cloning: A Laboratory Manual, Id.* (2001); Davis et al., *Basic Methods in Molecular Biology*, Elsevier (1986); and Chu et al., *Gene* 13:197 (1981). Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed wherein it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The term "percent sequence identity" in the context of nucleic acid sequences refers to the residues in two sequences which are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, GAP or BESTFIT, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (Pearson, *Meth. Enzymol.* 183:63-98 (1990); Pearson, *Meth. Mol. Biol.* 132:185-219 (2000); Pearson, *Meth. Enzymol.* 266:227-258 (1996); Pearson, J. Mol. Biol. 276:71-84 (1998); herein incorporated by reference). Unless specified otherwise, default parameters for a particular program or algorithm are used. For instance, percent sequence identity between nucleic acid sequences can be determined using FASTA with its default parameters (a word size of 6 and the NOPAM factor for the scoring matrix) or using GAP with its default parameters as provided in GCG Version 6.1, herein incorporated by reference.

A reference to a nucleic acid sequence encompasses its complement unless otherwise specified. Thus, a reference to a nucleic acid molecule having a particular sequence should be understood to encompass its complementary strand, with its complementary sequence.

The term "substantial similarity" or "substantial sequence similarity" when referring to a nucleic acid or fragment thereof, indicates that, when optimally aligned with appropriate nucleotide insertions or deletions with another nucleic acid (or its complementary strand), there is nucleotide sequence identity in at least about 85%, preferably at least about 90%, and more preferably at least about 95%, at least 96%, at least 97%, at least 98% or at least 99% of the nucleotide bases, as measured by any well-known algorithm of sequence identity, such as FASTA, BLAST, or GAP as discussed above.

The terms "polypeptide" or "protein" means a macromolecule having the amino acid sequence of a native protein, that is a protein produced by a naturally-occurring and non-recombinant cell, or produced by a genetically-engineered or recombinant cell, and comprise molecules having the amino acid sequence of the native protein, or molecules having deletions from, additions to, and/or substitutions of one or more amino acids of the native sequence. The terms "polypeptide" and "protein" specifically encompass anti-LRP6 antibodies antigen-binding fragments, or sequences that have deletions from, additions to, and/or substitutions of one or more amino acid of anti-LRP6 antibodies or antigen-binding fragments. The term "polypeptide fragment" refers to a polypeptide that has an amino-terminal deletion, a carboxyl-terminal deletion, and/or an internal deletion as compared with the full-length native protein. Such fragments may also contain modified amino acids as compared with the native protein. In certain embodiments, fragments are about 5 to 500 amino acids long. For example, fragments may be at least 5, 6, 8, 10, 14, 20, 50, 70, 100, 110, 150, 200, 250, 300, 350, 400, 450 or 500 amino acids long. Useful polypeptide fragments include immunologically functional fragments of antibodies, including binding domains. In the case of anti-LRP6 antibodies, useful fragments include but are not limited to a CDR region, a variable domain of a heavy or light chain, a portion of an antibody chain or just its variable region including two CDRs, and the like.

The term "isolated protein" referred to herein, means that a subject protein (1) is free of at least some other proteins with which it would normally be found, (2) is essentially free of other proteins from the same source, e.g., from the same species, (3) is expressed by a cell from a different species, (4)

has been separated from at least about 50% of polynucleotides, lipids, carbohydrates, or other materials with which it is associated in nature, (5) is operably associated (by covalent or noncovalent interaction) with a polypeptide with which it is not associated in nature, or (6) does not occur in nature. Genomic DNA, cDNA, mRNA or other RNA, of synthetic origin, or any combination thereof may encode such an isolated protein. Preferably, the isolated protein is substantially free from proteins or polypeptides or other contaminants that are found in its natural environment that would interfere with its therapeutic, diagnostic, prophylactic, research or other use.

A "variant" of a polypeptide comprises an amino acid sequence wherein one or more amino acid residues are inserted into, deleted from and/or substituted into the amino acid sequence relative to another polypeptide sequence. Unless otherwise indicated, the term "variants" includes fusion proteins.

A "derivative" of a polypeptide is a polypeptide (e.g., an antibody) that has been chemically modified in some manner distinct from insertion, deletion, or substitution variants, e.g., via conjugation to another chemical moiety.

The term "antibody" refers to an intact immunoglobulin of any isotype, or a fragment thereof, that can compete with the intact antibody for specific binding to the target antigen, and includes chimeric, humanized, fully human, and bispecific antibodies. An intact antibody generally will comprise at least two full-length heavy chains and two full-length light chains, but in some instances may include fewer chains such as antibodies naturally occurring in camelids which may comprise only heavy chains. Antibodies may be derived solely from a single source, or may be "chimeric," that is, different portions of the antibody may be derived from two different antibodies. For example, the CDR regions may be derived from a rat or murine source, while the framework region of the V region is derived from a different animal source, such as a human. The antibodies or binding fragments thereof may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below.

The term "light chain" includes a full-length light chain and fragments thereof having sufficient variable region sequence to confer binding specificity. A full-length light chain includes a variable region domain (abbreviated herein as $V_L$), and a constant region domain (abbreviated herein as $C_L$). The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain (abbreviated herein as $V_H$), and three constant region domains (abbreviated herein as $C_H1$, $C_H2$, and $C_H3$). The $V_H$ domain is at the amino-terminus of the polypeptide, and the $C_H$ domains are at the carboxy-terminus, with the $C_H3$ being closest to the —COOH end. Heavy chains may be of any isotype, including IgG (including $IgG_1$, $IgG_2$, $IgG_3$, and $IgG_4$ subtypes), IgA (including $IgA_1$ and $IgA_2$ subtypes), IgM, and IgE.

The $V_H$ and $V_L$ regions can be further subdivided into regions of hypervariability, termed "complementarity determining regions" or "CDR", interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3. CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An amino acid sequence which is substantially the same as a heavy or light chain CDR exhibits a considerable amount or extent of sequence identity when compared to a reference sequence and contributes favorably to specific binding of an antigen bound specifically by an antibody having the reference sequence. Such identity is definitively known or recognizable as representing the amino acid sequence of the particular human monoclonal antibody. Substantially the same heavy and light chain CDR amino acid sequence can have, for example, minor modifications or conservative substitutions of amino acids so long as the ability to bind a particular antigen is maintained.

The term "CDR" or "complementarity determining region" means the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987) and additionally by MacCallum et al., *J. Mol. Biol.* 262:732-745 (1996), which are incorporated herein by reference, where the definitions include overlapping or subsets of amino acid residues when compared against each other. Nevertheless, application of either definition to refer to a CDR of an antibody or functional fragment thereof is intended to be within the scope of the term as defined and used herein. The exact amino acid residue numbers which encompass a particular CDR will vary depending on the structure of the CDR. Those skilled in the art can routinely determine which residues comprise a particular CDR given the variable region amino acid sequence of the antibody. Those skilled in the art can compare two or more antibody sequences by defining regions or individual amino acid positions of the respective sequences with the same CDR definition.

The term "antibody" includes both glycosylated and non-glycosylated immunoglobulins of any isotype or subclass or combination thereof, including human (including CDR-grafted antibodies), humanized, chimeric, multi-specific, monoclonal, polyclonal, and oligomers thereof, irrespective of whether such antibodies are produced, in whole or in part, via immunization, through recombinant technology, by way of in vitro synthetic means, or otherwise. Thus, the term "antibody" includes those that are prepared, expressed, created or isolated by recombinant means, such as (a) antibodies isolated from an animal (e.g., a mouse) that is transgenic for human immunoglobulin genes or a hybridoma prepared therefrom, (b) antibodies isolated from a host cell transfected to express the antibody, (c) antibodies isolated from a recombinant, combinatorial library, and (d) antibodies prepared, expressed, created or isolated by any other means that involve splicing of immunoglobulin gene sequences of two distinct species of animals. In certain embodiments, however, such antibodies can be subjected to in vitro mutagenesis (or, when an animal transgenic for human immunoglobulin sequences is used, in vivo somatic mutagenesis) and thus the amino acid sequences of the $V_H$ and $V_L$ regions of the antibodies are sequences that, while derived from and related to the germline $V_H$ and $V_L$ sequences of a particular species (e.g., human), may not naturally exist within that species' antibody germline repertoire in vivo.

The term "antigen-binding fragment" of an antibody means one or more fragments of an antibody that retain the ability to specifically bind to an antigen (e.g., LRP6) that is specifically bound by a reference antibody, as disclosed herein. An "antigen-binding fragment" of an antibody may include, for example, polypeptides comprising individual heavy or light chains and fragments thereof, such as $V_L$, $V_H$, and Fd regions (consisting of the $V_H$ and $C_H1$ domains); monovalent fragments, such as Fv, Fab, and Fab' regions; bivalent fragments, such as $F(ab')_2$; single chain antibodies, such as single chain Fv (scFv) regions; Fc fragments; diabodies; maxibodies (bivalent scFv fused to the amino terminus of the Fc ($C_H2$-$C_H3$ domains)) and complementary determining region (CDR) domains. Such terms are described, for example, in Harlow and Lane, *Antibodies: A Laboratory Manual*, Cold Spring Harbor Laboratory, NY (1989); *Molec. Biology and Biotechnology: A Comprehensive Desk Reference* (Myers, R. A. (ed.), New York: VCH Publisher, Inc.); Huston et al., *Cell Biophysics*, 22:189-224 (1993); Pluckthun and Skerra, *Meth. Enzymol.*, 178:497-515 (1989) and in Day, E. D., *Advanced Immunochemistry*, 2d ed., Wiley-Liss, Inc. New York, N.Y. (1990), which are incorporated herein by reference.

The term "antigen-binding fragment" also includes, for example, fragments produced by protease digestion or reduction of a human monoclonal antibody and by recombinant DNA methods known to those skilled in the art. One skilled in the art knows that the exact boundaries of a fragment of a human monoclonal antibody can be variable, so long as the fragment maintains a functional activity. Using well-known recombinant methods, one skilled in the art can engineer a nucleic acid to express a functional fragment with any endpoints desired for a particular application. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., *Science* 242:423-426 (1988); and Huston et al., *Proc. Natl. Acad. Sci. USA* 85:5879-5883 (1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Such fragments include those obtained by amino-terminal and/or carboxy-terminal deletions, but where the remaining amino acid sequence is substantially identical to the corresponding positions in the naturally-occurring sequence deduced, for example, from a full-length cDNA sequence. Antigen-binding fragments also include fragments of an antibody which retain at least one (e.g., 1, 2, 3 or more) light chain sequences for a particular complementarity determining region (CDR) (e.g., at least one or more of CDR1, CDR2, and/or CDR3 from the heavy and/or light chain). Fusions of CDR containing sequences to an Fc region (or a $C_H2$ or $C_H3$ region thereof) are included within the scope of this definition including, for example, scFv fused, directly or indirectly, to an Fc region are included herein. An antigen-binding fragment is inclusive of, but not limited to, those derived from an antibody or fragment thereof (e.g., by enzymatic digestion or reduction of disulfide bonds), produced synthetically using recombinant methods, created via in vitro synthetic means (e.g., Merrifield resins), combinations thereof, or through other methods. Antigen-binding fragments may also comprise multiple fragments, such as CDR fragments, linked together synthetically, chemically, or otherwise, in the form of oligomers. Thus, antigen-binding fragments include polypeptides produced by any number of methods which comprise at least one CDR from a $V_H$ or $V_L$ chain of an anti-LRP6 antibody (e.g., derived from monoclonal antibodies 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1).

The term "$V_L$ fragment" means a fragment of the light chain of a monoclonal antibody which includes all or part of the light chain variable region, including the CDRs. A $V_L$ fragment can further include light chain constant region sequences.

The term "$V_H$ fragment" means a fragment of the heavy chain of a monoclonal antibody which includes all or part of the heavy chain variable region, including the CDRs. A $V_H$ fragment can further include heavy chain constant region sequences.

The term "Fd fragment" means a fragment of the heavy chain of a monoclonal antibody which includes all or part of the $V_H$ heavy chain variable region, including the CDRs. An Fd fragment can further include $C_H1$ heavy chain constant region sequences.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domain.

The term "Fv fragment" means a monovalent antigen-binding fragment of a monoclonal antibody, including all or part of the variable regions of the heavy and light chains, and absent of the constant regions of the heavy and light chains. The variable regions of the heavy and light chains include, for example, the CDRs.

The term "Fab fragment" means a monovalent antigen-binding fragment of an antibody consisting of the $V_L$, $V_H$, $C_L$ and $C_H1$ domains, which is larger than an Fv fragment. For example, a Fab fragment includes the variable regions, and all or part of the first constant domain of the heavy and light chains.

The term "Fab' fragment" means a monovalent antigen-binding fragment of a monoclonal antibody that is larger than a Fab fragment. For example, a Fab' fragment includes all of the light chain, all of the variable region of the heavy chain, and all or part of the first and second constant domains of the heavy chain.

The term "$F(ab')_2$ fragment" means a bivalent antigen-binding fragment of a monoclonal antibody comprising two Fab fragments linked by a disulfide bridge at the hinge region. An $F(ab')_2$ fragment includes, for example, all or part of the variable regions of two heavy chains and two light chains, and can further include all or part of the first constant domains of two heavy chains and two light chains.

"Single-chain antibodies" are Fv molecules in which the heavy and light chain variable regions have been connected by a flexible linker to form a single polypeptide chain, which forms an antigen-binding fragment. Single chain antibodies are discussed in detail in International Patent Application Publication No. WO 88/01649 and U.S. Pat. Nos. 4,946,778 and 5,260,203, the disclosures of which are herein incorporated by reference.

A "domain antibody" is an antigen-binding fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

The term "bivalent antibody" means an antibody that comprises two antigen binding sites. In some instances, the two binding sites have the same antigen specificities. However, bivalent antibodies may be bispecific (see below).

The term "bispecific antibody" means an antibody that binds to two or more distinct epitopes. For example, the antibody may bind to, or interact with, (a) a cell surface antigen and (b) an Fc receptor on the surface of an effector cell. The term "multispecific antibody" or "heterospecific antibody" means an antibody that binds to more than two distinct epitopes. For example, the antibody may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific antibodies or antigen-binding fragments thereof which are directed to LRP6 epitopes and to other targets, such as Fc receptors on effector cells. Bispecific antibodies are a species of multispecific antibody and may be produced by a variety of methods including, but not limited to, fusion of hybridomas or linking of Fab' fragments. See, e.g., Songsivilai and Lachmann, *Clin. Exp. Immunol.* 79:315 (1990); Kostelny et al., *J. Immunol.* 148:1547 (1992). The two binding sites of a bispecific antibody will bind to two different epitopes, which may reside on the same or different protein targets.

The term "bispecific antibodies" also includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Hollinger et al., *Proc Natl. Acad. Sci. USA* 90:6444-6448 (1993); Polijak et al., *Structure* 2:1121-1123 (1994).

The term "monoclonal antibody" or "mAb," as used herein, refers to an antibody obtained from a population of substantially homogeneous antibodies, e.g., the individual antibodies comprising the population are identical except for possible naturally occurring mutations that may be present in minor amounts. In contrast to polyclonal antibody preparations that typically include different antibodies against different determinants (epitopes), each monoclonal antibody is directed against a single determinant on the antigen. The term is not limited regarding the species or source of the antibody, nor is it intended to be limited by the manner in which it is made. The term encompasses whole immunoglobulins as well as fragments such as Fab, F(ab')$_2$, Fv, and other fragments, as well as chimeric and humanized homogeneous antibody populations, that exhibit immunological binding properties of the parent monoclonal antibody molecule.

The term "mouse monoclonal antibody" means a monoclonal antibody, as defined above, produced by immunizing a mouse, with an antigen of interest (e.g., LRP6). A "mouse monoclonal antibody" is produced using conventional methods well known in the art, from mouse-mouse hybridomas, described more fully below.

The term "rabbit monoclonal antibody" as used herein means a monoclonal antibody, as defined above, produced by immunizing a rabbit with an antigen of interest (e.g., LRP6). A "rabbit monoclonal antibody" can be produced using rabbit-rabbit hybridomas (e.g., fusions between an antibody-producing cell from the immunized rabbit with an immortalized cell from a rabbit), rabbit-mouse hybridomas (e.g., fusions between an antibody-producing cell from the immunized rabbit with an immortalized cell from a mouse), and the like.

The term "human monoclonal antibody" means a monoclonal antibody with substantially human CDR amino acid sequences produced, for example, by recombinant methods, by lymphocytes or by hybridoma cells.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851 (1984).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or nonhuman primate having the desired specificity, affinity, and capacity. In some instances, framework region (FR) residues of the immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., *Nature* 321:522 (1986); Riechmann et al., *Nature* 332:323 (1988); Presta, *Curr. Op. Struct. Biol.* 2:593 (1992); Vaswani and Hamilton, *Ann. Allergy, Asthma and Immunol.* 1:105 (1998); Harris, *Biochem. Soc. Transactions* 23; 1035 (1995); Hurle and Gross, *Curr. Op. Biotech.* 5:428 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding regions.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., *Bio/Technology* 10:779 (1992) describes affinity maturation by $V_H$ and $V_L$ domain shuffling. Random mutagenesis of CDR and/or framework residues is described by: Barbas et al., *Proc. Natl. Acad. Sci. USA* 91:3809 (1994); Schier et al., *Gene* 169:147 (1995); Yelton et al., *J. Immunol.* 155:1994 (1995); Jackson et al., *J. Immunol.* 154:3310 (1995); and Hawkins et al., *J. Mol. Biol.* 226:889 (1992).

"Immunoadhesions" or "immunoadhesins" are antibody-like molecules that combine the binding domain of a non-antibody polypeptide with the effector functions of an antibody or an antibody constant domain. The binding domain of the non-antibody polypeptide can be, for example, a ligand or cell surface receptor having ligand binding activity. Immunoadhesions for use as anti-LRP6 antibodies can contain at least the Fc receptor binding effector functions of the antibody constant domain.

"Immunologically reactive" means that the antibody of interest will bind with LRP6 antigens present in a biological sample.

The term "immunogenic sequence of an LRP6" means an LRP6 molecule that includes an amino acid sequence with at least one epitope such that the molecule is capable of stimulating the production of antibodies in an appropriate host.

The term "immunogenic composition" means a composition that comprises at least one immunogenic polypeptide (e.g., an LRP6 antigen or antibody).

The term "antigen" refers to a molecule or a portion of a molecule capable of being bound by a selective binding agent, such as an antibody, and additionally capable of being used in an animal to produce antibodies capable of binding to that antigen. An antigen may possess one or more epitopes that are capable of interacting with different antibodies.

The term "selective binding agent" refers to a molecule that binds to an antigen. Non-limiting examples include antibodies, antigen-binding fragments, scFv, Fab, Fab', F(ab')$_2$, single chain antibodies, peptides, peptide fragments and proteins.

The term "epitope" includes any determinant capable of binding with high affinity to an immunoglobulin or to a T-cell receptor. An epitope is a region of an antigen that is bound by an antibody that specifically targets that antigen, and when the antigen is a protein, includes specific amino acids that directly contact the antibody. Most often, epitopes reside on proteins, but in some instances, may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

Regions of a given polypeptide that include an epitope can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. *Proc. Natl. Acad. Sci. USA* 81:3998-4002 (1984); Geysen et al. *Proc. Natl. Acad. Sci. USA* 82:178-182 (1985); Geysen et al. *Molec. Immunol.* 23:709-715 (1986). Similarly, conformational epitopes are readily identified by determining spatial conformation of amino acids such as by, e.g., x-ray crystallography and two-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* 78:3824-3828 (1981) for determining antigenicity profiles, and the Kyte-Doolittle technique, Kyte et al., *J. Mol. Biol.* 157:105-132 (1982) for hydropathy plots.

An antibody is said to "specifically bind" its target antigen when the dissociation constant ($K_D$) is $\leq 10^{-8}$ M. The antibody specifically binds antigen with "high affinity" when the $K_D$ is $\leq 5 \times 10^{-9}$ M, and with "very high affinity" when the $K_D$ is $\leq 5 \times 10^{-10}$ M. In one embodiment of the invention, the antibody has a $K_D$ of $\leq 10^{-9}$ M and an off rate ($k_d$) of about $1 \times 10^{-4}$/sec. In one embodiment of the invention, the off rate if $<10^{-5}$/sec. In another embodiment of the invention, the antibody will bind LRP6 with a KD of between $10^{-8}$ and $10^{-10}$ M.

The term "surface plasmon resonance," as used herein, refers to an optical phenomenon that allows for the analysis of real-time biospecific interactions by detection of alterations in protein concentrations within a biosensor matrix, for example using the BIAcore system (Biacore International AB, Uppsala, Sweden). For further descriptions, see Jonsson et al., *Ann. Biol. Clin.* 51:19-26 (1993); Jonsson et al., *Biotechniques* 11:620-627 (1991); Johnsson et al., *J. Mol. Recognit.* 8:125-131 (1995); and Johnsson et al., *Anal. Biochem.* 198:268-277 (1991).

It is understood that the antibodies of the present invention may be modified, such that they are substantially identical to the antibody polypeptide sequences, or fragments thereof, and still bind the LRP6 epitopes provided herein. Polypeptide sequences are "substantially identical" when optimally aligned using such programs as GAP or BESTFIT using default gap weights, they share at least 80% sequence identity, at least 90% sequence identity, at least 95% sequence identity, at least 96% sequence identity, at least 97% sequence identity, at least 98% sequence identity, or at least 99% sequence identity.

As discussed herein, minor variations in the amino acid sequences of antibodies or antigen-binding regions thereof are contemplated as being encompassed by the present invention, providing that the variations in the amino acid sequence maintain at least 75%, more preferably at least 80%, at least 90%, at least 95%, at least 96%, at least 97%, at least 98% and most preferably at least 99% sequence identity. In particular, conservative amino acid replacements are contemplated. Conservative replacements are those that take place within a family of amino acids that are related in their side chains. Genetically encoded amino acids are generally divided into families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). More preferred families are: (1) aliphatic-hydroxy (serine, threonine); (2) amide-containing (asparagine, glutamine); (3) aliphatic (alanine, valine, leucine, isoleucine); and (4) aromatic (phenylalanine, tryptophan). For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al., *Science* 253:164 (1991). Thus, the foregoing examples demonstrate that those of skill in the art can recognize sequence motifs and structural conformations that may be used to define structural and functional domains in accordance with the invention.

The anti-LRP6 antibodies may also be generated using peptide analogs of the epitopic determinants disclosed herein, which analogs may consist of non-peptide compounds having properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p. 392 (1985); and Evans et al., *J. Med. Chem.* 30:1229 (1987).

The term "immune complex" refers to the combination formed when an antibody binds to an epitope on an antigen.

The term "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule to elicit a desired response in the individual. A therapeutically effective amount is also one in which any toxic or detrimental effects of the substance/molecule are outweighed by the therapeutically beneficial effects.

The term "cytotoxic agent" as used herein refers to a substance that inhibits or prevents the function of cells and/or causes destruction of cells. The term is intended to include radioactive isotopes (e.g., phosphorus-32, copper-67, arsenic-77, rhodium-105, palladium-109, silver-111, tin-121, iodine-125 or 131, holmium-166, lutetium-177, rhenium-186 or 188, iridium-194, gold-199, astatium-211, yttrium-90, samarium-153, or bismuth-212), chemotherapeutic agents, e.g., methotrexate, adriamicin, vinca alkaloids (vincristine, vinblastine, etoposide), doxorubicin, melphalan, mitomycin C, chloramucil, daunorubicin, or other intercalating agents, enzymes and fragments thereof such as nucleolytic enzymes, antibiotics, and toxins such as small molecule toxins or enzymatically active toxins of bacterial (e.g., *Diptheria* toxin, *Pseudomonas* endotoxin and exotoxin, *Staphylococcal* enterotoxin A), fungal (e.g., α-sarcin, restrictocin), plant (e.g., abrin, ricin, modeccin, viscumin, pokeweed anti-viral protein, saporin, gelonin, momoridin, trichosanthin, barley toxin) or animal origin, e.g., cytotoxic RNases, such as extracellular pancreatic RNases; DNase I, including fragments and/or variants thereof, and the various antitumor or anticancer agents disclosed below. Other cytotoxic agents are described below. A tumoricidal agent causes destruction of tumor cells.

The term "chemotherapeutic agent" means a chemical compound that non-specifically decreases or inhibits the growth, proliferation, and/or survival of cancer cells. Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous. Such agents are often administered, and are often most effective, in combination, e.g., in the formulation CHOP.

Examples of chemotherapeutic agents contemplated by the present invention include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1 and calicheamicin omega1 (see, e.g., Agnew, *Chem Intl. Ed. Engl.*, 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins;

mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE®), and doxetaxel (TAXOTERE®); chlorambucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above.

Also useful are combinations of two or more of the above such as CHOP (a combination of cyclophosphamide, doxorubicin, vincristine and prednisone) as well as the use of the constituents of CHOP either alone or in various combinations such as CO, CH, CP, COP, CHO, CHP, HO, HP, HOP, OP, etc.; CHOP and bleomycin (CHOP-BLEO); cyclophosphamide and fludarabine; cyclophosphamide, mitoxantrone, prednisone and vincristine; cyclophosphamide, dexamethasone, doxorubicin and vincristine (CAVD); CAV; cyclophosphamide, doxorubicin and prednisone; cyclophosphamide, mitoxantrone, prednisone and vincristine (CNOP); cyclophosphamide, methotrexate, leucovorin and cytarabine (COMLA); cyclophosphamide, dexamethasone, doxorubicin and prednisone; cylophosphamide, prednisone, procarbazine and vincristine (COPP); cylophosphamide, prednisone and vincristine (COP and CVP-1); cyclophosphamide and mitoxantrone; etoposide; mitoxantrone, ifosfamide and etoposide (MIV); cytarabine; methylprednisolone and cisplatin (ESHAP); methylprednisolone, cytarabine and cisplatin (ESAP); fludarabine, cytosine arabinoside (Ara-C) and G-CSF (FLAG); irinotecan, 5-FU (IFL); oxaliplatin, 5-FU, leucovorin (FOLFOX); oxaliplatin, irinotecan (IROX); leucovorin, 5-FU, irinotecan (FOLFIRI); methotrexate, leucovorin, doxorubicin, cyclophosphamide, vincristine, bleomycin and prednisone (MACOP-B); methotrexate, bleomycin, doxorubicin, cyclophosphamide, vincristine, and dexamethasone (m-BACOD); prednisone, cyclophosphamide, etoposide, cytarabine, bleomycin, vincristine, methotrexate and leucovorin (PROMACE-CYTABOM); etoposide, cyclophosphamide, vincristine, prednisone and bleomycin (VACOP-B); fludarabine and mitoxantrone; cisplatine, cytarabine and etoposide; desamethasone, fludarabine and mitoxantrone; chlorambucil and prednisone; busulfan and fludarabine; ICE; DVP; ATRA; Idarubicin, hoelzer chemotherapy regime; La La chemotherapy regime; ABVD; CEOP; 2-CdA; FLAG and IDA (with or without subsequent G-CSF treatment); VAD; M and P; C-Weekly; ABCM; MOPP; cisplatin, cytarabine and dexamethasone (DHAP), as well as the additional known chemotherapeutic regimens. Preparation and dosing schedules for such chemotherapeutic agents are also described in *Chemotherapy Service* Ed., M. C. Perry, Williams and Wilkins, Baltimore, Md. (1992).

Also included in this definition are anti-hormonal agents that act to regulate, reduce, block, or inhibit the effects of hormones that can promote the growth of cancer, and are often in the form of systemic or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); COX-2 inhibitors such as celecoxib (CELEBREX®; 4-(5-(4-methylphenyl)-3-(trifluoromethyl)-1H-pyrazol-1-yl)benzenesulfonamide; and pharmaceutically acceptable salts, acids or derivatives of any of the above.

The terms "radiation therapy" or "radiotherapeutic agents" mean the administration of radioactivity or radioactive compounds to a subject with cancer. Radiation decreases or inhibits the growth of dividing cells, such as cancer cells. Such therapy may include radiation from radioactive isotopes (e.g., phosphorous-32, copper-67, arsenic-77, rhodium-105, palladium-109, silver-111, tin-121, iodine-125 or 131, holmium-166, lutetium-177, rhenium-186 or 188, iridium-194, gold-199, astatium-21, yttrium-90, samarium-153, or bismuth-212). The radiation therapy may be whole body irradiation, or may be directed locally to a specific site or tissue in the body, such as the colon or small intestine.

The term "targeted anti-cancer agents" means molecules directed to specific proteins, lipids, or other cellular components. Such targeted anti-cancer agents include monoclonal antibodies or other types of antibodies (i.e., fragments, single chain antibodies, bi-specific antibodies) or molecules (such as peptibodies) that target antigens. Examples of such immunotherapeutic targeted antibodies include without limitation bevacizumab (AVASTIN®, Genentech, South San Francisco, Calif.), tositumomab (BEXXAR®, GlaxoSmithKline, United Kingdom), alemtuzumab (CAMPATH®, Genzyme, Cambridge, Mass.), cetuximab (ERBITUX®, ImClone Systems Inc., New York), trastuzumab (HERCEPTIN®, Genentech), gemtuzumab ozogamicin (MYLOTARG®, Wyeth, Madison, N.J.), rituximab (RITUXAN®, Biogen Idec, San Diego, Calif.), ibritumomab tiuxetan (ZEVALIN®, Biogen Idec), mitomomab (BEC2), C225, OncoLym, epratuzumab (Lymphocide), oregovomab (OVAREX®, ViRexx, Edmonton, Alberta, Canada), lintuzumab (SMART M195), apolizumab (SMART 1D10), VITAXIN® (Medimmune, Inc., Gaithersburg, Md.). Also captured by the term "targeted anti-cancer agents" are immunotoxins. By "immunotoxin" is meant an antibody- or antibody-like-toxin conjugate intended to destroy specific target cells (e.g., tumor cells) that bear antigens homologous to the antibody. Examples of toxins that are coupled to such antibodies include but are not limited to ricin A chain (RTA), blocked ricin (blR), saporin (SAP), pokeweed antiviral protein (PAP) and *Pseudomonas* exotoxin (PE), and other toxic compounds, such as radioisotopes and other chemotherapeutic drugs, as described above.

The term "immunotherapeutic agent" is used herein to denote an agent that is an immunopotentiator or an immunosuppressant and is useful for treating diseases and disorders including cancer. Such agents include, without limitation, various cytokines and lymphokines, such as a number of interleukins, including IL-1, IL-2, IL-3, IL-4, IL-5, IL-12 and muteins of these molecules; interferons, such as but not limited to IFN-α, IFN-β, IFN-γ and muteins thereof; colony stimulating factors such as GM-CSF and muteins of GM-CSF; tumor necrosis factors, such as TNF-α and TNF-β and muteins of these molecules. Also captured by the term "immunotherapeutic agent" are immunotoxins. By "immunotoxin" is meant an antibody-toxin conjugate intended to destroy specific target cells (e.g., tumor cells) which bear antigens homologous to the antibody. Examples of toxins that are coupled to such antibodies include but are not limited to ricin A chain (RTA), blocked ricin (blR), saporin (SAP), pokeweed antiviral protein (PAP) and *Pseudomonas* exotoxin (PE), and other toxic compounds, such as radioisotopes and other chemotherapeutic drugs, described further below.

The term "immunoconjugate" refers to the association of an antibody with another agent, such as a chemotherapeutic agent, a toxin, an immunotherapeutic agent, and the like. In this way, the agent of interest can be targeted directly to cells bearing the LRP6 cell surface receptor. The mode of association between the antibody and the agent of interest is immaterial. Thus, the antibody and agent may be associated through non-covalent interactions such as through electrostatic forces, or by covalent bonds. Various linkers, known in the art, can be employed in order to form the immunoconjugate. Additionally, the immunoconjugate can be provided in the form of a fusion protein that may be expressed from a polynucleotide encoding the immunoconjugate.

The term "agent" means any substance, naturally occurring or synthetic, and includes, without limitation, small molecules, single or double stranded oligonucleotide molecules such as aptamers, polynucleotides (DNA or RNA) interfering nucleic acid molecules (shRNA, siRNA, double stranded RNA, or microRNA), lipids, simple or complex sugars or other carbohydrates, peptide-nucleic acids, peptomimetics, peptides, single or multi chain polypeptides, antibodies, antibody fragments such as Fabs or Fc-fusion molecules, or peptibodies. Also included as agents are those substances that are chimeras, hybrids, or fusions of any of the foregoing, such as, for example, a peptide-lipid fusion molecule, a polypeptide linked to a sugar molecule such as polyethylene glycol, an aptamer fused to a lipid, and the like.

The term "anti-cancer agent" means any agent that can be used to treat a cell proliferative disorder such as cancer, including cytotoxic agents, chemotherapeutic agents, radiotherapy and radiotherapeutic agents, targeted anti-cancer agents, and immunotherapeutic agents.

As used herein, the terms "label" and "detectable label" refer to a molecule capable of detection, including, but not limited to, radioactive isotopes, fluorescers, semiconductor nanocrystals, chemiluminescers, chromophores, enzymes, enzyme substrates, enzyme cofactors, enzyme inhibitors, dyes, metal ions, metal sols, ligands (e.g., biotin, streptavidin or haptens) and the like. The term "fluorescer" refers to a substance or a portion thereof which is capable of exhibiting fluorescence in the detectable range. Particular examples of labels which may be used under the invention include, but are not limited to, horseradish peroxidase (HRP), fluorescein, FITC, rhodamine, dansyl, umbelliferone, dimethyl acridinium ester (DMAE), Texas red, luminol, NADPH and α- or β-galactosidase.

The term "anti-tumor activity" means a reduction in the rate of cell proliferation and hence a decline in growth rate of abnormal cells that arises during therapy. Such activity can be assessed using accepted animal models.

The term "subject" as used herein means a mammal, such as, but not limited to, domestic and farm animals and zoo, sports or pet animals, such as cow, monkey, horse, sheep, pig, cat, dog, mouse, rat, rabbit, guinea pig or human. Preferably the mammal is a human. A subject can be a human patient.

The term "biological sample" as used herein refers to a sample of tissue or fluid isolated from a subject such as, but not limited to, blood, plasma, platelets, serum, fecal matter, urine, bone marrow, bile, spinal fluid, lymph fluid, cerebrospinal fluid, samples of the skin, secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. The samples detailed above need not necessarily be in the form obtained directly from the source. For example, the sample can be treated prior to use, such as, for example, by heating, centrifuging, etc. prior to analysis.

The term "Wnt signaling pathway" means the canonical Wnt pathway in which members of the Wnt family of secreted protein ligands bind a receptor complex of LRP and Frizzled (FZD) allowing β-catenin to be translocated into the nucleus, interact with the LEF/TCF transcription factors and activate target gene expression.

The phrase "cell proliferation related disease or disorder" means those diseases or disorders in which cell proliferation is altered, i.e., either increased or decreased as compared with the homeostatic state.

The phrase "pharmaceutically acceptable" vehicle, carrier or adjuvant means a non-toxic agent that can be tolerated by a recipient patient at the dosages and concentrations employed. Often the pharmaceutical carrier is an aqueous pH buffered solution. Representative non-limiting examples of such agents include human serum albumin, gelatin, ion exchangers, alumina, lecithin, buffer substances such as phosphates, citrate, glycine, antioxidants such as ascorbic acid, potassium sorbate and other organic acids, and salts or electrolytes such as protamine sulfate. Suitable vehicles are, for example, water, saline, phosphate-buffered saline, dextrose, glycerol, ethanol, hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI Americas, Inc., Bridgewater, N.J.), polyethylene glycol (PEG), and PLURONIC® (BASF, Florham Park, N.J.). Other suitable agents are well known to those in the art. See, for example, *Remington's Pharmaceutical Sciences*, Mack Publishing Company, Easton, Pa., 19th edition, 1995. Actual methods of preparing such compositions are also known, or will be apparent, to those skilled in the art. See, e.g., *Remington's Pharmaceutical Sciences*, Mack Publishing Company, Easton, Pa., 19th edition, 1995.

Various aspects of the invention are described in further detail in the following sections and subsections.

II. LRP6 and the Wnt-Signaling Pathway

The Wnt signaling pathway is important in embryonic development and postnatal tissue maintenance. This is achieved by directing a specific set of genes that control temporal and spatial regulation of cell growth, movement and cell survival (reviewed in Barker and Clevers, *Nature Rev.* 5:997 (2006) herein incorporated by reference in its entirety). Proper regulation of this pathway is important for maintaining tissue homeostasis. Chronic activation of this pathway promotes uncontrolled cell growth and survival and can consequently drive the development of cell proliferative diseases, such as cancer. Alternatively, abnormal inhibition of this pathway can result in many disease states, for example loss of bone mass and other bone diseases. Wnt proteins initiate downstream signaling by interacting with a Frizzled receptor and one of two cell-surface receptors, which are members of the low-density-lipoprotein receptor (LDLR)-related proteins (LRPs): LRP5 and LRP6 (reviewed in He et al, *Development* 131:1663-1677 (2004), herein incorporated by reference in its entirety).

The role of LRP6 in canonical Wnt signaling was discovered via genetic studies. Mutant mice lacking LRP6 exhibited composite phenotypes similar to mutations in several individual Wnt genes (Pinson et al, *Nature* 407:535-538 (2000)). In *Xenopus* embryos, dominant-negative LRP6 blocked signaling by several Wnt proteins, whereas overexpression of LRP6 activated Wnt/β-catenin signaling (Tamai et al, *Nature* 407:530-535 (2000)). Furthermore, it has been shown that expression of either LRP6 or LRP5 is necessary for cells to respond to canonical Wnt signaling (reviewed in He et al., supra, 2004).

LRP5 and LRP6 are highly homologous and share 73% and 64% identity in their extra- and intracellular domains, respectively. They are widely co-expressed during embryogenesis and in adult tissues and share some functional redundancy. The extracellular domains of LRP5 and LRP6 comprise three basic domains: 1) a YWTD (tyrosine, tryptophan, threonine, aspartic acid)-type β-propeller domain, 2) an EGF (epidermal growth factor)-like domain, and 3) an LDLR type A (LA) domain. The YWTD-type β-propeller domain contains six YWTD repeats of 43-50 amino acid residues each and forms a six-bladed β-propeller structure. In LRP5 and LRP6, there are four YWTD-type β-propeller domains that are each followed by an EGF-like domain, which comprises about 40 amino acid residues with conserved cysteine residues, which in turn are followed by three LA domains. (Springer et al, *J. Mol. Biol.* 283:837-862 (1998); Jeon et al, *Nat. Struct. Biol.* 8:499-504 (2001)). The β-propeller-EGF-like domains appear to bind extracellular ligands. The extracellular domain of LRP6 is defined by amino acid residues 20 to 1375 and contains four propeller domains at amino acid residues 43-324, 352-627, 654-929, and 957-1250. Amino acid residues 32-1386 of LRP5 comprise the extracellular domain which contains four propeller domains at amino acid residues 75-336, 365-639, 667-941, and 969-1253.

LRP5 and LRP6 purportedly bind Axin directly via their intracellular domains thereby regulating β-catenin phosphorylation and degradation. LRP5/6 activity is modulated by secreted ligands Dkk1, Dkk2 and SOST/Sclerostin, which through their interaction with LRP5/6 antagonize Wnt activity. Dkk1 is a high affinity ligand for LRP5/6 and disrupts the binding of the FZD-LRP complex. Dkk1 appears to bind LRP6 via its C-terminal cysteine-rich domain which is also suggested to be required for Wnt antagonism (He et al, supra, 2004). Dkk1 has been demonstrated to interact with the region of LRP6 encompassing the third and fourth propeller domains which is distinct from the Wnt binding region of LRP6. Dkk1 also binds Kremen-1 and -2 which are single-pass transmembrane proteins. The interaction of Dkk1 and LRP5/6 with Kremen-1 internalizes the complex for degradation thereby reducing the number of Wnt coreceptors available for signaling.

Wnt signaling has been shown to be involved in normal skeletogenesis and cancer-related bone diseases. Activating mutations in LRP5 have been demonstrated to cause osteoporosis-pseudoglioma syndrome which is characterized by low bone mineral density and skeletal fragility (Gong et al, *Cell* 107:513-523 (2001)). On the other hand, mutations in LRP5 that prevent binding of Dkk1 have been implicated in the syndrome of hereditary high bone density (Boyden et al, *New Engl J Med* 346:1513-1521 (2002)). Dkk1 has also been implicated in normal skeletal development. Mice lacking Dkk1 grow extra digits, while increased expression of Dkk1 results in a loss of bony structures (Mukhopadhyay et al, *Dev Cell* 1:423-434 (2001)). In addition, plasma cells from multiple myeloma patients express Dkk1 whereas those from normal patients do not. The expression of Dkk1 positively correlates with the presence of bone lesions in multiple myeloma. Osteolytic lesions have also been found in prostate cancer patients (Tian et al, *New Engl J Med* 349:2483-2494 (2003); Politou et al, *Int. J Cancer* 119:1728-1731 (2006)).

Maintenance of bone mass is influenced by the balance achieved between bone forming cells (osteoblasts) and bone resorbing cells (osteoclasts). According to Diarra et al (*Nat Med* 13:156-163 (2007)), Dkk1 appears to be involved in bone loss in inflammatory joint disease such as rheumatoid arthritis, osteoarthritis and ankylosing spondylitis by inhibiting differentiation of osteoblasts and promoting the activity of osteoclasts. In situations where higher than normal levels of Dkk1 are present, Dkk1 appears to be involved in the bone destructive phenotype entailing joint instability common to diseases such as rheumatoid arthritis. In situations where lower than normal levels of Dkk1 are present, the bone anabolic reaction in the joint may be enhanced, leading to joint ankylosis in osteoarthritis and ankylosing spondylosis (Diarra et al, supra, 2007).

Modulation of LRP6 and/or Dkk1 resulting in activation of Wnt signaling may be useful to treat conditions such as bone disorders including, but not limited to osteoarthritis, rheumatoid arthritis, ankylosing spondylosis, and osteolytic lesions caused by a variety of diseases including osteoarthritis and multiple myeloma. Additional conditions that may benefit from these treatments include, but are not limited to, gastrointestinal disorders, such as irritable bowel disease, peptic ulcers, and mucositis, and wound healing, as Wnt/LRP6 signaling has been shown to regulate tissue homeostasis and repair in these tissues.

III. Anti-LRP6 Antibodies and Antigen-Binding Fragments

A variety of selective binding agents useful for regulating the activity of LRP6 are provided. These agents include, for instance, antibodies and antigen-binding fragments thereof that contain an antigen binding domain (e.g., single chain antibodies, domain antibodies, immunoadhesions, and polypeptides with an antigen-binding region) that specifically bind to an LRP6 polypeptide (e.g., a human, rat and/or murine LRP6 polypeptide).

The present invention provides isolated anti-LRP6 antibodies that bind to human LRP6 epitopes. In a preferred embodiment, the LRP6 epitope is substantially the same epitope as a human LRP6 epitope defined by amino acids 43-324 of SEQ ID NO: 2 (e.g., SEQ ID NO: 13 or 16). In another embodiment, the isolated anti-LRP6 antibodies and antigen-binding fragments thereof bind to a human LRP6 epitope, or substantially the same epitope, defined by amino acids 43-324 of SEQ ID NO: 2. In another embodiment, an isolated antibody or antigen-binding fragment thereof specifically binds to a human LRP6 epitope, or substantially the same epitope, defined by amino acids 43-324 of SEQ ID NO: 2. In another embodiment, a monoclonal antibody or antigen-binding fragment thereof specifically binds to a human LRP6 epitope, or substantially the same epitope, defined by amino acids 43-324 of SEQ ID NO: 2. Such antibodies or antigen-binding fragments thereof can be prepared by any one of a number of processes disclosed below, for example, by immunizing an animal with at least a first LRP6 antigenic composition and selecting from the immunized animal an antibody that substantially cross-reacts with the anti-LRP6 monoclonal antibodies provided herein.

In another embodiment, the LRP6 epitope is substantially the same epitope as a human LRP6 epitope defined by amino acids 263-283 of SEQ ID NO: 2 (e.g., SEQ ID NO: 371). In another embodiment, isolated anti-LRP6 antibodies and antigen-binding fragments thereof bind to a human LRP6 epitope, or substantially the same epitope, defined by amino acids 263-283 of SEQ ID NO: 2. In another embodiment, an isolated antibody or antigen-binding fragment thereof specifically binds to a human LRP6 epitope, or substantially the same epitope, defined by amino acids 263-283 of SEQ ID NO: 2. In another embodiment, a monoclonal antibody or antigen-binding fragment thereof specifically binds to a human LRP6 epitope, or substantially the same epitope, defined by amino acids 263-283 of SEQ ID NO: 2. Such antibodies or antigen-binding fragments thereof can be prepared by any one of a number of processes disclosed below, for example, by immunizing an animal with at least a first LRP6 antigenic composition and selecting from the immunized animal an antibody that substantially cross-reacts with the anti-LRP6 monoclonal antibodies provided herein.

In another embodiment, the LRP6 epitope is substantially the same epitope as a human LRP6 epitope defined by amino acids 352-627 of SEQ ID NO: 2 (e.g., SEQ ID NO: 370). In another embodiment, isolated anti-LRP6 antibodies and antigen-binding fragments thereof bind to a human LRP6 epitope, or substantially the same epitope, defined by amino acids 352-627 of SEQ ID NO: 2. In another embodiment, an isolated antibody or antigen-binding fragment thereof specifically binds to a human LRP6 epitope, or substantially the same epitope, defined by amino acids 352-627 of SEQ ID NO: 2. In another embodiment, a monoclonal antibody or antigen-binding fragment thereof specifically binds to a human LRP6 epitope, or substantially the same epitope, defined by amino acids 352-627 of SEQ ID NO: 2. Such antibodies or antigen-binding fragments thereof can be prepared by any one of a number of processes disclosed below, for example, by immunizing an animal with at least a first LRP6 antigenic composition and selecting from the immunized animal an antibody that substantially cross-reacts with the anti-LRP6 monoclonal antibodies provided herein.

Some of the antibodies and antigen-binding fragments that are provided include (a) one or more light chain (LC) complementary determining regions (CDRs) selected from the group consisting of:
(i) a LC CDR1 with at least 80% sequence identity to SEQ ID NO: 114, 126, 138, 150, 162, 174, 186, 198, 210, 222, 234, 246, 258, 282, 294, 306, 318, 330, 342, 354, or 366;
(ii) a LC CDR2 with at least 80% sequence identity to SEQ ID NO: 115, 127, 139, 151, 163, 175, 187, 199, 211, 223, 235, 247, 259, 283, 295, 307, 319, 331, 343, 355, or 367; and
(iii) a LC CDR3 with at least 80% sequence identity to SEQ ID NO: 116, 128, 140, 152, 164, 176, 188, 200, 212, 224, 236, 248, 260, 284, 296, 308, 320, 332, 344, 356, or 368;
(b) one or more heavy chain (HC) CDRs selected from the group consisting of:
(i) a HC CDR1 with at least 80% sequence identity to SEQ ID NO: 108, 120, 132, 144, 156, 168, 180, 192, 204, 216, 228, 240, 252, 264, 270, 276, 288, 300, 312, 324, 336, 348, or 360;
(ii) a HC CDR2 with at least 80% sequence identity to SEQ ID NO: 109, 121, 133, 145, 157, 169, 181, 193, 205, 217, 229, 241, 253, 265, 271, 277, 289, 301, 313, 325, 337, 349, or 361; and
(iii) a HC CDR3 with at least 80% sequence identity to SEQ ID NO: 110, 122, 134, 146, 158, 170, 182, 194, 206, 218, 230, 242, 254, 266, 272, 278, 290, 302, 314, 326, 338, 350, or 362; or
(c) one or more LC CDRs of (a) and one or more HC CDRs of (b).

Such antibodies or antigen-binding fragments thereof may specifically bind an LRP6 polypeptide. Certain antibodies or fragments include one, two, three, four, five or six of the foregoing CDRs. In a particular embodiment, the CDRs are arranged as in monoclonal antibodies 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1.

The light chain and heavy chains of other antibodies or fragments are as described above but have at least 90% sequence identity to the foregoing sequences. Still other antibodies or antigen-binding fragments thereof have a light chain in which CDR1 has the amino acid sequence as set forth in SEQ ID NO: 114, 126, 138, 150, 162, 174, 186, 198, 210, 222, 234, 246, 258, 282, 294, 306, 318, 330, 342, 354 or 366, CDR2 has the amino acid sequence as set forth in SEQ ID NO: 115, 127, 139, 151, 163, 175, 187, 199, 211, 223, 235, 247, 259, 283, 295, 307, 319, 331, 343, 355 or 367, and/or CDR3 has the amino acid sequence as set forth in SEQ ID NO: 116, 128, 140, 152, 164, 176, 188, 200, 212, 224, 236, 248, 260, 284, 296, 308, 320, 332, 344, 356, or 368. Some antibodies or antigen-binding fragments thereof may also have a heavy chain in which CDR1 has the amino acid sequence as set forth in SEQ ID NO: 108, 120, 132, 144, 156, 168, 180, 192, 204, 216, 228, 240, 252, 264, 270, 276, 288, 300, 312, 324, 336, 348, or 360, CDR2 has the amino acid sequence as set forth in SEQ ID NO: 109, 121, 133, 145, 157, 169, 181, 193, 205, 217, 229, 241, 253, 265, 271, 277, 289, 301, 313, 325, 337, 349, or 361, and/or CDR3 has the amino acid sequence as set forth in SEQ ID NO: 110, 122, 134, 146, 158, 170, 182, 194, 206, 218, 230, 242, 254, 266, 272, 278, 290, 302, 314, 326, 338, 350, or 362.

The antibodies encompassed by the present invention include IgA, IgG$_{1-4}$, IgE, IgM, and IgD antibodies. In a preferred embodiment, the antibody is an IgG and is an IgG$_1$, IgG$_2$, IgG$_3$, or IgG$_4$ subtype. In another preferred embodiment, the anti-LRP6 antibody is the same class and subclass as antibodies 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1.

The class and subclass of anti-LRP6 antibodies may be identified by any method known in the art. In general, the class and subclass of an antibody may be identified using antibodies that are specific for a particular class and subclass of antibody. Such antibodies are available commercially. The class and subclass can be determined by ELISA, Western blot, as well as other techniques. Alternatively, the class and subclass may be determined by sequencing all or a portion of the constant domains of the heavy and/or light chains of the antibodies, comparing their amino acid sequences to the known amino acid sequences of various classes and subclasses of immunoglobulins, and determining the class and subclass of the antibodies.

In another aspect of the invention, the anti-LRP6 antibody demonstrates both species and molecule selectivity. In one embodiment, the anti-LRP6 antibody binds to human, cynomologous, rhesus or chimpanzee LRP6. Following the teachings of the specification, one may determine the species selectivity for the anti-LRP6 antibody using methods well known in the art. For instance, one may determine species selectivity using Western blot, FACS, ELISA or RIA.

A. Naturally Occurring Antibody Structure

Some of the selective binding agents that are provided have the structure typically associated with naturally occurring antibodies. The structural units of these antibodies typically comprise one or more tetramers, each composed of two identical couplets of polypeptide chains, though some species of mammals also produce antibodies having only a single heavy chain. In a typical antibody, each pair or couplet includes one full-length "light" chain (in certain embodiments, about 25 kD) and one full-length "heavy" chain (in certain embodiments, about 50-70 kD). Each individual immunoglobulin chain is composed of several "immunoglobulin (Ig) domains," each consisting of roughly 90 to 110 amino acids and expressing a characteristic folding pattern. These domains are the basic units of which antibody polypeptides are composed. The amino-terminal portion of each chain typically includes a variable domain that is responsible for antigen recognition. The carboxy-terminal portion is more conserved evolutionarily than the other end of the chain and is referred to as the "constant region" or "C region". Human light chains generally are classified as kappa ($\kappa$) and lambda ($\lambda$) light chains, and each of these contains one variable domain and one constant domain. Heavy chains are typically classified as mu ($\mu$), delta ($\delta$), gamma ($\gamma$), alpha ($\alpha$), or epsilon ($\epsilon$) chains and these define the antibody's isotype as IgM, IgD, IgG, IgA, and IgE, respectively. IgG has several subtypes, including, but not limited to, $IgG_1$, $IgG_2$, $IgG_3$, and $IgG_4$. IgM subtypes include $IgM_1$ and $IgM_2$. IgA subtypes include $IgA_1$ and $IgA_2$. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that may be responsible for effector function. The number of heavy chain constant region domains will depend on the isotype. IgG heavy chains, for example, each contains three C region domains known as $C_H1$, $C_H2$, and $C_H3$. The antibodies that are provided may have any of these isotypes and subtypes. In certain embodiments of the invention, the anti-LRP6 antibodies are of the $IgG_1$, $IgG_2a$ or $IgG_2b$ subtypes.

In full-length light and heavy chains, the variable and constant regions are joined by a "J" region of about 12 or more amino acids, with the heavy chain also including a "D" region of about 10 or more amino acids. See, e.g., *Fundamental Immunology*, $2^{nd}$ ed., Ch. 7 (Paul, W., ed) 1989, New York: Raven Press (herein incorporated by reference in its entirety for all purposes). The variable regions of each light/heavy chain pair typically form the antigen binding site.

Variable regions of immunoglobulin chains generally exhibit the same overall structure, comprising relatively conserved framework regions (FR) joined by three hypervariable regions, more often called "complementarity determining regions" or CDRs. The CDRs from the two chains of each heavy chain/light chain pair mentioned above typically are aligned by the framework regions to form a structure that binds specifically with a specific epitope on the target protein (e.g., LRP6). From N-terminal to C-terminal, naturally occurring light and heavy chain variable regions both typically conform to the following order of these elements: FR1, CDR1, FR2, CDR2, FR3, CDR3 and FR4. A numbering system has been devised for assigning numbers to amino acids that occupy positions in each of these domains. This numbering system is defined in Kabat et al., *Sequences of Proteins of Immunological Interest* (1991, National Institutes of Health Publication No. 91-3242, $5^{th}$ ed., U.S. Department of Health and Human Services, Bethesda, Md.) or Chothia and Lesk, *J. Mol. Biol.* 196:901-917 (1987); Chothia et al., *Nature* 342:878-883 (1989).

As a specific example of such antibodies, in one embodiment, the anti-LRP6 antibody is a monoclonal antibody derived from mice. Exemplary antibodies capable of binding to the aforementioned epitope are the monoclonal antibodies 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1 (see, Examples below), each of which comprises a light chain and a heavy chain.

B. Variable Domains of Antibodies

Also provided are antibodies that comprise a light chain variable region selected from the group consisting of $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, $V_L17$, $V_L18$, $V_L19$, $V_L20$, $V_L21$, $V_L22$, or $V_L23$ and/or a heavy chain variable region selected from the group consisting of $V_H1$ and $V_H2$, $V_H3$, $V_H4$, $V_H5$, $V_H6$, $V_H7$, $V_H8$, $V_H9$, $V_H10$, $V_H11$, $V_H12$, $V_H13$, $V_H14$, $V_H15$, $V_H16$, $V_H17$, $V_H18$, $V_H19$, $V_H20$, $V_H21$, $V_H22$, or $V_H23$ as shown in Table 1 below, and antigen-binding regions, derivatives, muteins and variants of these light and heavy chain variable regions.

Antibodies of this type can generally be designated by the formula "$V_L x V_H y$," wherein "x" is the number of the light chain variable region and "y" corresponds to the number of the heavy chain variable region as listed in Table 1. In general, x and y are each 1, 2, 3, 4, 5, 6, 7, 8, 9, 10, 11, 12, 13, 14, 15, 16, 17, 18, 19, 20, 21, 22, or 23.

TABLE 1

| Antibody Designation | Abbreviated Name | Chain Type | NT Sequence (SEQ ID NO:) | AA Sequence (SEQ ID NO:) |
|---|---|---|---|---|
| 77.2 | $V_H1$ | Heavy | 17 | 18 |
| 77.2 | $V_L1$ | Light | 19 | 20 |
| 135.16 | $V_H2$ | Heavy | 21 | 22 |
| 135.16 | $V_L2$ | Light | 23 | 24 |
| 213.7 | $V_H3$ | Heavy | 25 | 26 |
| 213.7 | $V_L3$ | Light | 27 | 28 |
| 240.8 | $V_H4$ | Heavy | 29 | 30 |

TABLE 1-continued

| Antibody Designation | Abbreviated Name | Chain Type | NT Sequence (SEQ ID NO:) | AA Sequence (SEQ ID NO:) |
|---|---|---|---|---|
| 240.8 | $V_L4$ | Light | 31 | 32 |
| 413.1 | $V_H5$ | Heavy | 33 | 34 |
| 413.1 | $V_L5$ | Light | 35 | 36 |
| 421.1 | $V_H6$ | Heavy | 37 | 38 |
| 421.1 | $V_L6$ | Light | 39 | 40 |
| 498.3 | $V_H7$ | Heavy | 41 | 42 |
| 498.3 | $V_L7$ | Light | 43 | 44 |
| 537.2 | $V_H8$ | Heavy | 45 | 46 |
| 537.2 | $V_L8$ | Light | 47 | 48 |
| 606.4 | $V_H9$ | Heavy | 49 | 50 |
| 606.4 | $V_L9$ | Light | 51 | 52 |
| 620.1 | $V_H10$ | Heavy | 53 | 54 |
| 620.1 | $V_L10$ | Light | 55 | 56 |
| 856.6 | $V_H11$ | Heavy | 57 | 58 |
| 856.6 | $V_L11$ | Light | 59 | 60 |
| 923.3 | $V_H12$ | Heavy | 61 | 62 |
| 923.3 | $V_L12$ | Light | 63 | 64 |
| 931.1 | $V_H13$ | Heavy | 65 | 66 |
| 931.1 | $V_L13$ | Light | 67 | 68 |
| 993.9 | $V_H14$ | Heavy | 69 | 70 |
| 993.9 | $V_L14$ | Light | N/D | N/D |
| 995.5 | $V_H15$ | Heavy | 71 | 72 |
| 995.5 | $V_L15$ | Light | N/D | N/D |
| 1115.3 | $V_H16$ | Heavy | 73 | 74 |
| 1115.3 | $V_L16$ | Light | 75 | 76 |
| 1213.2 | $V_H17$ | Heavy | 77 | 78 |
| 1213.2 | $V_L17$ | Light | 79 | 80 |
| 1253.12 | $V_H18$ | Heavy | 81 | 82 |
| 1253.12 | $V_L18$ | Light | 83 | 84 |
| 1281.1 | $V_H19$ | Heavy | 85 | 86 |
| 1281.1 | $V_L19$ | Light | 87 | 88 |
| 1293.11 | $V_H20$ | Heavy | 89 | 90 |
| 1293.11 | $V_L20$ | Light | 91 | 92 |
| 1433.8 | $V_H21$ | Heavy | 93 | 94 |
| 1433.8 | $V_L21$ | Light | 95 | 96 |
| 1470.2 | $V_H22$ | Heavy | 97 | 98 |
| 1470.2 | $V_L22$ | Light | 99 | 100 |
| 1903.1 | $V_H23$ | Heavy | 101 | 102 |
| 1903.1 | $V_L23$ | Light | 103 | 104 |

*N/D = not determined

Thus, $V_L2V_H1$ refers to an antibody with a light chain variable region domain comprising the amino acid sequence of $V_L2$ and a heavy chain variable region comprising the amino acid sequence of $V_H1$. In some instances, the foregoing antibodies include two light chain variable region domains and two heavy chain variable region domains (e.g., $V_L1_2V_H1_2$, etc.).

As a specific example of such antibodies, certain antibodies or antigen-binding fragments thereof comprise the variable region of the light chain or the variable region of the heavy chain of 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1, wherein the light chain variable region consists of the amino acids shown in SEQ ID NO: 20, 24, 28, 32, 36, 40, 44, 48, 52, 56, 60, 64, 68, 76, 80, 84, 88, 92, 96, 100, or 104 and the heavy chain variable region consists of the amino acids shown in SEQ ID NO: 18, 22, 26, 30, 34, 38, 42, 46, 50, 54, 58, 62, 66, 70, 72, 74, 78, 82, 86, 90, 94, 98, or 102. In one aspect of this embodiment, the antibody consists of two identical heavy chains and two identical light chains.

Certain antibodies or antigen-binding fragments thereof comprise a light chain variable domain comprising a sequence of amino acids that differs from the sequence of a light chain variable domain selected from $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, $V_L17$, $V_L18$, $V_L19$, $V_L20$, $V_L21$, $V_L22$, or $V_L23$ at only 1, 2, 3, 4, 5, 6, 7, 8, 9, 10, 11, 12, 13, 14, or 15 amino acid residues, wherein each such sequence difference is independently either a deletion, insertion, or substitution of one amino acid. The light chain variable region in some antibodies comprises a sequence of amino acids that has at least 70%, at least 75%, at least 80%, at least 85%, at least 90%, at least 95%, at least 96%, at least 97%, at least 98% or at least 99% sequence identity to the amino acid sequences of the light chain variable regions of $V_L1$, $V_L2$, $V_L3$, $V_L4$, $V_L5$, $V_L6$, $V_L7$, $V_L8$, $V_L9$, $V_L10$, $V_L11$, $V_L12$, $V_L13$, $V_L14$, $V_L15$, $V_L16$, $V_L17$, $V_L18$, $V_L19$, $V_L20$, $V_L21$, $V_L22$, or $V_L23$.

Some antibodies or antigen-binding fragments thereof that are provided comprise a heavy chain variable domain comprising a sequence of amino acids that differs from the sequence of a heavy chain variable domain selected from $V_H1$ and $V_H2$, $V_H3$, $V_H4$, $V_H5$, $V_H6$, $V_H7$, $V_H8$, $V_H9$, $V_H10$, $V_H11$, $V_H12$, $V_H13$, $V_H14$, $V_H15$, $V_H16$, $V_H17$, $V_H18$, $V_H19$, $V_H20$, $V_H21$, $V_H22$ or $V_H23$ only at 1, 2, 3, 4, 5, 6, 7, 8, 9, 10, 11, 12, 13, 14 or 15 amino acid residues, wherein each such sequence difference is independently either a deletion, insertion, or substitution of one amino acid. The heavy chain variable region in some antibodies comprises a sequence of amino acids that has at least 70%, at least 75%, at least 80%, at least 85%, at least 90%, at least 95%, at least 96%, at least 97%, at least 98% or at least 99% sequence identity to the amino acid sequences of the heavy chain variable region of $V_H1$ and $V_H2$, $V_H3$, $V_H4$, $V_H5$, $V_H6$, $V_H7$, $V_H8$, $V_H9$, $V_H10$, $V_H11$, $V_H12$, $V_H13$, $V_H14$, $V_H15$, $V_H16$, $V_H17$, $V_H18$, $V_H19$, $V_H20$, $V_H21$, $V_H22$ or $V_H23$. Still other antibodies or antigen-binding fragments thereof include variant forms of a variant light chain and a variant heavy chain as just described. An alignment of the variable domains of the antibodies listed in Table 1 is seen in FIGS. 4 (heavy chain alignment) and 5 (light chain alignment).

C. CDRs of Antibodies

Complementarity determining regions (CDRs) and framework regions (FR) of a given antibody may be identified using the system described by Kabat et al., 1991, supra. Certain antibodies that are disclosed herein comprise one or more amino acid sequences that are identical or have substantial sequence identity to the amino acid sequences of one or more of the CDRs as summarized in Table 2.

TABLE 2

| Antibody Designation | Chain | CDR | NT Sequence (SEQ ID NO:) | AA Sequence (SEQ ID NO:) |
|---|---|---|---|---|
| 77.2 | Heavy | CDR1 | 105 | 108 |
| 77.2 | Heavy | CDR2 | 106 | 109 |
| 77.2 | Heavy | CDR3 | 107 | 110 |
| 77.2 | Light | CDR1 | 111 | 114 |
| 77.2 | Light | CDR2 | 112 | 115 |
| 77.2 | Light | CDR3 | 113 | 116 |
| 135.16 | Heavy | CDR1 | 117 | 120 |
| 135.16 | Heavy | CDR2 | 118 | 121 |
| 135.16 | Heavy | CDR3 | 119 | 122 |
| 135.16 | Light | CDR1 | 123 | 126 |
| 135.16 | Light | CDR2 | 124 | 127 |
| 135.16 | Light | CDR3 | 125 | 128 |
| 213.7 | Heavy | CDR1 | 129 | 132 |
| 213.7 | Heavy | CDR2 | 130 | 133 |
| 213.7 | Heavy | CDR3 | 131 | 134 |
| 213.7 | Light | CDR1 | 135 | 138 |
| 213.7 | Light | CDR2 | 136 | 139 |
| 213.7 | Light | CDR3 | 137 | 140 |
| 240.8 | Heavy | CDR1 | 141 | 144 |
| 240.8 | Heavy | CDR2 | 142 | 145 |
| 240.8 | Heavy | CDR3 | 143 | 146 |
| 240.8 | Light | CDR1 | 147 | 150 |
| 240.8 | Light | CDR2 | 148 | 151 |
| 240.8 | Light | CDR3 | 149 | 152 |
| 413.1 | Heavy | CDR1 | 153 | 156 |
| 413.1 | Heavy | CDR2 | 154 | 157 |

TABLE 2-continued

| Antibody Designation | Chain | CDR | NT Sequence (SEQ ID NO:) | AA Sequence (SEQ ID NO:) |
|---|---|---|---|---|
| 413.1 | Heavy | CDR3 | 155 | 158 |
| 413.1 | Light | CDR1 | 159 | 162 |
| 413.1 | Light | CDR2 | 160 | 163 |
| 413.1 | Light | CDR3 | 161 | 164 |
| 421.1 | Heavy | CDR1 | 165 | 168 |
| 421.1 | Heavy | CDR2 | 166 | 169 |
| 421.1 | Heavy | CDR3 | 167 | 170 |
| 421.1 | Light | CDR1 | 171 | 174 |
| 421.1 | Light | CDR2 | 172 | 175 |
| 421.1 | Light | CDR3 | 173 | 176 |
| 498.3 | Heavy | CDR1 | 177 | 180 |
| 498.3 | Heavy | CDR2 | 178 | 181 |
| 498.3 | Heavy | CDR3 | 179 | 182 |
| 489.3 | Light | CDR1 | 183 | 186 |
| 489.3 | Light | CDR2 | 184 | 187 |
| 489.3 | Light | CDR3 | 185 | 188 |
| 537.2 | Heavy | CDR1 | 189 | 192 |
| 537.2 | Heavy | CDR2 | 190 | 193 |
| 537.2 | Heavy | CDR3 | 191 | 194 |
| 537.2 | Light | CDR1 | 195 | 198 |
| 537.2 | Light | CDR2 | 196 | 199 |
| 537.2 | Light | CDR3 | 197 | 200 |
| 606.4 | Heavy | CDR1 | 201 | 204 |
| 606.4 | Heavy | CDR2 | 202 | 205 |
| 606.4 | Heavy | CDR3 | 203 | 206 |
| 606.4 | Light | CDR1 | 207 | 210 |
| 606.4 | Light | CDR2 | 208 | 211 |
| 606.4 | Light | CDR3 | 209 | 212 |
| 620.1 | Heavy | CDR1 | 213 | 216 |
| 620.1 | Heavy | CDR2 | 214 | 217 |
| 620.1 | Heavy | CDR3 | 215 | 218 |
| 620.1 | Light | CDR1 | 219 | 222 |
| 620.1 | Light | CDR2 | 220 | 223 |
| 620.1 | Light | CDR3 | 221 | 224 |
| 856.6 | Heavy | CDR1 | 225 | 228 |
| 856.6 | Heavy | CDR2 | 226 | 229 |
| 856.6 | Heavy | CDR3 | 227 | 230 |
| 856.6 | Light | CDR1 | 231 | 234 |
| 856.6 | Light | CDR2 | 232 | 235 |
| 856.6 | Light | CDR3 | 233 | 236 |
| 923.3 | Heavy | CDR1 | 237 | 240 |
| 923.3 | Heavy | CDR2 | 238 | 241 |
| 923.3 | Heavy | CDR3 | 239 | 242 |
| 923.3 | Light | CDR1 | 243 | 246 |
| 923.3 | Light | CDR2 | 244 | 247 |
| 923.3 | Light | CDR3 | 245 | 248 |
| 931.1 | Heavy | CDR1 | 249 | 252 |
| 931.1 | Heavy | CDR2 | 250 | 253 |
| 931.1 | Heavy | CDR3 | 251 | 254 |
| 931.1 | Light | CDR1 | 255 | 258 |
| 931.1 | Light | CDR2 | 256 | 259 |
| 931.1 | Light | CDR3 | 257 | 260 |
| 993.9 | Heavy | CDR1 | 261 | 264 |
| 993.9 | Heavy | CDR2 | 262 | 265 |
| 993.9 | Heavy | CDR3 | 263 | 266 |
| 993.9 | Light | CDR1 | N/D | N/D |
| 993.9 | Light | CDR2 | N/D | N/D |
| 993.9 | Light | CDR3 | N/D | N/D |
| 995.5 | Heavy | CDR1 | 267 | 270 |
| 995.5 | Heavy | CDR2 | 268 | 271 |
| 995.5 | Heavy | CDR3 | 269 | 272 |
| 995.5 | Light | CDR1 | N/D | N/D |
| 995.5 | Light | CDR2 | N/D | N/D |
| 995.5 | Light | CDR3 | N/D | N/D |
| 1115.3 | Heavy | CDR1 | 273 | 276 |
| 1115.3 | Heavy | CDR2 | 274 | 277 |
| 1115.3 | Heavy | CDR3 | 275 | 278 |
| 1115.3 | Light | CDR1 | 279 | 282 |
| 1115.3 | Light | CDR2 | 280 | 283 |
| 1115.3 | Light | CDR3 | 281 | 284 |
| 1213.2 | Heavy | CDR1 | 285 | 288 |
| 1213.2 | Heavy | CDR2 | 286 | 289 |
| 1213.2 | Heavy | CDR3 | 287 | 290 |
| 1213.2 | Light | CDR1 | 291 | 294 |
| 1213.2 | Light | CDR2 | 292 | 295 |
| 1213.2 | Light | CDR3 | 293 | 296 |
| 1253.12 | Heavy | CDR1 | 297 | 300 |
| 1253.12 | Heavy | CDR2 | 298 | 301 |
| 1253.12 | Heavy | CDR3 | 299 | 302 |
| 1253.12 | Light | CDR1 | 303 | 306 |
| 1253.12 | Light | CDR2 | 304 | 307 |
| 1253.12 | Light | CDR3 | 305 | 308 |
| 1281.1 | Heavy | CDR1 | 309 | 312 |
| 1281.1 | Heavy | CDR2 | 310 | 313 |
| 1281.1 | Heavy | CDR3 | 311 | 314 |
| 1281.1 | Light | CDR1 | 315 | 318 |
| 1281.1 | Light | CDR2 | 316 | 319 |
| 1281.1 | Light | CDR3 | 317 | 320 |
| 1293.11 | Heavy | CDR1 | 321 | 324 |
| 1293.11 | Heavy | CDR2 | 322 | 325 |
| 1293.11 | Heavy | CDR3 | 323 | 326 |
| 1293.11 | Light | CDR1 | 327 | 330 |
| 1293.11 | Light | CDR2 | 328 | 331 |
| 1293.11 | Light | CDR3 | 329 | 332 |
| 1433.8 | Heavy | CDR1 | 333 | 336 |
| 1433.8 | Heavy | CDR2 | 334 | 337 |
| 1433.8 | Heavy | CDR3 | 335 | 338 |
| 1433.8 | Light | CDR1 | 339 | 342 |
| 1433.8 | Light | CDR2 | 340 | 343 |
| 1433.8 | Light | CDR3 | 341 | 344 |
| 1470.2 | Heavy | CDR1 | 345 | 348 |
| 1470.2 | Heavy | CDR2 | 346 | 349 |
| 1470.2 | Heavy | CDR3 | 347 | 350 |
| 1470.2 | Light | CDR1 | 351 | 354 |
| 1470.2 | Light | CDR2 | 352 | 355 |
| 1470.2 | Light | CDR3 | 353 | 356 |
| 1903.1 | Heavy | CDR1 | 357 | 360 |
| 1903.1 | Heavy | CDR2 | 358 | 361 |
| 1903.1 | Heavy | CDR3 | 359 | 362 |
| 1903.1 | Light | CDR1 | 363 | 366 |
| 1903.1 | Light | CDR2 | 364 | 367 |
| 1903.1 | Light | CDR3 | 365 | 368 |

N/D = not determined

The antibodies and antigen-binding fragments that are provided can each include one, two, three, four, five or six of the CDRs listed above. Certain antibodies have variant forms of the CDRs listed in Table 2, with one or more (e.g., 2, 3, 4, 5 or 6) of the CDRs each having at least 80%, at least 85%, at least 90%, at least 95%, at least 96%, at least 97%, at least 98% or at least 99% sequence identity to a CDR sequence listed in Table 2. For example, the antibody or antigen-binding region may include both a light chain CDR3 and a heavy chain CDR3 that each have at least 80%, at least 85%, at least 90%, at least 95%, at least 96%, at least 97%, at least 98% or at least 99% sequence identity to the light chain CDR3 and heavy chain CDR3, respectively, listed in Table 2. The invention also provides for antibodies that have CDR sequences that differ from the CDR sequences listed in Table 2 such that the amino acid sequence for any given CDR differs from the sequence listed in Table 2 by no more than 1, 2, 3, 4, or 5 amino acid residues. Differences from the listed sequences usually are conservative substitutions (see below).

As a specific example, the antibodies and antigen-binding fragments that are provided may comprise one or more of the following CDR sequences from the 77.2 light chain:

CDR1: amino acids 44-59 of SEQ ID NO: 20, which also corresponds to SEQ ID NO: 114 (encoded by nucleotides 130-177 of SEQ ID NO: 19 (SEQ ID NO: 111));

CDR2: amino acids 75-81 of SEQ ID NO: 20, which also corresponds to SEQ ID NO: 115 (encoded by nucleotides 223-243 of SEQ ID NO: 19 (SEQ ID NO: 112)); and CDR3: amino acids 114-122 of SEQ ID NO: 20, which also corresponds to SEQ ID NO: 116 (encoded by nucleotides 340-366 of SEQ ID NO: 19 (SEQ ID NO: 113)).

Additional antibodies and antigen-binding fragments of the invention may comprise one or more of the following CDR sequences from the 77.2 heavy chain:

CDR1: amino acids 45-54 of SEQ ID NO: 18, which also corresponds to SEQ ID NO: 108 (encoded by nucleotides 133-162 of SEQ ID NO: 17 (SEQ ID NO: 105));

CDR2: amino acids 69-85 of SEQ ID NO: 18, which also corresponds to SEQ ID NO: 109 (encoded by nucleotides 205-255 of SEQ ID NO: 17 (SEQ ID NO: 106)); and CDR3: amino acids 118-133 of SEQ ID NO: 18, which also corresponds to SEQ ID NO: 110 (encoded by nucleotides 352-399 of SEQ ID NO: 17 (SEQ ID NO: 107)).

As another specific example, the antibodies and antigen-binding fragments that are provided may comprise one or more of the following CDR sequences from the 135.16 light chain:

CDR1: amino acids 48-58 of SEQ ID NO: 24, which also corresponds to SEQ ID NO: 126 (encoded by nucleotides 142-174 of SEQ ID NO: 23 (SEQ ID NO: 123));

CDR2: amino acids 74-80 of SEQ ID NO: 24, which also corresponds to SEQ ID NO: 127 (encoded by nucleotides 222-240 of SEQ ID NO: 23 (SEQ ID NO: 124)); and CDR3: amino acids 113-121 of SEQ ID NO: 24, which also corresponds to SEQ ID NO: 128 (encoded by nucleotides 337-363 of SEQ ID NO: 23 (SEQ ID NO: 125)).

Additional antibodies and antigen-binding fragments of the invention may comprise one or more of the following CDR sequences from the 135.16 heavy chain:

CDR1: amino acids 45-54 of SEQ ID NO: 22, which also corresponds to SEQ ID NO: 120 (encoded by nucleotides 133-162 of SEQ ID NO: 21 (SEQ ID NO: 117));

CDR2: amino acids 69-85 of SEQ ID NO: 22, which also corresponds to SEQ ID NO: 121 (encoded by nucleotides 205-255 of SEQ ID NO: 21 (SEQ ID NO: 118)); and CDR3: amino acids 118-129 of SEQ ID NO: 22, which also corresponds to SEQ ID NO: 122 (encoded by nucleotides 352-387 of SEQ ID NO: 21 (SEQ ID NO: 119)).

As another specific example, the antibodies and antigen-binding fragments that are provided may comprise one or more of the following CDR sequences from the 213.7 light chain:

CDR1: amino acids 45-54 of SEQ ID NO: 28, which also corresponds to SEQ ID NO: 138 (encoded by nucleotides 133-162 of SEQ ID NO: 27 (SEQ ID NO: 135));

CDR2: amino acids 70-76 of SEQ ID NO: 28, which also corresponds to SEQ ID NO: 139 (encoded by nucleotides 208-228 of SEQ ID NO: 27 (SEQ ID NO: 136)); and CDR3: amino acids 109-117 of SEQ ID NO: 28, which also corresponds to SEQ ID NO: 140 (encoded by nucleotides 325-351 of SEQ ID NO: 27 (SEQ ID NO: 137)).

Additional antibodies and antigen-binding fragments of the invention may comprise one or more of the following CDR sequences from the 213.7 heavy chain:

CDR1: amino acids 45-54 of SEQ ID NO: 26, which also corresponds to SEQ ID NO: 132 (encoded by nucleotides 133-162 of SEQ ID NO: 25 (SEQ ID NO: 129));

CDR2: amino acids 69-85 of SEQ ID NO: 26, which also corresponds to SEQ ID NO: 133 (encoded by nucleotides 205-255 of SEQ ID NO: 25 (SEQ ID NO: 130)); and CDR3: amino acids 118-129 of SEQ ID NO: 26, which also corresponds to SEQ ID NO: 134 (encoded by nucleotides 352-387 of SEQ ID NO: 25 (SEQ ID NO: 131)).

As another specific example, the antibodies and antigen-binding fragments that are provided may comprise one or more of the following CDR sequences from the 240.8 light chain:

CDR1: amino acids 45-54 of SEQ ID NO: 32, which also corresponds to SEQ ID NO: 150 (encoded by nucleotides 130-162 of SEQ ID NO: 31 (SEQ ID NO: 147));

CDR2: amino acids 70-76 of SEQ ID NO: 32, which also corresponds to SEQ ID NO: 151 (encoded by nucleotides 208-228 of SEQ ID NO: 31 (SEQ ID NO: 148)); and CDR3: amino acids 109-117 of SEQ ID NO: 32, which also corresponds to SEQ ID NO: 152 (encoded by nucleotides 325-351 of SEQ ID NO: 31 (SEQ ID NO: 149)).

Additional antibodies and antigen-binding fragments of the invention may comprise one or more of the following CDR sequences from the 240.8 heavy chain:

CDR1: amino acids 45-54 of SEQ ID NO: 30, which also corresponds to SEQ ID NO: 144 (encoded by nucleotides 133-162 of SEQ ID NO: 29 (SEQ ID NO: 141));

CDR2: amino acids 69-85 of SEQ ID NO: 30, which also corresponds to SEQ ID NO: 145 (encoded by nucleotides 205-255 of SEQ ID NO: 29 (SEQ ID NO: 142)); and CDR3: amino acids 118-128 of SEQ ID NO: 30, which also corresponds to SEQ ID NO: 146 (encoded by nucleotides 352-384 of SEQ ID NO: 29 (SEQ ID NO: 143)).

As another specific example, the antibodies and antigen-binding fragments that are provided may comprise one or more of the following CDR sequences from the 413.1 light chain:

CDR1: amino acids 46-55 of SEQ ID NO: 36, which also corresponds to SEQ ID NO: 162 (encoded by nucleotides 139-165 of SEQ ID NO: 35 (SEQ ID NO: 159));

CDR2: amino acids 71-77 of SEQ ID NO: 36, which also corresponds to SEQ ID NO: 163 (encoded by nucleotides 211-231 of SEQ ID NO: 35 (SEQ ID NO: 160)); and CDR3: amino acids 110-118 of SEQ ID NO: 36, which also corresponds to SEQ ID NO: 164 (encoded by nucleotides 328-354 of SEQ ID NO: 35 (SEQ ID NO: 161)).

Additional antibodies and antigen-binding fragments of the invention may comprise one or more of the following CDR sequences from the 413.1 heavy chain:

CDR1: amino acids 58-67 of SEQ ID NO: 34, which also corresponds to SEQ ID NO: 156 (encoded by nucleotides 172-201 of SEQ ID NO: 33 (SEQ ID NO: 153));

CDR2: amino acids 82-98 of SEQ ID NO: 34, which also corresponds to SEQ ID NO: 157 (encoded by nucleotides 244-294 of SEQ ID NO: 33 (SEQ ID NO: 154)); and CDR3: amino acids 131-142 of SEQ ID NO: 34, which also corresponds to SEQ ID NO: 158 (encoded by nucleotides 391-426 of SEQ ID NO: 33 (SEQ ID NO: 155)).

As another specific example, the antibodies and antigen-binding fragments that are provided may comprise one or more of the following CDR sequences from the 421.1 light chain:

CDR1: amino acids 44-53 of SEQ ID NO: 40, which also corresponds to SEQ ID NO: 174 (encoded by nucleotides 130-159 of SEQ ID NO: 39 (SEQ ID NO: 171));

CDR2: amino acids 69-75 of SEQ ID NO: 40, which also corresponds to SEQ ID NO: 175 (encoded by nucleotides 205-225 of SEQ ID NO: 39 (SEQ ID NO: 172)); and CDR3: amino acids 108-116 of SEQ ID NO: 40, which also corresponds to SEQ ID NO: 176 (encoded by nucleotides 322-348 of SEQ ID NO: 39 (SEQ ID NO: 173)).

Additional antibodies and antigen-binding fragments of the invention may comprise one or more of the following CDR sequences from the 421.1 heavy chain:

CDR1: amino acids 45-54 of SEQ ID NO: 38, which also corresponds to SEQ ID NO: 168 (encoded by nucleotides 133-162 of SEQ ID NO: 37 (SEQ ID NO: 165));

CDR2: amino acids 69-75 of SEQ ID NO: 38, which also corresponds to SEQ ID NO: 169 (encoded by nucleotides 205-225 of SEQ ID NO: 37 (SEQ ID NO: 166)); and CDR3: amino acids 108-116 of SEQ ID NO: 38, which also corresponds to SEQ ID NO: 170 (encoded by nucleotides 322-348 of SEQ ID NO: 37 (SEQ ID NO: 167)).

As another specific example, the antibodies and antigen-binding fragments that are provided may comprise one or more of the following CDR sequences from the 498.3 light chain:

CDR1: amino acids 44-54 of SEQ ID NO: 44, which also corresponds to SEQ ID NO: 186 (encoded by nucleotides 130-162 of SEQ ID NO: 43 (SEQ ID NO: 183));

CDR2: amino acids 70-76 of SEQ ID NO: 44, which also corresponds to SEQ ID NO: 187 (encoded by nucleotides 208-228 of SEQ ID NO: 43 (SEQ ID NO: 184)); and CDR3: amino acids 109-117 of SEQ ID NO: 44, which also corresponds to SEQ ID NO: 188 (encoded by nucleotides 325-351 of SEQ ID NO: 43 (SEQ ID NO: 185)).

Additional antibodies and antigen-binding fragments of the invention may comprise one or more of the following CDR sequences from the 489.3 heavy chain:

CDR1: amino acids 45-54 of SEQ ID NO: 42, which also corresponds to SEQ ID NO: 180 (encoded by nucleotides 133-162 of SEQ ID NO: 41 (SEQ ID NO: 177));

CDR2: amino acids 69-85 of SEQ ID NO: 42, which also corresponds to SEQ ID NO: 181 (encoded by nucleotides 205-255 of SEQ ID NO: 41 (SEQ ID NO: 178)); and CDR3: amino acids 118-127 of SEQ ID NO: 42, which also corresponds to SEQ ID NO: 182 (encoded by nucleotides 352-381 of SEQ ID NO: 41 (SEQ ID NO: 179)).

As another specific example, the antibodies and antigen-binding fragments that are provided may comprise one or more of the following CDR sequences from the 537.2 light chain:

CDR1: amino acids 46-55 of SEQ ID NO: 48, which also corresponds to SEQ ID NO: 198 (encoded by nucleotides 136-165 of SEQ ID NO: 47 (SEQ ID NO: 195));

CDR2: amino acids 71-77 of SEQ ID NO: 48, which also corresponds to SEQ ID NO: 199 (encoded by nucleotides 211-231 of SEQ ID NO: 47 (SEQ ID NO: 196)); and CDR3: amino acids 110-118 of SEQ ID NO: 48, which also corresponds to SEQ ID NO: 200 (encoded by nucleotides 328-354 of SEQ ID NO: 47 (SEQ ID NO: 197)).

Additional antibodies and antigen-binding fragments of the invention may comprise one or more of the following CDR sequences from the 537.2 heavy chain:

CDR1: amino acids 44-54 of SEQ ID NO: 46, which also corresponds to SEQ ID NO: 192 (encoded by nucleotides 130-162 of SEQ ID NO: 45 (SEQ ID NO: 189));

CDR2: amino acids 69-84 of SEQ ID NO: 46, which also corresponds to SEQ ID NO: 193 (encoded by nucleotides 205-252 of SEQ ID NO: 45 (SEQ ID NO: 190)); and CDR3: amino acids 117-127 of SEQ ID NO: 46, which also corresponds to SEQ ID NO: 194 (encoded by nucleotides 349-381 of SEQ ID NO: 45 (SEQ ID NO: 191)).

As another specific example, the antibodies and antigen-binding fragments that are provided may comprise one or more of the following CDR sequences from the 606.4 light chain:

CDR1: amino acids 44-54 of SEQ ID NO: 52, which also corresponds to SEQ ID NO: 210 (encoded by nucleotides 130-162 of SEQ ID NO: 51 (SEQ ID NO: 207));

CDR2: amino acids 70-76 of SEQ ID NO: 52, which also corresponds to SEQ ID NO: 211 (encoded by nucleotides 208-228 of SEQ ID NO: 51 (SEQ ID NO: 208)); and CDR3: amino acids 109-117 of SEQ ID NO: 52, which also corresponds to SEQ ID NO: 212 (encoded by nucleotides 325-351 of SEQ ID NO: 51 (SEQ ID NO: 209)).

Additional antibodies and antigen-binding fragments of the invention may comprise one or more of the following CDR sequences from the 606.4 heavy chain:

CDR1: amino acids 45-54 of SEQ ID NO: 50, which also corresponds to SEQ ID NO: 204 (encoded by nucleotides 133-162 of SEQ ID NO: 49 (SEQ ID NO: 201));

CDR2: amino acids 69-85 of SEQ ID NO: 50, which also corresponds to SEQ ID NO: 205 (encoded by nucleotides 205-255 of SEQ ID NO: 49 (SEQ ID NO: 202)); and CDR3: amino acids 118-127 of SEQ ID NO: 50, which also corresponds to SEQ ID NO: 207 (encoded by nucleotides 352-381 of SEQ ID NO: 49 (SEQ ID NO: 203)).

As another specific example, the antibodies and antigen-binding fragments that are provided may comprise one or more of the following CDR sequences from the 620.1 light chain:

CDR1: amino acids 44-60 of SEQ ID NO: 56, which also corresponds to SEQ ID NO: 222 (encoded by nucleotides 130-180 of SEQ ID NO: 55 (SEQ ID NO: 219));

CDR2: amino acids 76-82 of SEQ ID NO: 56, which also corresponds to SEQ ID NO: 223 (encoded by nucleotides 226-246 of SEQ ID NO: 55 (SEQ ID NO: 220)); and CDR3: amino acids 115-123 of SEQ ID NO: 56, which also corresponds to SEQ ID NO: 224 (encoded by nucleotides 343-369 of SEQ ID NO: 55 (SEQ ID NO: 221)).

Additional antibodies and antigen-binding fragments of the invention may comprise one or more of the following CDR sequences from the 620.1 heavy chain:

CDR1: amino acids 58-67 of SEQ ID NO: 54, which also corresponds to SEQ ID NO: 216 (encoded by nucleotides 172-201 of SEQ ID NO: 53 (SEQ ID NO: 213));

CDR2: amino acids 82-98 of SEQ ID NO: 54, which also corresponds to SEQ ID NO: 217 (encoded by nucleotides 244-294 of SEQ ID NO: 53 (SEQ ID NO: 214)); and CDR3: amino acids 131-142 of SEQ ID NO: 54, which also corresponds to SEQ ID NO: 218 (encoded by nucleotides 391-426 of SEQ ID NO: 53 (SEQ ID NO: 215)).

As another specific example, the antibodies and antigen-binding fragments that are provided may comprise one or more of the following CDR sequences from the 856.6 light chain:

CDR1: amino acids 28-37 of SEQ ID NO: 60, which also corresponds to SEQ ID NO: 234 (encoded by nucleotides 82-111 of SEQ ID NO: 59 (SEQ ID NO: 231));

CDR2: amino acids 53-59 of SEQ ID NO: 60, which also corresponds to SEQ ID NO: 235 (encoded by nucleotides 157-177 of SEQ ID NO: 59 (SEQ ID NO: 232)); and CDR3: amino acids 92-100 of SEQ ID NO: 60, which also corresponds to SEQ ID NO: 236 (encoded by nucleotides 274-300 of SEQ ID NO: 59 (SEQ ID NO: 233)).

Additional antibodies and antigen-binding fragments of the invention may comprise one or more of the following CDR sequences from the 856.6 heavy chain:

CDR1: amino acids 45-54 of SEQ ID NO: 58, which also corresponds to SEQ ID NO: 228 (encoded by nucleotides 133-162 of SEQ ID NO: 57 (SEQ ID NO: 225));

CDR2: amino acids 69-85 of SEQ ID NO: 58, which also corresponds to SEQ ID NO: 229 (encoded by nucleotides 205-255 of SEQ ID NO: 57 (SEQ ID NO: 226)); and CDR3: amino acids 118-129 of SEQ ID NO: 58, which also corresponds to SEQ ID NO: 230 (encoded by nucleotides 352-387 of SEQ ID NO: 57 (SEQ ID NO: 227)).

As another specific example, the antibodies and antigen-binding fragments that are provided may comprise one or more of the following CDR sequences from the 923.3 light chain:

CDR1: amino acids 44-54 of SEQ ID NO: 64, which also corresponds to SEQ ID NO: 246 (encoded by nucleotides 130-162 of SEQ ID NO: 63 (SEQ ID NO: 243));

CDR2: amino acids 70-76 of SEQ ID NO: 64, which also corresponds to SEQ ID NO: 247 (encoded by nucleotides 208-228 of SEQ ID NO: 63 (SEQ ID NO: 244)); and CDR3: amino acids 109-117 of SEQ ID NO: 64, which also corresponds to SEQ ID NO: 248 (encoded by nucleotides 325-351 of SEQ ID NO: 63 (SEQ ID NO: 245)).

Additional antibodies and antigen-binding fragments of the invention may comprise one or more of the following CDR sequences from the 923.3 heavy chain:

CDR1: amino acids 45-54 of SEQ ID NO: 62, which also corresponds to SEQ ID NO: 240 (encoded by nucleotides 133-162 of SEQ ID NO: 61 (SEQ ID NO: 237));

CDR2: amino acids 69-85 of SEQ ID NO: 62, which also corresponds to SEQ ID NO: 241 (encoded by nucleotides 205-255 of SEQ ID NO: 61 (SEQ ID NO: 238)); and CDR3: amino acids 118-128 of SEQ ID NO: 62, which also corresponds to SEQ ID NO: 242 (encoded by nucleotides 352-384 of SEQ ID NO: 61 (SEQ ID NO: 239)).

As another specific example, the antibodies and antigen-binding fragments that are provided may comprise one or more of the following CDR sequences from the 931.1 light chain:

CDR1: amino acids 44-54 of SEQ ID NO: 68, which also corresponds to SEQ ID NO: 258 (encoded by nucleotides 130-162 of SEQ ID NO: 67 (SEQ ID NO: 255));

CDR2: amino acids 70-76 of SEQ ID NO: 68, which also corresponds to SEQ ID NO: 259 (encoded by nucleotides 208-228 of SEQ ID NO: 67 (SEQ ID NO: 256)); and CDR3: amino acids 109-117 of SEQ ID NO: 68, which also corresponds to SEQ ID NO: 260 (encoded by nucleotides 325-351 of SEQ ID NO: 67 (SEQ ID NO: 257)).

Additional antibodies and antigen-binding fragments of the invention may comprise one or more of the following CDR sequences from the 931.1 heavy chain:

CDR1: amino acids 45-54 of SEQ ID NO: 66, which also corresponds to SEQ ID NO: 252 (encoded by nucleotides 133-162 of SEQ ID NO: 65 (SEQ ID NO: 249));

CDR2: amino acids 69-85 of SEQ ID NO: 66, which also corresponds to SEQ ID NO: 253 (encoded by nucleotides 205-255 of SEQ ID NO: 65 (SEQ ID NO: 250)); and CDR3: amino acids 118-127 of SEQ ID NO: 66, which also corresponds to SEQ ID NO: 254 (encoded by nucleotides 352-381 of SEQ ID NO: 65 (SEQ ID NO: 251)).

Additional antibodies and antigen-binding fragments of the invention may comprise one or more of the following CDR sequences from the 993.9 heavy chain:

CDR1: amino acids 44-54 of SEQ ID NO: 70, which also corresponds to SEQ ID NO: 264 (encoded by nucleotides 130-162 of SEQ ID NO: 69 (SEQ ID NO: 261));

CDR2: amino acids 69-74 of SEQ ID NO: 70, which also corresponds to SEQ ID NO: 265 (encoded by nucleotides 205-222 of SEQ ID NO: 69 (SEQ ID NO: 262)); and CDR3: amino acids 117-127 of SEQ ID NO: 70, which also corresponds to SEQ ID NO: 266 (encoded by nucleotides 349-381 of SEQ ID NO: 69 (SEQ ID NO: 263)).

Additional antibodies and antigen-binding fragments of the invention may comprise one or more of the following CDR sequences from the 995.5 heavy chain:

CDR1: amino acids 45-55 of SEQ ID NO: 72, which also corresponds to SEQ ID NO: 270 (encoded by nucleotides 133-165 of SEQ ID NO: 71 (SEQ ID NO: 267));

CDR2: amino acids 70-85 of SEQ ID NO: 72, which also corresponds to SEQ ID NO: 271 (encoded by nucleotides 208-255 of SEQ ID NO: 71 (SEQ ID NO: 268)); and CDR3: amino acids 118-128 of SEQ ID NO: 72, which also corresponds to SEQ ID NO: 272 (encoded by nucleotides 352-384 of SEQ ID NO: 71 (SEQ ID NO: 269)).

As another specific example, the antibodies and antigen-binding fragments that are provided may comprise one or more of the following CDR sequences from the 1115.3 light chain:

CDR1: amino acids 44-54 of SEQ ID NO: 76, which also corresponds to SEQ ID NO: 282 (encoded by nucleotides 133-162 of SEQ ID NO: 75 (SEQ ID NO: 279));

CDR2: amino acids 70-76 of SEQ ID NO: 76, which also corresponds to SEQ ID NO: 283 (encoded by nucleotides 208-228 of SEQ ID NO: 75 (SEQ ID NO: 280)); and CDR3: amino acids 109-117 of SEQ ID NO: 76, which also corresponds to SEQ ID NO: 284 (encoded by nucleotides 325-351 of SEQ ID NO: 75 (SEQ ID NO: 281)).

Additional antibodies and antigen-binding fragments of the invention may comprise one or more of the following CDR sequences from the 1115.3 heavy chain:

CDR1: amino acids 45-54 of SEQ ID NO: 74, which also corresponds to SEQ ID NO: 276 (encoded by nucleotides 133-162 of SEQ ID NO: 73 (SEQ ID NO: 273));

CDR2: amino acids 69-85 of SEQ ID NO: 74, which also corresponds to SEQ ID NO: 277 (encoded by nucleotides 205-255 of SEQ ID NO: 73 (SEQ ID NO: 274)); and CDR3: amino acids 118-128 of SEQ ID NO: 74, which also corresponds to SEQ ID NO: 278 (encoded by nucleotides 352-384 of SEQ ID NO: 73 (SEQ ID NO: 275)).

As another specific example, the antibodies and antigen-binding fragments that are provided may comprise one or more of the following CDR sequences from the 1213.2 light chain:

CDR1: amino acids 44-54 of SEQ ID NO: 80, which also corresponds to SEQ ID NO: 294 (encoded by nucleotides 130-162 of SEQ ID NO: 79 (SEQ ID NO: 291));

CDR2: amino acids 70-76 of SEQ ID NO: 80, which also corresponds to SEQ ID NO: 295 (encoded by nucleotides 208-228 of SEQ ID NO: 79 (SEQ ID NO: 292)); and CDR3: amino acids 109-117 of SEQ ID NO: 80, which also corresponds to SEQ ID NO: 296 (encoded by nucleotides 323-351 of SEQ ID NO: 79 (SEQ ID NO: 293)).

Additional antibodies and antigen-binding fragments of the invention may comprise one or more of the following CDR sequences from the 1213.2 heavy chain:

CDR1: amino acids 45-54 of SEQ ID NO: 78, which also corresponds to SEQ ID NO: 288 (encoded by nucleotides 133-162 of SEQ ID NO: 77 (SEQ ID NO: 285));

CDR2: amino acids 69-85 of SEQ ID NO: 78, which also corresponds to SEQ ID NO: 289 (encoded by nucleotides 205-255 of SEQ ID NO: 77 (SEQ ID NO: 286)); and CDR3: amino acids 118-127 of SEQ ID NO: 78, which also corresponds to SEQ ID NO: 290 (encoded by nucleotides 352-381 of SEQ ID NO: 771 (SEQ ID NO: 287)).

As another specific example, the antibodies and antigen-binding fragments that are provided may comprise one or more of the following CDR sequences from the 1253.12 light chain:

CDR1: amino acids 46-55 of SEQ ID NO: 84, which also corresponds to SEQ ID NO: 306 (encoded by nucleotides 136-165 of SEQ ID NO: 83 (SEQ ID NO: 303));

CDR2: amino acids 71-77 of SEQ ID NO: 84, which also corresponds to SEQ ID NO: 307 (encoded by nucleotides 211-231 of SEQ ID NO: 83 (SEQ ID NO: 304)); and CDR3: amino acids 110-118 of SEQ ID NO: 84, which also corresponds to SEQ ID NO: 308 (encoded by nucleotides 328-354 of SEQ ID NO: 83 (SEQ ID NO: 305)).

Additional antibodies and antigen-binding fragments of the invention may comprise one or more of the following CDR sequences from the 1253.12 heavy chain:

CDR1: amino acids 61-70 of SEQ ID NO: 82, which also corresponds to SEQ ID NO: 300 (encoded by nucleotides 181-210 of SEQ ID NO: 81 (SEQ ID NO: 297));

CDR2: amino acids 85-101 of SEQ ID NO: 82, which also corresponds to SEQ ID NO: 301 (encoded by nucleotides 253-303 of SEQ ID NO: 81 (SEQ ID NO: 298)); and CDR3: amino acids 134-142 of SEQ ID NO: 82, which also corresponds to SEQ ID NO: 302 (encoded by nucleotides 400-426 of SEQ ID NO: 81 (SEQ ID NO: 299)).

As another specific example, the antibodies and antigen-binding fragments that are provided may comprise one or more of the following CDR sequences from the 1281.1 light chain:

CDR1: amino acids 44-59 of SEQ ID NO: 88, which also corresponds to SEQ ID NO: 318 (encoded by nucleotides 130-177 of SEQ ID NO: 87 (SEQ ID NO: 315));

CDR2: amino acids 75-81 of SEQ ID NO: 88, which also corresponds to SEQ ID NO: 319 (encoded by nucleotides 225-243 of SEQ ID NO: 87 (SEQ ID NO: 316)); and CDR3: amino acids 104-122 of SEQ ID NO: 88, which also corresponds to SEQ ID NO: 320 (encoded by nucleotides 310-366 of SEQ ID NO: 87 (SEQ ID NO: 317)).

Additional antibodies and antigen-binding fragments of the invention may comprise one or more of the following CDR sequences from the 1281.1 heavy chain:

CDR1: amino acids 45-54 of SEQ ID NO: 86, which also corresponds to SEQ ID NO: 312 (encoded by nucleotides 133-162 of SEQ ID NO: 85 (SEQ ID NO: 309));

CDR2: amino acids 69-85 of SEQ ID NO: 86, which also corresponds to SEQ ID NO: 313 (encoded by nucleotides 205-255 of SEQ ID NO: 85 (SEQ ID NO: 310)); and CDR3: amino acids 118-133 of SEQ ID NO: 86, which also corresponds to SEQ ID NO: 314 (encoded by nucleotides 352-399 of SEQ ID NO: 85 (SEQ ID NO: 311)).

As another specific example, the antibodies and antigen-binding fragments that are provided may comprise one or more of the following CDR sequences from the 1393.11 light chain:

CDR1: amino acids 46-55 of SEQ ID NO: 92, which also corresponds to SEQ ID NO: 330 (encoded by nucleotides 136-165 of SEQ ID NO: 91 (SEQ ID NO: 327));

CDR2: amino acids 71-77 of SEQ ID NO: 92, which also corresponds to SEQ ID NO: 331 (encoded by nucleotides 211-231 of SEQ ID NO: 91 (SEQ ID NO: 328)); and CDR3: amino acids 100-118 of SEQ ID NO: 92, which also corresponds to SEQ ID NO: 332 (encoded by nucleotides 298-354 of SEQ ID NO: 91 (SEQ ID NO: 329)).

Additional antibodies and antigen-binding fragments of the invention may comprise one or more of the following CDR sequences from the 1293.11 heavy chain:

CDR1: amino acids 61-70 of SEQ ID NO: 90, which also corresponds to SEQ ID NO: 324 (encoded by nucleotides 181-210 of SEQ ID NO: 89 (SEQ ID NO: 321));

CDR2: amino acids 85-101 of SEQ ID NO: 90, which also corresponds to SEQ ID NO: 325 (encoded by nucleotides 253-303 of SEQ ID NO: 89 (SEQ ID NO: 322)); and CDR3: amino acids 134-142 of SEQ ID NO: 90, which also corresponds to SEQ ID NO: 326 (encoded by nucleotides 400-426 of SEQ ID NO: 89 (SEQ ID NO: 323)).

As another specific example, the antibodies and antigen-binding fragments that are provided may comprise one or more of the following CDR sequences from the 1433.8 light chain:

CDR1: amino acids 21-36 of SEQ ID NO: 96, which also corresponds to SEQ ID NO: 342 (encoded by nucleotides 61-108 of SEQ ID NO: 95 (SEQ ID NO: 339));

CDR2: amino acids 52-58 of SEQ ID NO: 96, which also corresponds to SEQ ID NO: 343 (encoded by nucleotides 154-174 of SEQ ID NO: 95 (SEQ ID NO: 340)); and CDR3: amino acids 91-99 of SEQ ID NO: 96, which also corresponds to SEQ ID NO: 344 (encoded by nucleotides 371-397 of SEQ ID NO: 95 (SEQ ID NO: 341)).

Additional antibodies and antigen-binding fragments of the invention may comprise one or more of the following CDR sequences from the 1433.8 heavy chain:

CDR1: amino acids 45-54 of SEQ ID NO: 94, which also corresponds to SEQ ID NO: 336 (encoded by nucleotides 133-162 of SEQ ID NO: 93 (SEQ ID NO: 333));

CDR2: amino acids 69-85 of SEQ ID NO: 94, which also corresponds to SEQ ID NO: 337 (encoded by nucleotides 205-255 of SEQ ID NO: 93 (SEQ ID NO: 334)); and CDR3: amino acids 118-133 of SEQ ID NO: 94, which also corresponds to SEQ ID NO: 338 (encoded by nucleotides 352-399 of SEQ ID NO: 93 (SEQ ID NO: 335)).

As another specific example, the antibodies and antigen-binding fragments that are provided may comprise one or more of the following CDR sequences from the 1470.2 light chain:

CDR1: amino acids 44-54 of SEQ ID NO: 100, which also corresponds to SEQ ID NO: 354 (encoded by nucleotides 130-162 of SEQ ID NO: 99 (SEQ ID NO: 351));

CDR2: amino acids 70-76 of SEQ ID NO: 100, which also corresponds to SEQ ID NO: 355 (encoded by nucleotides 208-228 of SEQ ID NO: 99 (SEQ ID NO: 352)); and CDR3: amino acids 109-117 of SEQ ID NO: 100, which also corresponds to SEQ ID NO: 356 (encoded by nucleotides 325-351 of SEQ ID NO: 99 (SEQ ID NO: 353)).

Additional antibodies and antigen-binding fragments of the invention may comprise one or more of the following CDR sequences from the 1470.2 heavy chain:

CDR1: amino acids 45-54 of SEQ ID NO: 98, which also corresponds to SEQ ID NO: 348 (encoded by nucleotides 133-162 of SEQ ID NO: 97 (SEQ ID NO: 345));

CDR2: amino acids 69-85 of SEQ ID NO: 98, which also corresponds to SEQ ID NO: 349 (encoded by nucleotides 205-255 of SEQ ID NO: 97 (SEQ ID NO: 346)); and CDR3: amino acids 118-127 of SEQ ID NO: 98, which also corresponds to SEQ ID NO: 350 (encoded by nucleotides 352-381 of SEQ ID NO: 97 (SEQ ID NO: 347)).

As another specific example, the antibodies and antigen-binding fragments that are provided may comprise one or more of the following CDR sequences from the 1903.1 light chain:

CDR1: amino acids 48-58 of SEQ ID NO: 104, which also corresponds to SEQ ID NO: 366 (encoded by nucleotides 142-174 of SEQ ID NO: 103 (SEQ ID NO: 363));

CDR2: amino acids 74-80 of SEQ ID NO: 104, which also corresponds to SEQ ID NO: 367 (encoded by nucleotides 222-240 of SEQ ID NO: 103 (SEQ ID NO: 364)); and CDR3: amino acids 113-121 of SEQ ID NO: 104, which also corresponds to SEQ ID NO: 368 (encoded by nucleotides 337-363 of SEQ ID NO: 103 (SEQ ID NO: 365)).

Additional antibodies and antigen-binding fragments of the invention may comprise one or more of the following CDR sequences from the 1903.1 heavy chain:

CDR1: amino acids 45-54 of SEQ ID NO: 102, which also corresponds to SEQ ID NO: 360 (encoded by nucleotides 133-162 of SEQ ID NO: 101 (SEQ ID NO: 357));

CDR2: amino acids 69-85 of SEQ ID NO: 102, which also corresponds to SEQ ID NO: 361 (encoded by nucleotides 205-255 of SEQ ID NO: 101 (SEQ ID NO: 358)); and CDR3: amino acids 118-127 of SEQ ID NO: 102, which also corresponds to SEQ ID NO: 362 (encoded by nucleotides 352-381 of SEQ ID NO: 101 (SEQ ID NO: 359)).

Certain antibodies that are disclosed herein comprise one or more amino acid sequences that comprise one or more CDRs that begin at least one amino acid before (N-terminal to) the beginning amino acid of the CDRs as summarized in Table 2. Yet other antibodies that are disclosed herein comprise one or more amino acid sequences that comprise one or more CDRs that begin at least two, at least three, or at least four amino acids before (N-terminal to) the beginning amino acid of the CDRs as summarized in Table 2. Certain other antibodies that are disclosed herein comprise one or more amino acid sequences that comprise one or more CDRs that end at least one amino acid after (C-terminal to) the last amino acid of the CDRs as summarized in Table 2. Yet other antibodies that are disclosed herein comprise one or more amino acid sequences that comprise one or more CDRs that end at least two, at least three, or at least four amino acids after (C-terminal to) the last amino acid of the CDRs as summarized in Table 2. Other antibodies disclosed herein comprise one or more amino acid sequences that comprise a combination of one or more CDRs with one, two, three or four amino acid differences at the start and/or stop of the CDRs as summarized in Table 2.

Polypeptides comprising one or more of the light or heavy chain CDRs may be produced by using a suitable vector to express the polypeptides in a suitable host cell as described in greater detail below.

The heavy and light chain variable regions and the CDRs that are disclosed in Tables 1 and 2 can be used to prepare any of the various types of antigen-binding fragments that are known in the art including, but not limited to, domain antibodies, Fab fragments, Fab' fragments, F(ab')$_2$ fragments, Fv fragments, single-chain antibodies, and scFvs.

D. Antibodies and Binding Epitopes

When an antibody is said to bind an epitope within specified residues, such as LRP6, for example, what is meant is that the antibody binds with high affinity to a polypeptide consisting of the specified residues (e.g., a specified segment of LRP6). Such an antibody does not necessarily contact every residue within LRP6. Nor does every single amino acid substitution or deletion within LRP6 necessarily significantly affect binding affinity. Epitope specificity of an antibody can be determined in a variety of ways. One approach, for example, involves testing a collection of overlapping peptides of about 15 amino acids spanning the sequence of LRP6 and differing in increments of a small number of amino acids (e.g., 3 to 30 amino acids). The peptides are immobilized in separate wells of a microtiter dish. Immobilization can be effected by biotinylating one terminus of the peptides. Optionally, different samples of the same peptide can be biotinylated at the N or C terminus and immobilized in separate wells for purposes of comparison. This is useful for identifying end-specific antibodies. Optionally, additional peptides can be included terminating at a particular amino acid of interest. This approach is useful for identifying end-specific antibodies to internal fragments of LRP6. An antibody or antigen-binding fragment is screened for binding to each of the various peptides. The epitope is defined as occurring with a segment of amino acids that is common to all peptides to which the antibody shows high affinity binding. Details regarding a specific approach for defining an epitope are set forth in Example 3.

Antibodies and antigen-binding fragments thereof that bind to an epitope that is located in the carboxy-terminal portion of the first propeller domain of LRP6 (e.g., SEQ ID NO: 13, 16 or 371) or the second propeller domain (e.g., SEQ ID NO: 27; see FIG. 3) are also provided. Exemplary antibodies capable of binding to the aforementioned epitope are the monoclonal antibodies 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1, each of which comprise a light chain and a heavy chain.

In one aspect of the invention, peptides comprising or consisting of amino acids 43-324 of SEQ ID NO: 2 (e.g., SEQ ID NO: 13 or 16) are provided. Other peptides comprise or consist of amino acids 43-627 of SEQ ID NO: 2 (e.g., SEQ ID NO: 15), or amino acids 263-283 of SEQ ID NO: 2 (e.g. SEQ ID NO: 317), or amino acids 352-627 of SEQ ID NO: 2 (e.g., SEQ ID NO: 370) are provided. Such peptides are shorter than the full-length protein sequence of a native LRP6 (e.g., the peptides may include one or more of the forgoing regions and be 8, 9, 10, 11, 12, 13, 14, 15, 20, 21, 22, 23, 24, 25, 30, 40, 50, 75, 100, 150, or 200 amino acids in length). These peptides may be fused to another peptide to increase immunogenicity and thus be in the form of a fusion protein.

E. Monoclonal Antibodies

The antibodies that are provided include monoclonal antibodies that bind to LRP6. Monoclonal antibodies may be produced using any technique known in the art, e.g., by immortalizing spleen cells harvested from a transgenic or non-transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag41, Sp210-Ag14, FO, NSO/U, MPC-11, MPC11-X45-GTG 1.7 and 5194/5XXO Bul; examples of cell lines used in rat fusions include R210.RCY3, Y3-Ag1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a transgenic animal having human immunoglobulin sequences) with an LRP6 immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a LRP6 polypeptide. Such hybridoma cell lines, and anti-LRP6 monoclonal antibodies produced by them, are encompassed by the present invention.

Monoclonal antibodies secreted by a hybridoma cell line can be purified using any technique known in the art. Hybridomas or mAbs may be further screened to identify mAbs with particular properties, such as blocking LRP6 activity, enhancing LRP6 activity, enhancing Wnt activity or antagonizing Dkk1 activity.

F. Chimeric and Humanized Antibodies

Chimeric and humanized antibodies based upon the foregoing sequences are also provided. Monoclonal antibodies for use as therapeutic agents may be modified in various ways prior to use. One example is a "chimeric" antibody, which is an antibody composed of protein segments from different antibodies that are covalently joined to produce functional immunoglobulin light or heavy chains or antigen-binding fragments thereof. Generally, a portion of the heavy chain and/or light chain is identical with, or homologous to, a corresponding sequence in antibodies derived from a particular species or belonging to a particular antibody class or subclass, while the remainder of the chain(s) is/are identical or homologous to a corresponding sequence in antibodies derived from another species or belonging to another antibody class or subclass. For methods relating to chimeric antibodies, see, for example, U.S. Pat. No. 4,816,567; and Morrison et al. *Proc. Natl. Acad. Sci. USA* 81:6851-6855 (1985), which are hereby incorporated by reference. CDR grafting is described, for example, in U.S. Pat. Nos. 6,180,370, 5,693,762, 5,693,761, 5,585,089, and 5,530,101, which are all hereby incorporated by reference for all purposes.

Generally, the goal of making a chimeric antibody is to create a chimera in which the number of amino acids from the intended patent species is maximized. One example is the "CDR-grafted" antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the V region or selected CDRs from a rodent antibody often are grafted into a human antibody, replacing the naturally-occurring V regions or CDRs of the human antibody.

One useful type of chimeric antibody is a "humanized" antibody. Generally, a humanized antibody is produced from a monoclonal antibody raised initially in a non-human animal. Certain amino acid residues in this monoclonal antibody, typically from non-antigen recognizing portions of the antibody, are modified to be homologous to corresponding residues in a human antibody or corresponding isotype. Preferably, anti-LRP6 humanized antibodies contain minimal sequence derived from non-human immunoglobulin sequences. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. See, for example, U.S. Pat. Nos. 5,225,539; 5,585,089; 5,693,761; 5,693,762; 5,859,205. In some instances, framework residues of the human immunoglobulin are replaced by corresponding non-human residues (see, for example, U.S. Pat. Nos. 5,585,089; 5,693,761; 5,693,762). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., *Nature* 331:522-525 (1986); Riechmann et al., *Nature* 332:323-329 (1988); and Presta, *Curr. Op. Struct. Biol.* 2:593-596 (1992); Verhoeyen et al., *Science* 239:1534-36 (1988)).

In one aspect of the invention, the CDRs of the light and heavy chain variable regions of the antibodies provided herein (see Table 2) are grafted to framework regions (FRs) from antibodies from the same, or a different, phylogenetic species. For example, the CDRs of the light and heavy chain variable regions of the 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1 antibody can be grafted to consensus human FRs. To create consensus human FRs, FRs from several human heavy chain or light chain amino acid sequences may be aligned to identify a consensus amino acid sequence. In other embodiments, the FRs of the 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1 antibody heavy or light chain are replaced with the FRs from a different heavy chain or light chain. In one aspect of the invention, rare amino acids in the FRs of the heavy and light chains of anti-LRP6 antibody are not replaced, while the rest of the FR amino acids are replaced. A "rare amino acid" is a specific amino acid that is in a position in which this particular amino acid is not usually found in an FR. Alternatively, the grafted variable regions from the 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1 antibody may be used with a constant region that is different from the constant region of 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1. In another aspect of this embodiment, the CDRs of the light and heavy chain variable regions of the 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1 antibody can be used. In other embodiments of the invention, the grafted variable regions are part of a single chain Fv antibody.

In certain embodiments, constant regions from species other than human can be used along with the human variable region(s) to produce hybrid antibodies.

Also encompassed are xenogeneic or modified anti-LRP6 antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. No. 5,939,598.

Antibody fragments that retain the ability to recognize the antigen of interest, will also find use herein. A number of antibody fragments are known in the art which comprise antigen-binding sites capable of exhibiting immunological binding properties of an intact antibody molecule. For example, functional antibody fragments can be produced by cleaving a constant region, not responsible for antigen binding, from the antibody molecule, using e.g., pepsin, to produce F(ab')$_2$ fragments. These fragments can contain two antigen binding sites, but lack a portion of the constant region from each of the heavy chains. Similarly, if desired, Fab fragments, comprising a single antigen binding site, can be produced, e.g., by digestion of polyclonal or monoclonal antibodies with papain. Functional fragments, including only the variable regions of the heavy and light chains, can also be produced, using standard techniques such as recombinant production or preferential proteolytic cleavage of immunoglobulin molecules. These fragments are known as Fv. See, e.g., Inbar et al., *Proc. Nat. Acad. Sci. USA* 69:2659-2662 (1972); Hochman et al., *Biochem.* 15:2706-2710 (1976); and Ehrlich et al., *Biochem.* 19:4091-4096 (1980).

A phage-display system can be used to expand antibody molecule populations in vitro. Saiki, et al., *Nature* 324:163 (1986); Scharf et al., *Science* 233:1076 (1986); U.S. Pat. Nos. 4,683,195 and 4,683,202; Yang et al., *J Mol Biol.* 254:392 (1995); Barbas, III et al., *Methods: Comp. Meth Enzymol.* 8:94 (1995); Barbas, III et al., *Proc Natl Acad Sci USA* 88:7978 (1991).

Once generated, the phage display library can be used to improve the immunological binding affinity of the Fab molecules using known techniques. See, e.g., Figini et al., *J. Mol. Biol.* 239:68 (1994). The coding sequences for the heavy and light chain portions of the Fab molecules selected from the phage display library can be isolated or synthesized, and cloned into any suitable vector or replicon for expression. Any suitable expression system can be used, including those described above.

Single chain antibodies are also within the scope of the present invention. A single-chain Fv ("sFv" or "scFv") polypeptide is a covalently linked $V_H$-$V_L$ heterodimer which is expressed from a gene fusion including $V_H$- and $V_L$-encoding genes linked by a peptide-encoding linker. Huston et al., *Proc. Nat. Acad. Sci. USA* 85:5879-5883 (1988). A number of methods have been described to discern and develop chemical structures (linkers) for converting the naturally aggregated, but chemically separated, light and heavy polypeptide chains from an antibody V region into an scFv molecule which will fold into a three-dimensional structure substantially similar to the structure of an antigen-binding site. See, e.g., U.S. Pat. Nos. 5,091,513, 5,132,405 and 4,946,778. The scFv molecules may be produced using methods described in the art. See, e.g., Huston et al., *Proc. Nat. Acad. Sci. USA* 85:5879-5883 (1988); U.S. Pat. Nos. 5,091,513, 5,132,405 and 4,946,778. Design criteria include determining the appropriate length to span the distance between the C-terminus of one chain and the N-terminus of the other, wherein the linker is generally formed from small hydrophilic amino acid residues that do not tend to coil or form secondary structures. Such methods have been described in the art and are well known. See, e.g., U.S. Pat. Nos. 5,091,513, 5,132,405 and 4,946,778. Suitable linkers generally comprise polypeptide chains of alternating sets of glycine and serine residues, and may include glutamic acid and lysine residues inserted to enhance solubility.

"Mini-antibodies" or "minibodies" are also within the scope of the present invention. Minibodies are scFv polypeptide chains that include oligomerization domains at their C-termini, separated from the sFv by a hinge region. Pack et al., *Biochem.* 31:1579-1584 (1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al., *Biochem.* 31:1579-1584 (1992); Cumber et al., *J. Immunology* 149B:120-126 (1992).

G. Fully Human Antibodies

Fully human antibodies are also provided. Methods are available for making fully human antibodies specific for a given antigen without exposing human beings to the antigen ("fully human antibodies"). One means for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derivatized mAbs to humans as therapeutic agents.

In one embodiment, human antibodies may be produced in a non-human transgenic animal, e.g., a transgenic mouse capable of producing multiple isotypes of human antibodies to LRP6 (e.g., IgG, IgA, and/or IgE) by undergoing V-D-J recombination and isotype switching. Accordingly, aspects of the invention include not only antibodies, antibody fragments, and pharmaceutical compositions thereof, but also non-human transgenic animals, B-cells, host cells, and hybridomas which produce anti-LRP6 monoclonal antibodies. Methods of using the anti-LRP6 antibodies or antigen-binding fragments to detect a cell expressing LRP6, either in vivo or in vitro, are also encompassed by the invention. Further, the present invention encompasses pharmaceutical preparations containing the anti-LRP6 antibodies, and methods of treating physiological disorders, e.g., bone diseases and other disorders modulated by Wnt signaling, including but not limited to, gastrointestinal diseases such as inflammatory bowel disease, ulcerative colitis and radiation- or chemotherapy-induced mucositis, and wound healing, by administering the anti-LRP6 antibodies or antigen-binding fragments provided herein.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, for example, Jakobovits et al., *Proc. Natl. Acad. Sci. USA* 90:2551-2555 (1993); Jakobovits et al., *Nature* 362:255-258 (1993); Bruggermann et al., *Year in Immunol.* 7:33 (1993). In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, International Patent Application Publication Nos. WO 96/33735 and WO 94/02602, which are hereby incorporated by reference in their entirety. Additional methods relating to transgenic mice for making human antibodies are described in U.S. Pat. Nos. 5,545,807;

6,713,610; 6,673,986; 6,162,963; 6,300,129; 6,255,458; 5,877,397; 5,874,299 and 5,545,806; in International Patent Application Publication Nos. WO 91/10741 and WO 90/04036; and in European Patent Nos. EP 546073B1 and EP 546073A1, all of which are hereby incorporated by reference in their entirety for all purposes.

The transgenic mice described above, referred to herein as "HuMAb" mice, contain a human immunoglobulin gene minilocus that encodes unrearranged human heavy (μ and γ) and κ light chain immunoglobulin sequences, together with targeted mutations that inactivate the endogenous μ and κ chain loci (Lonberg et al., *Nature* 368:856-859 (1994)). Accordingly, the mice exhibit reduced expression of mouse IgM or κ chains and in response to immunization, the introduced human heavy and light chain transgenes undergo class switching and somatic mutation to generate high affinity human IgG κ monoclonal antibodies (Lonberg et al., supra; Lonberg and Huszar, *Intern. Ref. Immunol.* 13:65-93 (1995); Harding and Lonberg, *Ann. N.Y. Acad. Sci.* 764:536-546 (1995)). The preparation of HuMAb mice is described in detail in Taylor et al., *Nucl. Acids Res.* 20:6287-6295 (1992); Chen et al., *Int. Immunol.* 5:647-656 (1993); Tuaillon et al., *J. Immunol.* 152:2912-2920 (1994); Lonberg et al., supra; Lonberg, *Handbook of Exp. Pharmacol.* 113:49-101 (1994); Taylor et al., *Int. Immunol.* 6:579-591 (1994); Lonberg and Huszar, *Intern. Ref. Immunol.* 13:65-93 (1995); Harding and Lonberg, *Ann. N.Y. Acad. Sci.* 764:536-546 (1995); Fishwild et al., *Nat. Biotechnol.* 14:845-851 (1996); the foregoing references are herein incorporated by reference in their entirety for all purposes. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807; as well as International Patent Application Publication Nos. WO 93/1227; WO 92/22646; and WO 92/03918, the disclosures of all of which are hereby incorporated by reference in their entirety for all purposes. Technologies utilized for producing human antibodies in these transgenic mice are disclosed also in WO 98/24893, and Mendez et al., *Nat. Genetics* 15:146-156 (1997), which are herein incorporated by reference. For example, the HCo7 and HCo12 transgenic mice strains can be used to generate human anti-LRP6 antibodies.

Using hybridoma technology, antigen-specific human mAbs with the desired specificity can be produced and selected from the transgenic mice such as those described above. Such antibodies may be cloned and expressed using a suitable vector and host cell, or the antibodies can be harvested from cultured hybridoma cells.

Fully human antibodies can also be derived from phage-display libraries (as disclosed in Hoogenboom et al., *J. Mol. Biol.* 227:381 (1991); and Marks et al., *J. Mol. Biol.* 222:581 (1991)). Phage-display techniques mimic immune selection through the display of antibody repertoires on the surface of filamentous bacteriophage, and subsequent selection of phage by their binding to an antigen of choice. One such technique is described in International Patent Application Publication No. WO 99/10494 (herein incorporated by reference), which describes the isolation of high affinity and functional agonistic antibodies for MPL⁻ and msk⁻ receptors using such an approach.

H. Bispecific or Bifunctional Antibodies

The antibodies that are provided also include bispecific and bifunctional antibodies that include one or more CDRs or one or more variable regions as described above. A bispecific or bifunctional antibody in some instances is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai and Lachmann, *Clin. Exp. Immunol.* 79:315-321 (1990); Kostelny et al., *J. Immunol.* 148:1547-1553 (1992).

I. Various Other Forms

Some of the antibodies or antigen-binding fragments that are provided are variant forms of the antibodies and fragments disclosed above (e.g., those having the sequences listed in Tables 1 and 2). For instance, some of the antibodies or antigen-binding fragments are ones having one or more conservative amino acid substitutions in one or more of the heavy or light chains, variable regions or CDRs listed in Tables 1 and 2.

Naturally-occurring amino acids may be divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of the classes for a member from another class. Such substituted residues may be introduced into regions of the antibody that are homologous with human antibodies, or into the non-homologous regions of the molecule.

In making such changes, according to certain embodiments, the hydropathic profile of a protein is calculated by assigning each amino acid a numerical value ("hydropathy index") and then repetitively averaging these values along the peptide chain. Each amino acid has been assigned a hydropathic index on the basis of its hydrophobicity and charge characteristics. They are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (1.6); histidine (−3.2); glutamate (−3.5); glutamine (−3.5); aspartate (−3.5); asparagine (−3.5); lysine (−3.9); and arginine (−4.5).

The importance of the hydropathic profile in conferring interactive biological function on a protein is understood in the art (see, for example, Kyte et al., *J. Mol. Biol.* 157:105-131 (1982)). It is known that certain amino acids may be substituted for other amino acid shaving a similar hydropathic index or score and still retain a similar biological activity. In making changes based upon the hydropathic index, in certain embodiments, the substitution of amino acids whose hydropathic indices are within ±2 is included. In some aspects of the invention, those which are within ±1 are included, and in other aspects of the invention, those within ±0.5 are included).

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding, that is, with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, in certain embodiments, the substitution of amino acids whose hydrophilicity values are within ±2 are included, in other embodiments, whose which are within ±1 are included, and in still other embodiments, those within ±0.5 are included. In some instances, one may also identify epitopes from primary amino acid sequences on the basis of hydrophilicity. These regions are also referred to as "epitopic core regions."

Exemplary conservative amino acid substitutions are set forth in Table 3.

TABLE 3

| Original Residues | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, Gln, Asn, 1,4 diamine-butryic acid |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

A skilled artisan will be able to determine suitable variants of polypeptides as set forth herein using well-known techniques. One skilled in the art may identify suitable areas of the molecule that may be changed without destroying activity by targeting regions not believed to be important for activity. The skilled artisan also will be able to identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three-dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. These variants can then be screened using assays for LRP6 binding, LRP6 activating activity, Wnt activating activity or Dkk1 antagonistic activity (see Examples below) thus yielding information gathered from such routine experiments, one skilled in the art can readily determine the amino acid positions where further substitutions should be avoided either alone or in combination with other mutations.

A number of scientific publications have been devoted to the prediction of secondary structure. See, Moult, *Curr. Op. Biotech* 7:422-427 (1996); Chou et al., *Biochemistry* 13:222-245 (1974); Chou et al., *Biochemistry* 13:211-222 (1974); Chou et al., *Adv. Enzymol. Relat. Areas Mol. Biol.* 47:45-148 (1978); Chou et al., *Ann. Rev. Biochem.* 47:251-276 (1979); and Chou et al., *Biophys J.* 26:367-384 (1979). Moreover, computer programs are currently available to assist with predicting secondary structure. One method of predicting secondary structure is based upon homology modeling. For example, two polypeptides or proteins that have a sequence identity of greater than 30% or similarity of greater than 40% often have similar structural topologies. The growth of the protein structural database (PDB) has provided enhanced predictability of secondary structure, including the potential number of folds within a polypeptide's or protein's structure. See, Holm et al., *Nucl. Acids Res.* 27:244-247 (1999). It has been suggested (Brenner et al., *Curr. Op. Struct. Biol.* 7:369-376 (1997)) that there are a limited number of folds in a given polypeptide or protein and that once a critical number of structures have been resolved, structural prediction will become dramatically more accurate.

Additional methods of predicting secondary structure include "threading" (Jones, *Curr. Opin. Struct. Biol.* 7:377-87 (1997); Sippl et al., *Structure* 4:15-19 (1996)), "profile analysis" (Bowie et al., *Science* 253:164-170 (1991); Gribskov et al., *Proc. Natl. Acad. Sci. USA* 84:4355-4358 (1987)), and "evolutionary linkage" (See, Holm, 1999, supra; and Brenner, 1997, supra).

In some embodiments of the invention, amino acid substitutions are made that: (1) reduce susceptibility to proteolysis, (2) reduce susceptibility to oxidation, (3) alter binding affinity for forming protein complexes, (4) alter ligand or antigen binding affinities, and/or (5) confer or modify other physicochemical or functional properties on such polypeptides. For example, single or multiple amino acid substitutions (in certain embodiments, conservative amino acid substitutions) may be made in the naturally-occurring sequence. Substitutions can be made in that portion of the antibody that lies outside the domain(s) forming intermolecular contacts. In such embodiments, conservative amino acid substitutions can be used that do not substantially change the structural characteristics of the parent sequence (e.g., one or more replacement amino acids that do not disrupt the secondary structure that characterizes the parent or native antibody). Examples of art-recognized polypeptide secondary and tertiary structures are described in *Proteins, Structures and Molecular Principles* (Creighton, Ed.), 1984, W.H. New York: Freeman and Company; *Introduction to Protein Structure* (Brandon and Tooze, eds.), 1991 New York: Garland Publishing; and Thornton et al., *Nature* 354:105 (1991), each of which is incorporated herein by reference in its entirety for all purposes.

The invention also encompasses glycosylation variants of the anti-LRP6 antibodies wherein the number and/or type of glycosylation site(s) has been altered compared to the amino acid sequences of the parent polypeptide. In certain embodiments, antibody protein variants comprise a greater or a lesser number of N-linked glycosylation sites than the native antibody. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate or alter this sequence will prevent addition of an N-linked carbohydrate chain present in the native polypeptide. For example, the glycosylation can be reduced by the deletion of an Asn or by substituting the Asn with a different amino acid. In other embodiments, one or more new N-linked glycosylation sites are created. Antibodies typically have an N-linked glycosylation site in the Fc region.

Additional preferred antibody variants include cysteine variants wherein one or more cysteine residues in the parent or native amino acid sequence are deleted from or substituted with another amino acid (e.g., serine). Cysteine variants are useful, inter alia, when antibodies must be refolded into a biologically active conformation. Cysteine variants may have fewer cysteine residues than the native antibody, and typically have an even number to minimize interactions resulting from unpaired cysteines.

The heavy and light chains, variable region domains and CDRs that are disclosed can be used to prepare polypeptides that contain an antigen-binding fragment that can specifically bind to a LRP6 molecule. For example, one or more of the CDRs listed in Table 2 can be incorporated into a molecule (e.g., a polypeptide) covalently or noncovalently to make an immunoadhesion. An immunoadhesion may incorporate the CDR(s) as part of a larger polypeptide chain, may covalently link the CDR(s) to another polypeptide chain, or may incorporate the CDR(s) noncovalently. The CDR(s) enable the immunoadhesion to bind specifically to a particular antigen of interest (e.g., an LRP6 polypeptide or epitope thereof).

Mimetics (e.g., "peptide mimetics" or "peptidomimetics") based upon the variable region domains and CDRs that are described herein are also provided. These analogs can be peptides, non-peptides or combinations of peptide and non-peptide regions. Fauchere, *Adv. Drug Res.* 15:29 (1986); Veber and Freidiner, *TINS* p. 392 (1985); and Evans et al., *J. Med. Chem.* 30:1229 (1987), which are incorporated herein by reference in their entirety for any purpose. Peptide mimetics that are structurally similar to therapeutically useful peptides may be used to produce a similar therapeutic or prophylactic effect. Such compounds are often developed with the aid of computerized molecular modeling. Generally, peptidomimetics are proteins that are structurally similar to an antibody displaying a desired biological activity, such as the ability to bind LRP6, but have one or more peptide linkages optionally replaced by a linkage selected from: —$CH_2NH$—, —$CH_2S$—, —$CH_2$—$CH_2$—, —$CH$=$CH$—(cis and trans), —$COCH_2$—, —$CH(OH)CH_2$—, and —$CH_2SO$— by methods well known in the art. Systematic substitution of one or more amino acids of a consensus sequence with a D-amino acid of the same type (e.g., D-lysine in place of L-lysine) may be used in certain embodiments of the invention to generate more stable proteins. In addition, constrained peptides comprising a consensus sequence or a substantially identical consensus sequence variation may be generated by methods known in the art (Rizo and Gierasch, *Ann. Rev. Biochem.* 61:387 (1992), incorporated herein by reference), for example, by adding internal cysteine residues capable of forming intramolecular disulfide bridges which cyclize the peptide.

Derivatives of the antibodies and antigen binding fragments that are described herein are also provided. The derivatized antibody or fragment may comprise any molecule or substance that imparts a desired property to the antibody or fragment, such as increased half-life in a particular use. The derivatized antibody can comprise, for example, a detectable (or labeling) moiety (e.g., a radioactive, colorimetric, antigenic or enzymatic molecule, a detectable bead [such as a magnetic or electrodense (e.g., gold) bead], or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly (n-vinyl pyrrolidone), polyethylene glycols, propropylene glycol homopolymers, polypropylene oxide/ethylene oxide co-polymers, polyoxyethylated polyols and polyvinyl alcohols.

Other derivatives include covalent or aggregative conjugates of anti-LRP6 antibodies, or antigen-binding fragments thereof, with other proteins or polypeptides, such as by expression of recombinant fusion proteins comprising heterologous polypeptides fused to the N-terminus or C-terminus of an anti-LRP6 antibody polypeptide. For example, the conjugated peptide may be a heterologous signal (or leader) polypeptide, e.g., the yeast alpha-factor leader, or a peptide such as an epitope tag (e.g., V5-His). Anti-LRP6 antibody-containing fusion proteins can comprise peptides added to facilitate purification or identification of the anti-LRP6 antibody (e.g., poly-His). An anti-LRP6 antibody polypeptide also can be linked to the FLAG® (Sigma-Aldrich, St. Louis, Mo.) peptide as described in Hopp et al., *Bio/Technology* 6:1204 (1988), and U.S. Pat. No. 5,011,912. The FLAG® peptide is highly antigenic and provides an epitope reversibly bound by a specific monoclonal antibody enabling reversibly rapid assay and facile purification of expressed recombinant protein. Reagents useful for preparing fusion proteins in which the FLAG® peptide is fused to a given polypeptide are commercially available (Sigma, St. Louis, Mo., USA).

Oligomers that contain one or more anti-LRP6 antibody polypeptide may be employed as LRP6 agonists or antagonists. Oligomers may be in the form of covalently-linked or non-covalently linked dimers, trimers, or higher oligomers. Oligomers comprising two or more anti-LRP6 antibody polypeptides are contemplated for use, with one example being a homodimer. Other oligomers include heterodimers, homotrimers, heterotrimers, homotetramers, heterotetramers, etc.

One embodiment is directed to oligomers comprising multiple anti-LRP6 antibody polypeptides joined via covalent or non-covalent interactions between peptide moieties fused to the anti-LRP6 antibody polypeptides. Such peptides may be peptide linkers (spacers), or peptides that have the property of promoting oligomerization. Leucine zippers and certain polypeptides derived from antibodies are among the peptides that can promote oligomerization of anti-LRP6 antibody polypeptides attached thereto, as described in more detail below.

In particular embodiments, the oligomers comprise from two to four anti-LRP6 polypeptides. The anti-LRP6 antibody moieties of the oligomer may be in any of the forms described above, e.g., variants or fragments. Preferably, the oligomers comprise anti-LRP6 antibody polypeptides that have LRP6 binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., *Proc. Natl. Acad. Sci. USA* 88:10535 (1991); Byrn et al., *Nature* 344:677 (1990); and Hollenbaugh et al., 1992 "Construction of Immunoglobulin Fusion Proteins," in *Current Protocols in Immunology*, Suppl 4, pages 10.19.1-10.19.11.

One embodiment of the present invention is directed to a dimer comprising two fusion proteins created by fusing a LRP6 binding fragment of an anti-LRP6 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in International Patent Application Publication No. WO 93/10151 and U.S. Pat. Nos. 5,426,048 and 5,262,522 (each of which is herein incorporated by reference), is a single chain polypeptide extending from the N-terminal hinge region to the native C-terminus of the Fc region of a human $IgG_1$ antibody. Another useful Fc polypeptide is the Fc mutein described in U.S. Pat. No. 5,457,035 and in Baum et al., *EMBO J.* 13:3992-4001 (1994). The amino acid sequence of this mutein is identical to that of the native Fc sequence presented in WO 93/10151, except that amino acid 19 has been changed from Leu to Glu, and amino acid 22 has been changed from Gly to Ala. The mutein exhibits reduced affinity for Fc receptors.

In other embodiments, the variable portion of the heavy and/or light chains of an anti-LRP6 antibody such as disclosed herein may be substituted for the variable portion of an antibody heavy and/or light chain.

Alternatively, the oligomer is a fusion protein comprising multiple anti-LRP6 antibody polypeptides, with or without peptide linkers (spacer peptides). Among the suitable peptide linkers are those described in U.S. Pat. Nos. 4,751,180 and 4,935,233.

Another method for preparing oligomeric anti-LRP6 antibody derivatives involves use of a leucine zipper. Leucine zipper domains are peptides that promote oligomerization of the proteins in which they are found. Leucine zippers were originally identified in several DNA-binding proteins (Landschulz et al., *Science* 240:1759 (1988)), and have since been found in a variety of different proteins. Among the known leucine zippers are naturally occurring peptides and derivatives thereof that dimerize or trimerize. Examples of leucine zipper domains suitable for producing soluble oligomeric proteins are described in International Patent Application Publication No. WO 94/10308, and the leucine zipper derived from lung surfactant protein D (SPD) described in Hoppe et al., *FEBS Lett.* 344:191 (1994), hereby incorporated by reference. The use of a modified leucine zipper that allows for stable trimerization of a heterologous protein fused thereto is described in Fanslow et al., *Semin. Immunol.* 6:267-78 (1994). In one approach, recombinant fusion proteins comprising an anti-LRP6 antibody fragment or derivative fused to a leucine zipper peptide are expressed in suitable host cells, and the soluble anti-LRP6 antibody fragments or derivatives that form are recovered from the culture supernatant.

Some antibodies that are provided have a binding affinity ($k_a$) for LRP6 of at least $10^4$ or $10^5$ $M^{-1}sec^{-1}$ measured, for instance, as described in the examples below. Other antibodies have a $k_a$ of at least $10^6$, $10^7$, $10^8$ or $10^9$ $M^{-1}sec^{-1}$. Certain antibodies that are provided have a low disassociation rate. Some antibodies, for instance, have a $k_{off}$ of $1\times10^{-4}$ $s^{-1}$, $1\times10^{-5}$ $s^{-1}$ or lower. In another embodiment, the $K_{off}$ is the same as an antibody having combinations of variable region domains according to the formula $V_L x V_H y$, wherein x=the number of the light chain variable region and y=the number of the heavy chain variable region as listed in Table 1, wherein x and y are each 1, 2, 3, 4, 5, 6, 7, 8, 9, 10, 11, 12, 13, 14, 15, 16, 17, 18, 19, 20, 21, 22, or 23.

In another aspect, the present invention provides an anti-LRP6 antibody or antigen-binding fragment having a half-life of at least one day in vitro or in vivo (e.g., when administered to a human subject). In one embodiment, the antibody or antigen-binding fragment has a half-life of at least three days. In another embodiment, the antibody or antigen-binding fragment has a half-life of four days or longer. In another embodiment, the antibody or antigen-binding fragment has a half life of eight days or longer. In another embodiment, the antibody or antigen-binding fragment is derivatized or modified such that it has a longer half-life as compared to the underivatized or unmodified antibody. In another embodiment, the antibody contains point mutations to increase serum half life, such as described in International Patent Application Publication No. WO 00/09560, which is herein incorporated by reference.

J. Immunoconjugates

The invention also pertains to immunoconjugates, or antibody-drug conjugates (ADC), comprising an antibody or antigen-binding fragment thereof conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In one embodiment of the invention, an anti-LRP6 antibody may be conjugated to various therapeutic substances in order to target the LRP6 cell surface antigen. Examples of conjugated agents include, but are not limited to, metal chelate complexes, drugs, toxins and other effector molecules, such as cytokines, lymphokines, chemokines, immunomodulators, radiosensitizers, asparaginase, carboranes and radioactive halogens. Additionally, enzymes useful for activating a pro-drug or increasing the target-specific toxicity of a drug can be conjugated to the antibodies. Such substances are described in further detail below.

The use of antibody-drug conjugates for the local delivery of cytotoxic or cytostatic agents, i.e. drugs to kill or inhibit tumor cells in the treatment of cancer (Syrigos and Epenetos, *Anticancer Res.* 19:605-614 (1999); Niculescu-Duvaz and Springer, *Adv. Drg. Del. Rev.* 26:151-172 (1997); U.S. Pat. No. 4,975,278) theoretically allows targeted delivery of the drug moiety to tumors, and intracellular accumulation therein, where systematic administration of these unconjugated drug agents may result in unacceptable levels of toxicity to normal cells as well as the tumor cells sought to be eliminated (Baldwin et al., *Lancet* 1:603-5 (1986); Thorpe, (1985) "Antibody Carriers of Cytotoxic Agents in Cancer Therapy: A Review," In: *Monoclonal Antibodies '84: Biological and Clinical Applications*, A. Pincera et al., (eds.) pp. 475-506). Maximal efficacy with minimal toxicity is sought thereby. Both polyclonal antibodies and monoclonal antibodies have been reported as useful in these strategies (Rowland et al., *Cancer Immunol. Immunother.* 21:183-87 (1986)). Drugs used in these methods include danuomycin, doxorubicin, methotrexate and vindesine (Rowland et al., (1986) supra). Toxins used in antibody-toxin conjugates include bacterial toxins such as diphtheria toxin, plant toxins such as ricin, small molecule toxins such as geldamanycin (Mandler et al., *J. Nat. Cancer Inst.* 92:1573-1581 (2000); Mandler et al., *Bioorganic Med. Chem. Lett.* 10:1025-1028 (2000); Mandler et al., *Bioconjugate Chem.* 13:786-791 (2002)), maytansinoids (European Patent No. EP 1391213; Liu et al., *Proc. Natl. Acad. Sci. USA* 93:8618-8623 (1996)), and calicheamicin (Lode et al., *Cancer Res.* 58:2928 (1998); Rinman et al., *Cancer Res.* 53:3336-3342 (1993)). The toxins may effect their cytotoxin and cytostatic effects by mechanisms including tubulin binding, DNA binding, or topoisomerase inhibition. Some cytotoxic drugs tend to be inactive or less active when conjugated to large antibodies or protein receptor ligands.

The antibodies provided herein may be used in combination with various chemotherapeutic agents, toxins and regimens. The agents and/or toxins can either be administered before, after or concurrently with the antibodies of the invention. Alternatively, if appropriate, the agents and toxins can be conjugated to the antibodies of the invention to target the agent directly to tumor cells.

A variety of radionuclides are available for the production of radioconjugated antibodies. Goodwin and Meares, *Cancer Supplement* 80:2675-2680 (1997) have described the use of yttrium-90-labeled monoclonal antibodies in various strategies to maximize the dose to tumor while limiting normal tissue toxicity. Other known cytotoxic radionuclides include, but are not limited to phosphorus-32, copper-67, arsenic-77, rhodium-105, palladium-109, silver-111, tin-121, iodine-125 or 131, holmium-166, lutetium-177, rhenium-186 or 188, iridium-194, gold-199, astatium-211, yttrium-90, samarium-153, or bismuth-212, all of which can be used to label antibodies directed against the LRP6 cell surface antigen for the treatment of cancer. When the conjugate is used for detection, it may comprise a radioactive atom for scintigraphic studies, for example technetium-99m or iodine-123, or a spin label for nuclear magnetic resonance (NMR) imaging (also known as magnetic resonance imaging (MRI)), such as iodine-123, iodine-131, iodine-111, fluorine-19, carbon-13, nitrogen-15, oxygen-17, gadolinium, manganese or iron.

The anti-LRP6 antibodies or antigen-binding fragments thereof can be conjugated to radionuclides using an indirect labeling or indirect labeling approach. The anti-LRP6 antibodies may be labeled by an "indirect labeling" or "indirect labeling approach" wherein a chelating agent is covalently attached to an antibody and at least one radionuclide is inserted into the chelating agent. See, for example, the chelating agents and radionuclides described in Srivastava and Mease, *Int. J. Rad. Appl. Instrum. B.* 18:589-603 (1991). Alternatively, the anti-LRP6 antibody may be labeled using "direct labeling" or a "direct labeling approach", where a label, such as a radionuclide is covalently attached directly to an antibody (typically via an amino acid residue). For example, the peptide may be biosynthesized or may be synthesized by chemical amino acid synthesis using amino acid precursors involving, for example, fluorine-19 in place of hydrogen. Labels such as technetium-99m, iodine-123, rhenium-186, rhenium-188, and indium-111 can be attached via a cysteine residue in the peptide. Yttrium-90 can be attached via a lysine residue. The iodogen method (Franker et al., *Biochem. Biophys. Res. Commun.* 80:49-57 (1978)) can be used to incorporate iodine-123. "Monoclonal Antibodies in Immunoscintigraphy" (Chantal, CRC Press, 1989, which is herein incorporated by reference in its entirety) describes other methods in detail.

Conjugates of an anti-LRP6 antibody and a cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl)hexanediamine), bis-diazonium derivatives (such as bos(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). $^{14}$C-labeled 1-isothiocyanatobenzyl-3-methyldiethylene triaminepentaacetic acid (MX-DTPA) is an exemplary chelating agent for conjugation of radionucleotide to the antibody. See, International Patent Application Publication No. WO 94/11026.

Further, the invention provides an embodiment wherein the anti-LRP6 antibody or antigen-binding fragment thereof is linked to an enzyme that converts a prodrug into a cytotoxic drug. The enzymes cleave the non-toxic "prodrug" into the toxic "drug", which leads to tumor cell death. Suitable prodrug enzymes include thymidine kinase (TK), xanthine-guanine phosphoribosyltransferase (GPT) gene from *E. coli* or *E. coli* cytosine deaminase (CD), or hypoxanthine phosphoribosyl transferase (HPRT). Additional representative examples of enzymes and associated prodrug molecules include alkaline phosphatase and various toxic phosphorylated compounds such as phenolmustard phosphate, doxorubicin phosphate, mitomycin phosphate and etoposide phosphate; β-galactosidase and N-[4-(β-D-galactopyranosyl)benzyloxycarbonyl]-daunorubicin; azoreductase and azobenzene mustards; β-glucosidase and amygdalin; β-glucuronidase and phenolmustard-glucuronide and epirubicin-glucuronide; carboxypeptidase A and methotrexate-alanine; cytochrome P450 and cyclophosphamide or ifosfamide; DT diaphorase and 5-(aziridine-1-yl)-2,4,dinitrobenzamide (CB1954) (Cobb et al., *Biochem. Pharmacol* 18:1519 (1969), Knox et al., *Cancer Metastasis Rev.* 12:195 (1993)); β-glutamyl transferase and β-glutamyl p-phenylenediamine mustard; nitroreductase and CB1954 or derivatives of 4-nitrobenzyloxycarbonyl; glucose oxidase and glucose; xanthine oxidase and hypoxanthine; and plasmin and peptidyl-p-phenylenediamine-mustard.

Conjugates of an antibody and one or more small molecule toxins, such as calcheamicin, maytansinoids, a trichothecene, and CC1065, and the derivatives of these toxins that have toxin activity, are also contemplated herein.

The present invention further contemplates an immunoconjugate formed between an antibody and a compound with nucleolytic activity (e.g., a ribonuclease or a DNA endonuclease such as deoxyribonuclease; DNase).

Additionally, the anti-LRP6 antibodies can be attached to various labels in order to screen biological samples such as blood, tissues and/or tumors for the presence or absence of the proteins, as an indication of disease, as described further below.

K. Preparation of Antibody Drug Conjugates

In the antibody drug conjugates (ADC) of the invention, an antibody (Ab) is conjugated to one or more drug moieties (D), e.g., about 1 to about 20 drug moieties per antibody, through a linker (L). The ADC of Formula I (see below) may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody.

Ab-(L-D)$_P$      (I)

Nucleophilic groups on antibodies include, but are not limited to: (i) N-terminal amine groups, (ii) side chain amine groups, e.g., lysine, (iii) side chain thiol groups, e.g., cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e., cysteine bridges. Antibodies may be made reactive for conjugation with linker reagents by treatment with a reducing agent such as DTT (dithiolthreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody drug conjugates may also be produced by modification of the antibody to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium metaperiodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan and Stroh, *Bioconjugate Chem.* 3:138-146 (1992); U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine, carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such as streptavidin) for utilization in tumor or cancer cell pre-targeting" wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

IV. LRP6 Nucleic Acids

A. Nucleic Acids

Polynucleotide sequences encoding the anti-LRP6 antibodies and immunoreactive fragments thereof, described above, are readily obtained using standard techniques, well known in the art, such as those techniques described above with respect to the recombinant production of the LRP6 cell surface receptor.

Nucleic acids that encode one or both chains of an anti-LRP6 antibody, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing are also provided. The nucleic acids can be any length. They can be, for example, 5, 10, 15, 20, 25, 30, 35, 40, 45, 50, 75, 100, 125, 175, 200, 250, 300, 350, 400, 450, 500, 750, 1000, 1500, 3000, 5000 or more nucleotides in length, and/or can comprise one or more additional sequences, for example, regulatory sequences, and/or be a part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids that encode the epitope to which certain of the antibodies provided herein are also provided. Thus, nucleic acids that encode SEQ ID NO: 16, 370 and 371 are included as are those that encode SEQ ID NO: 13 and 15. Nucleic acids encoding fusion proteins that include these peptides are also provided.

DNA encoding anti-LRP6 antibody polypeptides (e.g., heavy or light chain, variable domain only, or full-length) may be isolated from B cells of mice that have been immunized with LRP6 or an immunogenic fragment thereof. The DNA may be isolated by conventional procedures such as polymerase chain reaction (PCR). Phage display is another example of a known technique whereby derivatives of antibodies may be prepared. In one approach, polypeptides that are components of an antibody of interest are expressed in any suitable recombinant expression system, and the expressed polypeptides are allowed to assemble to form antibody molecules.

Exemplary nucleic acids that encode the light and heavy chains, variable regions and CDRs of the antibodies and antigen-binding fragments are provided in Tables 1 and 2 above. Due to the degeneracy of the genetic code, each of the polypeptide sequences listed in Tables 1 and 2 is also encoded by a large number of other nucleic acid sequences besides those listed in Tables 1 and 2. The present invention provides each degenerate nucleotide sequence encoding each anti-LRP6 antibody or antigen-binding fragment thereof.

Nucleic acid molecules encoding anti-LRP6 antibodies or antigen-binding fragments thereof are provided. In one embodiment, the nucleic acid molecule encodes a heavy and/or light chain of an anti-LRP6 immunoglobulin. In a preferred embodiment, a single nucleic acid molecule encodes a heavy chain of an anti-LRP6 immunoglobulin and another nucleic acid molecule encodes the light chain of an anti-LRP6 immunoglobulin. In a more preferred embodiment, the encoded immunoglobulin is a human immunoglobulin, preferably a human IgG. The encoded light chain may be a λ chain or a κ chain.

The invention provides nucleic acid molecules comprising a nucleic acid sequence that encodes the amino acid sequence of the variable region of the light chain ($V_L$) of 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1. The invention also provides nucleic acid molecules comprising a nucleic acid sequence that encodes the amino acid sequence of one or more of the CDRs of any one of the light chains of 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1. In a preferred embodiment, the nucleic acid molecule comprises a nucleic acid sequence that encodes the amino acid sequence of all of the CDRs of any one of the light chains of 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1. In another embodiment, the nucleic acid molecule comprises a nucleic acid sequence that encodes the amino acid sequence of one of SEQ ID NO: 20, 24, 28, 32, 36, 40, 44, 48, 52, 56, 60, 64, 68, 76, 80, 84, 88, 92, 96, 100, or 104, or comprises a nucleic acid sequence of one of SEQ ID NO: 19, 23, 27, 31, 35, 39, 43, 47, 51, 55, 59, 63, 67, 75, 79, 83, 87, 91, 95, 99, or 103. In another preferred embodiment, the nucleic acid molecule comprises a nucleic acid sequence that encodes the amino acid sequence of one or more of the CDRs of any one of SEQ ID NO: 20, 24, 28, 32, 36, 40, 44, 48, 52, 56, 60, 64, 68, 76, 80, 84, 88, 92, 96, 100, or 104, or comprises a nucleic acid sequence of one or more of the CDRs of any one of SEQ ID NO: 19, 23, 27, 31, 35, 39, 43, 47, 51, 55, 59, 63, 67, 75, 79, 83, 87, 91, 95, 99, or 103. In a more preferred embodiment, the nucleic acid molecule comprises a nucleic acid sequence that encodes the amino acid sequence of all of the CDRs of any one of SEQ ID NO: 20, 24, 28, 32, 36, 40, 44, 48, 52, 56, 60, 64, 68, 76, 80, 84, 88, 92, 96, 100, or 104, or comprises a nucleic acid sequence of all the CDRs of any one of SEQ ID NO: 19, 23, 27, 31, 35, 39, 43, 47, 51, 55, 59, 63, 67, 75, 79, 83, 87, 91, 95, 99, or 103.

The invention also provides nucleic acid molecules that encode an amino acid sequence of a $V_L$ that has an amino acid sequence that is at least 70%, at least 75%, at least 80%, at least 85%, at least 90%, at least 95%, at least 96%, at least 97%, at least 98%, or at least 99% identical to a $V_L$ described above, particularly to a $V_L$ that comprises an amino acid sequence of one of SEQ ID NO: 20, 24, 28, 32, 36, 40, 44, 48, 52, 56, 60, 64, 68, 76, 80, 84, 88, 92, 96, 100, or 104. The invention also provides a nucleic acid sequence that is at least 70%, at least 75%, at least 80%, at least 85%, at least 90%, at least 95%, at least 96%, at least 97%, at least 98%, or at least 99% identical to a nucleic acid sequence of one of SEQ ID NO: 19, 23, 27, 31, 35, 39, 43, 47, 51, 55, 59, 63, 67, 75, 79, 83, 87, 91, 95, 99, or 103. In another embodiment, the invention provides a nucleic acid molecule encoding a $V_L$ that hybridizes under stringent conditions to a nucleic acid molecule encoding a $V_L$ as described above, particularly a nucleic acid molecule that comprises a nucleic acid sequence encoding an amino acid sequence of SEQ ID NO: 20, 24, 28, 32, 36, 40, 44, 48, 52, 56, 60, 64, 68, 76, 80, 84, 88, 92, 96, 100, or 104. The invention also provides a nucleic acid sequence encoding a $V_L$ that hybridizes under stringent conditions to a nucleic acid molecule comprising a nucleic acid sequence of one of SEQ ID NO: 19, 23, 27, 31, 35, 39, 43, 47, 51, 55, 59, 63, 67, 75, 79, 83, 87, 91, 95, 99, or 103.

The invention also provides a nucleic acid molecule encoding the variable region of the heavy chain ($V_H$) of 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1. In one embodiment, the nucleic acid molecule comprises a nucleic acid sequence that encodes the amino acid sequence of the $V_H$ of 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1. In another embodiment, the nucleic acid molecule comprises a nucleic acid sequence that encodes the amino acid sequence of one or more of the CDRs of the heavy chain of 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1. In a preferred embodiment, the nucleic acid molecule comprises a nucleic acid sequence that encodes the amino acid sequences of all of the CDRs of the heavy chain of 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1. In another preferred embodiment, the nucleic acid molecule comprises a nucleic acid sequence that encodes the amino acid sequence of one of SEQ ID NO: 18, 22, 26, 30, 34, 38, 42, 46, 50, 54, 58, 62, 66, 70, 72, 74, 78, 82, 86, 90, 94, 98, 102, or that comprises a nucleic acid sequence of one of SEQ ID NO: 17, 21, 25, 29, 33, 37, 41, 45, 49, 53, 57, 61, 65, 69, 71, 73, 77, 81, 85, 89, 93, 97, 101. In another preferred embodiment, the nucleic acid molecule comprises a nucleic acid sequence that encodes the amino acid sequence of one or more of the CDRs of any one of SEQ ID NO: 18, 22, 26, 30, 34, 38, 42, 46, 50, 54, 58, 62, 66, 70, 72, 74, 78, 82, 86, 90, 94, 98, 102, or comprises a nucleic acid sequence of one or more of the CDRs of any one of SEQ ID NO: 17, 21, 25, 29, 33, 37, 41, 45, 49, 53, 57, 61, 65, 69, 71, 73, 77, 81, 85, 89, 93, 97, 101. In a preferred embodiment, the nucleic acid molecule comprises a nucleic acid sequence that encodes the amino acid sequences of all of the CDRs of any one of SEQ ID NO: 18, 22, 26, 30, 34, 38, 42, 46, 50, 54, 58, 62, 66, 70, 72, 74, 78, 82, 86, 90, 94, 98, 102, or comprises a nucleic acid sequence of all of the CDRs for any one of SEQ ID NO: 17, 21, 25, 29, 33, 37, 41, 45, 49, 53, 57, 61, 65, 69, 71, 73, 77, 81, 85, 89, 93, 97, 101.

In another embodiment, the nucleic acid molecule encodes an amino acid sequence of a $V_H$ that is at least 70%, at least 75%, at least 80%, at least 85%, at least 90%, at least 95%, at least 96%, at least 97%, at least 98%, or at least 99% identical to one of the amino acid sequences encoding a $V_H$ as described immediately above, particularly to a $V_H$ that comprises an amino acid sequence of one of SEQ ID NO: 18, 22, 26, 30, 34, 38, 42, 46, 50, 54, 58, 62, 66, 70, 72, 74, 78, 82, 86, 90, 94, 98, 102. In another embodiment, the nucleic acid molecule encoding a $V_H$ is one that hybridizes under stringent conditions to a nucleic acid sequence encoding a $V_H$ as described above, particularly to a $V_H$ that comprises an amino acid sequence of one of SEQ ID NO: 18, 22, 26, 30, 34, 38, 42, 46, 50, 54, 58, 62, 66, 70, 72, 74, 78, 82, 86, 90, 94, 98, 102. The invention also provides a nucleic acid sequence encoding a $V_H$ that hybridizes under stringent conditions to a nucleic acid molecule comprising a nucleic acid sequence of one of SEQ ID NO: 17, 21, 25, 29, 33, 37, 41, 45, 49, 53, 57, 61, 65, 69, 71, 73, 77, 81, 85, 89, 93, 97, 101.

The nucleic acid molecule encoding either or both of the entire heavy and light chains of an anti-LRP6 antibody or the variable regions thereof may be obtained from any source that produces an anti-LRP6 antibody. Methods of isolating mRNA encoding an antibody are well-known in the art. See e.g., Sambrook et al., supra. The mRNA may be used to produce cDNA for use in the polymerase chain reaction (PCR) or cDNA cloning of antibody genes. In one embodiment of the invention, the nucleic acid molecules may be obtained from a hybridoma that expresses an anti-LRP6 antibody as described above, preferably a hybridoma that has as one of its fusion partners a transgenic animal cell that expresses human immunoglobulin genes, such as a XENOMOUSE® (Amgen, Thousand Oaks, Calif., USA), non-human mouse transgenic animal, or a non-human, non-mouse transgenic animal. In another embodiment, the hybridoma is derived from a non-human, non-transgenic animal, which may be used, e.g., for humanized antibodies.

A nucleic acid molecule encoding the entire heavy chain of an anti-LRP6 antibody may be constructed by fusing a nucleic acid molecule encoding the variable domain of a heavy chain or an antigen-binding domain thereof with a constant domain of a heavy chain. Similarly, a nucleic acid molecule encoding the light chain of an anti-LRP6 antibody may be constructed by fusing a nucleic acid molecule encoding the variable domain of a light chain or an antigen-binding fragment thereof with a constant domain of a light chain. The nucleic acid molecules encoding the $V_H$ and $V_L$ chain may be converted to full-length antibody genes by inserting them into expression vectors already encoding heavy chain constant and light chain constant regions, respectively, such that the $V_H$ segment is operatively linked to the heavy chain constant region ($C_H$) segment(s) within the vector and the $V_L$ segment is operatively linked to the light chain constant region ($C_L$) segment within the vector. Alternatively, the nucleic acid molecules encoding the $V_H$ or $V_L$ chains are converted into full-length antibody genes by linking, e.g., ligating, the nucleic acid molecule encoding a $V_H$ chain to a nucleic acid molecule encoding a $C_H$ chain using standard molecule biological techniques. The same may be achieved using nucleic acid molecules encoding $V_L$ and $C_L$ chains. The sequences of human heavy and light chain constant region genes are known in the art. See, e.g., Kabat et al., 1991, supra. Nucleic acid molecules encoding the full-length heavy and/or light chains may then be expressed from a cell into which they have been introduced and the anti-LRP6 antibody isolated.

In another embodiment, a nucleic acid molecule encoding either the heavy chain of an anti-LRP6 antibody or an antigen-binding fragment thereof or the light chain of an anti-LRP6 antibody or an antigen-binding fragment thereof may be isolated from a non-human, non-mouse animal that expresses human immunoglobulin genes and has been immunized with a LRP6 antigen. In another embodiment, the nucleic acid molecule may be isolated from an anti-LRP6 antibody producing cell derived from a non-transgenic animal or from a human patient who produces anti-LRP6 antibodies. Methods of isolating mRNA from the anti-LRP6 antibody-producing cells may be isolated by standard techniques, cloned and/or amplified using PCR and library construction techniques, and screened using standard protocols to obtain nucleic acid molecules encoding anti-LRP6 heavy and light chains.

The nucleic acid molecules may be used to recombinantly express large quantities of anti-LRP6 antibodies, as described below. The nucleic acid molecules may also be used to produce chimeric antibodies, single chain antibodies, immunoadhesins, diabodies, mutated antibodies and antibody derivatives. If the nucleic acid molecules are derived from a non-human, non-transgenic animal, the nucleic acid molecules may be used for antibody humanization.

The invention further provides nucleic acids that hybridize to other nucleic acids (e.g., nucleic acids comprising a nucleotide sequence listed in Tables 1-2) under particular hybridization conditions. Methods for hybridizing nucleic acids are well-known in the art. See, e.g., *Current Protocols in Molecular Biology*, John Wiley and Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C. in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequence that are at least 65%, at least 70%, at least 75%, at least 80%, at least 85%, at least 90%, at least 95%, at least 96%, at least 97%, at least 98% or at least 99% identical to each other typically remain hybridized to each other.

The basic parameters affecting the choice of hybridization conditions and guidance for devising suitable conditions are set forth by, for example, Sambrook, Fritsch, and Maniatis (*Molecular Cloning: A Laboratory Manual*, Cold Spring Harbor Laboratory Press, Cold Spring Harbor, N.Y., chapters 9 and 11 (1989); *Current Protocols in Molecular Biology*, Ausubel et al., eds., John Wiley and Sons, Inc., sections 2.10 and 6.3-6.4 (1995), both of which are herein incorporated by reference in their entirety for all purposes) and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an anti-LRP6 antibody or antibody derivative) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. Alternatively, one or more mutations can be introduced into a nucleic acid that selectively change the biological activity of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody.

In another aspect, the present invention provides nucleic acid molecules that are suitable for use as primers or hybridization probes for the detection of the nucleic acid sequences provided herein. A nucleic acid molecule may comprise only a portion of a nucleic acid sequence encoding a full-length polypeptide of an anti-LRP6 antibody, for example, a fragment that can be used as a probe or primer or a fragment encoding an active portion (e.g., an LRP6 binding portion) of the polypeptide.

In another embodiment, the nucleic acid molecules may be used as probes or PCR primers for specific antibody sequences. For instance, a nucleic acid molecule probe may be used in diagnostic methods or a nucleic acid molecule PCR primer may be used to amplify regions of DNA that could be used, inter alia, to isolate nucleic acid sequences for use in producing variable domains of anti-LRP6 antibodies. In a preferred embodiment, the nucleic acid molecules are oligonucleotides. In a more preferred embodiment, the oligonucleotides are from highly variable regions of the heavy and light chains of the antibody of interest. In an even more preferred embodiment, the oligonucleotides encode all or part of one or more of the CDRs.

Probes based on the sequence of a nucleic acid provided herein can be used to detect the nucleic acid or similar nucleic acids, for example, transcripts encoding a polypeptide of an anti-LRP6 antibody. The probe can comprise a label group, e.g., a radioisotope, a fluorescent compound, an enzyme, or an enzyme co-factor. Such probes can be used to identify a cell that expresses the polypeptide.

B. Vectors

The invention provides vectors comprising the nucleic acid molecules that encode the heavy chain or the antigen-binding portion thereof. Also provided are vectors comprising the nucleic acid molecules that encode the light chain or antigen-binding portion thereof. In addition, vectors comprising nucleic acid molecules encoding fusion proteins, modified antibodies, antibody fragments, and probes thereof are provided herein.

Also provided are vectors comprising a nucleic acid encoding a polypeptide of an anti-LRP6 antibody or a portion thereof (e.g., a fragment containing one or more CDRs or one or more variable region domains). Examples of vectors include, but are not limited to, plasmids, viral vectors, non-episomal mammalian vectors and expression vectors, for example, recombinant expression vectors. The recombinant expression vectors may comprise a nucleic acid in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., Simian Virus 40 (SV40) early gene enhancer, Rous sarcoma virus (RSV) promoter and cytomegalovirus (CMV) promoter), those that direct expression of the nucleotide sequence only in certain host cells (e.g., tissue-specific regulatory sequences, see Voss et al., *Trends Biochem. Sci.* 11:287 (1986); Maniatis et al., *Science* 236:1237 (1986), incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems. It will be appreciated by those skilled in the art that the design of the expression vector can depend on such factors as the choice of the host cell to be transformed, the level of expression of protein desired, etc. The expression vectors may be introduced into host cells to thereby produce proteins or peptides, including fusion protein or peptides, encoded by nucleic acids as described herein.

To express the antibodies, or antigen-binding fragments thereof, DNAs encoding partial or full-length light and heavy chains, obtained as described above, are inserted into expression vectors such that the genes area operatively linked to transcriptional and translational control sequences. Expression vectors include plasmids, retroviruses, cosmids, YACs, EBV-derived episomes, and the like. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors. In a preferred embodiment, both genes are inserted into the same expression vector. The antibody genes are inserted into the expression vector by standard methods (e.g., ligation of complementary restriction sites on the antibody gene fragment and vector, or blunt end ligation if no restriction sites are present).

A convenient vector is one that encodes a functionally complete human $C_H$ or $C_L$ immunoglobulin sequence, with appropriate restriction sites engineered so that any $V_H$ or $V_L$ sequence can be easily inserted and expressed, as described above. In such vectors, splicing usually occurs between the splice donor site in the inserted J region and the splice acceptor site preceding the human C region, and also at the splice regions that occur within the human $C_H$ exons. Polyadenylation and transcription termination occur at native chromosomal sites downstream of the coding regions. The recombinant expression vector can also encode a signal peptide that facilitates secretion of the antibody chain from a host cell. The antibody chain gene may be cloned into the vector such that the signal peptide is linked in-frame to the amino terminus of the antibody chain gene. The signal peptide can be an immunoglobulin signal peptide or a heterologous signal peptide (e.g., a signal peptide from a non-immunoglobulin protein).

In addition to the antibody chain genes, the recombinant expression vectors carry regulatory sequences that control the expression of the antibody chain genes in a host cell. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, CMV (such as the CMV promoter/enhancer), SV40 (such as the SV40 promoter/enhancer), adenovirus (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062 4,510,245, and 4,968,615.

In addition to the antibody chain genes and regulatory sequences, the recombinant expression vectors may carry additional sequences, such as sequences that regulate replication of the vector in host cells (e.g., origins of replication)

and selectable marker genes. The selectable marker gene facilitates selection of host cells into which the vector has been introduced (see e.g., U.S. Pat. Nos. 4,399,216, 4,634,665, and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neomycin gene (for G418 selection).

C. Host Cells

In another aspect, the present invention provides host cells into which a recombinant expression vector has been introduced. A host cell can be any prokaryotic cell (for example, *E. coli*) or eukaryotic cell (for example, yeast (for example, *Pichia pastoris*), insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

V. PREPARATION OF ANTIBODIES

As explained above, the LRP6 antigen is used to produce antibodies for therapeutic, diagnostic and purification purposes. These antibodies may be polyclonal or monoclonal antibody preparations, monospecific antisera, human antibodies, or may be hybrid or chimeric antibodies, such as humanized antibodies, altered antibodies, F(ab')$_2$ fragments, Fab fragments, Fv fragments, single-domain antibodies, dimeric or trimeric antibody fragment constructs, minibodies, or functional fragments thereof which bind to the antigen in question. Antibodies are produced using techniques well known to those of skill in the art and disclosed in, for example, U.S. Pat. Nos. 4,011,308; 4,722,890; 4,016,043; 3,876,504; 3,770,380; and 4,372,745.

For example, the LRP6 antigens can be used to produce LRP6-specific polyclonal and monoclonal antibodies for use in diagnostic and detection assays, for purification and for use as therapeutics. LRP6-specific polyclonal and monoclonal antibodies bind with high affinity to LRP6 antigens. The non-human antibodies that are provided can be, for example, derived from any antibody-producing animal, such as mouse, rat, rabbit, goat, donkey, or non-human primate (such as monkey (e.g., cynomologous or rhesus monkey) or ape (e.g., chimpanzee)). Serum from the immunized animal is collected and the antibodies are purified from the plasma by, for example, precipitation with ammonium sulfate, followed by chromatography, preferably affinity chromatography. Techniques for producing and processing polyclonal antisera are known in the art.

Non-human antibodies can be used, for instance, in in vitro cell culture and cell-culture based applications, or any other application where an immune response to the antibody does not occur or is insignificant, can be prevented, is not a concern, or is desired. In certain embodiments of the invention, the antibodies may be produced by immunizing with full-length LRP6 (i.e., SEQ ID NO: 2) or with the extracellular domain (i.e. SEQ ID NO: 3). Alternatively, the certain non-human antibodies may be raised by immunizing with amino acids 43-324 of SEQ ID NO: 2 (i.e., SEQ ID NO: 13 or 16), amino acids 263-283 of SEQ ID NO: 2 (i.e. SEQ ID NO: 271), or amino acids 43-627 of SEQ ID NO: 2 (i.e., SEQ ID NO: 15) which are segments of human LRP6 that form part of the epitope to which certain antibodies provided herein bind. In yet further embodiments, anti-LRP6 antibodies may be raised by immunizing non-human animals with amino acids 43-324 of SEQ ID NO: 2 (i.e., SEQ ID NO: 13 or 16), or amino acids 43-627 of SEQ ID NO: 2 (i.e., SEQ ID NO: 15). The antibodies may be polyclonal, monoclonal, or may be synthesized in host cells by expressing recombinant DNA.

Fully human antibodies may be prepared as described above by immunizing transgenic animals containing human immunoglobulin loci or by selecting a phage display library that is expressing a repertoire of human antibodies.

Mouse and/or rabbit monoclonal antibodies directed against epitopes present in the LRP6 antigen can also be readily produced. In order to produce such monoclonal antibodies, the mammal of interest, such as a rabbit or mouse, is immunized, such as by mixing or emulsifying the antigen in saline, preferably in an adjuvant such as Freund's complete adjuvant (FCA), and injecting the mixture or emulsion parenterally (generally subcutaneously or intramuscularly). The animal is generally boosted 2-6 weeks later with one or more injections of the antigen in saline, preferably using Freund's incomplete adjuvant (FIA).

The anti-LRP6 monoclonal antibodies (mAbs) can be produced by a variety of techniques, including conventional monoclonal antibody methodology, e.g., the standard somatic cell hybridization technique of Kohler and Milstein, *Nature* 256:495 (1975), herein incorporated by reference in its entirety for all purposes. Alternatively, other techniques for producing monoclonal antibodies can be employed, for example, the viral or oncogenic transformation of B-lymphocytes. One suitable animal system for preparing hybridomas is the murine system, which is a very well-established procedure. Immunization protocols and techniques for isolation of immunized splenocytes for fusion are known in the art. For such procedures, B cells from immunized mice are fused with a suitable immortalized fusion partner, such as a murine myeloma cell line. If desired, rats or other mammals can be immunized instead of mice and B cells from such animals can be fused with the murine myeloma cell line to form hybridomas. Alternatively, a myeloma cell line from a source other than mouse may be used. Fusion procedures for making hybridomas are also well-known.

Antibodies may also be generated by in vitro immunization, using methods known in the art. See, e.g., James et al., *J. Immunol. Meth.* 100:5-40 (1987). Polyclonal antisera are then obtained from the immunized animal. However, rather than bleeding the animal to extract serum, the spleen (and optionally several large lymph nodes) is removed and dissociated into single cells. If desired, the spleen cells (splenocytes) may be screened (after removal of nonspecifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated splenocytes, are then induced to fuse with cells from an immortalized cell line (also termed a "fusion partner"), to form hybridomas. Typically, the fusion partner includes a property that allows selection of the resulting hybridomas using specific media. For example, fusion partners can be hypoxanthine/aminopterin/thymidine (HAT)-sensitive.

If rabbit-rabbit hybridomas are desired, the immortalized cell line will be from a rabbit. Such rabbit-derived fusion partners are known in the art and include, for example, cells of lymphoid origin, such as cells from a rabbit plasmacytoma as described in Spieker-Polet et al., *Proc. Natl. Acad. Sci. USA* 92:9348-9352 (1995) and U.S. Pat. No. 5,675,063, or the TP-3 fusion partner described in U.S. Pat. No. 4,859,595, incorporated herein by reference in their entireties. If a rabbit-mouse hybridoma or a rat-mouse or mouse-mouse hybridoma, or the like, is desired, the mouse fusion partner will be derived from an immortalized cell line from a mouse, such as a cell of lymphoid origin, typically from a mouse myeloma cell line. A number of such cell lines are known in the art and are available from ATCC (American Type Culture Collection, Manassas, Va., USA).

Fusion is accomplished using techniques well known in the art. Chemicals that promote fusion are commonly referred to as fusogens. These agents are extremely hydrophilic and facilitate membrane contact. One particularly preferred method of cell fusion uses polyethylene glycol (PEG). Another method of cell fusion is electrofusion. In this method, cells are exposed to a predetermined electrical discharge that alters the cell membrane potential. Additional methods for cell fusion include bridged-fusion methods. In this method, the antigen is biotinylated and the fusion partner is avidinylated. When the cells are added together, an antigen-reactive B cell-antigen-biotin-avidin-fusion partner bridge is formed. This permits the specific fusion of an antigen-reactive cell with an immortalizing cell. The method may additionally employ chemical or electrical means to facilitate cell fusion.

Following fusion, the cells are cultured in a selective medium (e.g., HAT medium). In order to enhance antibody secretion, an agent that has secretory stimulating effects can optionally be used, such as IL-6. See, e.g., Liguori et al., *Hybridoma* 20:189-198 (2001). The resulting hybridomas can be plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice). For example, hybridomas producing LRP6-specific antibodies can be identified using RIA or ELISA and isolated by cloning in semi-solid agar or by limiting dilution. Clones producing the desired antibodies can be isolated by another round of screening.

An alternative technique for generating the anti-LRP6 monoclonal antibodies is the selected lymphocyte antibody method (SLAM). This method involves identifying a single lymphocyte that is producing an antibody with the desired specificity or function within a large population of lymphoid cells. The genetic information that encodes the specificity of the antibody (i.e., the immunoglobulin $V_H$ and $V_L$ DNA) is then rescued and cloned. See, e.g., Babcook et al., *Proc. Natl. Acad. Sci. USA* 93:7843-7848 (1996), for a description of this method.

For further descriptions of rabbit monoclonal antibodies and methods of making the same from rabbit-rabbit and rabbit-mouse fusions, see, e.g., U.S. Pat. Nos. 5,675,063 (rabbit-rabbit); 4,859,595 (rabbit-rabbit); 5,472,868 (rabbit-mouse); and 4,977,081 (rabbit-mouse).

The single-chain antibodies that are provided may be formed by linking heavy and light chain variable domain (Fv region) fragments (see, e.g., Table 1) via an amino acid bridge (short peptide linker), resulting in a single polypeptide chain. Such single-chain Fvs (scFvs) may be prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., *Prot. Eng.* 10:423 (1997); Kort et al., *Biomol. Eng.* 18:95-108 (2001)). By combining different $V_L$ and $V_H$-comprising polypeptides, one can form multimeric scFvs that bind to different epitopes (Kriangkum et al., *Biomol. Eng.* 18:31-40 (2001)). Techniques developed for the production of single-chain antibodies include those described in U.S. Pat. No. 4,946,778; Bird, *Science* 242:423 (1988); Huston et al., *Proc. Natl. Acad. Sci. USA* 85:5879 (1988); Ward et al., *Nature* 334:544 (1989); de Graff et al., *Methods Mol. Biol.* 178:379-87 (2002)). Single-chain antibodies derived from antibodies provided herein include, but are not limited to scFvs comprising the variable domain combinations designated by the formula "$V_L x V_H y$," wherein "x" is the number of the light chain variable region and "y" corresponds to the number of the heavy chain variable region as listed in Table 1. In general, x and y are each 1, 2, 3, 4, 5, 6, 7, 8, 9, 10, 11, 12, 13, 14, 15, 16, 17, 18, 19, 20, 21, 22, or 23.

Antibodies provided herein that are of one subclass can be changed to antibodies of a different subclass using subclass switching methods. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See, e.g., Lantto et al., *Methods Mol. Biol.* 178:303-16 (2002).

Accordingly, the antibodies that are provided include those comprising, for example, the following variable domain combinations designated by the formula "$V_L x V_H y$," (see definition above) having a desired isotype (for example, IgA, $IgG_1$, $IgG_2$, $IgG_3$, $IgG_4$, IgE, and IgD) as well as Fab or $F(ab')_2$ fragments thereof. Moreover, if an $IgG_4$ is desired, it may also be desired to introduce a point mutation (e.g. CPSCP→CPPCP) in the hinge region as described in Bloom et al., *Protein Sci.* 6:407 (1997), incorporated by reference herein) to alleviate a tendency to form intra-H chain disulfide bonds that can lead to heterogeneity in the $IgG_4$ antibodies.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., *BioTechnology* 10:770 (1992).

Conservative modifications may be made to the heavy and light chains (and corresponding modifications to the encoding nucleic acids) to produce an anti-LRP6 antibody having functional and biochemical characteristics. Methods for achieving such modifications are described above.

Antibodies and functional fragments thereof may be further modified in various ways. For example, if they are to be used for therapeutic purposes, they may be conjugated with polyethylene glycol (PEGylated) to prolong the serum half-life or to enhance protein delivery. Alternatively, the V region of the subject antibodies or fragments thereof may be fused with the Fc region of a different antibody molecule. The Fc region used for this purpose may be modified so that it does not bind complement, thus reducing the likelihood of inducing cell lysis in the patient when the fusion protein is used as a therapeutic agent. In addition, the subject antibodies or functional fragments thereof may be conjugated with human serum albumin to enhance the serum half-life of the antibody of fragment thereof. Another useful fusion is transthyretin (TTR). TTR has the capacity to form a tetramer, thus an antibody-TTR fusion protein can form a multivalent antibody which may increase its binding avidity.

Alternatively, substantial modifications in the functional and/or biochemical characteristics of the antibodies and fragments described herein may be achieved by creating substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulkiness of the side chain. A "conservative amino acid substitution" may involve a substitution of a native amino acid residue with a normative residue that has little or no effect on the polarity or charge of the amino acid residue at that position. Furthermore, any native residue in the polypeptide may also be substituted with alanine, as has been previously described for alanine scanning mutagenesis.

Amino acid substitutions (whether conservative or non-conservative) of the subject antibodies can be implemented by those skilled in the art by applying routine techniques. Amino acid substitutions can be used to identify important residues of the antibodies provided herein, or to increase or decrease the affinity of these antibodies for human LRP6 or for modifying the binding affinity of other anti-LRP6 antibodies described herein.

VI. EXPRESSION OF ANTI-LRP6 ANTIBODIES

The anti-LRP6 antibodies and antigen-binding fragments can be prepared by any of a number of conventional techniques. For example, anti-LRP6 antibodies may be produced by recombinant expression systems, using any technique known in the art. See, for example, *Monoclonal Antibodies, Hybridomas: A New Dimension in Biological Analyses*, Kennet et al. (eds.) Plenum Press, N.Y. (1980); *Antibodies: A Laboratory Manual*, Harlow and Lane (eds.), Cold Spring Harbor Laboratory Press, Cold Spring Harbor, N.Y. (1988).

The antibodies may be expressed in hybridoma cell lines or in cell lines other than hybridomas. Expression constructs encoding the antibodies may be used to transform a mammalian, insect, or microbial host cell. Transformation may be performed using any known method for introducing polynucleotides into a host cell, including, for example packaging the polynucleotide in a virus or bacteriophage and transducing a host cell with the construct by transfection procedures known in the art, as exemplified by U.S. Pat. Nos. 4,399,216, 4,912,040, 4,740,461, and 4,959,455 (which patents are hereby incorporated herein by reference for any purpose). The optimal transformation procedure used will depend upon which type of host cell is being transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide (s) in liposomes, mixing nucleic acid with positively-charged lipids, and direct microinjection of the DNA into nuclei.

Recombinant expression constructs typically comprise a nucleic acid molecule encoding a polypeptide comprising one or more of the following: a heavy chain constant region (e.g., $C_H1$, $C_H2$ and/or $C_H3$); a heavy chain variable region; a light chain constant region; a light chain variable region; one or more CDRs of the light or heavy chain of the anti-LRP6 antibody. These nucleic acid sequences are inserted into an appropriate expression vector using standard ligation techniques. In one embodiment, the 77.2, 135.16, 213.7, 240.8, 413.1, 421.1, 498.3, 537.2, 606.4, 620.1, 856.6, 923.3, 931.1, 993.3, 995.5, 1115.3, 1213.2, 1253.12, 1281.1, 1293.11, 1433.8, 1470.2, or 1903.1 heavy or light chain constant region is appended to the C-terminus of the LRP6-specific heavy or light chain variable region and is ligated into an expression vector. The vector is typically selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964, which is hereby incorporated by reference). Suitable expression vectors can be purchased, for example, from Invitrogen Life Technologies or BD Biosciences. Other useful vectors for cloning and expressing the anti-LRP6 antibodies and fragments include those described in Bianchi and McGrew, *Biotech. Biotechnol. Bioeng.* 84:439-44 (2003), herein incorporated by reference. Additional suitable expression vectors are discussed, for example, in *Methods Enzymol*, vol. 185 (D. V. Goeddel, ed.), 1990, New York: Academic Press, herein incorporated by reference.

Typically, expression vectors used in any of the host cells contain sequences for plasmid or virus maintenance and for cloning and expression of exogenous nucleotide sequences. Such sequences, collectively referred to as "flanking sequences" typically include one or more of the following operatively linked nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

Optionally, the vector may contain a "tag"-encoding sequence, that is, an oligonucleotide molecule located at the 5' or 3' end of the coding sequence, the oligonucleotide sequence encoding polyHis (such as hexaHis), or another "tag" for which commercially available antibodies exist, such as V5-His, FLAG®, HA (hemaglutinin from influenza virus), or myc. The tag is typically fused to the antibody protein upon expression, and can serve as a means for affinity purification of the antibody from the host cell. Affinity purification can be accomplished, for example, by column chromatography using antibodies against the tag as an affinity matrix. Optionally, the tag can subsequently be removed from the purified antibody polypeptide by various means such as using certain peptidases for cleavage.

Flanking sequences in the expression vector may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors provided herein may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, QIAGEN® column chromatography (Qiagen, Chatsworth, Calif., USA), or other methods known to the skilled artisan. The selection of suitable enzymes to accomplish this purpose will be readily apparent to those skilled in the art.

An origin of replication is typically a part of prokaryotic expression vectors, particularly those purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass., USA.) is suitable for most gram-negative bacteria and various origins of replication (e.g., SV40, polyoma, adenovirus, vesicular stomatitis virus (VSV), or papilloma viruses such as HPV or BPV) are useful for cloning vectors in mammalian cells. Generally, a mammalian origin of replication is not needed for mammalian expression vectors (for example, the SV40 origin is often used only because it contains the early promoter).

The expression and cloning vectors of the present invention will typically contain a promoter that is recognized by the host organism and operably linked to nucleic acid encoding an anti-LRP6 antibody or antigen-binding fragment thereof. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continuous gene product production; that is, there is little or no experimental control over gene expression. A large number of promoters, recognized by a variety of potential host cells, are well known. A suitable promoter is operably linked to the DNA encoding an anti-LRP6 antibody by removing the promoter from the source DNA by restriction enzyme digestion or amplifying the promoter by polymerase chain reaction and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably SV40. Other suitable mammalian promoters include heterologous mammalian promoters, for example, heat-shock promoters and the actin promoter.

Particular promoters useful in the practice of the recombinant expression vectors of the invention include, but are not limited to: the SV40 early promoter region (Bemoist and Chambon, *Nature* 290:304-10 (1981)); the CMV promoter; the promoter contained in the 3' long terminal repeat of Rous sarcoma virus (Yamamoto, et al., *Cell* 22:787-97 (1980)); the herpes thymidine kinase promoter (Wagner et al., *Proc. Natl. Acad. Sci. U.S.A.* 78:1444-45 (1981)); the regulatory sequences of the metallothionine gene (Brinster et al., *Nature* 296:39-42 (1982)); prokaryotic expression vectors such as the beta-lactamase promoter (VIIIa-Kamaroff et al., *Proc. Natl. Acad. Sci. U.S.A.,* 75:3727-31 (1978)); or the tac promoter (DeBoer et al., *Proc. Natl. Acad. Sci. U.S.A.* 80:21-25 (1983)). Also available for use are the following animal transcriptional control regions, which exhibit tissue specificity and have been utilized in transgenic animals: the elastase I gene control region that is active in pancreatic acinar cells (Swift et al., *Cell* 38:63946 (1984); Ornitz et al., *Cold Spring Harbor Symp. Quant. Biol.* 50:399409 (1986); MacDonald, *Hepatology* 7:425-515 (1987)); the insulin gene control region that is active in pancreatic beta cells (Hanahan, *Nature* 315:115-22 (1985)); the mouse mammary tumor virus control region that is active in testicular, breast, lymphoid and mast cells (Leder et al., *Cell* 45:485-95 (1986)); the albumin gene control region that is active in liver (Pinkert et al., *Genes Devel.* 1:268-76 (1987)); the alpha-feto-protein gene control region that is active in liver (Krumlauf et al., *Mol. Cell. Biol.* 5:1639-48 (1985); Hammer et al., *Science* 235:53-58 (1987)); the alpha 1-antitrypsin gene control region that is active in the liver (Kelsey et al., *Genes Devel.* 1:161-71 (1987)); the beta-globin gene control region that is active in myeloid cells (Mogram et al., *Nature* 315:338-40 (1985); Kollias et al., *Cell* 46:89-94 (1986)); the myelin basic protein gene control region that is active in oligodendrocyte cells in the brain (Readhead et al., *Cell* 48:703-12 (1987)); the myosin light chain-2 gene control region that is active in skeletal muscle (Sani, *Nature* 314:283-86 (1985)); the gonadotropic releasing hormone gene control region that is active in the hypothalamus (Mason et al., *Science* 234:1372-78 (1986)); and most particularly the immunoglobulin gene control region that is active in lymphoid cells (Grosschedl et al., *Cell* 38:647-58 (1984); Adames et al., *Nature* 318 533-38 (1985); Alexander et al., *Mol. Cell Biol.* 7:1436-44 (1987)).

An enhancer sequence may be inserted into the vector to increase the transcription in higher eukaryotes of a nucleic acid encoding an anti-LRP6 antibody or antigen-binding fragment thereof. Enhancers are cis-acting elements of DNA, usually about 10-300 bp in length, that act on promoters to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). An enhancer sequence from a virus also can be used. The SV40 enhancer, the cytomegalovirus early promoter enhancer, the polyoma enhancer, and adenovirus enhancers are exemplary enhancing elements for the activation of eukaryotic promoters.

While an enhancer may be spliced into the vector at a position 5' or 3' to a nucleic acid molecule, it is typically placed at a site 5' to the promoter.

In expression vectors, a transcription termination sequence is typically located 3' of the end of a polypeptide-coding region and serves to terminate transcription. A transcription termination sequence used for expression in prokaryotic cells typically is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes used in expression vectors encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Examples of selectable markers include the kanamycin resistance gene, the ampicillin resistance gene and the tetracycline resistance gene. A bacterial neomycin resistance gene can also be used for selection in both prokaryotic and eukaryotic host cells.

Other selection genes can be used to amplify the gene that will be expressed. Amplification is a process whereby genes that cannot in single copy be expressed at high enough levels to permit survival and growth of cells under certain selection conditions are reiterated in tandem within the chromosomes of successive generations of recombinant cells. Examples of suitable amplifiable selectable markers for mammalian cells include dihydrofolate reductase (DHFR) and promoterless thymidine kinase. In the use of these markers mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively increased, thereby permitting survival of only those cells in which the selection gene has been amplified. Under these circumstances, DNA adjacent to the selection gene, such as DNA encoding an anti-LRP6 antibody, is co-amplified with the selection gene. As a result, increased quantities of anti-LRP6 antibody polypeptides are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, for example where glycosylation is desired in a eukaryotic host cell expression system, various presequences can be manipulated to improve glycosylation or yield. For example, the peptidase cleavage site of a particular signal peptide can be altered, or pro-sequences added, which also may affect glycosylation. The final protein product may have in the −1 position (relative to the first amino acid of the mature protein) one or more additional amino acids incident to expression which may not have been totally removed. For example, the final protein product may have one or two amino acid residues found in the peptidase cleavage site attached to the amino-terminus. Alternatively, use of some enzyme cleavage sites may result in a slightly truncated yet active form of the desired polypeptide if the enzyme cuts at such area within the mature polypeptide.

Where a commercially available expression vector lacks some of the desired flanking sequences as described above, the vector can be modified by individually ligating these sequences into the vector. After the vector has been chosen and modified as desired, a nucleic acid molecule encoding an anti-LRP6 antibody or antigen-binding fragment thereof is inserted into the proper site of the vector.

The completed vector containing sequences encoding the anti-LRP6 antibody or antigen-binding region thereof is inserted into a suitable host cell for amplification and/or polypeptide expression. The transformation of an expression vector for an anti-LRP6 antibody or antigen-binding fragment thereof into a selected host cell may be accomplished by well-known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan.

The transformed host cell, when cultured under appropriate conditions, synthesizes an anti-LRP6 antibody or antigen-binding fragment thereof that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, many immortalized cell lines available from the American Type Culture Collection (ATCC), such as Chinese hamster ovary (CHO) cells, human embryonic kidney (HEK) cells, HEK293 cells, HeLa cells, baby hamster kidney (BHK) cells, monkey kidney cells (COS), human hepatocellular carcinoma cells (e.g., Hep G2), and a number of other cell lines. In certain embodiments, the best cell line for expressing a particular DNA construct may be selected by testing various cell lines to determine which ones have the highest levels of expression levels and produce antibodies that bind LRP6.

VII. PHARMACEUTICAL COMPOSITIONS

A. Exemplary Formulations

In certain embodiments, the invention also provides compositions comprising the subject anti-LRP6 antibodies or antigen-binding fragments thereof together with one or more of the following: a pharmaceutically acceptable diluent; a carrier; a solubilizer; an emulsifier; a preservative; and/or an adjuvant. Such compositions may contain an effective amount of the anti-LRP6 antibody or antigen-binding fragment thereof that are provided herein in the preparation of a pharmaceutical composition of medicament is also included. Such compositions can be used in the treatment of a variety of diseases such as listed below.

The anti-LRP6 antibodies and antigen-binding fragments thereof may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease or disorder targeted. The compositions also preferably include pharmaceutically acceptable vehicles, carriers or adjuvants, well known in the art.

A "pharmaceutically acceptable" vehicle, carrier or adjuvant is a non-toxic agent that can be tolerated by a recipient patient. Representative non-limiting examples of such agents include human serum albumin, ion exchangers, alumina, lecithin, buffer substances such as phosphates, glycine, sorbic acid, potassium sorbate, and salts or electrolytes such as protamine sulfate. Suitable vehicles are, for example, water, saline, phosphate-buffered saline, dextrose, glycerol, ethanol, or the like, and combinations thereof. Other suitable agents are well-known to those in the art. See, for example, *Remington's Pharmaceutical Sciences*, Mack Publishing Company, Easton, Pa., 19th edition, 1995. Actual methods of preparing such compositions are also known, or will be apparent, to those skilled in the art. See, e.g., *Remington's Pharmaceutical Sciences*, 1995, supra.

Acceptable formulation components for pharmaceutical preparations are nontoxic to recipients at the dosages and concentrations employed. In addition to the antibodies and antigen-binding regions that are provided, compositions according to the invention may contain components for modifying, maintaining or preserving, for example, the pH, osmolarity, viscosity, clarity, color, isotonicity, odor, sterility, stability, rate of dissolution or release, adsorption or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences*, 1995, supra), hereby incorporated by reference in its entirety for all purposes.

The primary vehicle or carrier in a pharmaceutical composition may be either aqueous or non-aqueous in nature. Suitable vehicles or carriers for such compositions include water for injection, physiological saline solution or artificial cerebrospinal fluid, possibly supplemented with other materials common in compositions for parenteral administration. Neutral buffered saline or saline mixed with serum albumin are further exemplary vehicles. Compositions comprising anti-LRP6 antibodies or antigen-binding fragments thereof may be prepared for storage by mixing the selected composition having the desired degree of purity with optional formulation agents in the form of a lyophilized cake or an aqueous solution. Further the anti-LRP6 antibodies or antigen-binding fragments thereof may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefore.

The pharmaceutical composition to be used for in vivo administration typically is sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

Additional pharmaceutical methods may be employed to control the duration of action of an antibody in a therapeutic application. Control release preparations can be prepared through the use of polymers to complex or adsorb the antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10:1446 (1992). The rate of release of an antibody from such a matrix depends upon the molecular weight of the protein, the amount of antibody within the matrix, and the size of dispersed particles. Saltzman et al., *Biophys. J.* 55:163 (1989); Sherwood et al., supra. Other solid dosage forms are described in *Remington's Pharmaceutical Sciences*, 1995, supra.

The above compositions can be administered using conventional modes of delivery including, but not limited to, intravenous, intraperitoneal, oral, intralymphatic, subcutaneous administration, intraarterial, intramuscular, intrapleural, intrathecal, and by perfusion through a regional catheter. Local administration to a tumor in question, will also find use with the present invention. Eye drops can be used for intraocular administration. When administering the compositions by injection, the administration may be by continuous infusion or by single or multiple boluses. Intravenous injection provides a useful mode of administration due to the thoroughness of the circulation in rapidly distributing antibodies. For parenteral administration, the antibodies may be administered in a pyrogen-free, parenterally acceptable aqueous solution comprising the desired anti-LRP6 antibodies or antigen-binding fragments thereof in a pharmaceutically acceptable vehicle. A particularly suitable vehicle for parenteral injection is sterile distilled water in which the anti-LRP6 antibodies or antigen-binding fragments thereof are formulated as a sterile, isotonic solution, properly preserved.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The present invention provides kits for producing multi-dose or single-dose administration units. For example, kits according to the invention may each contain both a first container having a dried protein and a second container having an aqueous diluent, including for example single and multi-chambered pre-filled syringes (e.g., liquid syringes, lyosyringes or needle-free syringes).

The subject compositions comprising anti-LRP6 antibodies or antigen-binding fragments thereof also may be used ex vivo. In such instances, cells, tissues or organs that have been removed from the patient are exposed to or cultured with the anti-LRP6 antibody or antigen-binding fragment thereof. The cultured cells may then be implanted back into the patient or a different patient or used for other purposes.

In certain embodiments, anti-LRP6 antibodies or antigen-binding fragments thereof can be delivered by implanting certain cells that have been genetically engineered, using methods such as those described herein, to express and secrete the polypeptide. Such cells may be animal or human cells, and may be autologous, heterologous, or xenogenic, or may be immortalized. In order to decrease the chance of an immunological response, the cells may be encapsulated to avoid infiltration of surrounding tissues. Encapsulation materials are typically biocompatible, semi-permeable polymeric enclosures or membranes that allow the release of the protein product(s) but prevent the destruction of the cells by the patient's immune system or by other detrimental factors from the surrounding tissues.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of an anti-LRP6 antibody, protein or other active ingredient provided herein is administered orally, the antibody, protein or other active ingredient will be in the form of a tablet, capsule, powder, solution or elixir. When administered in tablet form, the pharmaceutical composition may additionally contain a solid carrier such as a gelatin or an adjuvant. The tablet, capsule, and powder contain from about 5 to 95% antibody, protein or other active ingredient, and preferably from about 25 to 90% antibody, protein or other active ingredient. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of antibody, protein or other active ingredient, and preferably from about 1 to 50% antibody, protein or other active ingredient.

When a therapeutically effective amount of an antibody, protein or other active ingredient provided herein is administered by intravenous, cutaneous or subcutaneous injection, the antibody, protein or other active ingredient will be in the form of a pyrogen-free, parenterally acceptable aqueous solution. The preparation of such parenterally acceptable antibody, protein or other active ingredient solutions, having due regard to pH, isotonicity, stability, and the like, is within the skill in the art. A preferred pharmaceutical composition for intravenous, cutaneous, or subcutaneous injection should contain, in addition to the antibody, protein or other active ingredient, an isotonic vehicle such as Sodium Chloride Injection, Ringers Injection, Dextrose Injection, Dextrose and Sodium Chloride Injection, Lactated Ringers Injection, or other vehicle as known in the art. The pharmaceutical composition may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for hydrophobic compounds is a co-solvent system comprising benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for antibody, protein or other active ingredient stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the active ingredients provided herein may be provided as salts with pharmaceutically compatible counter ions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition may be in the form of a complex of the antibody, protein(s) or other active ingredient along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention.

The pharmaceutical composition may be in the form of a liposome in which the anti-LRP6 antibody is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithins, phospholipids, saponin, bile acids, and the like. Preparation of such liposomal formulations is within the level of skill in the art, as disclosed, for example, in U.S. Patent Nos. 4,235,871; 4,501,728; 4,837,028; and 4,737,323, all of which are incorporated herein by reference.

The amount of antibody, protein or other active ingredient in the pharmaceutical composition will depend upon the nature and severity of the condition being treated, and on the nature of prior treatments which the patient has undergone. Ultimately, the attending physician will decide the amount of antibody, protein or other active ingredient with which to treat each individual patient. Initially, the attending physician will administer low doses of antibody, protein or other active ingredient and observe the patient's response. Larger doses of antibody, protein or other active ingredient may be administered until the optimal therapeutic effect is obtained for the patient, and at that point the dosage is not increased further. It is contemplated that the various pharmaceutical compositions used to practice the method of the present invention should contain about 0.01 µg to about 100 mg (preferably about 0.1 µg to about 10 mg, more preferably about 0.1 µg to about 1 mg) of antibody, protein or other active ingredient per kg body weight. For compositions of the present invention which are useful for bone, cartilage, tendon or ligament regeneration, the therapeutic method includes administering the composition topically, systematically (i.e., via intravenous, intraperitoneal, intramuscular, or oral administration), or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than an antibody, protein or other active ingredient which may also optionally be included in the composition as described above, may alternatively or additionally, be administered simultaneously or sequentially with the composition in the methods provided herein. Preferably for bone and/or cartilage formation, the composition would include a matrix capable of delivering the protein-containing or other active ingredient-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalcium phosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5-20 weight percent, preferably 1-10 weight percent based on total formulation weight, which represents the amount necessary to prevent desorption of the antibody or protein from the polymer matrix and to provide appropriate handling of the composition, yet not so much that the progenitor cells are prevented from infiltrating the matrix, thereby providing the antibody or protein the opportunity to assist the osteogenic activity of the progenitor cells. In further compositions, the antibodies, proteins or other active ingredient may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-$\alpha$ and TGF-$\beta$), and insulin-like growth factor (IGF).

The therapeutic compositions are also presently valuable for veterinary applications. Particularly domestic animals and thoroughbred horses, in addition to humans, are desired patients for such treatment with antibodies, proteins or other active ingredient of the present invention. The dosage regimen of an antibody- or protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

B. Dosage

For purposes of therapy, antibodies are administered to a patient in a therapeutically effective amount. A "therapeutically effective amount" is one that is physiologically significant. An agent is physiologically significant if its presence results in a detectable change in the physiology or disease or disorder state of a recipient. A "prophylactically effective amount" refers to an amount that is effective to prevent, hinder or retard the onset of a disease state or symptom.

Therapeutically effective doses will be easily determined by one of skill in the art and will depend on the severity and course of the disease, the patient's health and response to treatment, the patient's age, weight, height, sex, previous medical history and the judgment of the treating physician. Typically, it is desirable to provide the recipient with a dosage of antibody component or immunoconjugate which is in the range of from about 1 pg/kg to 10 mg/kg (amount of agent/body weight of patient), although a lower or higher dosage also may be administered as circumstances dictate. In preferred embodiments, anti-LRP6 antibodies are administered at low protein doses, such as 20 mg to 2 g protein per dose, given once, or repeatedly, parenterally. Alternatively, antibodies are administered in doses of 20 to 1000 mg protein per dose, or 20 to 500 mg protein per dose, or 20 to 100 mg protein per dose.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amount is well within the capability of those skilled in the art, especially in light of the detailed disclosure provided herein. For any compound used in the methods of the invention, the therapeutically effective dose can be estimated initially from appropriate in vitro assays. For example, a dose can be formulated in animal models to achieve a circulating concentration range that can be used to more accurately determine useful doses in humans. For example, a dose can be formulated in animal models to achieve a circulating concentration range that includes the $IC_{50}$ as determined in cell culture (i.e., the concentration of the test compound which achieves a half-maximal inhibition of the protein's biological activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p. 1. Dosage amount and interval may be adjusted individually to provide plasma levels of the active moiety which are sufficient to maintain the desired effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

The amount of composition administered will, of course, be dependent on the subject being treated, on the subject's age and weight, the severity of the affliction, the manner of administration and the judgment of the prescribing physician.

C. Routes of Administration

Suitable routes of administration of anti-LRP6 antibodies for the treatment of bone diseases and disorders may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of anti-LRP6 antibodies or other active ingredient used in the pharmaceutical composition or to practice the methods of the present invention can be carried out in a variety of conventional ways, such as oral ingestion, inhalation, topical application or cutaneous, subcutaneous, intraperitoneal (IP), parenteral or intravenous injection.

Alternatively, one may administer the compound in a local rather than systemic manner, for example, via injection of the compound directly into the tissue, often in a depot or sustained release formulation.

The compounds provided herein are administered by any route that delivers an effective dosage to the desired site of action. The determination of a suitable route of administration and an effective dosage for a particular indication is within the level of skill in the art. Preferably for bone disorders, one administers the anti-LRP6 antibodies systemically. Suitable dosage ranges for the anti-LRP6 antibodies can be extrapolated from these dosages or from similar studies in appropriate animal models. Dosages can then be adjusted as necessary by the clinician to provide maximal therapeutic benefit. Alternatively, bone disorders and diseases may be treated via local administration of the anti-LRP6 antibodies.

VIII. DIAGNOSTIC ASSAYS

Antibodies of the present invention can be used in vivo, i.e., injected into subjects, for diagnostic or therapeutic uses. The use of antibodies for in vivo diagnosis is well known in the art. Sumerdon et al., *Nucl. Med. Biol* 17:247-254 (1990) have described an optimized antibody-chelator for the radioimmunoscintographic imaging of carcinoembryonic antigen (CEA)-expressing tumors using Indium-111 as the label. Griffin et al., *J Clin Onc* 9:631-640 (1991) have described the use of this agent in detecting tumors in patients suspected of having recurrent colorectal cancer. The use of similar agents with paramagnetic ions as labels for magnetic resonance imaging is known in the art (R. B. Lauffer, *Magnetic Resonance in Medicine* 22:339-342 (1991). Thus, antibodies directed against the LRP6 antigen can be injected into subjects suspected of having a disease or disorder in which LRP6, Wnt or Dkk1 is implicated for the purpose of diagnosing or staging the disease status of the patient. The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used. Localization of the label within the patient allows determination of the presence and/or spread of the disease.

The antibodies generated against LRP6 can also be used in standard in vitro immunoassays, to screen biological samples such as blood, tissues and/or tumors for the presence or absence of LRP6. Thus, the anti-LRP6 antibodies produced as described above, can be used in diagnostic assays. The anti-LRP6 antibodies can be used as either the capture component and/or the detection component in the assays, as described further below. Thus, the presence of LRP6 antigen can be determined by the presence of LRP6 antigens and/or anti-LRP6 antibodies.

For example, the presence of LRP6 cell surface receptors can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as enzyme-linked immunosorbent assays ("ELISAs"); biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods for detecting the formation of a complex between the antigens and the antibodies described above.

Assays can also be conducted in solution, such that the antigens and antibodies thereto form complexes under precipitating conditions. The precipitated complexes can then be separated from the test sample, for example, by centrifugation. The reaction mixture can be analyzed to determine the presence or absence of antibody-antigen complexes using any of a number of standard methods, such as those immunodiagnostic methods described above. The antigens and antibodies can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

IX. THERAPEUTIC USES

The present invention provides antibodies or antigen-binding fragments thereof that bind to LRP6 epitopes that are useful for the treatment of human diseases and pathological conditions. Anti-LRP6 antibodies may be used in combination with other therapeutic agents to enhance their therapeutic effects or decrease potential side effects.

Supplemental active compounds can also be incorporated into the compositions. In certain embodiments, an anti-LRP6 antibody of antigen-binding fragment can be co-formulated with one or more additional therapeutic agents, such as a chemotherapeutic agent, an antineoplastic agent, or an anti-tumor agent. These agents include without limitation, antibodies that bind other targets (e.g., antibodies that bind one or more growth factors, cytokines, or cell surface receptors), LRP6 binding proteins, antineoplastic agents, chemotherapeutic agents, anti-tumor agents, antisense oligonucleotides against LRP6, LRP6 peptide analogs, and/or one or more chemical agents that inhibit LRP6 production or activity, which are known in the art.

In another aspect, the anti-LRP6 antibody may be co-administered with other therapeutic agents, such as antineoplastic drugs or molecules, to a patient who has a hyperproliferative disorder, such as cancer (for example multiple myeloma or prostate cancer with associated osteolytic lesions) or a tumor. In one aspect, the invention relates to a method for the treatment of the hyperproliferative disorder in a mammal comprising administering to said mammal a therapeutically effective amount of a compound of the invention in combination with an anti-tumor agent selected from the group consisting of, but not limited to, mitotic inhibitors, alkylating agents, anti-metabolites, intercalating agents, growth factor inhibitors, cell cycle inhibitors, enzymes, topoisomerase inhibitors, biological response modifiers, anti-hormones, kinase inhibitors, matrix metalloprotease inhibitors, genetic therapeutics and anti-androgens. In a more preferred embodiment, the antibody may be administered with an antineoplastic agent, such as adriamycin or taxol. In another preferred embodiment, the antibody or combination therapy is administered along with radiotherapy, chemotherapy, photodynamic therapy, surgery or other immunotherapy. In yet another preferred embodiment, the antibody will be administered with another antibody. For example, an anti-LRP6 antibody may be administered with an antibody or other agent that is known to inhibit tumor or cancer cell proliferation, e.g., an antibody or agent that inhibits erbB2 receptor, EGF-R, CD20 or VEGF.

In yet another aspect, the anti-LRP6 mAbs may be administered with other therapeutic agents, such as anti-inflammatory agents including but not limited to steroids, glucocorticoids, corticosteroids, NSAIDS, including cyclooxygenase inhibitors, aspirin, analgesics including paracetamol (acetaminophen), and capsaicin, to a patient with a bone or joint inflammatory disease, such as rheumatoid arthritis, osteoarthritis, ankylosing spondylosis.

In yet another aspect, the anti-LRP6 mAbs may be administered with other therapeutic agents, such as agents that treat osteoporosis including but not limited to bisphosphonates, including alendronate (FOSAMAX® (Merck, Whitehouse Station, N.J.), ibandronate (BONIVA®, Roche, Nutley, N.J.), risedronate (ACTONEL® (Procter & Gamble Pharmaceuticals, Cincinnati, Ohio); selective estrogen receptor modulators (SERM) including raloxifene (EVISTA®, Eli Lilly, Indianapolis, Ind.); calcitonin, including CALCIMAR® (Rhône-Poulenc-Rorer, Collegeville, Pa.) and MIACAL-CIN® (Novartis, East Hanover, N.J.); parathyroid hormone, including teriparatide; estrogen replacement therapy (ERT), hormone replacement therapy (HRT, estrogen with progestin), testosterone, and calcium with vitamin D, for the treatment of bone disorders characterized by low bone density, such as osteoporosis.

Co-administration of the anti-LRP6 antibody or antigen-binding fragments thereof with an additional therapeutic agent (combination therapy) encompasses administering a pharmaceutical composition comprising an anti-LRP6 antibody and the additional therapeutic agent and administering two or more separate pharmaceutical compositions, one composition comprising an anti-LRP6 antibody and the other(s) comprising the additional therapeutic agent(s). Further, although co-administration or combination therapy generally means that the antibody and additional therapeutic agents are administered at the same time as one another, it also encompasses instances in which the antibody and additional therapeutic agents are administered at different times. For instance, the antibody may be administered once every three days, while the additional therapeutic agent is administered once daily. Alternatively, the antibody may be administered prior to or subsequent to treatment of the disorder with the additional therapeutic agent. Similarly, administration of the anti-LRP6 antibody may be administered prior to or subsequent to other therapy, such as radiotherapy, chemotherapy, photodynamic therapy, surgery or other immunotherapy The antibody and one or more additional therapeutic agents (the combination therapy) may be administered once, twice or at least the period of time until the condition is treated, palliated or cured. Preferably, the combination therapy is administered multiple times. The combination therapy may be administered from three times daily to once every six months. The administering may be on a schedule such as three times daily, twice daily, once daily, once every two days, once every three days, once weekly, once every two weeks, once every month, once every two months, once every three months, once every six months, or may be administered continuously via a minipump. The combination therapy may be administered via an oral, mucosal, buccal, intranasal, inhalable, intravenous, subcutaneous, intramuscular, parenteral, intratumor or topical route.

In one aspect, the present invention provides reagents and methods useful for treating diseases and conditions characterized by reduced levels of Wnt/LRP6 signaling activity and/or increased levels of Wnt inhibitors, such as the LRP5/6 inhibitor Dkk1. In a particular embodiment, the antibodies and derivatives thereof are used in vivo to enhance LRP6 signaling and/or block Dkk1 activity to treat, prevent or diagnose a variety of bone diseases. These diseases include osteoporosis, osteogenesis imperfecta, Paget's disease of bone, myeloma bone disease including osteolytic lesions associated with multiple myeloma, bone spurs (osteophytes), osteoarthritis, diffuse idiopathic skeletal hyperstosis, plantar fasciitis, spondylosis (including cervical and lumbar), spinal stenosis, craniocynostossi, echondroma, fibrous dysplasia, Klippel-Feil syndrome, osteitis condensans ilii, osteochondritis dissecans, osteomyelitis, osteopetroses (marble bone diseases), renal osteodystrophy, unicameral bone cyst, osteomalacia, hyperostosis, and van Buchem disease.

The diseases treatable by methods of the present invention preferably occur in mammals. Mammals include, for example, humans and other primates, as well as pet or companion animals such as dogs and cats, laboratory animals such as rats, mice and rabbits, and farm animals such as horses, pigs, sheep and cattle.

The present invention also provides methods of modulating stem cell growth by administering anti-LRP6 antibodies that promote LRP6 activity and/or inhibit Dkk1 activity. For example, such anti-LRP6 antibodies may serve to stimulate proliferation of intestinal epithelial cells including crypt cells and for regeneration of oral and gastrointestinal tissue, i.e., for the treatment of injuries sustained by the epithelial layer which involve degeneration, death or trauma to epithelial cells. More specifically, an anti-LRP6 antibody that promotes LRP6 activity and/or inhibits Dkk1 activity can be used in the treatment of diseases of the gastrointestinal tract as recited herein. Similarly, such anti-LRP6 antibodies can also be used to promote expansion and/or differentiation of other stem cell populations such as, but not limited to, hematopoietic, neuronal, and embryonic stem cells.

In one aspect, the present invention provides compositions and methods useful for treating diseases and conditions wherein epithelialization is desired. Anti-LRP6 antibodies that promote LRP6 activity and/or inhibit Dkk1 activity can be used to increase cytoprotection, proliferation or differentiation of epithelial cells of the oral and gastrointestinal tract. Specifically, anti-LRP6 antibodies that promote LRP6 activity and/or inhibit Dkk1 activity can be useful to treat or prevent diseases or conditions that include without limitation, gastrointestinal diseases, mucositis of the gastrointestinal tract, mucositis of the oropharynx, lips and esophagus (oral mucositis), inflammatory bowel disease, short bowel syndrome, gastric and duodenal ulcers, erosions of the gastrointestinal tract including erosive gastritis, esophagitis, esophageal reflux and other conditions including wounds, burns, ophthalmic disorders, and any disorder where stimulation of epithelial cell proliferation or regeneration is desired. Treatment of diseases that result in insufficient production of mucus throughout the oral and gastrointestinal tract is also contemplated.

Anti-LRP6 antibodies that promote LRP6 activity and/or inhibit Dkk1 activity can also be useful to promote better or faster closure of non-healing wounds, including without limitation, pressure ulcers, ulcers associated with vascular insufficiency, surgical and traumatic wounds and the like. Assays for wound healing activity include, without limitation, those described in Winter, Epidermal Wound Healing, pp. 71-112 (Maibach and Rovee, eds), Year Book Medical Publishers, Inc., Chicago, as modified by Eaglstein and Mertz, *J. Invest. Dermatol.* 71:382-84 (1978).

The invention further provides methods for treating wounded tissue comprising administering to a subject in need thereof. The anti-LRP6 antibodies that promote LRP6 activity and/or inhibit Dkk1 activity may be administered alone or in combination with other compositions including but not limited to growth factors, antioxidant vitamins, antibiotics, and cellulosic materials. The present invention provides methods for treating wounds on external surfaces such as the skin and mucous membranes as well as treating internal lesions. For example, the methods and compositions of the present invention may be used to treat wounds associated with surgical incisions and other localized injury to internal tissues.

In yet another embodiment, anti-LRP6 antibodies that promote LRP6 activity and/or inhibit Dkk1 activity may enhance hematopoietic recovery after chemotherapy or radiation therapy by stimulating the growth or proliferation of hematopoietic stem cells. Such anti-LRP6 antibodies may also be used to stimulate bone marrow transplant engraftment by stimulating hematopoietic stem cell proliferation.

Anti-LRP6 antibodies that promote LRP6 activity and/or inhibit Dkk1 activity may also be useful in treating disorders wherein epithelial stem cell proliferation is desired, for example in stimulating hair growth.

Anti-LRP6 antibodies that promote LRP6 activity and/or inhibit Dkk1 activity may also be useful in stimulating the growth, expansion or differentiation of stem cells in vivo or in vitro to expand stem cell populations. Expanded stem cell populations can also be used for cell-based therapies in which stem cells are induced to differentiate into specific cell types required to repair damaged or destroyed cells or tissue. Examples of diseases and disorders that can be treated using stem cell-based therapies include, but are not limited to: organ regeneration or generation; neural diseases and disorders such as Parkinson's disease, Alzheimer's disease, spinal cord injury, stroke, neurodegenerative diseases, multiple sclerosis; burns; heart disease; diabetes; bone and cartilage diseases and disorders including osteoporosis and osteoarthritis; kidney diseases, gastrointestinal diseases and disorders, rheumatoid arthritis, sickle cell disease; and cancer such as multiple myeloma, breast and prostate cancer that have associated osteolytic lesions.

X. ARTICLES OF MANUFACTURE

In another embodiment of the invention, an article of manufacture containing materials useful for the treating diseases or disorders implicating LRP6 is provided. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an anti-LRP6 antibody (e.g., 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, or 1903.1). Alternatively, or additionally, the article of manufacture may further comprise a second container comprising a pharmaceutically-acceptable buffer, such as bacteriostatic water for injection (BWFI), phosphate-buffered saline (PBS), Ringer's solution and dextrose solution. It may further include other materials desirable from a commercial and user standpoint, including other buffers, diluents, filters, needles and syringes.

Further details of the invention are illustrated by the following non-limiting Examples. The disclosures of all citations in the specification are expressly incorporated herein by reference.

EXAMPLE 1

Generation and Characterization of Anti-LRP6 Monoclonal Antibodies

A. Generation of Hybridomas

Recombinant human LRP6 (hLRP6) protein containing the complete extracellular domain was purchased from R&D systems (Minneapolis, Minn.). Using standard protocols (see Kohler and Milstein, *Nature* 256:495-497 (1975) herein incorporated by reference in its entirety), immunizations of Balb/c mice with the extracellular domain of LRP6 (SEQ ID NO: 3) and subsequent fusions with SP20-Ag14 cells (ATCC) resulted in a total of 170 hybridoma supernatants containing antibodies which bound to LRP6 in an ELISA screen, 64 of which scored positive by FACS analysis on 293 Tcells transiently transfected with hLRP6.

B. ELISA Screen of Hybridoma Supernatants for Binding to LRP6

Human LRP6-Fc (R&D Systems) was coated at 1 μg/ml in Carbonate-Bicarbonate buffer (Sigma #C-3041) on Maxi-Sorp 96-well plates (Nunc) and incubated overnight at 4° C. After three washes with 300 μg/well TBST (0.1 M Tris-HCl, 0.15 M NaCl, 0.05% Tween-20), wells were blocked using 300 μg/well 2% BSA (Sigma #A9647) in PBS for one hour at room temperature. Hybridoma supernatants were diluted 1:2 in Iscove's Media (Gibco #31980-030) with 10% FBS (Gibco #20012-027) and 100 μl was added to each well followed by incubation for 2 hours on a plate shaker at room temperature. Three washes with TBST were followed by addition of 100 μl of secondary antibody, goat anti-mouse Ig-HRP (BioRad #170-6516), diluted 1:10,000 in 0.5% BSA/PBS and incubated for one hour on a plate shaker. After five washes with TBST, 100 μl TMB substrate (KPL #50-76-03) were added and color was allowed to develop for 10 min. Plates were read at 450 nm on a SpectraMax plate reader (Molecular Devices, Sunnyvale, Calif.).

C. FACS Screening of Hybridoma Supernatants for Binding to LRP6 Expressing Cells Briefly, 293 T cells were transiently transfected with HA-tagged hLRP6 plasmid (SEQ ID NO: 4) using Fugene transfection reagent (Roche), according to manufacturer's instructions. Transfected cells were collected 48 hours post transfection and resuspended at $5\times10^6$ cells/ml in blocking buffer (10% heat-inactivated human serum, BioWhittaker, in PBS) and 100 μl were added to each well of a round-bottom 96-well plate and incubated for 15 min on ice. 100 μl of hybridoma supernatant was added to each well and plates were incubated for an additional 20 min on ice. Cells were centrifuged for 5 min at 1500 rpm, supernatant was removed and cells were washed twice in cold FACS buffer (1% BSA in PBS). The pellet was resuspended in 100 μl blocking buffer containing 0.25 μg of secondary antibody (goat anti-mouse PE-conjugated, BD Pharmingen) and incubated for 15 min on ice. Cells were analyzed for fluorescence in FL-2 using an Automated Microsampler from Cytek hooked up to a FACScalibur system (Becton Dickinson, Franklin Lakes, N.J.).

Based on isotype and ability to recognize LRP6 expressed on cells by FACS, 23 hits were subcloned, re-screened, selected for scale-up and purified using a protein G column. The monoclonal antibodies isolated and described herein were annotated as follows: 77.2, 135.16, 213.7, 240.8, 413.1, 421.1, 498.3, 537.2, 606.4, 620.1, 856.6, 923.3, 931.1, 993.9, 995.5, 1115.3, 1213.2, 1253.12, 1281.1, 1293.11, 1433.8, 1470.2, and 1903.1. These antibodies were subsequently used in detailed expression analysis and efficacy studies (discussed below).

D. Generation of Anti-LRP6 Chimeric Monoclonal Antibodies

Chimeric monoclonal antibodies (mAbs) against LRP6 are generated as follows: RNA is isolated from hybridoma fusion cells expressing the anti-LRP6 mAb of interest. Using standard RACE/RT-PCR techniques, the heavy and light variable regions are cloned into two separate expression vectors in fusion with cDNA encoding for human IgG1 constant regions. The resulting plasmids are co-transfected into CHO cells and stable cell lines are selected secreting full-length chimeric mAbs. Conditioned medium of these cell lines are subjected to protein G purification to yield purified chimeric mAbs.

Example 2

Affinity Measurements for Anti-LRP6 Monoclonal Antibodies

Kinetic rate constants ($k_a$ and $k_d$) were determined using surface plasmon resonance, and affinities ($K_D$) were then calculated from the rate constants ($k_d/k_a$). Surface plasmon resonance was carried out on a BIAcore system (Biacore International AB, Uppsala, Sweden). Each murine anti-LRP6 mAb sample was diluted 100 fold and captured onto an anti-mouse sensor chip surface. The running buffer contained 10 mM HEPES, 150 mM NaCl, 0.005% Tween-20 and 0.1 mg/ml BSA. Following the capturing step, the Fc-antigen was injected at 45 nM as the highest concentration in a 3-fold dilution series. The association and dissociation phases were monitored for 8 and 60 minutes, respectively. The antigen response data were fit into a 1:1 interaction model. The apparent binding constants were reported within each plot (see FIG. 2 and summarized in Table 4. The analysis was carried out in HBS, pH 7.4 buffer at 25° C. (Canziani et al, *Anal. Biochem.* 352:301-307 (2004)).

TABLE 4

| mAb | $k_a$ (M$^{-1}$s$^{-1}$) | $k_d$ (s$^{-1}$) | $K_D$ |
|---|---|---|---|
| 77.2 | 6.32(2)e4 | 3.5(2)e-5 | 550(40) pM |
| 135.16 | 2.63(1)e4 | 1.9(1)e-5 | 730(30) pM |
| 213.7 | 5.563(9)e4 | 9.6(1)e-5 | 1.72(2) nM |
| 240.8 | 6.11(1)e3 | 4(1)e-5 | 6.55(1) nM |
| 413.1 | 4.7(2)e3 | 8.47(8)e-5 | 18.0(7) nM |
| 421.1 | 3.54(3)e4 | 1.14(4)e-4 | 3.2(1) nM |
| 498.3 | 5.05(2)e4 | 5.0(3)e-5 | 980(50) pM |
| 606.4 | 5.32(1)e4 | 5.7(1)e-5 | 1.08(2) nM |
| 537.2 | 3.517(6)e4 | 3.15(6)e-5 | 900(20) pM |
| 620.1 | 4.46(2)e4 | 7.7(2)e-5 | 1.73(4) nM |
| 856.6 | 4.74(2)e4 | 4.5(2)e-5 | 950(30) pM |
| 923.3 | 3.16(1)e4 | 7.4(1)e-5 | 2.33(4) nM |
| 931.1 | 5.63(1)e4 | 6.3(1)e-5 | 1.12(2) nM |
| 993.9 | 2.80(1)e4 | 5.7(1)e-5 | 2.05(3) nM |
| 995.5 | 4.138(9)e4 | 4.51(9)e-5 | 1.09(4) nM |
| 1115.3 | 3.675(9)e4 | 5.34(9)e-5 | 1.45(2) nM |
| 1213.2 | 5.88(1)e4 | 6.3(1)e-5 | 1.07(2) nM |
| 1253.12 | 3.40(3)e4 | 7.3(3)e-5 | 2.15(7) nM |
| 1281.1 | 4.55(2)e4 | 8.3(2)e-5 | 1.83(4) nM |
| 1293.11 | 2.2(3)e3 | 1.24(1)e-4 | 57(8) nM |
| 1433.8 | 4.56(2)e4 | 7.7(2)e-5 | 1.68(4) nM |
| 1903.1 | 3.37(4)e4 | 9.4(4)e-5 | 2.79(9) nM |

Example 3

Epitope Mapping of Anti-LRP6 Monoclonal Antibodies

Figure 3A:
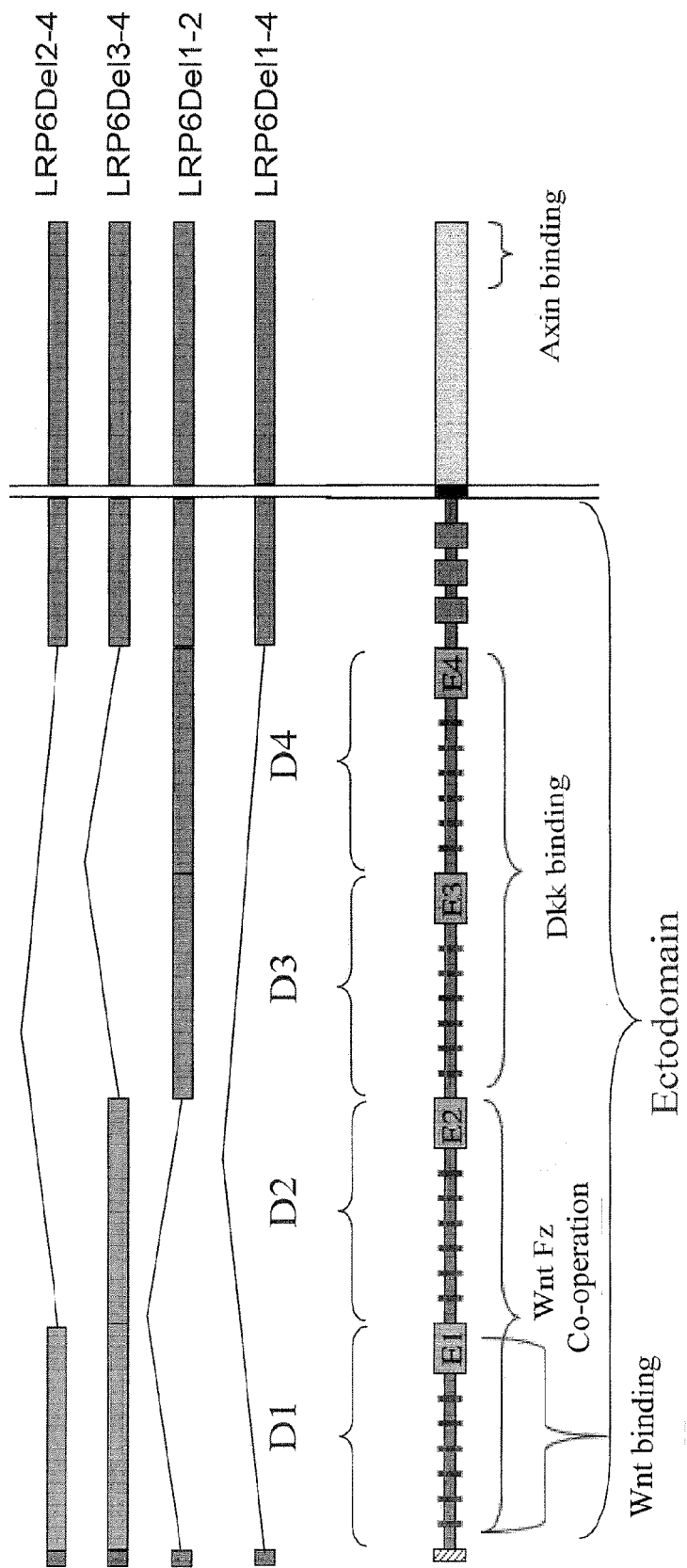
FIG. 3: A) Schematic of constructs used to map the LRP6 epitope that binds anti-LRP6 mAbs; B) FACS analysis of anti-LRP6 mAb binding to the LRP6 deletion constructs; C) Schematic of constructs used to map the C-terminal region of propeller domain 1 of LRP6 that binds anti-LRP mAb 135.16; D) FACS analysis of anti-LRP6 mAb 135.16 binding to propeller domain 1 of LRP6; E) Schematic of LRP6 propeller domain 1, amino acid sequence of mouse and human C-terminal region of LRP6 propeller domain 1 (residues 236-283), and ribbon model of LRP6 indicating position of Ser$^{243}$; F) FACS analysis of anti-LRP6 mAb 135.16 binding to LRP6 propeller domain 1 with the indicated amino acid substitutions.
Figure 3B:
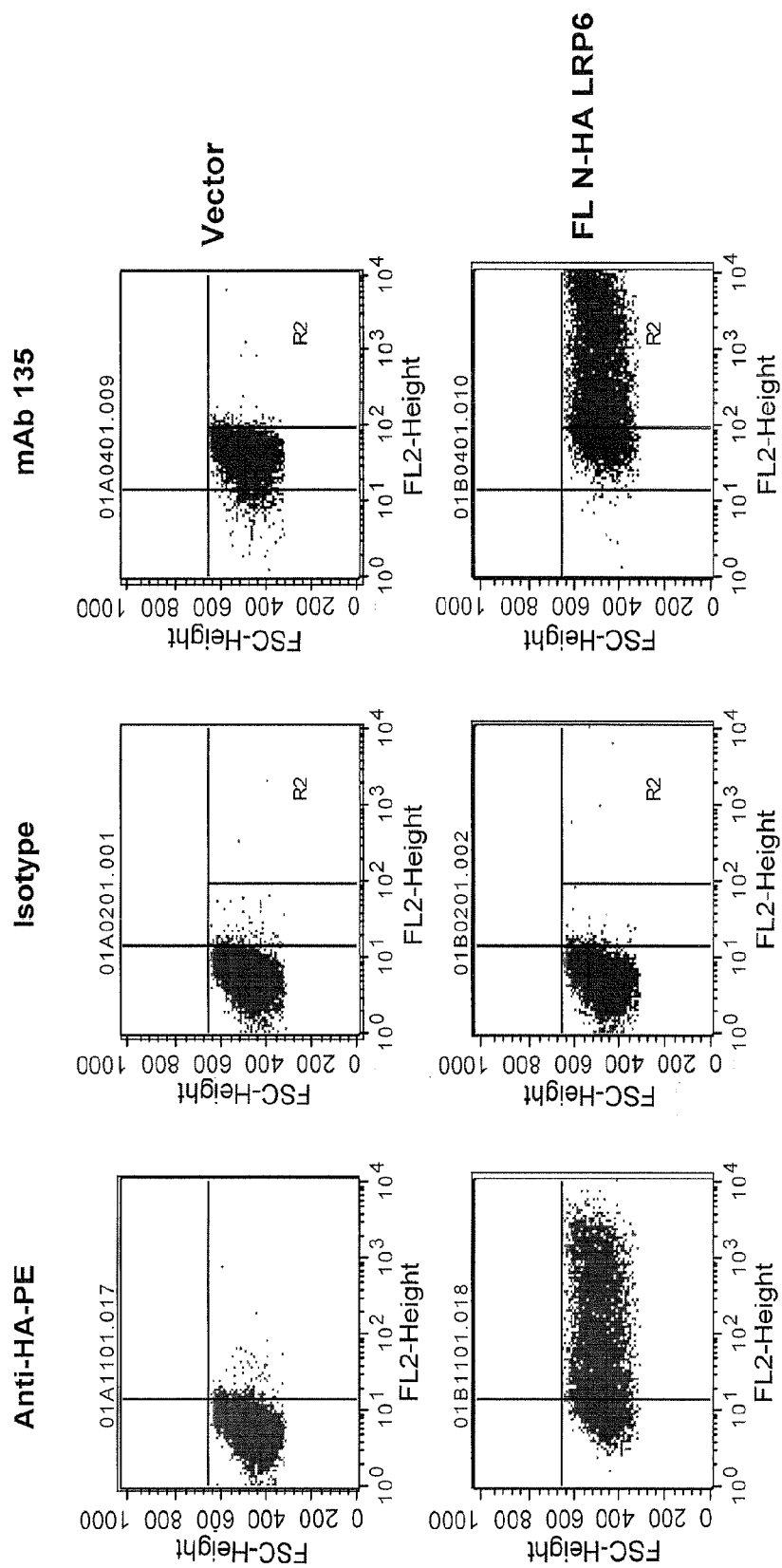
Figure 3C:
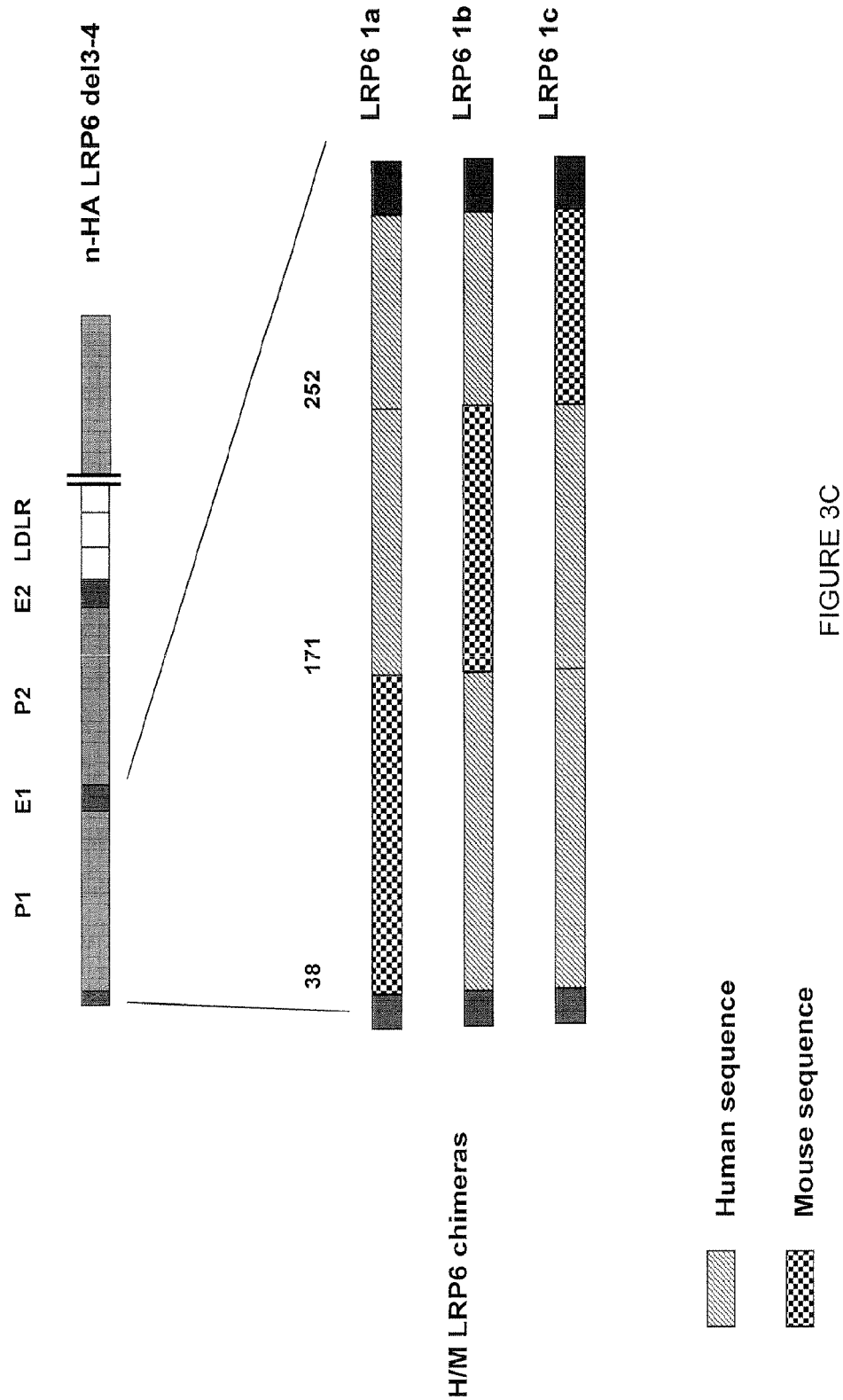

To identify the region of LRP6 that is recognized by LRP6 mAbs, a series of LRP6 propeller domain deletion constructs were made (SEQ ID NO: 6-15) and expressed in 293 cells. Binding of anti-LRP6 mAbs was determined by flow cytometry. LRP6 mAb135.16 bound to full-length LRP6 (SEQ ID NO: 5), LRP6Δ2-4 (SEQ ID NO: 13) and LRP6Δ3-4 (SEQ ID NO: 15); however mAb135.16 did not bind LRP6Δ1-2 (SEQ ID NO: 7). Therefore, the results demonstrated binding of the anti-LRP6 mAb 135.16 to a region containing the first propeller domain (propeller domain 1) defined by SEQ ID NO: 16 or amino acids 43-324 of SEQ ID NO: 2 (FIGS. 3A & B). The other antibodies disclosed herein, were mapped in the same way and results are summarized in Table 5. Amino acid sequence alignments of the heavy and light chain variable domains of the anti-LRP6 mAbs disclosed herein are shown in FIGS. 4 and 5, respectively.

To further characterize the panel of LRP6 mAbs that bound to the first propeller domain of LRP6, competition experiments were carried by ELISA, using biotinylated mAb135.16. mAb135 was biotinylated using standard procedures and LRP6 antibodies were incubated on ELISA plates coated with LRP6-Fc as described above, in the presence of biontinylated mAb135 at 0.01 or 0.1 ug/ml. After three washes with TBST, wells were incubated with streptavidin-HRP (1:5000 in 0.5% BSA/PBS) for 1 hr at room temperature on a plate shaker. After five washes with TBST, 100 μl TMB substrate (KPL #50-76-03) were added and color was allowed to develop for 10 min. Plates were read at 450 nm on a SpectraMax plate reader (Molecular Devices). Loss of binding of biotinylated mAb135.16 in the presence of the unlabeled test hybridoma supernatant and/or purified antibody, indicated that the test mAb bound to an epitope similar to or overlapping with the epitope recognized by mAb135.16. Six LRP6 antibodies were found to bind an epitope similar to or overlapping with the epitope recognized by mAb135, summarized in Table 5.

TABLE 5

| Activating LRP6 mAb | Dkk1 antagonizing mAb | mAb that bind mAb 135.16 overlapping epitope | Domain mapping* |
| --- | --- | --- | --- |
| 77.2 | 77.2 | | Propeller domain 2 |
| 213.7 | 213.7 | | Propeller domain 1 |
| 240.8 | 240.8 | | Propeller domain 1 |
| 421.1 | 421.1 | 421.1 | Propeller domain 2 |
| 498.3 | 498.3 | | Propeller domain 1 |
| 606.4 | 606.4 | | Propeller domain 1 |
| 856.6 | 856.6 | 856.6 | Propeller domain 1 |
| 923.3 | 923.3 | | Propeller domain 1 |
| 931.1 | 931.1 | | Propeller domain 1 |
| 993.9 | | | Not determined |
| 995.5 | | | Not determined |
| 1115.3 | 1115.3 | | Propeller domain 1 |
| 1213.2 | 1213.2 | | Propeller domain 1 |
| 1253.12 | 1253.12 | 1253.12 | Propeller domain 1 |
| 1281.1 | | | Propeller domain 1 |
| 1293.11 | 1293.11 | 1293.11 | Propeller domain 1 |
| 1433.8 | | | Propeller domain 1 |
| 1470.2 | 1470.2 | | Propeller domain 1 |
| 1903.1 | 1903.1 | | Propeller domain 1 |
| 135.16 | 135.16 | | Propeller domain 1 |
| 413.1 | 413.1 | 413.1 | Propeller domain 1 |
| 620.1 | 620.1 | 620.1 | Propeller domain 1 |
| 537.2 | | | Not determined |

*Propeller domain 1 = SEQ ID NO: 16; Propeller domain 2 = SEQ ID NO: 370

Figure 3D:
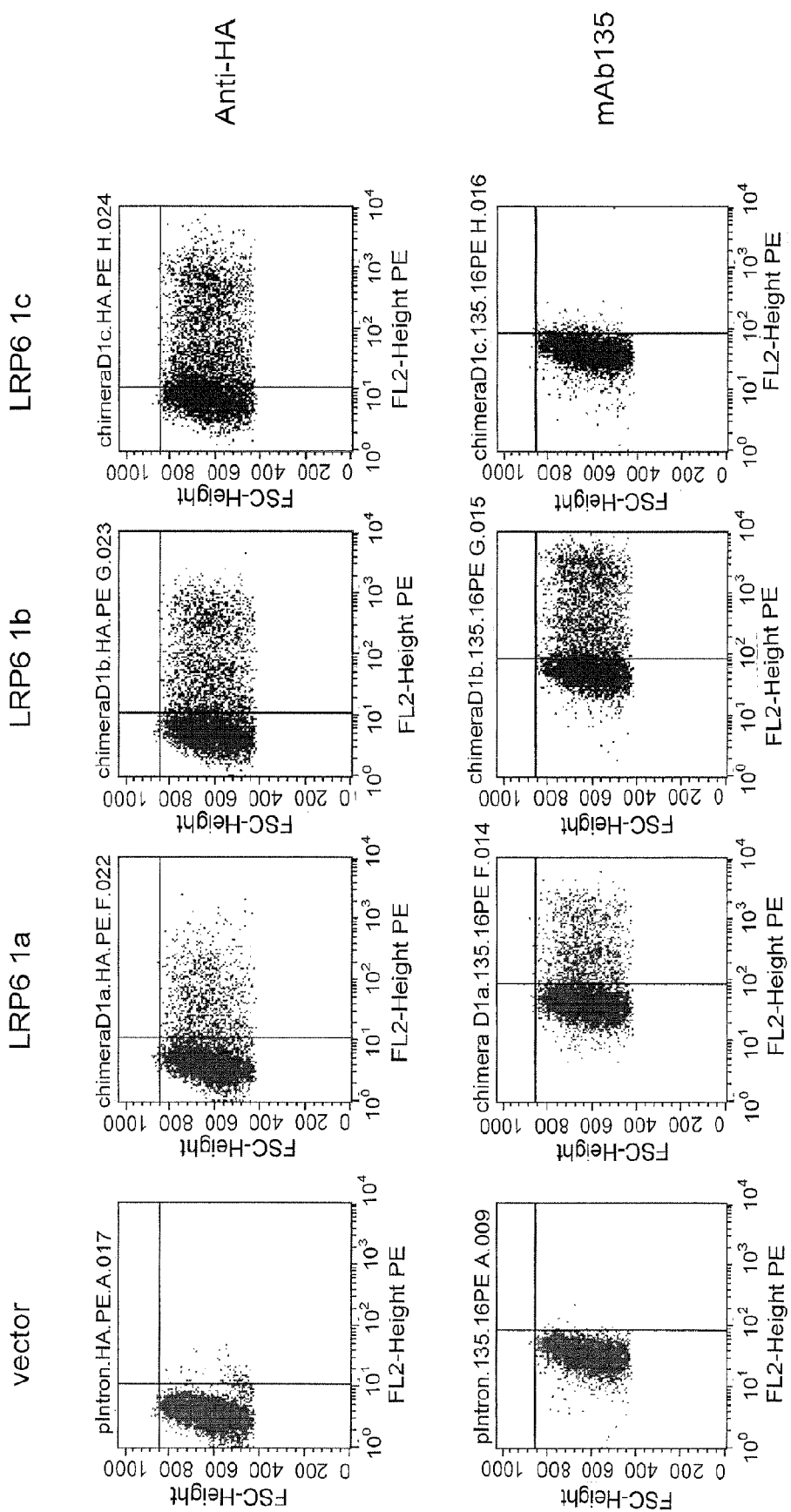
Figure 3E:
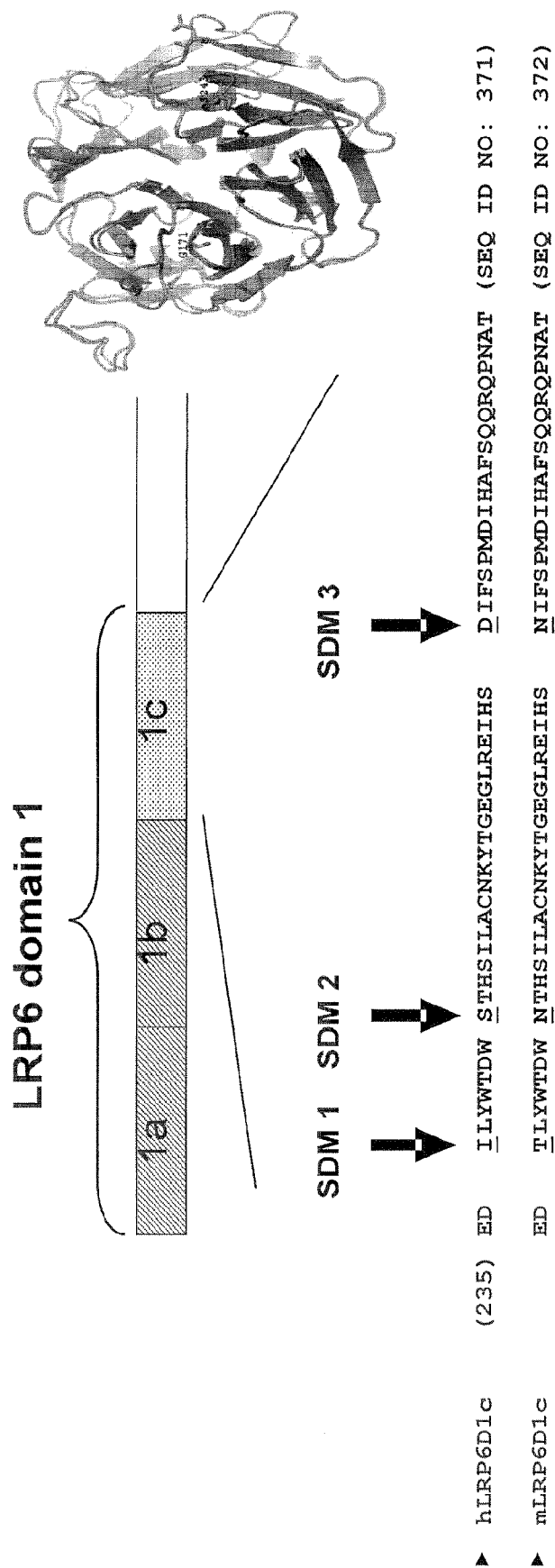
Figure 3F:
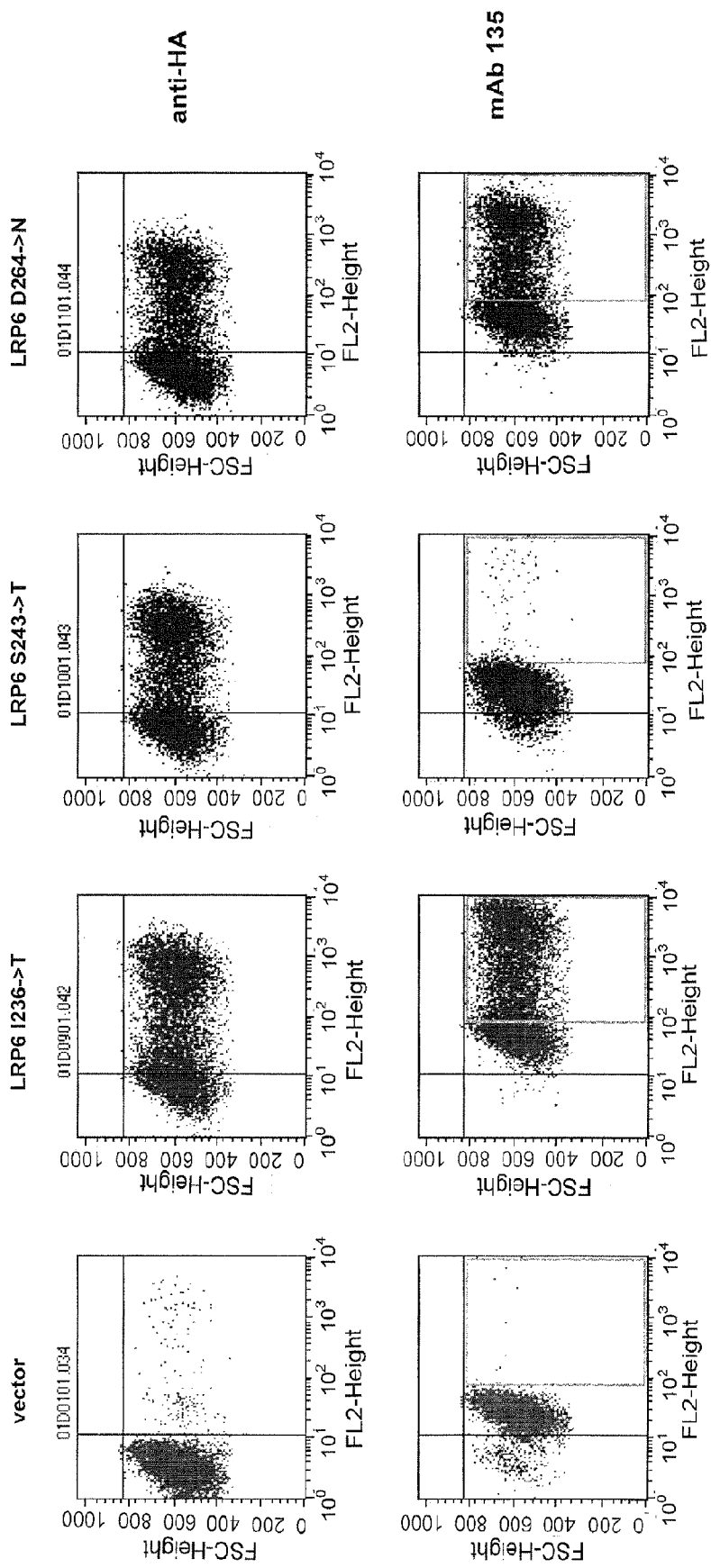

To further define the epitope to which the anti-LRP6 mAbs bound, human/mouse chimeric constructs were made of propeller domain 1. Since mAb 135.16 did not bind to mouse LRP6, various portions of the human LRP6 propeller domain 1 were substituted with the corresponding mouse sequence (SEQ ID NO: 373 is the mouse LRP6 polypeptide). Binding of the anti-LRP6 mAb to the constructs was determined by FACS analysis as described above. As can be seen in FIG. 3D, the anti-LRP6 mAb 135.16 did not bind to construct 1c in which residues 252 to 283 were replaced by the mouse sequence. Analysis of the differences between the mouse and human sequences in region 1c showed that three amino acid residues differ between human and mouse: I236T, S243N and D264N. Each of these three residues in the human sequence was individually changed to the mouse residue and analyzed for binding. As can be seen in FIG. 3F, anti-LRP6 mAb 135.16 required $Ser^{243}$ for binding.

Example 4

TCF-Luciferase Assay for Testing the Activity of Anti-LRP6 Monoclonal Antibodies To investigate the effect of the anti-LRP6 mAbs disclosed herein on canonical Wnt signaling, a stable 293 cell line expressing a TCF luciferase reporter plasmid was used.

Figure 6:
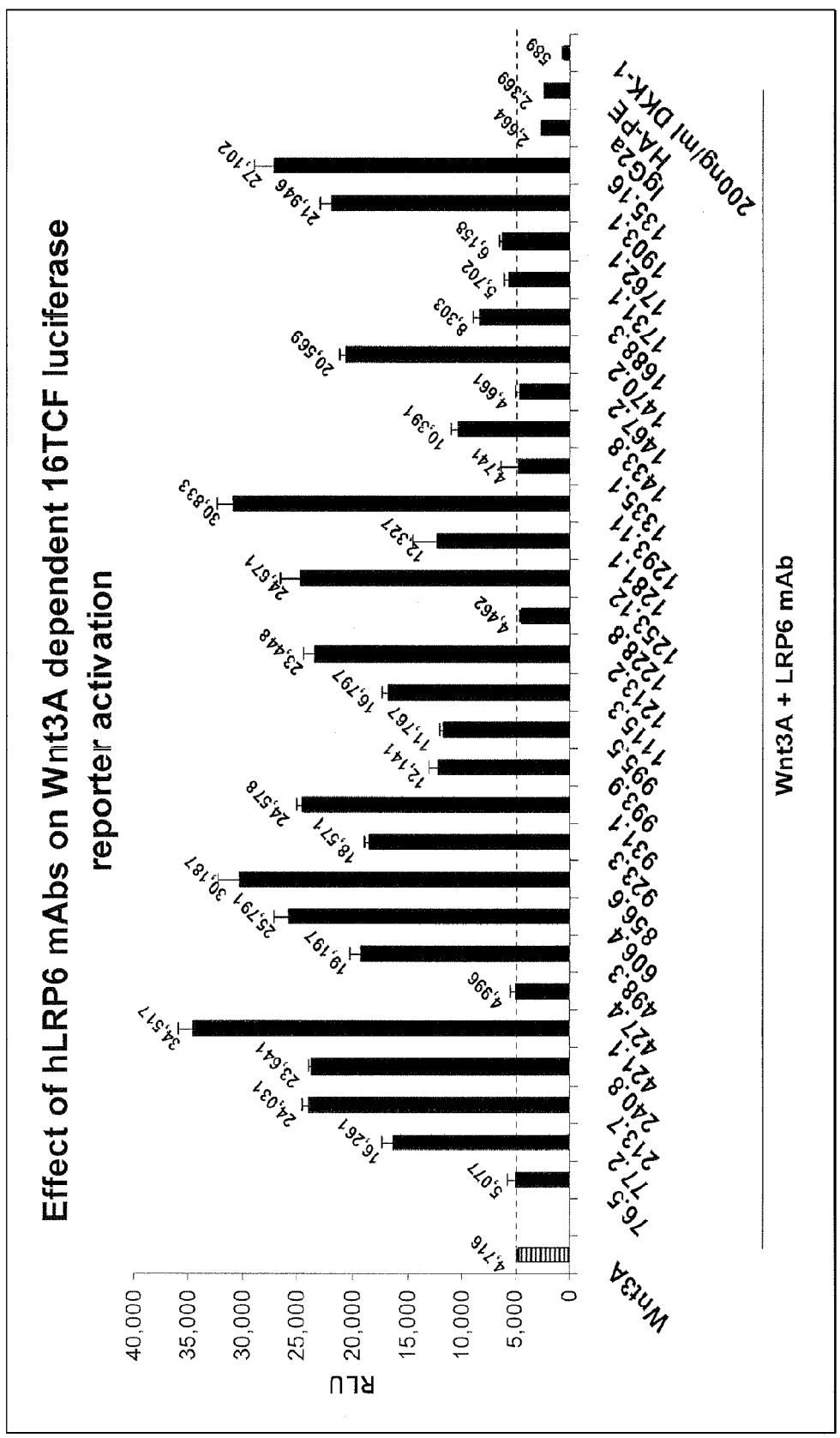
FIG. 6: Effect of anti-LRP6 mAbs on Wnt3A-dependent 16TCF luciferase reporter activation.

A 16TCF luciferase reporter construct was generated by cloning 16 repeats of a TCF consensus site (AGATCAAAGG (SEQ ID NO: 369) into the pTA-Luc vector (Clontech, Mountain View, Calif.). A geneticin selectable marker was inserted into the vector and used to select a stable clone (A6) exhibiting minimal basal reporter activation. 293 A6 cells were seeded in 96-well plates in DEMEM containing 10% fetal bovine serum (FBS) (Invitrogen, Carlsbad, Calif.), starved for 8 hours in DEMEM containing 0.1% FBS, treated in triplicate for 18 hours with the indicated antibodies (10 μg/ml) in the presence or absence of recombinant Wnt3A (200 ng/ml; purchased from R&D Systems). Reporter activity was determined 18 hours post treatment, using a Veritas luminometer (Turner Biosystems, Sunnyvale, Calif.). As shown in FIG. 6 and summarized in Table 5, treatment with mAbs 77.2, 213.7, 240.8, 421.1, 498.3, 606.4, 856.6, 923.3, 931.1, 993.9, 995.5, 1115.3, 1213.2, 1253.12, 1281.1, 1293.11, 1433.8, 1470.2, 1903.1, 135.16, 413.1, 620.1, or 537.2 resulted in a 2-7 fold increase in Wnt3A dependent reporter activation, relative to cells treated with Wnt3A alone. LRP6 antibodies did not induce reporter activation in the absence of Wnt3A, indicating that LRP6 antibodies can not induce reporter activation by themselves (data not shown).

Figure 7:
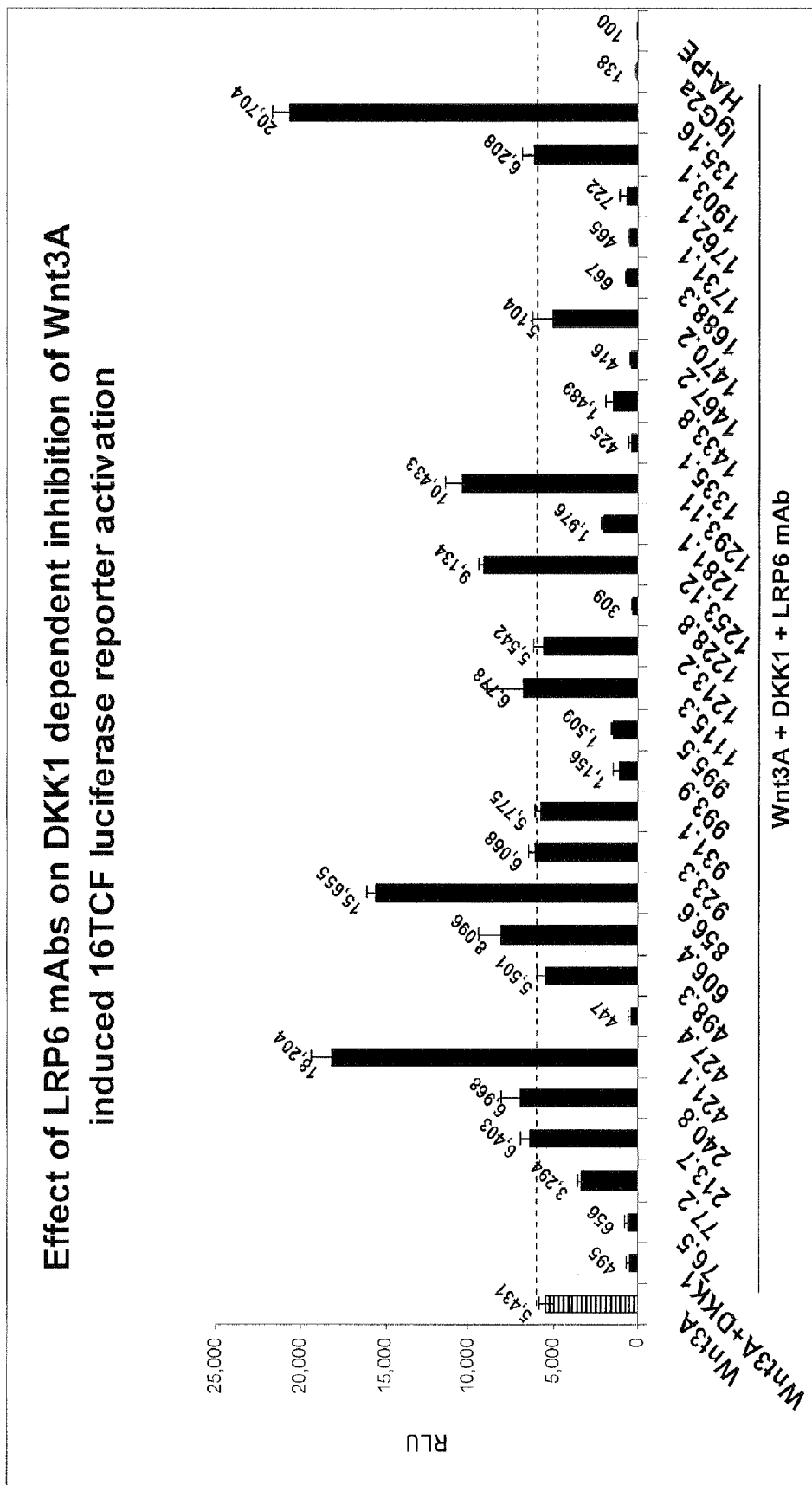
FIG. 7: Effect of anti-LRP6 mAbs on Dkk1-dependent inhibition of Wnt3A-induced 16TCF luciferase reporter activation.

Canonical Wnt signaling can be inhibited by the soluble protein Dkk1, which prevents Wnt binding to LRP5/6 and causes Kremen-dependent internalization of LRP5/6 receptors (reviewed in He et al., supra, 2004). To determine whether LRP6 specific antibodies would affect Dkk1-dependent inhibition of LRP6 function, the effect of the antibodies on Dkk1-dependent inhibition of Wnt3a mediated reporter activation was determined in the TCF reporter assay, by treating Wnt3A stimulated reporter cells with Dkk1 (200 ng/ml, purchased from R&D Systems), in the presence or absence of LRP6 activating antibodies. As shown in FIG. 7 and summarized in Table 5, co-treatment of cells with Wnt3A and Dkk1 completely inhibited Wnt3A dependent reporter activation. However, in the presence of LRP6 mAbs 77.2, 213.7, 240.8, 421.1, 498.3, 606.4, 856.6, 923.3, 931.1, 1115.3, 1213.2, 1253.12, 1293.11, 1470.2, 1903.1, 135.16, 413.1 or 620.1, Wnt3A dependent reporter activation was restored to levels at or above those observed in cells treated with Wnt3A alone, indicating that these LRP6 mAb can inhibit Dkk1 function and can be used as Dkk1 antagonists.

Figure 8:
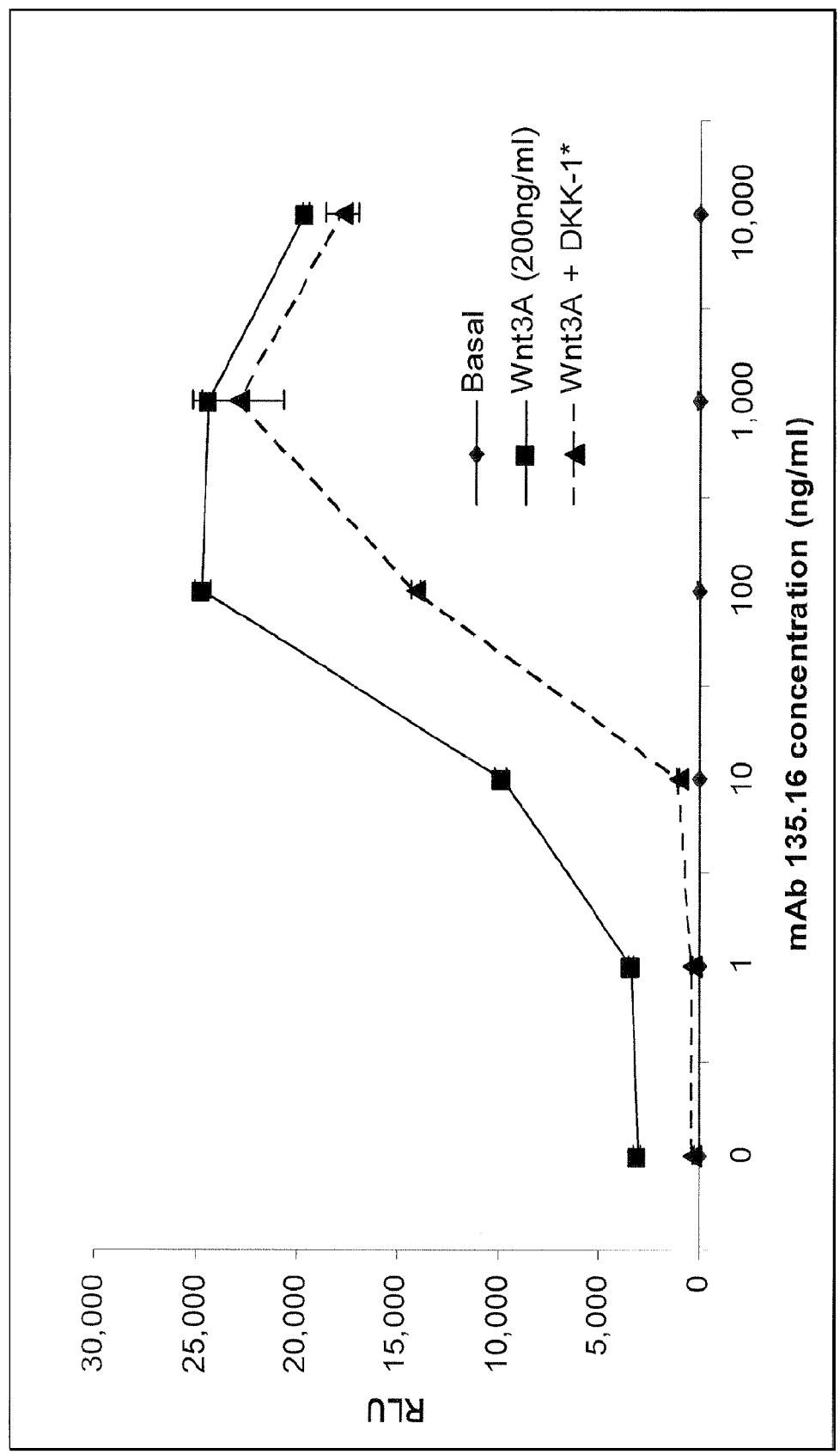
FIG. 8: Characterization of the dose response of anti-LRP6 mAb 135.16 on Wnt3A dependent 16TCF luciferase reporter activation in the absence (squares) or presence of Dkk1 (triangles).

To further characterize the activity of Wnt signaling activating anti-LRP6 antibodies, more detailed 16TCF luciferase reporter assays were carried out using the LRP6 activating antibody mAb135.16. 293 A6 reporter cells were treated with media only, recombinant Wnt3A, or recombinant Wnt3A plus recombinant Dkk1, in the presence or absence of a dose range of mAb135.16 or isotype control antibody. As shown in FIG. 8, co-treatment with mAb135.16 enhanced Wnt3A dependent reporter activation in a dose-dependent manner. Furthermore, Dkk1-dependent inhibition of Wnt3A dependent reporter activation was reversed by mAb135.16 in a dose-dependent manner, to levels at or above observed with treatment with Wnt3A alone.

Figure 9:
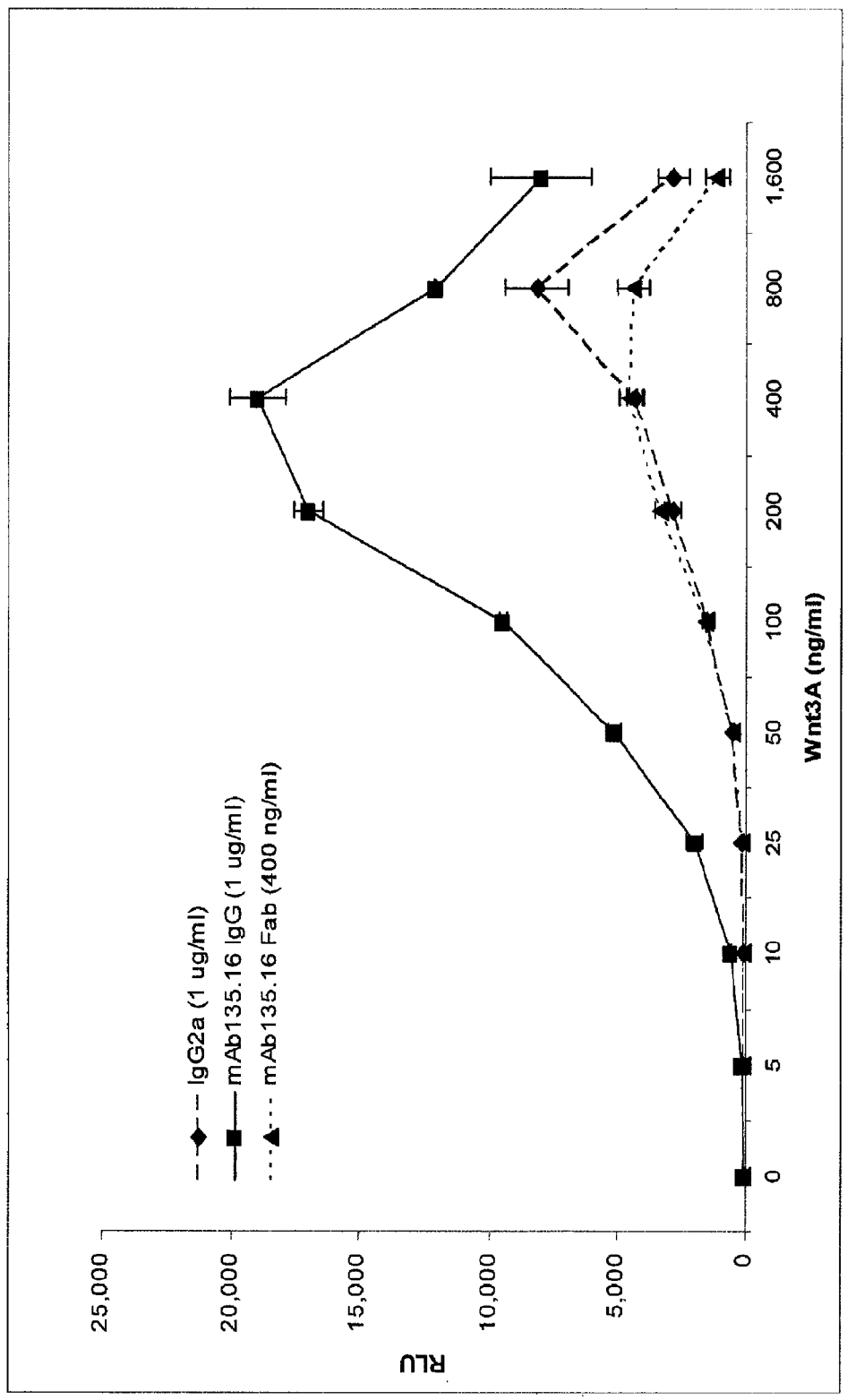
FIG. 9: Effect of anti-LRP6 mAb 135.16 whole antibody (squares) or Fab fragment (triangles) on the dose response of Wnt3a-dependent 16TCF luciferase reporter activation.
Figure 10:
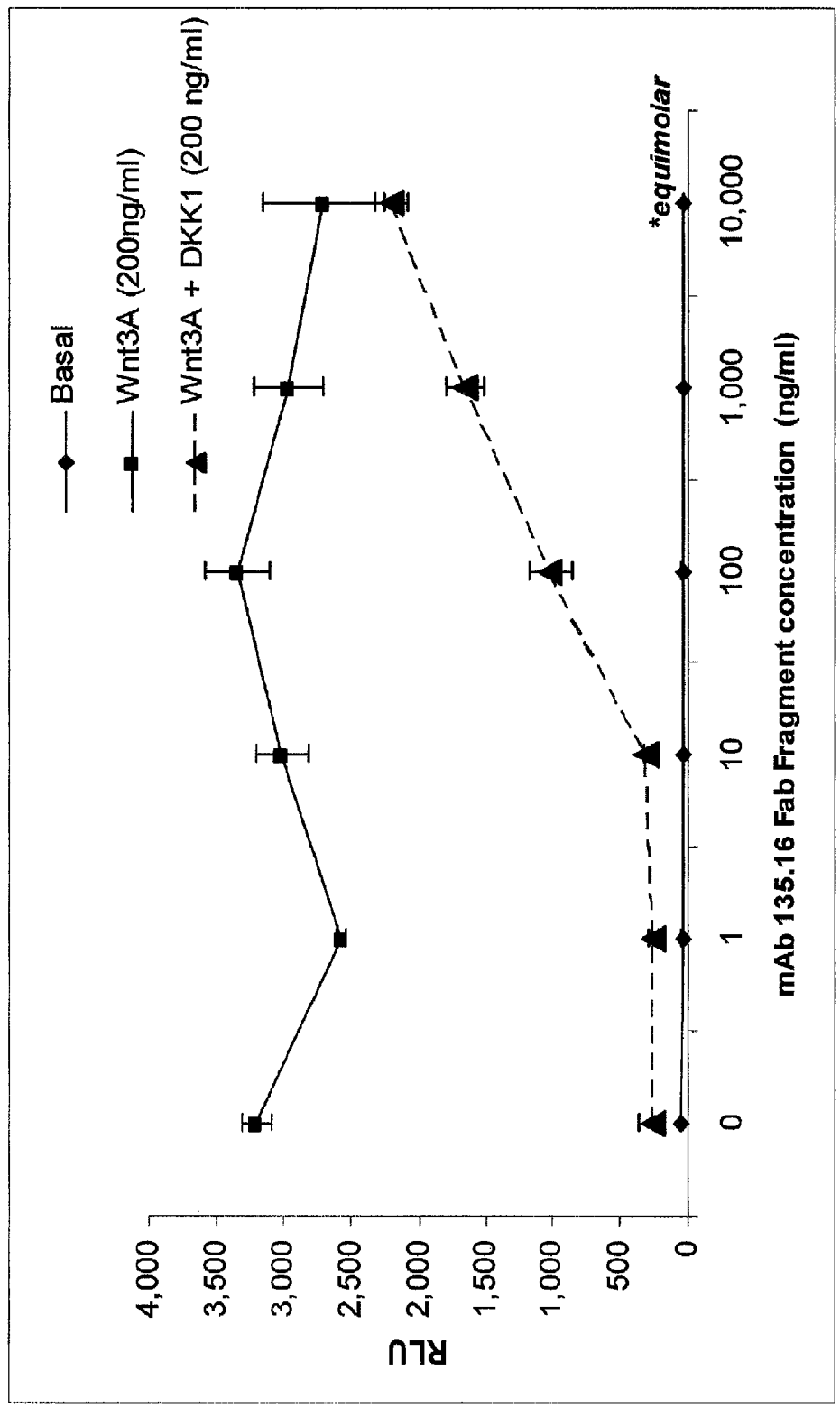
FIG. 10: Effect of anti-LRP6 mAb 135.16 Fab fragment on Dkk1-dependent inhibition of Wnt3A-induced 16TCF luciferase reporter activity.

293 A6 cells were then treated with a dose range of Wnt3A in the absence or presence of mAb135.16 or control antibody. As shown in FIG. 9, co-treatment with mAb135.16 not only enhanced the level of reporter activation in the presence of Wnt3A, but also made the cells more sensitive to Wnt3A treatment, as reporter activation could be observed at lower doses of Wnt3A. However, Fab fragments of mAb 135.16 were unable to enhance Wnt3A dependent 16TCF luciferase reporter activation. Finally, 293 A6 cells were treated with Wnt3A with or without Dkk1, in the presence or absence of Fab fragments of mAb135.16. As shown in FIG. 10, mAb 135.16 Fab fragments reversed inhibition of Wnt3A dependent reporter activity by Dkk1. These results imply that the enhancement of Wnt3A activity by activating LRP6 antibodies such as mAb135.16, requires antibody-mediated dimerization of LRP6 through binding of bivalent antibody to the first domain of LRP6. In contrast, the ability of LRP6 antibodies to antagonize Dkk1 activity does not require antibody mediated dimerization of LRP6, suggesting that inhibition of Dkk1-dependent LRP6 functions by LRP6 activating antibodies such as mAb 135.16, may result from blocking an additional Dkk1 binding site in the first propeller domain of LRP6. In this context, it is interesting to note that the high bone mass mutations identified in LRP5 that render LRP5 insensitive to Dkk1, also reside in the first propeller domain of LRP5, suggesting that the first domains of LRP5/6 may regulate sensitivity of these receptors to the Dkk1 inhibitor.

Example 5

Effect of Anti-LRP6 mAbs on Dkk1-Dependent Internalization of LRP6

Figure 11:
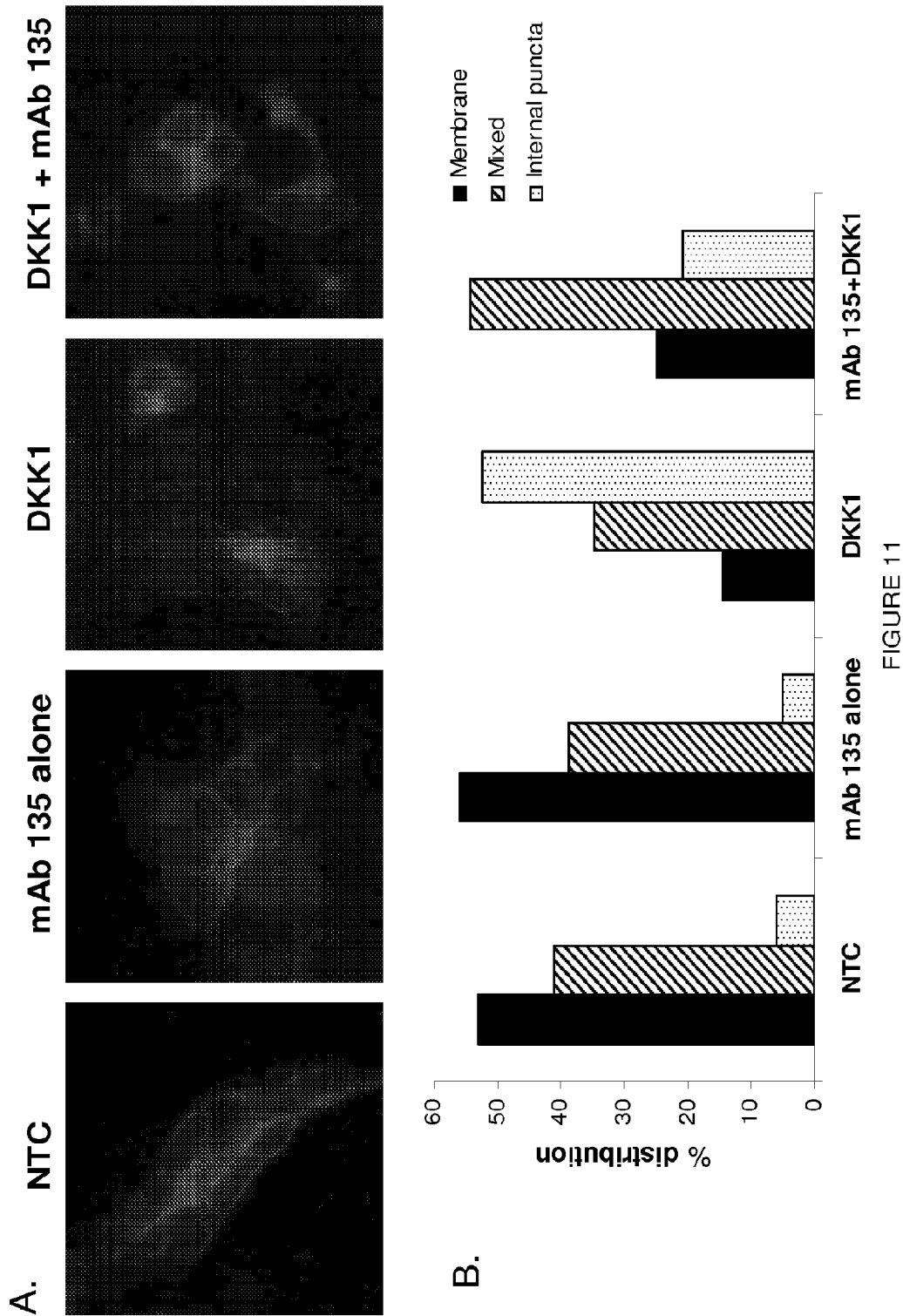
FIG. 11: Anti-LRP6 mAb 135.16 antagonizes Dkk1-dependent internalization of LRP6. A) Immunofluorescence microscopy of LRP6 internalization in HEK293 cells transfected with HA-tagged LRP6 and wildtype Kremen1 and treated with mAb 135.16 alone, Dkk1 alone, mAb 135.16 followed by Dkk1, or no treatment (NTC). B) Quantitative analysis of the immunofluorescence results as described in A.

To assess the functional consequence of inhibiting Dkk1 binding to LRP6, Dkk1-dependent internalization of LRP6 was examined by immunofluoroescence microscopy as described in Binnerts et al (*Proc. Natl. Acad. Sci. USA* 104: 14700-14705 (2007)). Briefly, HEK293 cells were co-transfected with HA-tagged LRP6 and wild-type Kremen1 proteins and analyzed using anti-HA antibodies to determine the location of the HA-tagged LRP6. LRP6 was mostly localized to the cell surface in untreated cells, whereas treatment with Dkk1 for 30 min caused LRP6 to internalize and localize into distinct intracellular punctae. In contrast, pre-treatment with anti-LRP6 mAb135 prevented Dkk1-dependent internalization of LRP6 and restored normal LRP6 cell surface levels (see FIG. 11). These results suggest that pre-incubation with anti-LRP6 mAbs result in functional inhibition of Dkk1/Kremen1-dependent internalization of LRP6.

Example 6

Models for Bone Diseases

Anti-LRP6 antibodies are tested for reduction of bone loss using a rat bone loss model as described in Kulkarni et al, *J. Bone Miner. Res.* 21:910-920 (2006). Briefly, 3- to 6-month old virgin Sprague-Dawley female rats are anesthetized by pentobarbital sodium and subjected to bilateral ovariectomy (OVX) or sham operation. Animals are caged in pairs and maintained on rodent chow and tap water ad libitum. OVX rats are permitted to lose bone for 1 month to establish osteopenia before the initiation of treatments. Anti-LRP6 antibodies are administered to the rats at 10 mg/kg three times a week intraperitoneally for 1-2 months. Animals are weighed every 2 weeks, and the dosing volumes are adjusted accordingly. One day after the last dose, the animals are sacrificed by $CO_2$ inhalation. Femurs are removed and cleaned of soft tissue, and fixed in 10% formalin for 48 hours and stored at 4° C. in 70% ethanol. Additionally, lumbar vertebrae L5 are removed and processed for biomechanical analyses.

Bone mineral density and geometric parameters of the harvested femurs are measured by peripheral quantitative computed tomography (pQCT). A two-dimensional scout view of the femur is obtained first and a distal growth plate of the femur is identified as a landmark. Measurements are performed at the metaphysic and mid-diaphysis of the femur, at 1.4 mm and 5.5 mm proximal to the growth plate, respectively. Analyses of the scans are performed using the manufacturer-supplied software.

Proximal tibias and tibial shaft are stained for 4 days in Villanueva osteochrome bone stain for osteoid staining (Polysciences, Warrington, Pa.) and dehydrated in a graded ethanol, defatted in acetone, and embedded in methyl methacrylate. Longitudinal sections of 210 μm thickness are cut using a diamond wafering saw and further hand ground to 20 μm sections of proximal tibia metaphysis (PTM) and 30 μm of tibial shaft (TX). For PTM analyses, the measurements are performed on the entire marrow region within the cortical shell between 1 and 4 mm distal to the growth plate-metaphyseal junction using an Image Analysis System (Osteomeasure). Trabecular area, perimeter, single and double-labeling surfaces, eroded surface, osteoid surface, labeling and wall width are measured and trabecular number, thickness, separation, mineralizing surface, mineral appositional rate, bone formation rate/bone volume, surface reference and activation frequency are calculated. Osteoclast number is measured on the entire marrow region within the cortical shell between 0.67 and 2 mm under ×20 magnification. The osteoclast number is normalized to trabecular bone surface. For analysis of cortical bone, TX, cross-sectional area, marrow area, eroded surface, single- and double-labeling surfaces, and labeling width are measured. These parameters are used to calculate the percent cortical bone are, marrow area, mineralizing surface, mineral appositional rate, and bone formation rate/surface reference as described in Parfitt et al., *J. Bone Miner. Res.* 2:595-610 (1987) and Ma et al, *Bone* 17:549-554 (1995).

Excised L5 vertebrae are used to evaluate the biomechanical properties of bones treated with anti-LRP6 antibodies. Mechanical properties of the L5 vertebrae are analyzed after the posterior processes are removed, and the ends of the centrum are made parallel using a diamond wafering saw. Veterbral specimens are loaded to failure in compression, using the materials testing device and analyzed using Test Works 4 software (MTS Corp., Minneapolis, Minn.). The compressive load is applied through a pivoting platen to correct for possible nonparallel alignment of the faces of the vertebral body. Specimens are tested in a saline solution at 37° C. after equilibration. Parameters measured from the load-displacement curve include ultimate load (Fu), stiffness, and energy (area under the curve). The modulus of toughness is calculated by normalizing energy by the area.

Example 7

Murine Model for Wound Healing

Anti-LRP6 antibodies that cross-react with mouse LRP6 are tested for stimulating wound closure using a murine wound healing model (described in Fathke et al, *BMC Cell Biology* 7: (2006). All animal procedures are in accordance with the Institutional Animal Care and Use Committee. Briefly, either male C57Bl/6J mice (Jackson Labs), male TOPGAL mice (DasGupta and Fuchs, *Development* 126: 4557-4568 (1999)) or male BATGAL mice (Maretto et al, *Proc. Natl. Acad. Sci. USA* 100:3299-3304 (2003)) between 8-12 weeks of age are used for the wounding experiments. Mice are anesthetized by intraperitoneal injection of a ketamine and xylazine mixture (15 mg/kg and 1 mg/kg, respectively, Phoenix Pharmaceuticals, Inc.). The dorsal hair is removed and skin is prepared for generation of a standardized 1.5 cm² full thickness wound (including the panniculus carnosus muscle) on the midback. The wound is covered with a transparent semi-occlusive dressing (Tegaderm, 3M) to prevent dessication. Anti-LRP6 antibodies are administered to the mice via subcutaneous, intravenous or topical administration daily. On days 3, 7, 14, 21 and 30, wounds are excised and processed for histology and immunohistochemistry.

Wounds are digitally photographed at the time of generation (day 0) and again on days 3, 7, 14, 21 and 30, or until wound closure. Wound area is measured using NIH Image. Wound size is determined by using histologic sections cut at a right angle to the skin surface across the wound. Serial sections are observed, and the section at the center of the wound, with the largest wound diameter, is chosen to measure wound size. A grid is used to measure the size of the epidermal and mesenchymal (or dermal) component of each wound.

Wounds are excised, bisected along the cranial-caudal axis and either frozen in OCT (Tissue-Tek, Sakura) or placed in 10% formalin overnight. Frozen tissues are cut at 10 μm sections, post fixed in 100% cold acetone, blocked for 1 hour with goat serum and then incubated with a PE-labeled anti-CD5 antibody (BD-Pharmigen, CA) for one hour. Tissues are counterstained for 5 min with DAPI (Molecular Probes, OR) to visualize nuclei. For tissues fixed in formalin, tissues are embedded, cut and stained with hematoxylin and eosin for further analysis.

Example 8

Murine Model for Osteolytic Lesions in Multiple Myeloma

Anti-LRP6 antibodies are tested for treatment of osteolytic lesions in multiple myeloma using a murine model such as the SCID-rab mouse model for human primary multiple myeloma (Yata and Yaccoby, *Leukemia*, 18:1891-1897 (2004)). Briefly, 4-week old rabbits are sacrificed and their femora and tibiae are cut into two pieces keeping the proximal and distal ends closed. The bone is inserted subcutaneously into 6- to 8-week old CB.17/Icr-SCID mice thorugh a small (5 mm) incision. The incision is closed with sterile surgical staples and engraftment of the bones is allowed to take place for 6 to 8 weeks. For each experiment, 3 to $10 \times 10^6$ unseparated human myeloma bone marrow cells containing more than 20% plasma cells in 100 μl PBS are injected directly into the implanted rabbit bone. Mice are periodically bled from the tail vein and changes in levels of circulating human immunoglobulin (hIg) of the M-protein isotype is used as an indicator of multiple myeloma growth (determined by ELISA as described in Yaccoby et al, *Blood* 92:2908-2913 (1998) and Yaccoby and Epstein, *Blood*, 94:3576-3582 (1999), both of which are herein incorporated by reference in their entirety). When hIg levels reach 50 μg/ml or higher, two mice injected with cells from the same patient are used for study. Mice are treated with the anti-LRP6 antibodies via subcutaneous injection at 100 μg antibody in 100 μl PBS into the surrounding area of the implanted bone. Mice receive treatment 5 days a week for 4 to 6 weeks.

Mice are anesthetized with ketamine plus xylazine. Radiographs taken with an AXR Minishot-100 beryllium source instrument (Associated X-Ray Imaging, Haverhill, Mass.) use a 10 second exposure at 40 kV. Changes in bone mineral density of the implanted bone and mouse femur are determined using a PIXImus DEXA (GE Medical Systems, LUNAR, Madison, Wis.).

For closer analysis of the bone structure, mice are sacrificed and the bones are fixed in 10% phosphate-buffered formalin for 24 hours. Rabbit and murine bones are further decalcified with 10% (w/v) EDTA, pH 7.0. The bones are embedded in paraffin for sectioning. Sections (5 μm) are deparaffinized in xylene, rehydrated with ethanol, and rinsed in PBS, and then undergo antigen retrieval using microwave. After peroxidase quenching with 3% hydrogen peroxide for 10 min, sections are incubated with 5 μg/ml mouse anti-bovine ostecalcin monoclonal antibody and mouse IgG control antibody (QED Bioscience, San Diego, Calif.) and the assay is completed with the use of the Dako immunoperoxidase kit (Dako, Carpinteria, Calif.). Sections are lightly counterstained with hematoxylin. According to the manufacturer, the osteocalcin antibody cross-reacts with human and rabbit tissues but not with mouse tissues. Tartrate-resistant acti phosphatase (TRAP) staining of deparaffinized bone sections are performed with an acid phosphatase kit (Sigma, St. Louis, Mo.). Osteocalcin-expressing osteoblasts and TRAP$^+$ multinucleated osteoclasts in 4 nonoverlapping, millimeter-square areas are counted.

---

We claim:

1. An isolated antibody or antigen-binding fragment thereof, comprising a heavy chain variable region comprising an amino acid sequence selected from the group consisting of SEQ ID NO: 18, 22, 26, 30, 34, 38, 42, 46, 50, 54, 58, 62, 66, 70, 72, 74, 78, 82, 86, 90, 94, 98 and 102, wherein said antibody or antigen-binding fragment thereof specifically binds to an LPR6 polypeptide comprising the amino acid sequence of SEQ ID NO: 2.

2. An isolated antibody or antigen-binding fragment thereof, comprising a light chain variable region comprising an amino acid sequence selected from the group consisting of SEQ ID NO: 20, 24, 28, 32, 36, 40, 44, 48, 52, 56, 60, 64, 68, 76, 80, 84, 88, 92, 96, 100 and 104, wherein said antibody or antigen-binding fragment thereof specifically binds to an LPR6 polypeptide comprising the amino acid sequence of SEQ ID NO: 2.

3. An isolated antibody or antigen-binding fragment thereof, selected from the group consisting of,
(a) an antibody or antigen-binding fragment thereof comprising a heavy chain variable region comprising the amino acid sequence of SEQ ID NO: 18, and a light chain variable region comprising the amino acid sequence of SEQ ID NO: 20;
(b) an antibody or antigen-binding fragment thereof comprising a heavy chain variable region comprising the amino acid sequence of SEQ ID NO: 22, and a light chain variable region comprising the amino acid sequence of SEQ ID NO: 24;
(c) an antibody or antigen-binding fragment thereof comprising a heavy chain variable region comprising the amino acid sequence of SEQ ID NO: 26, and a light chain variable region comprising the amino acid sequence of SEQ ID NO: 28;
(d) an antibody or antigen-binding fragment thereof comprising a heavy chain variable region comprising the amino acid sequence of SEQ ID NO: 30, and a light chain variable region comprising the amino acid sequence of SEQ ID NO: 32;
(e) an antibody or antigen-binding fragment thereof comprising a heavy chain variable region comprising the amino acid sequence of SEQ ID NO: 34, and a light chain variable region comprising the amino acid sequence of SEQ ID NO: 36;
(f) an antibody or antigen-binding fragment thereof comprising a heavy chain variable region comprising the amino acid sequence of SEQ ID NO: 38, and a light chain variable region comprising the amino acid sequence of SEQ ID NO: 40;
(g) an antibody or antigen-binding fragment thereof comprising a heavy chain variable region comprising the amino acid sequence of SEQ ID NO: 42, and a light chain variable region comprising the amino acid sequence of SEQ ID NO: 44;
(h) an antibody or antigen-binding fragment thereof comprising a heavy chain variable region comprising the amino acid sequence of SEQ ID NO: 46, and a light chain variable region comprising the amino acid sequence of SEQ ID NO: 48;
(i) an antibody or antigen-binding fragment thereof comprising a heavy chain variable region comprising the amino acid sequence of SEQ ID NO: 50, and a light chain variable region comprising the amino acid sequence of SEQ ID NO: 52;
(j) an antibody or antigen-binding fragment thereof comprising a heavy chain variable region comprising the amino acid sequence of SEQ ID NO: 54, and a light chain variable region comprising the amino acid sequence of SEQ ID NO: 56;
(k) an antibody or antigen-binding fragment thereof comprising a heavy chain variable region comprising the amino acid sequence of SEQ ID NO: 58, and a light chain variable region comprising the amino acid sequence of SEQ ID NO: 60;
(l) an antibody or antigen-binding fragment thereof comprising a heavy chain variable region comprising the amino acid sequence of SEQ ID NO: 62, and a light chain variable region comprising the amino acid sequence of SEQ ID NO: 64,
(m) an antibody or antigen-binding fragment thereof comprising a heavy chain variable region comprising the amino acid sequence of SEQ ID NO: 66, and a light chain variable region comprising the amino acid sequence of SEQ ID NO: 68;
(n) an antibody or antigen-binding fragment thereof comprising a heavy chain variable region comprising the amino acid sequence of SEQ ID NO: 74, and a light chain variable region comprising the amino acid sequence of SEQ ID NO: 76;
(o) an antibody or antigen-binding fragment thereof comprising a heavy chain variable region comprising the amino acid sequence of SEQ ID NO: 78, and a light chain variable region comprising the amino acid sequence of SEQ ID NO: 80;
(p) an antibody or antigen-binding fragment thereof comprising a heavy chain variable region comprising the amino acid sequence of SEQ ID NO 82, and a light chain variable region comprising the amino acid sequence of SEQ ID NO: 84;
(q) an antibody or antigen-binding fragment thereof comprising a heavy chain variable region comprising the amino acid sequence of SEQ ID NO: 86, and a light chain variable region comprising the amino acid sequence of SEQ ID NO: 88;
(r) an antibody or antigen-binding fragment thereof comprising a heavy chain variable region comprising the amino acid sequence of SEQ ID NO: 90, and a light chain variable region comprising the amino acid sequence of SEQ ID NO: 92;
(s) an antibody or antigen-binding fragment thereof comprising a heavy chain variable region comprising the amino acid sequence of SEQ ID NO: 94, and a light chain variable region comprising the amino acid sequence of SEQ ID NO: 96;
(o) an antibody or antigen-binding fragment thereof comprising a heavy chain variable region comprising the amino acid sequence of SEQ ID NO: 98, and a light chain variable region comprising the amino acid sequence of SEQ ID NO: 100; and (v) an antibody or antigen-binding fragment thereof comprising a heavy chain variable region comprising the amino acid sequence of SEQ ID NO: 102, and a light chain variable region comprising the amino acid sequence of SEQ ID NO: 104, wherein sad antibody or antigen-binding fragment thereof specifically binds to an LPR6polypeptide comprising the amino acid sequence of SEQ ID NO: 2.

4. An isolated antibody or antigen-binding fragment thereof, selected from the group consisting of:

(a) an antibody or antigen-binding fragment thereof, comprising three heavy chain. complementarity determining regions (CDRs) comprising the amino acid sequences of SEQ ID NOs: 108-110, and three light chain CDRs comprising the amino acid sequences of SEQ ID NOs: 114-116;

(b) an antibody or antigen-binding fragment thereof comprising three heavy chain CDRs comprising the amino acid sequences of SEQ ID NOs: 120-122, and three light chain CDRs comprising the amino acid sequences of SEQ ID NOs: 126-128;

(c) an antibody or antigen-binding fragment thereof comprising three heavy chain CDRs comprising the amino acid sequences of SEC ID NOs: 132-134, and three light chain CDRs comprising the amino acid sequences of SEQ ID NOs: 138-140;

(d) an antibody or antigen-binding fragment thereof comprising three heavy chain CDRs comprising the amino acid sequences of SEQ ID NOs: 144-146, and three light chain CDRs comprising the amino acid sequences of SEQ ID NOs: 150-152;

(e) an antibody or antigen-binding fragment thereof comprising three heavy chain CDRs comprising the amino acid sequences of SEQ ID NOs: 156-158, and three light chain CDRs comprising the amino acid sequences of SEQ ID NOs: 162-164;

(f) an antibody or antigen-binding fragment thereof comprising three heavy chain CDRs comprising the amino acid sequences of SEQ ID NOs: 168-170, and three light chain CDRs comprising the amino acid sequences of SEQ ID NOs: 174-176;

(g) an antibody or antigen-binding fragment thereof comprising three heavy chain GDRs comprising the ammo acid sequences of SEQ ID NOs: 180-182, and three light chain CDRs comprising the amino acid sequences of SEQ ID NOs: 186-188;

(h) an antibody or antigen-binding fragment thereof comprising three heavy chain CDRs comprising the amino acid sequences of SEQ ID NOs: 192-194, and three light chain CDRs comprising the amino acid sequences of SEQ NOs: 198-200;

(i) an antibody or antigen-binding fragment thereof comprising three heavy chain CDRs comprising the amino acid sequences of SEQ ID NOs: 204-206, and three light chain CDRs comprising the amino acid sequences of SEQ NOs: 210-212;

(j) an antibody or antigen-binding fragment thereof comprising three heavy Chain CDRs comprising the amino acid sequences of SEQ ID NOs: 216-218, and three light chain CDRs comprising the amino acid sequences of SEQ ID NOs: 222-224;

(k) an antibody or antigen-binding fragment thereof comprising three heavy chain CDRs comprising the amino acid sequences of SEQ ID NOs: 228-230, and three light chain CDRs comprising the amino acid sequences of SEQ ID NOs: 234-236;

(l) an antibody or antigen-binding fragment thereof comprising three heavy chain CDRs comprising the amino acid sequences of SEQ ID NOs: 240-242, and throe light chain CDRs comprising the amino acid sequences of SEQ NOs: 246-248;

(m) an antibody or antigen-binding fragment thereof comprising three heavy chain CDRs comprising the amino acid sequences of SEQ ID NOs: 252-254, and three light chain CDRs comprising the amino acid sequences of SEQ ID NOs: 258-260, (n) an antibody or antigen-binding fragment thereof comprising three heavy chain CDRs comprising the amino acid sequences of SEQ ID NOs: 276-278, and three light chain CDRs comprising the amino acid sequences of SEQ ID NOs: 282-284;

(o) an antibody or antigen-binding fragment thereof comprising three light chain CDRs comprising the amino acid sequences of SEQ ID NOs: 288-290, and throe light chain CDRs comprising the amino acid sequences of SEQ ID NOs: 294-296;

(p) an antibody or antigen-binding fragment thereof comprising three heavy chain CDRs comprising the amino acid sequences of SEQ ID NOs: 300-302, and three light chain CDRs comprising the amino acid sequences of SEQ ID NOs: 306-308;

(q) an antibody or antigen-binding fragment thereof comprising three heavy chain CDRs comprising the amino acid sequences of SEQ ID NOs: 312-314, and three light chain CDRs comprising the amino acid sequences of SEQ ID NOs: 318-320;

(r) an antibody or antigen-binding fragment thereof comprising three heavy chain CDRs comprising the amino acid sequences of SEQ ID NOs: 324-326, and throe light chain CDRs comprising the amino acid sequences of SEQ ID NOs: 330-332;

(s) an antibody or antigen-binding fragment thereof comprising three heavy chain CDRs comprising, the amino acid sequences of SEQ ID NOs: 336-338, and three light chain CDRs comprising the amino acid sequences of SEQ ID NOs: 342-344;

(t) an antibody or antigen-binding fragment thereof comprising three heavy chain CDRs comprising the amino acid sequences of SEQ ID NOs: 348-350, and three light chain CDRs comprising the amino acid sequences of SEQ ID NOs: 354-356; and (v) an antibody or antigen-binding fragment thereof comprising three heavy chain CDRs comprising the amino acid sequences of SEQ ID NOs: 360-362, and three light chain CDRs comprising the amino acid sequences of SEQ ID NOs; 366-368;

wherein said antibody or antigen-binding fragment thereof specifically binds to an LPR6polypeptide comprising the amino acid sequence of SEQ ID NO: 2.

5. The isolated antibody or antigen-binding fragment thereof according to claim 1, 2, 3 or 4, wherein said antigen or antigen-binding fragment thereof binds to an epitope within residues 43-627, 43-324, 263-283 or 352-627 of an LRP6 polypeptide comprising the amino acid sequence of SEQ ID NO: 2.

6. The isolated antibody or antigen-binding fragment thereof according to claim 1, 2, 3 or 4, wherein said antigen or antigen-binding fragment thereof binds to an epitope of an LRP6 polypeptide comprising an amino acid sequence selected from the group consisting of SEQ ID NOs; 13, 15, 16, 27, 370 and 371, 7. The isolated antibody or antigen-binding fragment thereof according to claim 1, 2, 3 or 4 selected from the group consisting of a single-Fv antibody, an Fab antibody, an (Fab')$_2$ antibody, a fully human antibody, a humanized antibody, and a chimeric antibody.

8. A nucleic acid molecule encoding the antibody or antigen binding fragment thereof, according to claim 1, 2, 3 or 4.

9. An isolated cell line that produces an antibody or antigen- binding fragment thereof, according to claim 1, 2, 3 or 4.

10. A method of detecting the level of an LRP6 polypeptide comprising the amino acid sequence of SEQ ID NO: 2 in a biological sample, the method comprising; contacting the sample with an antibody or antigen-binding fragment thereof, according to claim 1.

11. The isolated antibody or antigen-binding fragment thereof, according to claim 3, wherein said antibody or antigen-binding fragment comprises a heavy chain variable region comprising the amino acid sequence of SEQ ID NO: 22, and the light chain variable sequence comprising the amino acid sequence of SEQ ID NO: 24.

12. The isolated antibody or antigen-binding fragment thereof, according to claim 4, wherein said antibody or antigen-binding fragment comprises three heavy chain CDRs comprising the amino acid sequences of SEQ ID NOs: 120-122, and three light chain CDRs comprising the amino acid sequences of SEQ ID NOs: 126-128.

13. The isolated antibody or antigen-binding fragment thereof, according to claim 12, wherein the antibody or antigen-binding fragment thereof binds LPR6 with a $K_D$ of less than or equal to $10^9$M.

* * * * *